US009029337B2

(12) United States Patent
Freier et al.

(10) Patent No.: US 9,029,337 B2
(45) Date of Patent: May 12, 2015

(54) MODULATION OF FACTOR 7 EXPRESSION

(75) Inventors: Susan M. Freier, San Diego, CA (US);
Brett P. Monia, Encinitas, CA (US);
Hong Zhang, Carlsbad, CA (US);
Jeffrey R. Crosby, Carlsbad, CA (US);
Chenguang Zhao, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 1219 days.

(21) Appl. No.: 12/741,959

(22) PCT Filed: Nov. 5, 2008

(86) PCT No.: PCT/US2008/082526
§ 371 (c)(1),
(2), (4) Date: Aug. 12, 2010

(87) PCT Pub. No.: WO2009/061851
PCT Pub. Date: May 14, 2009

(65) Prior Publication Data
US 2010/0298417 A1 Nov. 25, 2010

Related U.S. Application Data

(60) Provisional application No. 60/986,928, filed on Nov. 9, 2007.

(51) Int. Cl.
*C12N 15/11* (2006.01)
*C12N 15/113* (2010.01)

(52) U.S. Cl.
CPC ........ *C12N 15/1137* (2013.01); *C12N 2310/11* (2013.01); *C12N 2310/315* (2013.01); *C12N 2310/321* (2013.01); *C12N 2310/3341* (2013.01); *C12N 2310/341* (2013.01); *C12Y 304/21021* (2013.01)

(58) Field of Classification Search
USPC ...................................... 514/44 A
See application file for complete search history.

(56) References Cited

U.S. PATENT DOCUMENTS

| 5,801,154 | A | 9/1998 | Baracchini et al. | |
|---|---|---|---|---|
| 6,582,908 | B2 | 6/2003 | Fodor et al. | |
| 7,871,985 | B2* | 1/2011 | de Fougerolles et al. | 514/44 R |
| 2001/0053519 | A1 | 12/2001 | Fodor et al. | |
| 2003/0228597 | A1 | 12/2003 | Cowsert et al. | |
| 2005/0208588 | A1* | 9/2005 | Ravikumar et al. | 435/7.1 |
| 2006/0003322 | A1* | 1/2006 | Bentwich | 435/6 |
| 2006/0058266 | A1* | 3/2006 | Manoharan et al. | 514/81 |
| 2006/0252039 | A1* | 11/2006 | Fontcuberta et al. | 435/6 |
| 2007/0031844 | A1 | 2/2007 | Khvorova et al. | |
| 2010/0331392 | A1* | 12/2010 | Monia et al. | 514/44 A |

FOREIGN PATENT DOCUMENTS

| WO | WO 00/40595 | 7/2000 |
|---|---|---|
| WO | WO 01/30395 | 5/2001 |
| WO | WO 2004/016754 | 2/2004 |
| WO | WO 2005/042552 | 5/2005 |
| WO | WO2010/055041 A1 * | 5/2010 |

OTHER PUBLICATIONS

Applicant's arguments filed on Feb. 17, 2011, pp. 1-15, U.S. Appl. No. 12/488,394.*
Mouritzen et al. Nature Methods 2:313-17, 2005.*
Hagen et al., "Characterization of a cDNA coding for human factor VII" PNAS (1986) 83(8):2412-2416.
O'Hara et al., "Nucleotide sequence of the gene coding for human factor VII, a vitamin K-dependent protein participating in blood coagulation" PNAS (1987) 84(15):5158-5162.
Crosby et al., "Antisense Oligonucleotide Mediated Depiction of Factor VII Provides Protection from Ferric Chlroide Induced Thrombosis without Increased Bleeding Risk in Mice" Blood (2008) 112(11):1058.
Crosby et al., "FXII Antisense Oligonucleotide Mediated Depletion Results in Effective Anticoagulation without Bleeding Risk" Blood (2010) 116(21):497.
Savi et al., "Effect of Aspirin and Clopidogrel on Platelet-Dependent Tissue Factor Expression in Endothelial Cells" Thrombosis Research (1994) 73(2):117-124.
European Search Report for application EP 10800570 dated May 31, 2013.
Becker et al., "Nucleic Acid Aptamers in Therapeutic Anticoagulation Technology, Development and Clinical Application" Thrombosis and Haemostasis (2005) 93(6):1014-1020.
Branch et al., "A good antisense molecule is hard to find," TIBS (1998) 23:45-50.
Crooke et al., "Basic Principles of Antisense Therapeutics" Antisense Research and Application (1998) Chapter 1:1-50.
New England Biolabs 1998/99 Catalog (cover page and pp. 121 and 284).
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Shirk et al., "Inhibitors of Factor VIIa/tissue factor" Arteriosclerosis, Thrombosis, and Vascular Biology (2007) 27(9):1895-1900.
International Search Report for application No. PCT/US2008/082526 dated Jun. 4, 2009.
Ollivier et al., "Tissue Factor-Dependent Vascular Endothelial Growth Factor Production by Human Fibroblasts in Response to Activated Factor VII" Blood (1998) 91(8):2698-2703.
International Search Report for application No. PCT/US2010/042187 dated Dec. 22, 2010.

* cited by examiner

*Primary Examiner* — Brian Whiteman
(74) *Attorney, Agent, or Firm* — Knobbe, Martens, Olson & Bear, LLP

(57) ABSTRACT

Disclosed herein are antisense compounds and methods for decreasing Factor 7 and treating or preventing thromboembolic complications, hyperproliferative disorders, or inflammatory conditions in an individual in need thereof. Examples of disease conditions that can be ameliorated with the administration of antisense compounds targeted to Factor 7 include thrombosis, embolism, and thromboembolism, such as, deep vein thrombosis, pulmonary embolism, myocardial infarction, stroke, cancer, rheumatoid arthritis, and fibrosis.

27 Claims, No Drawings

MODULATION OF FACTOR 7 EXPRESSION

RELATED APPLICATIONS

This application is a 35 U.S.C. §371 national phase application of international application serial no. PCT/US2008/082526, filed on Nov. 5, 2008, which is a non-provisional of and claims priority to U.S. patent application Ser. No. 60/986,928, filed on Nov. 9, 2007, the disclosure of each of which is incorporated herein by reference in its entirety.

SEQUENCE LISTING

The present application is being filed along with a Sequence Listing in electronic format. The Sequence Listing is provided as a file entitled BIOL0099WOSEQ.txt created Nov. 5, 2008, which is 180 Kb in size. The information in the electronic format of the sequence listing is incorporated herein by reference in its entirety.

FIELD OF THE INVENTION

Embodiments of the present invention provide methods, compounds, and compositions for reducing expression of Factor 7 mRNA and protein in an animal. Such methods, compounds, and compositions are useful to treat, prevent, or ameliorate thromboembolic complications, hyperproliferative disorders, and inflammatory conditions.

BACKGROUND OF THE INVENTION

The circulatory system requires mechanisms that prevent blood loss, as well as those that counteract inappropriate intravascular obstructions. Generally, coagulation comprises a cascade of reactions culminating in the conversion of soluble fibrinogen to an insoluble fibrin gel. The steps of the cascade involve the conversion of an inactive zymogen to an activated enzyme. The active enzyme then catalyzes the next step in the cascade.

Coagulation Cascade

The coagulation cascade may be initiated through two branches, the tissue factor pathway (also "extrinsic pathway"), which is the primary pathway, and the contact activation pathway (also "intrinsic pathway").

The tissue factor pathway is initiated by the cell surface receptor tissue factor (TF, also referred to as factor III), which is expressed constitutively by extravascular cells (pericytes, cardiomyocytes, smooth muscle cells, and keratinocytes) and expressed by vascular monocytes and endothelial cells upon induction by inflammatory cytokines or endotoxin. (Drake et al., *Am J Pathol* 1989, 134:1087-1097). TF is the high affinity cellular receptor for coagulation factor VIIa, a serine protease. In the absence of TF, VIIa has very low catalytic activity, and binding to TF is necessary to render VIIa functional through an allosteric mechanism. (Drake et al., *Am J Pathol* 1989, 134:1087-1097). The TF-VIIa complex activates factor X to Xa. Xa in turn associates with its co-factor factor Va into a prothrombinase complex which in turn activates prothrombin, (also known as factor II or factor 2) to thrombin (also known as factor IIa, or factor 2a). Thrombin activates platelets, converts fibrinogen to fibrin and promotes fibrin cross-linking by activating factor XIII, thus forming a stable plug at sites where TF is exposed on extravascular cells. In addition, thrombin reinforces the coagulation cascade response by activating factors V and VIII.

The contact activation pathway is triggered by activation of factor XII to XIIa. Factor XIIa converts XI to XIa, and XIa converts IX to IXa. IXa associates with its cofactor VIIIa to convert X to Xa. The two pathways converge at this point as factor Xa associates factor Va to activate prothrombin (factor II) to thrombin (factor IIa).

Inhibition of Coagulation

At least three mechanisms keep the coagulation cascade in check, namely the action of activated protein C, antithrombin, and tissue factor pathway inhibitor. Activated protein C is a serine protease that degrades cofactors Va and VIIIa. Protein C is activated by thrombin with thrombomodulin, and requires coenzyme Protein S to function. Antithrombin is a serine protease inhibitor (serpin) that inhibits serine proteases: thrombin, Xa, XIIa, XIa and IXa. Tissue factor pathway inhibitor inhibits the action of Xa and the TF-VIIa complex. (Schwartz A L et al., *Trends Cardiovasc Med.* 1997; 7:234-239.)

Disease

Thrombosis is the pathological development of blood clots, and an embolism occurs when a blood clot migrates to another part of the body and interferes with organ function. Thromboembolism may cause conditions such as deep vein thrombosis, pulmonary embolism, myocardial infarction, and stroke. Significantly, thromboembolism is a major cause of morbidity affecting over 2 million Americans every year. (Adcock et al. *American Journal of Clinical Pathology.* 1997; 108:434-49). While most cases of thrombosis are due to acquired extrinsic problems, for example, surgery, cancer, immobility, some cases are due to a genetic predisposition, for example, antiphospholipid syndrome and the autosomal dominant condition, Factor V Leiden. (Bertina R M et al. *Nature* 1994; 369:64-67.)

Treatment

The most commonly used anticoagulants, warfarin, heparin, and low molecular weight heparin (LMWH) all possess significant drawbacks.

Warfarin is typically used to treat patients suffering from atrial fibrillation. The drug interacts with vitamin K—dependent coagulation factors which include factors II, VII, IX and X. Anticoagulant proteins C and S are also inhibited by warfarin. Drug therapy using warfarin is further complicated by the fact that warfarin interacts with other medications, including drugs used to treat atrial fibrillation, such as amiodarone. Because therapy with warfarin is difficult to predict, patients must be carefully monitored in order to detect any signs of anomalous bleeding.

Heparin functions by activating antithrombin which inhibits both thrombin and factor X. (Bjork I, Lindahl U. *Mol Cell Biochem.* 1982 48: 161-182.) Treatment with heparin may cause an immunological reaction that makes platelets aggregate within blood vessels that can lead to thrombosis. This side effect is known as heparin-induced thrombocytopenia (HIT) and requires patient monitoring. Prolonged treatment with heparin may also lead to osteoporosis. LMWH can also inhibit Factor 2, but to a lesser degree than unfractioned heparin (UFH). LMWH has been implicated in the development of HIT.

Thus, current anticoagulant agents lack predictability and specificity and, therefore, require careful patient monitoring to prevent adverse side effects, such as bleeding complications. There are currently no anticoagulants which target only the intrinsic or extrinsic pathway.

SUMMARY OF THE INVENTION

Provided herein are antisense compounds, compositions, and methods for the treatment and prevention of clotting disorders.

Antisense compounds described herein may comprise an oligonucleotide consisting of 12 to 30 nucleosides targeted to a Factor 7 nucleic acid. In certain embodiments, the Factor 7 nucleic acid may be any of the sequences as set forth in nucleotides 1255000 to 1273000 of GENBANK® Accession No. NT_027140.6, GENBANK® Accession No. NM_019616.2, and GENBANK® Accession No. DB184141.1.

The antisense compound may be a single-stranded or double-stranded oligonucleotide. The antisense compound may be 100, 95, 90, 85, 80, 75, or 70% complementary to the Factor 7 nucleic acid.

The antisense oligonucleotide may be modified, wherein at least one internucleoside linkage is a modified internucleoside linkage. The internucleoside linkage may be a phosphorothioate internucleoside linkage.

The antisense oligonucleotide may be modified, wherein at least one nucleoside comprises a modified sugar. The modified sugar may be a bicyclic sugar. The modified sugar may comprise a 2'-O-methoxyethyl.

The antisense oligonucleotide may be modified, wherein at least one nucleoside comprises a modified nucleobase. The modified nucleobase may be a 5-methylcytosine.

The antisense oligonucleotide may be a 5-10-5 MOE gapmer. The antisense oligonucleotide may consist of 20 linked nucleosides.

Compositions described herein may comprise an oligonucleotide consisting of 12 to 30 linked nucleosides, targeted to a Factor 7 nucleic acid or a salt thereof and a pharmaceutically acceptable carrier or diluent.

The composition may be a single-stranded or double-stranded oligonucleotide.

Methods described herein may comprise administering to an animal a compound comprising an oligonucleotide consisting of 12 to 30 linked nucleosides targeted to a Factor 7 nucleic acid.

Administration of the compound may slow or stop coagulation. The compound may be co-administered with any of aspirin, clopidogrel, dipyridamole, heparin, lepirudin, ticlopidine, and warfarin. Administration of the compound and a second drug may be concomitant.

Administration of the compound and/or the second drug may be by parenteral administration. Parenteral administration may be any of subcutaneous or intravenous administration.

In another embodiment, the methods described herein may also comprise identifying a human with a clotting disorder and administering to a human a therapeutically effective amount of a compound comprising an oligonucleotide consisting of 12 to 30 linked nucleosides targeted to a Factor 7 nucleic acid.

Also described is a compound comprising an antisense oligonucleotide consisting of 12 to 30 linked nucleosides that will bind within the range of nucleobases 1147 to 1227, 9169 to 9278, 10982 to 11058, 11075 to 11117, 12084 to 12117, 12387 to 13796, 13847 to 13907, 14017 to 14051, 14093 to 14134, 14172 to 14287, 14331 to 14402, 14664 to 14746, 15098 to 15570, 15609 to 15819, 15899 to 15905, or 15957 to 15982 of SEQ ID NO: 1, encoding a Factor 7 nucleic acid.

The antisense oligonucleotide may be 90, 95, or 100% complementary to SEQ ID NO: 1, encoding a Factor 7 nucleic acid. The antisense oligonucleotide may be fully complementary to SEQ ID NO: 1.

The antisense oligonucleotide may hybridize exclusively within the range of nucleobases 1147 to 1227, 9169 to 9278, 10982 to 11058, 11075 to 11117, 12084 to 12117, 12387 to 13796, 13847 to 13907, 14017 to 14051, 14093 to 14134, 14172 to 14287, 14331 to 14402, 14664 to 14746, 15098 to 15570, 15609 to 15819, 15899 to 15905, or 15957 to 15982 of SEQ ID NO: 1, encoding a Factor 7 nucleic acid.

Also described is a compound comprising an antisense oligonucleotide consisting of 12 to 30 linked nucleosides that will bind within the range of nucleobases 102 to 131 or 652 to 682 of SEQ ID NO: 2, encoding a Factor 7 nucleic acid.

The antisense oligonucleotide may be 90, 95, or 100% complementary to SEQ ID NO: 2, encoding a Factor 7 nucleic acid. The antisense oligonucleotide may be fully complementary to SEQ ID NO: 2.

The compound may hybridize exclusively within the range of nucleobases 102 to 131 or 652 to 682 of SEQ ID NO: 2, encoding a Factor 7 nucleic acid.

Embodiments of the present invention provide, a compound comprising a modified oligonucleotide consisting of 12 to 30 linked nucleosides comprising a nucleobase sequence comprising at least 12 contiguous nucleobases of a nucleobase sequence of SEQ ID NOs: 4 to 159 and 168 to 611.

In certain embodiments, the nucleobase sequence is SEQ ID NO: 53.

In certain embodiments, the nucleobase sequence of the modified oligonucleotide is at least 80% complementary to the nucleobase sequence of any of SEQ ID NO: 1, SEQ ID NO: 2, SEQ ID NO: 3, and SEQ ID NO: 167.

In certain embodiments, the nucleobase sequence of the modified oligonucleotide is at least 90% complementary to the nucleobase sequence of any of SEQ ID NO: 1, SEQ ID NO: 2, SEQ ID NO: 3, and SEQ ID NO: 167.

In certain embodiments, the nucleobase sequence of the modified oligonucleotide is 100% complementary to the nucleobase sequence of any of SEQ ID NO: 1, SEQ ID NO: 2, SEQ ID NO: 3, and SEQ ID NO: 167.

In certain embodiments, the modified oligonucleotide comprises:
(i) a gap segment consisting of linked deoxynucleosides;
(ii) a 5' wing segment consisting of linked nucleosides;
(iii) a 3' wing segment consisting of linked nucleosides;
  wherein the gap segment is positioned immediately adjacent to and between the 5' wing segment and the 3' wing segment and wherein each nucleoside of each wing segment comprises a modified sugar.

In certain embodiments, the modified oligonucleotide comprises:
(i) a gap segment consisting of ten linked deoxynucleosides;
(ii) a 5' wing segment consisting of five linked nucleosides;
(iii) a 3' wing segment consisting of five linked nucleosides;
  wherein the gap segment is positioned immediately adjacent and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide comprises:
(i) a gap segment consisting of fourteen linked deoxynucleosides;
(ii) a 5' wing segment consisting of three linked nucleosides;
(iii) a 3' wing segment consisting of three linked nucleosides;
  wherein the gap segment is positioned immediately adjacent and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide comprises:

(i) a gap segment consisting of thirteen linked deoxynucleosides;
(ii) a 5' wing segment consisting of two linked nucleosides;
(iii) a 3' wing segment consisting of five linked nucleosides;
wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide comprises:
(i) a gap segment consisting of twelve linked deoxynucleosides;
(ii) a 5' wing segment consisting of two linked nucleosides;
(iii) a 3' wing segment consisting of two linked nucleosides;
wherein the gap segment is positioned between the 5' wing segment and the 3' wing segment, wherein each nucleoside of each wing segment comprises a 2'-O-methoxyethyl sugar; and wherein each internueleoside linkage is a phosphorothioate linkage.

Embodiments of the present invention provide a composition comprising a modified oligonucleotide consisting of 12 to 30 linked nucleosides comprising a nucleobase sequence comprising at least 12 contiguous nucleobases of a nucleobase sequence of any of SEQ ID NOs: 4 to 159 and 168 to 611 or a salt thereof and a pharmaceutically acceptable carrier or diluent.

In certain embodiments, the nucleobase sequence is SEQ ID NO: 53.

Embodiments of the present invention provide a method comprising administering to an animal a modified oligonucleotide consisting of 12 to 30 linked nucleosides comprising a nucleobase sequence comprising at least 12 contiguous nucleobases of a nucleobase sequence of any of SEQ ID NOs: 4 to 159 and 168 to 611.

In certain embodiments, the nucleobase sequence is SEQ ID NO: 53.

In certain embodiments, the animal is a human.

In certain embodiments, the administering prevents deep vein thrombosis.

In certain embodiments, the administering prevents pulmonary embolism.

In certain embodiments, the administering treats a hyperproliferative disorder.

In certain embodiments, the administering treats an inflammatory condition.

Embodiments of the present invention provide a method comprising identifying an animal at risk for having thromboembolic complications and administering to the at risk animal a therapeutically effective amount of a compound comprising a modified oligonucleotide consisting of 12 to 30 linked nucleosides, wherein the modified oligonucleotide is complementary to a Factor 7 nucleic acid.

In certain embodiments, the thromboembolic complication is deep vein thrombosis, pulmonary embolism, or a combination thereof.

Embodiments of the present invention provide a compound comprising a modified oligonucleotide consisting of 12 to 30 linked nucleosides and having a nucleobase sequence, wherein the nucleobase sequence comprises an at least 12 consecutive nucleobase portion complementary to a equal number of nucleobases of nucleotides 15128 to 15223 of SEQ ID NO: 1, wherein the modified oligonucleotide is at least 80% complementary to SEQ ID NO: 1.

In certain embodiments, the modified oligonucleotide has a nucleobase sequence of SEQ ID NO: 53.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or", unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furanosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antidote compound" refers to a compound capable decreasing the intensity or duration of any antisense activity.

"Antidote oligonucleotide" means an antidote compound comprising an oligonucleotide that is complementary to and capable of hybridizing with an antisense compound.

"Antidote protein" means an antidote compound comprising a peptide.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" or "bicyclic nucleoside" or bicyclic nucleotide" refers to a nucleoside or nucleotide wherein the furanose portion of the nucleoside or nucleotide includes a bridge connecting two carbon atoms on the furanose ring, thereby forming a bicyclic ring system. As used herein, unless otherwise indicated, the term "methyleneoxy BNA" alone refers to β-D-methyleneoxy BNA.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Coagulation factor" means any of factors I, II, III, IV, V, VII, VIII, IX, X, XI, XII, or XIII in the blood coagulation cascade. "Coagulation factor nucleic acid" means any nucleic acid encoding a coagulation factor. For example, in certain embodiments, a coagulation factor nucleic acid includes, without limitation, a DNA sequence encoding a coagulation factor (including genomic DNA comprising introns and exons), an RNA sequence transcribed from DNA encoding a coagulation factor, and an mRNA sequence encoding a coagulation factor. "Coagulation factor mRNA" means an mRNA encoding a coagulation factor protein.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, in drugs that are injected the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Efficacy" means the ability to produce a desired effect. "Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Factor 7 nucleic acid" or "Factor VII nucleic acid" means any nucleic acid encoding Factor 7. For example, in certain embodiments, a Factor 7 nucleic acid includes, without limitation, a DNA sequence encoding Factor 7, an RNA sequence transcribed from DNA encoding Factor 7 (including genomic DNA comprising introns and exons), and an mRNA sequence encoding Factor 7. "Factor 7 mRNA" means an mRNA encoding a Factor 7 protein.

"Factor 7 specific inhibitor" refers to any agent capable of specifically inhibiting the expression of Factor 7 mRNA and/or Factor 7 protein at the molecular level. For example, Factor 7 specific inhibitors include nucleic acids (including antisense compounds), peptides, antibodies, small molecules, and other agents capable of inhibiting the expression of Factor 7 mRNA and/or Factor 7 protein. In certain embodiments, by specifically modulating Factor 7 mRNA expression and/or Factor 7 protein expression, Factor 7 specific inhibitors may affect other components of the coagulation cascade including downstream components. Similarly, in certain embodiments, Factor 7 specific inhibitors may affect other molecular processes in an animal.

"Factor 7 specific inhibitor antidote" means a compound capable of decreasing the effect of a Factor 7 specific inhibitor. In certain embodiments, a Factor 7 specific inhibitor antidote is selected from a Factor 7 peptide; a Factor 7 antidote oligonucleotide; including a Factor 7 antidote compound complementary to a Factor 7 antisense compound; and any compound or protein that affects the intrinsic or extrinsic coagulation pathway.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid. In certain such embodiments, an antisense oligonucleotide is a first nucleic acid and a target nucleic acid is a second nucleic acid.

"Gapmer" means an antisense compound in which an internal position having a plurality of nucleotides that supports RNaseH cleavage is positioned between external regions having one or more nucleotides that are chemically distinct from the nucleosides of the internal region. A "gap segment" means the plurality of nucleotides that make up the internal region of a gapmer. A "wing segment" means the external region of a gapmer.

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include, but are not limited to, an antisense compound and a target nucleic acid. In certain such embodiments, complementary nucleic acid molecules include, but are not limited to, an antisense oligonucleotide and a nucleic acid target.

"Hyperproliferative disorder" refers to disorders characterized by an abnormal or pathological proliferation of cells, for example, cancer, psoriasis, hyperplasia and the like.

"Identifying an animal at risk for thromboembolic complications" means identifying an animal having been diagnosed with a thromboembolic complication, or identifying an animal predisposed to develop a thromboembolic complication. Individuals predisposed to develop a thromboembolic complication include those having one or more risk factors for thromboembolic complications including immobility, surgery (particularly orthopedic surgery), malignancy, pregnancy, older age, use of oral contraceptives, and inherited or acquired prothrombotic clotting disorders. Such identification may be accomplished by any method including evaluating an individual's medical history and standard clinical tests or assessments.

"Immediately adjacent" means there are no intervening elements between the immediately adjacent elements.

"Individual" means a human or non-human animal selected for treatment or therapy.

"Individual in need thereof" refers to a human or non-human animal selected for treatment or therapy that is in need of such treatment or therapy.

"Inflammatory condition" refers to a disease, disease state, syndrome, or other condition resulting in inflammation. For example, rheumatoid arthritis and liver fibrosis are inflammatory conditions. Other examples of inflammatory conditions include sepsis, myocardial ischemia/reperfusion injury, adult respiratory distress syndrome, nephritis, graft rejection, inflammatory bowel disease, multiple sclerosis, arteriosclerosis, and vasculitis.

"Internucleoside linkage" refers to the chemical bond between nucleosides.

"Linked nucleosides" means adjacent nucleosides which are bonded together.

"Mismatch" or "non-complementary nucleobase" means a nucleobase of a first nucleic acid that is not capable of pairing with the corresponding nucleobase of a second or target nucleic acid.

"Modified internucleoside linkage" refers to a substitution and/or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, and/or a modified nucleobase.

"Modified sugar" refers to a substitution and/or any change from a natural sugar. "Modified sugar moiety" means a sugar moiety having any substitution and/or change from a natural sugar moiety.

"Motif" means the pattern of unmodified and modified nucleosides in an antisense compound, i.e. the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, and/or nucleobase modification.

"Nucleoside" means a nucleobase linked to a sugar.

"Nucleotide" means a nucleoside having a phosphate group covalently linked to the sugar portion of the nucleoside.

"Oligomeric compound" or "oligomer" means a polymer comprising linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes, but is not limited to, subcutaneous administration, intravenous administration, intramuscular administration, intraarterial administration, intraperitoneal administration, or intracranial administration, e.g. intrathecal or intracerebroventricular administration. "Subcutaneous administration" means administration just below the skin. "Intravenous administration" means administration into the veins.

"Peptide" means a molecule formed by linking at least two amino acids by amide bonds. Peptide refers to polypeptides and proteins.

"Pharmaceutical agent" means a substance provides a therapeutic benefit when administered to an individual. For example, in certain embodiments, an antisense oligonucleotide targeted to Factor 7 is a pharmaceutical agent. "Active pharmaceutical agent" means the substance or substances in a pharmaceutical composition that provides a desired effect.

"Pharmaceutical composition" means a mixture of substances suitable for administering to an individual. For example, a pharmaceutical composition may comprise one or more antisense oligonucleotides and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. "Prevent" also means reducing risk of developing a disease, disorder, or condition.

"Prodrug" means a therapeutic agent that is prepared in an inactive form that is converted to an active form (i.e., drug) within the body or cells thereof by the action of endogenous enzymes or other chemicals or conditions.

"Side effects" means physiological responses attributable to a treatment other than the desired effects. In certain embodiments, side effects include, without limitation, injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand. "Single-stranded modified oligonucleotide" means a modified oligonucleotide which is not hybridized to a complementary strand.

"Specifically hybridizable" means an antisense compound that hybridizes to a target nucleic acid to induce a desired effect, while exhibiting minimal or no effects on non-target nucleic acids. For example, specifically hybridizable refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Stringent hybridization conditions" means conditions under which a nucleic acid molecule, such as an antisense compound, will hybridize to a target nucleic acid sequence, but to a minimal number of other sequences. Stringent conditions are sequence-dependent and will vary in different circumstances. In the context of this invention, stringent conditions under which oligomeric compounds hybridize to a target sequence are determined by the nature and composition of the oligomeric compounds and the assays in which they are being investigated.

"Targeted" or "targeted to" means having a nucleobase sequence that will allow specific hybridization of an antisense compound to a target nucleic acid to induce a desired effect. In certain embodiments, a desired effect is reduction of a target nucleic acid. In certain embodiments, a desired effect is reduction of a Factor 7 mRNA.

"Targeting" means the process of design and selection of an antisense compound that will specifically hybridize to a target nucleic acid and induce a desired effect.

"Target nucleic acid," "target RNA," "target RNA transcript," and "nucleic acid target" all mean a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Target region" or "active target region" means a portion of a target nucleic acid to which one or more antisense compounds is targeted.

"Therapeutically effective amount" means an amount of a pharmaceutical agent that provides a therapeutic benefit to an individual.

"Thromboembolic complication" means any disease, disorder, or condition involving an embolism caused by a thrombus. Examples of such diseases, disorders, and conditions include the categories of thrombosis, embolism, and thromboembolism. In certain embodiments, such disease disorders, and conditions include deep vein thrombosis, pulmonary embolism, myocardial infarction, and stroke.

"Treat" refers to administering a pharmaceutical composition to effect an alteration or improvement of a disease, disorder, or condition.

"Unmodified nucleotide" means a nucleotide composed of naturally occuring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Embodiments of the present invention provide methods, compounds, and compositions for modulating expression of Factor 7 mRNA and protein. In certain embodiments, expression of Factor 7 mRNA and protein is decreased. In certain embodiments, Factor 7 specific inhibitors modulate expression of Factor 7 mRNA and protein. In certain embodiments, Factor 7 specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, Factor 7 mRNA levels are reduced. In certain embodiments, Factor 7 protein levels are reduced. Such reduction can occur in a time-dependent manner or in a dose-dependent manner.

Embodiments of the present invention provide methods, compounds, and compositions for the treatment, prevention, or amelioration of diseases, disorders, and conditions associated with Factor 7 in an individual in need thereof. In certain embodiments, such diseases, disorders, and conditions are thromboembolic complications. Such thromboembolic complications include the categories of thrombosis, embolism, and thromboembolism. In certain embodiments such thromboembolic complications include deep vein thrombosis, pulmonary embolism, myocardial infarction, and stroke.

Such diseases, disorders, and conditions can have one or more risk factors, causes, or outcomes in common. Certain risk factors and causes for development of a thromboembolic complication include immobility, surgery (particularly orthopedic surgery), malignancy, pregnancy, older age, use of oral contraceptives, atrial fibrillation, previous thromboembolic complication, chronic inflammatory disease, and inherited or acquired prothrombotic clotting disorders. Certain outcomes associated with development of a thromboembolic complication include decreased blood flow through an affected vessel, death of tissue, and death of the individual. Certain risk factors and causes for development of a hyperproliferative disorder include genetic factors, such as gene mutations and chromosomal aberrations, which may or may not be inherited; and environmental factors, which include, but are not limited to, exposure to known mutagens, such as high energy radiation from radioactive elements, X-rays, gamma rays, microwaves, and ultraviolet light; certain industrial chemicals; pollutants such as cigarette smoke; certain pesticides; drugs, and viruses. Certain outcomes associated with development of a hyperproliferative disorder include non-malignant tumors, pre-malignant tumors and malignant tissues in an individual. Certain risk factors and causes for development of an inflammatory condition include any noxious stimulus that causes a cellular response to an underlying pathophysiologic condition, which includes but is not limited to bacterial and viral infections, and allergens. Inflammation is mediated by cytokines, which are secreted by the host macrophages, T-lymphocytes, endothelial cells. Certain outcomes associated with development of an inflammatory condition include redness, pain, swelling at the affected area, loss of function, morbidity and mortality of the individual.

In certain embodiments, methods of treatment include administering a Factor 7 specific inhibitor to an individual in need thereof.

In certain embodiments, the present invention provides methods and compounds for the preparation of a medicament for the treatment, prevention, or amelioration of a disease, disorder, or condition associated with Factor 7. Factor 7 associated diseases, disorders, and conditions include thromboembolic complications, hyperproliferative disorders, and inflammatory conditions. Thromboembolic complications include thrombosis, embolism, thromboembolism, deep vein thrombosis, pulmonary embolism, myocardial infarction, and stroke. Hyperproliferative disorders include cancer. Inflammatory conditions include rheumatoid arthritis and fibrosis.

Embodiments of the present invention provide a Factor 7 specific inhibitor for use in treating, preventing, or ameliorating a Factor 7 associated disease. In certain embodiments, Factor 7 specific inhibitors are nucleic acids (including antisense compounds), peptides, antibodies, small molecules, and other agents capable of inhibiting the expression of Factor 7 mRNA and/or Factor 7 protein.

Embodiments of the present invention provide a Factor 7 specific inhibitor, as described herein, for use in treating, preventing, or ameliorating thromboembolic complications such as thrombosis, embolism, thromboembolism, deep vein thrombosis, pulmonary embolism, myocardial infarction, and stroke.

Embodiments of the present invention provide a Factor 7 specific inhibitor, as described herein, for use in treating, preventing, or ameliorating a thromboembolic complication, as described herein, by combination therapy with an additional agent or therapy, as described herein. Agents or therapies can be co-administered or administered concomitantly.

Embodiments of the present invention provide the use of a Factor 7 specific inhibitor, as described herein, in the manufacture of a medicament for treating, preventing, or ameliorating a thromboembolic complication, as described herein, by combination therapy with an additional agent or therapy, as described herein. Agents or therapies can be co-administered or administered concomitantly.

Embodiments of the present invention provide the use of a Factor 7 specific inhibitor, as described herein, in the manufacture of a medicament for treating, preventing, or ameliorating a thromboembolic complication, as described herein, in a patient who is subsequently administered an additional agent or therapy, as described herein.

Embodiments of the present invention provide a kit for treating, preventing, or ameliorating a thromboembolic complication, as described herein, wherein the kit comprises:
(i) a Factor 7 specific inhibitor as described herein; and alternatively
(ii) an additional agent or therapy as described herein.

A kit of the present invention may further include instructions for using the kit to treat, prevent, or ameliorate a thromboembolic complication, as described herein, by combination therapy, as described herein.

Embodiments of the present invention provide antisense compounds targeted to a Factor 7 nucleic acid. In certain embodiments, the human Factor 7 nucleic acid is any of the sequences set forth in GENBANK Accession No. NT_027140.6, truncated at 1255000 to 1273000 (incorporated herein as SEQ ID NO: 1), GENBANK Accession No. NM_019616.2, (incorporated herein as SEQ ID NO: 2), GENBANK Accession No. DB184141.1 (incorporated herein as SEQ ID NO: 3), and GENBANK® Accession No. NM_000131.3 (incorporated herein as SEQ ID NO: 167). In certain embodiments, the rhesus monkey Factor 7 nucleic acid is any of the sequences set forth in GENBANK Accession No NW_001104507.1, truncated at nucleotides 691000 to 706000 (incorporated herein as SEQ ID NO: 162) and GENBANK Accession No. 3360_061_B (incorporated herein as SEQ ID NO: 163). In certain embodiments, the murine Factor 7 nucleic acid is the sequence set forth in GENBANK Accession No. NT_039455.6, truncated at nucleotides 10024000 to 10037000 (incorporated herein as SEQ ID NO: 160).

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that it is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a Factor 7 nucleic acid is 12 to 30 subunits in length. In other words, antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments, a shortened or truncated antisense compound targeted to a Factor 7 nucleic acid has a single subunit deleted from the 5' end (5' truncation), or alternatively from the 3' end (3' truncation). A shortened or truncated antisense compound targeted to a Factor 7 nucleic acid may have two subunits deleted from the 5' end, or alternatively may have two subunits deleted from the 3' end, of the antisense compound. Alternatively, the deleted nucleosides may be dispersed throughout the antisense compound; for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other; for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a Factor 7 nucleic acid have chemically modified subunits arranged in patterns, or motifs, to confer to the antisense compounds properties, such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer, an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment supports cleavage of the target nucleic acid, while the wing segments comprise modified nucleosides to enhance stability, affinity, and exonuclease resistance. In certain embodiments, the regions of a gapmer are differentiated by the types of sugar moieties comprising each distinct region. The types of sugar moieties that are used to differentiate the regions of a gapmer may, in some embodiments, include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30, or more nucleotides. Thus, gapmers of the present invention include, but are not limited to, for example, 5-10-5, 4-8-4, 4-12-3, 4-12-4, 3-14-3, 2-13-5, 2-16-2, 1-18-1, 3-10-3, 2-10-2, 1-10-1 or 2-8-2.

In certain embodiments, the antisense compound has a "wingmer" motif, having a wing-gap or gap-wing configuration, i.e. an X-Y or Y-Z configuration, as described above, for the gapmer configuration. Thus, wingmer configurations of the present invention include, but are not limited to, for example, 5-10, 8-4, 4-12, 12-4, 3-14, 16-2, 18-1, 10-3, 2-10, 1-10, 8-2, 2-13, or 5-13.

In certain embodiments, antisense compounds targeted to a Factor 7 nucleic acid possess a 5-10-5 gapmer motif.

In certain embodiments, antisense compounds targeted to a Factor 7 nucleic acid possess a 3-14-3 gapmer motif.

In certain embodiments, antisense compounds targeted to a Factor 7 nucleic acid possess a 2-13-5 gapmer motif.

In certain embodiments, antisense compounds targeted to a Factor 7 nucleic acid possess a 2-12-2 gapmer motif In certain embodiments, an antisense compound targeted to a Factor 7 nucleic acid has a gap-widened motif.

In certain embodiments, a gap-widened antisense oligonucleotide targeted to a Factor 7 nucleic acid has a gap segment of fourteen 2'-deoxyribonucleotides positioned immediately adjacent to and between wing segments of three chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a Factor 7 nucleic acid has a gap segment of thirteen 2'-deoxyribonucleotides positioned immediately adjacent to and between a 5' wing segment of two chemically modified nucleosides and a 3' wing segment of five chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences

Nucleotide sequences that encode the Factor 7 gene sequence include, without limitation, the following: GEN-BANK® Accession No. NT_027140.6, truncated from 1255000 to 1273000, first deposited with GENBANK® on Jul. 17, 2001, incorporated herein as SEQ ID NO: 1; GEN-BANK Accession No. NM_019616.2, first deposited with GENBANK® on Oct. 3, 2000, and incorporated herein as SEQ ID NO: 2; GENBANK® Accession No. DB184141.1, first deposited with GENBANK® on Dec. 11, 2005, incorporated herein as SEQ ID NO: 3; GENBANK Accession No. NM_000131.3, first deposited with GENBANK® on Mar. 24, 1999, and incorporated herein as SEQ ID NO: 167; GEN-BANK Accession No. NT_039455.6, truncated at nucleotides 10024000 to 10037000, first deposited with GEN-BANK® on Feb. 24, 2003, and incorporated herein as SEQ ID NO: 160; GENBANK Accession No. NW_00104507.1, incorporated herein as SEQ ID NO: 162; and GENBANK Accession No. 3360_061_B, incorporated herein as SEQ ID NO: 163.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No.) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, a translation termination region, or other defined nucleic acid regions. The structurally defined regions for Factor 7 gene sequences can be obtained by accession number from sequence databases, such as NCBI, and such information is incorporated herein by reference. In certain embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region, such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in Factor 7 mRNA levels are indicative of inhibition of Factor 7 expression. Reductions in levels of a Factor 7 protein are also indicative of inhibition of target mRNA expression. Further, phenotypic changes are indicative of inhibition of Factor 7 expression. For example, a prolonged PT time can be indicative of inhibition of Factor 7 expression. In another example, prolonged aPTT time in conjunction with a prolonged PT time can be indicative of inhibition of Factor 7 expression. In another example, a decreased level of Platelet Factor 4 (PF-4) expression can be indicative of inhibition of Factor 7 expression. In another example, reduced formation of thrombus or increased time for thrombus formation can be indicative of inhibition of Factor 7 expression.

Hybridization

In some embodiments, hybridization occurs between an antisense compound disclosed herein and a Factor 7 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a Factor 7 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a Factor 7 nucleic acid).

Non-complementary nucleobases between an antisense compound and a Factor 7 nucleic acid may be tolerated provided that the antisense compound remains able to specifically hybridize to a target nucleic acid. Moreover, an antisense compound may hybridize over one or more segments of a Factor 7 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a Factor 7 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an antisense compound which is 18 nucleobases in length having 4 (four) non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a Factor 7 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to each nucleobase of the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a Factor 7 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a Factor 7 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA, which contains uracil in place of thymidine in a disclosed DNA sequence, would be considered identical to the DNA sequence since both uracil and thymidine pair with adenine. Shortened and lengthened versions of the antisense compounds described herein, as well as compounds having non-identical bases relative to the antisense compounds provided herein, are also contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties, such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a Factor 7 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise chemically modified ribofuranose ring moieties. Examples of chemically modified ribofuranose rings include, without limitation, addition of substituent groups (including 5' and 2' substituent groups, bridging of non-geminal ring atoms to form bicyclic nucleic acids (BNA), replacement of the ribosyl ring oxygen atom with S, N(R), or C(R1)(R)2 (R=H, C1-C12 alkyl or a protecting group) and combinations thereof. Examples of chemically modified sugars include 2'-F-5'-methyl substituted nucleoside (see PCT International Application WO 2008/101157, published on Aug. 21, 2008, for other disclosed 5',2'-bis substituted nucleosides) or replacement of the ribosyl ring oxygen atom with 'S' and with further substitution at the 2'-position (see U.S. Patent. Application US2005-0130923, published on Jun. 16, 2005) or alternatively 5'-substitution of a BNA (see PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-OCH$_3$ and 2'-O(CH$_2$)2OCH$_3$ substituent groups. The substituent at the 2' position can also be selected from allyl, amino, azido, thio, O-allyl, O—C1-C10 alkyl, OCF$_3$, O(CH$_2$)2SCH$_3$, O(CH$_2$)$_2$—O—N(Rm)(Rn), and O—CH$_2$—C(=O)—N(Rm)(Rn), where each Rm and Rn is, independently, H or substituted or unsubstituted C1-C10 alkyl.

Examples of bicyclic nucleic acids (BNAs) include, without limitation, nucleosides comprising a bridge between the 4' and the 2' ribosyl ring atoms. In certain embodiments, antisense compounds provided herein include one or more BNA nucleosides, wherein the bridge comprises one of the formulas: 4'-(CH$_2$)—O-2' (LNA); 4'-(CH$_2$)—S-2'; 4'-(CH$_2$)—O-2' (LNA); 4'-(CH$_2$)$_2$—O-2' (ENA); 4'-C(CH$_3$)$_2$—O-2' (see PCT/US2008/068922); 4'-CH(CH$_3$)⁻—O-2' and 4'-C⁻H(CH$_2$OCH$_3$)⁻—O-2' (see U.S. Pat. No. 7,399,845, issued on Jul. 15, 2008); 4'-CH$_2$—N(OCH$_3$)-2' (see PCT/US2008/064591); 4'-CH$_2$—O—N(CH$_3$)-2' (see U.S. Patent Application US2004-0171570, published Sep. 2, 2004); 4'-CH$_2$—N(R)—O-2' (see U.S. Pat. No. 7,427,672, issued on Sep. 23, 2008); 4'-CH$_2$—C(CH$_3$)-2' and 4'-CH$_2$—C⁻(=CH$_2$)-2' (see PCT/US2008/066154); and wherein R is, independently, H, C1-C12 alkyl, or a protecting group. Each of the foregoing BNAs include various stereochemical sugar configurations, including, for example, α-L-ribofuranose and β-D-ribofuranose (see PCT international application PCT/DK98/00393, published on Mar. 25, 1999 as WO 99/14226).

In certain embodiments, nucleosides are modified by replacement of the ribosyl ring with a sugar surrogate. Such modification includes, without limitation, replacement of the ribosyl ring with a surrogate ring system (sometimes referred to as DNA analogs), such as a morpholino ring, a cyclohexenyl ring, a cyclohexyl ring or a tetrahydropyranyl ring, such as one having one of the formulas:

Many other bicyclo and tricyclo sugar surrogate ring systems are also known in the art that can be used to modify nucleosides for incorporation into antisense compounds (see, for example, review article: Leumann, Christian J.). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds targeted to a Factor 7 nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly, 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a Factor 7 nucleic acid comprise one or more modified nucleobases. In certain embodiments, gap-widened antisense oligonucleotides targeted to a Factor 7 nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compounds targeted to a Factor 7 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment employed in the methods described herein is a pharmaceutical composition comprising an antisense compound targeted to a Factor 7 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602, published on Jan. 16, 2003.

Cell Culture and Antisense Compounds Treatment

The effects of antisense compounds on the level, activity or expression of Factor 7 nucleic acids can be tested in vitro in a variety of cell types. Cell types used for such analyses are available from commerical vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include HepG2 cells, HepB3 cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE® (Invitrogen, Carlsbad, Calif.). Antisense oligonucleotide is mixed with LIPOFECTAMINE® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTIN®. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.), according to the manufacturer's recommended protocols.

Analysis of Inhibition of Target Levels or Expression

Inhibition of levels or expression of a Factor 7 nucleic acid can be assayed in a variety of ways known in the art. For example, target nucleic acid levels can be quantitated by, e.g., Northern blot analysis, competitive reverse transcription polymerase chain reaction (RT-PCR), or quantitative real-time RT-PCR. RNA analysis can be performed on total cellular RNA or poly(A)+ mRNA. Methods of RNA isolation are well known in the art. Northern blot analysis is also routine in the art. Real-time RT-PCR can be conveniently accomplished using the commercially available ABI PRISM® 7600, 7700, or 7900 Sequence Detection System, available from PE-Applied Biosystems, Foster City, Calif., and used according to manufacturer's instructions.

Quantitative Real-Time RT-PCR Analysis of Target RNA Levels

Quantitation of target RNA levels may be accomplished by quantitative real-time RT-PCR using the ABI PRISM® 7600, 7700, or 7900 Sequence Detection System (PE-Applied Biosystems, Foster City, Calif.) according to manufacturer's instructions. Methods of real-time RT-PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT and real-time-PCR reactions are carried out by methods well known to those skilled in the art.

Gene (or RNA) target quantities obtained by real-time RT-PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real-time RT-PCR, by being run simultaneously with the target, multiplexing, or separately. Total RNA is quantified using RIBOGREEN® RNA quantification reagent (Invetrogen, Inc. Eugene, Oreg.). Methods of RNA quantification by RIBOGREEN® are taught in Jones, L. J., et al., (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a Factor 7 nucleic acid. Methods for designing real-time RT-PCR probes and primers are well known in the art, and may include the use of software such as PRIMER EXPRESS® Software (Applied Biosystems, Foster City, Calif.).

Analysis of Protein Levels

Antisense inhibition of Factor 7 nucleic acids can be assessed by measuring Factor 7 protein levels. Protein levels of Factor 7 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Miss.), or can be prepared via conventional monoclonal or polyclonal antibody generation methods well known in the art. Antibodies useful for the detection of human and mouse Factor 7 are commercially available.

In Vivo Testing of Antisense Compounds

Antisense compounds, for example, antisense oligonucleotides, are tested in animals to assess their ability to inhibit expression of Factor 7 and produce phenotypic changes, such as, prolonged PT, prolonged aPTT time, decreased quantity of Platelet Factor 4 (PF-4), reduced formation of thrombus or increased time for thrombus formation, and reduction of cellular proliferation. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from liver tissue and changes in Factor 7 nucleic acid expression are measured. Changes in Factor 7 protein levels are also measured using a thrombin generation assay. In addition, effects on clot times, e.g. PT and aPTT, are determined using plasma from treated animals.

Certain Indications

In certain embodiments, the invention provides methods of treating an individual comprising administering one or more pharmaceutical compositions of the present invention. In certain embodiments, the individual has a thromboembolic complication. In certain embodiments, the individual is at risk for a blood clotting disorder, including, but not limited to, infarction, thrombosis, embolism, thromboembolism, such as deep vein thrombosis, pulmonary embolism, myocardial infarction, and stroke. This includes individuals with an acquired problem, disease, or disorder that leads to a risk of thrombosis, for example, surgery, cancer, immobility, sepsis, atherosclerosis, atrial fibrillation, as well as genetic predisposition, for example, antiphospholipid syndrome and the autosomal dominant condition, Factor V Leiden. In certain embodiments, the individual has been identified as in need of anticoagulation therapy. Examples of such individuals include, but are not limited to, those undergoing major orthopedic surgery (e.g., hip/knee replacement or hip fracture surgery) and patients in need of chronic treatment, such as those suffering from atrial fibrillation to prevent stroke. In certain embodiments the invention provides methods for prophylactically reducing Factor 7 expression in an individual. Certain embodiments include treating an individual in need thereof by administering to an individual a therapeutically effective amount of an antisense compound targeted to a Factor 7 nucleic acid.

In certain embodiments, pharmaceutical compositions comprising an antisense compound targeted to Factor 7 are used for the preparation of a medicament for treating a patient suffering or susceptible to a thromboembolic complication.

In certain embodiments, the binding of Factor 7 with Tissue factor to form Tissue Factor-Factor 7a complex may lead to inflammatory conditions, such as liver fibrosis, rheumatoid arthritis, and tumor growth and metastasis.

In certain embodiments, the individual has an inflammatory condition leading to a fibrosis complication. In certain embodiments, the individual is at risk of an excessive collagen deposition and fibrosis disorder, including, but not limited to, liver fibrosis, arterial sclerosis, chronic glomerulonephritis, cutis keloid formation, progressive systemic sclerosis (PSS), liver fibrosis, pulmonary fibrosis, cystic fibrosis, chronic graft versus host disease, scleroderma (local and systemic), Peyronie's disease, penis fibrosis, urethrostenosis after the test using a cystoscope, inner accretion after surgery, myelofibrosis, idiopathic retroperitoneal fibrosis. In certain embodiments, the individual has been identified as in need of anti-fibrotic therapy. This includes individuals with a genetic or acquired problem, disease, or disorder that leads to a risk of fibrosis, for example, α1-antitrypsin deficiency, copper storage disease (Wilson's disease), fructosemia, galactosemia, glycogen storage diseases (such as, types II, IV, VI, IX, and X), iron overload syndromes (such as, hemochromatosis), lipid abnormalities (such as, Gaucher's disease), peroxisomal disorders (such as, Zellweger syndrome), Tyrsoninemia, congenital hepatic fibrosis, bacterial infection (such as, brucellosis), parasitic infection (such as, echinococcosis), viral infections (such as, chronic hepatitis B, C), disorders affecting hepatic blood flow (such as, Budd Chiari syndrome, heart failure, hepatic veno-occlusive disease, and portal vein thrombosis), alcohol, and drugs (such as amiodarone, chlorpromazine, Isoniazid, Methotrexate, Methyldopa, Oxyphenisatin, and Tolbutamide). In certain embodiments, the individual has been identified as in need of anti-fibrotic therapy. In such embodiments, the tissue factor-Factor 7a (TF/F7a) complex is identified to have the major procoagulant activity in fibrosis. In certain embodiments, the invention provides methods for prophylactically reducing Factor 7 expression in an individual. Certain embodiments include treating an individual in need thereof by administering to an individual a therapeutically effective amount of an antisense compound targeted to a Factor 7 nucleic acid.

In certain embodiments, pharmaceutical compositions comprising an antisense compound targeted to Factor 7 are used for the preparation of a medicament for treating a patient suffering or susceptible to a fibrotic complication.

In certain embodiments, the individual has an inflammatory rheumatoid arthritic complication. In certain embodiments, the individual is at risk for inflammation at the joints and rheumatoid arthritis. In such embodiments, the individual suffers from pain, swelling and tenderness at the joints, fatigue, lack of appetite, low-grade fever, muscle aches and stiffness. In certain embodiments, the individual has been identified as in need of anti-inflammatory arthritic therapy. This includes individuals suffering from rheumatoid arthritis, reactive arthritis, Reiter's syndrome, psoriatic arthritis, ankylosing spondylitis, and arthritis associated with inflammatory bowel disease. In certain embodiments, the individual has been identified as in need of anti-inflammatory therapy. In such embodiments, the tissue factor-Factor 7a (TF/F7a) complex is identified to have the major procoagulant activity in inducing arthritis. In certain embodiments the invention provides methods for prophylactically reducing Factor 7 expression in an individual. Certain embodiments include treating an individual in need thereof by administering to an individual a therapeutically effective amount of an antisense compound targeted to a Factor 7 nucleic acid.

In certain embodiments, pharmaceutical compositions comprising an antisense compound targeted to Factor 7 are used for the preparation of a medicament for treating a patient suffering or susceptible to an inflammatory arthritic complication.

In certain embodiments, the individual has a malignant complication. In certain embodiments, the individual is at risk for tumor growth, angiogenesis and metastasis. In such embodiments, the individual suffering from hemostatic abnormalities, such as disseminated intravascular coagulation and venous thromboembolism, may suffer additional complications, such as primary and metastatic tumor growths. In such embodiments, the seeding of tumor metastases is a coagulation-dependent process. In such embodiments, the tissue factor-Factor 7a (TF/F7a) complex is identified to have the major procoagulant activity in cancer. In certain embodiments, the individual has been identified as in need of anti-TF/F7a therapy. In certain embodiments the invention provides methods for prophylactically reducing Factor 7 expression in an individual. Certain embodiments include treating an individual in need thereof by administering to an individual a therapeutically effective amount of an antisense compound targeted to a Factor 7 nucleic acid.

In certain embodiments, pharmaceutical compositions comprising an antisense compound targeted to Factor 7 are used for the preparation of a medicament for treating a patient suffering or susceptible to a malignant complication.

In certain embodiments, administration of a therapeutically effective amount of an antisense compound targeted to a Factor 7 nucleic acid is accompanied by monitoring of Factor 7 levels in the serum of an individual, to determine an individual's response to administration of the antisense compound. An individual's response to administration of the antisense compound is used by a physician to determine the amount and duration of therapeutic intervention.

In certain embodiments, administration of an antisense compound targeted to a Factor 7 nucleic acid results in reduction of Factor 7 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a Factor 7 nucleic acid results in a change in a measure of blood clotting, as measured by a standard test, for example, but not limited to, activated partial thromboplastin time (aPTT) test, prothrombin time (PT) test, thrombin time (TCT), bleeding time, or D-dimer. In certain embodiments, administration of a Factor 7 antisense compound increases the measure by at least 15, 20, 25, 30, 35, 40, 45, 50, 55, 60, 65, 70, 75, 80, 85, 90, 95 or 99%, or a range defined by any two of these values. In some embodiments, administration of a Factor 7 antisense compound decreases the measure by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to Factor 7 are used for the preparation of a medicament for treating a patient suffering or susceptible to a thromboembolic complication.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease, disorder, or condition as the one or more pharmaceutical compositions of the present invention. In certain embodiments, such one or more other pharmaceutical agents are designed to treat a different disease, disorder, or condition as the one or more pharmaceutical compositions of the present invention. In certain embodiments, such one or more other pharmaceutical agents are designed to treat an undesired side effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention are co-administered with another pharmaceutical agent to produce a combinational effect. In certain embodiments, one or more pharmaceutical compositions of the present invention are co-administered with another pharmaceutical agent to produce a synergistic effect.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, pharmaceutical agents that may be co-administered with a pharmaceutical composition of the present invention include anticoagulant or antiplatelet agents. In certain embodiments, pharmaceutical agents that may be co-administered with a pharmaceutical composition of the present invention include, but are not limited to aspirin, clopidogrel, dipyridamole, ticlopidine, warfarin (and related coumarins), heparin, direct thrombin inhibitors (such as lepirudin, bivalirudin), apixaban, lovenox, and small molecular compounds that interfere directly with the enzymatic action of particular coagulation factors (e.g. rivaroxaban, which interferes with Factor Xa). In certain embodiments, the anticoagulant or antiplatelet agent is administered prior to administration of a pharmaceutical composition of the present invention. In certain embodiments, the anticoagulant or antiplatelet agent is administered following administration of a pharmaceutical composition of the present invention. In certain embodiments the anticoagulant or antiplatelet agent is administered at the same time as a pharmaceutical composition of the present invention. In certain embodiments the dose of a co-administered anticoagulant or antiplatelet agent is the same as the dose that would be administered if the anticoagulant or antiplatelet agent was administered alone. In certain embodiments the dose of a co-administered anticoagulant or antiplatelet agent is lower than the dose that would be administered if the anticoagulant or antiplatelet agent was administered alone. In certain embodiments the dose of a co-administered anticoagulant or antiplatelet agent is greater than the dose that would be administered if the anticoagulant or antiplatelet agent was administered alone.

In certain embodiments, the co-administration of a second compound enhances the anticoagulant effect of a first compound, such that co-administration of the compounds results in an anticoagulant effect that is greater than the effect of administering the first compound alone. In other embodiments, the co-administration results in anticoagulant effects that are additive of the effects of the compounds when administered alone. In certain embodiments, the co-administration results in anticoagulant effects that are supra-additive of the effects of the compounds when administered alone. In certain embodiments, the first compound is an antisense compound. In certain embodiments, the second compound is an antisense compound.

In certain embodiments, an antidote is administered anytime after the administration of a Factor 7 specific inhibitor. In certain embodiments, an antidote is administered anytime after the administration of an antisense oligonucleotide targeting Factor 7. In certain embodiments, the antidote is administered minutes, hours, days, weeks, or months after the administration of an antisense compound targeting Factor 7. In certain embodiments, the antidote is a complementary (e.g. a sense strand) to the antisense compound targeting Factor 7. In certain embodiments, the antidote is a Factor 7 or Factor 7a protein. In certain embodiments, the Factor 7 or Factor 7a, protein is a human Factor 7 or human Factor 7a protein.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human Factor 7 mRNA in HepB3 Cells

Antisense oligonucleotides targeted to a Factor 7 nucleic acid were tested for their effects on Factor 7 mRNA in vitro. Cultured HepB3 cells at a density of 4,000 cells per well were transfected using lipofectin reagent with 50 nM antisense oligonucleotide. After a treatment period of approximately 24 hours, RNA was isolated from the cells and Factor 7 mRNA levels were measured by real-time RT-PCR, as described herein. Factor 7 mRNA levels were adjusted according to total RNA content as measured by RIBOGREEN®. Results are presented as percent inhibition of Factor 7, relative to untreated control cells.

The chimeric antisense oligonucleotides in Table 1 were designed as 5-10-5 MOE gapmers. The gapmers are 20 nucleotides in length, wherein the central gap segment is comprised of ten 2'-deoxynucleotides and is flanked on both sides (in the 5' and 3' directions) by wings comprising five nucleotides each. Each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. Each gapmer listed in Table 1 is targeted to human gene sequences, SEQ ID NO: 1 (nucleotides 1255000 to 1273000 of GENBANK Accession No. NT_027140.6), SEQ ID NO: 2 (GENBANK Accession No. NM_019616.2), or SEQ ID NO: 3 (GENBANK Accession No. DB184141.1). "Human Target start site" indicates the 5'-most nucleotide to which the gapmer is targeted in the specified human gene sequence. "Human Target stop site" indicates the 3'-most nucleotide to which the gapmer is targeted in the specified human gene sequence.

TABLE 1

Inhibition of human Factor 7 mRNA levels by chimeric antisense oligonucleotides having 5-10-5 MOE wings and deoxy gap targeted to SEQ ID NO: 1, SEQ ID NO: 2, and SEQ ID NO: 3

| Oligo ID | Target SEQ ID NO | Target Start Site | Target Stop Site | Sequence (5' to 3') | % Inhibition | SEQ ID NO |
|---|---|---|---|---|---|---|
| 403090 | 1 | 14017 | 14036 | AGTCCTGGGTCATCAGCCGG | 69 | 4 |
| 403093 | 1 | 14231 | 14250 | GAGACCCTGGTGTACACCCC | 75 | 5 |
| 407594 | 1 | 1208 | 1227 | CCTGCAGCCAGGCAGCCCTG | 87 | 6 |
| 407595 | 1 | 2169 | 2188 | TCCTGAGGCCTTAGCGACCC | 71 | 7 |
| 407596 | 1 | 2206 | 2225 | GAGGCCCCGGCTTCCACGGC | 61 | 8 |
| 407597 | 1 | 1114 | 1133 | TGTTGACATTCCCCATGGGA | 39 | 9 |
| 407598 | 1 | 1147 | 1166 | CCATGATGAAATCTCTGCAG | 72 | 10 |
| 407599 | 1 | 1156 | 1175 | CCTGGGAGACCATGATGAAA | 73 | 11 |
| 407600 | 1 | 1190 | 1209 | TGAAGCCCAAGCAGAAGGCA | 61 | 12 |
| 407601 | 1 | 1196 | 1215 | CAGCCCTGAAGCCCAAGCAG | 52 | 13 |
| 407602 | 1 | 1207 | 1226 | CTGCAGCCAGGCAGCCCTGA | 81 | 14 |
| 407603 | 1 | 9073 | 9092 | TAAGAAATCCAGAACAGCTT | 54 | 15 |
| 407605 | 1 | 9169 | 9188 | TTGAGGCACACTGGTCCCCA | 58 | 16 |
| 407606 | 1 | 9204 | 9223 | CTGGTCCTTGCAGGAGCCCC | 89 | 17 |
| 407607 | 1 | 9209 | 9228 | TGGAGCTGGTCCTTGCAGGA | 76 | 18 |
| 407608 | 1 | 9217 | 9236 | TATAGGACTGGAGCTGGTCC | 13 | 19 |
| 407609 | 1 | 9226 | 9245 | AGAAGCAGATATAGGACTGG | 35 | 20 |
| 407610 | 1 | 9234 | 9253 | AGGGAGGCAGAAGCAGATAT | 31 | 21 |
| 407611 | 1 | 9259 | 9278 | TCTCACAGTTCCGGCCCTCG | 82 | 22 |
| 407612 | 1 | 10982 | 11001 | AGATCAGCTGGTCATCCTTG | 82 | 23 |
| 407613 | 1 | 11010 | 11029 | TGCTCACAGCCGCCGTTCTC | 66 | 24 |
| 407614 | 1 | 11018 | 11037 | TGCAGTACTGCTCACAGCCG | 78 | 25 |
| 407615 | 1 | 11088 | 11107 | GACACCCCGTCTGCCAGCAG | 65 | 26 |
| 407616 | 1 | 11093 | 11112 | TGCAGGACACCCCGTCTGCC | 64 | 27 |
| 407617 | 1 | 12084 | 12103 | TCCACATGGATATTCAACTG | 67 | 28 |
| 407618 | 1 | 12091 | 12110 | GTATTTTCCACATGGATAT | 42 | 29 |
| 407619 | 1 | 12098 | 12117 | AGAATAGGTATTTTCCACA | 64 | 30 |
| 407623 | 1 | 12795 | 12814 | TCCATTCACCAACAACAGGA | 69 | 31 |
| 407624 | 1 | 12842 | 12861 | GAGACCACCCAGATGGTGTT | 73 | 32 |
| 407625 | 1 | 12863 | 12882 | TTGTCGAAACAGTGGGCCGC | 100 | 33 |
| 407626 | 1 | 12871 | 12890 | TCTTGATTTTGTCGAAACAG | 82 | 34 |
| 407628 | 1 | 13777 | 13796 | TGATGACCTGCGCCACCCGC | 38 | 35 |
| 407629 | 1 | 13856 | 13875 | TCAGTGAGGACCACGGGCTG | 34 | 36 |

TABLE 1-continued

Inhibition of human Factor 7 mRNA levels by chimeric antisense oligonucleotides having 5-10-5 MOE wings and deoxy gap targeted to SEQ ID NO: 1, SEQ ID NO: 2, and SEQ ID NO: 3

| Oligo ID | Target SEQ ID NO | Target Start Site | Target Stop Site | Sequence (5' to 3') | % Inhibition | SEQ ID NO |
|---|---|---|---|---|---|---|
| 407630 | 1 | 13863 | 13882 | CACATGGTCAGTGAGGACCA | 29 | 37 |
| 407631 | 1 | 13869 | 13888 | GGGCACCACATGGTCAGTGA | 66 | 38 |
| 407632 | 1 | 13888 | 13907 | TCCGTTCGGGCAGGCAGAGG | 46 | 39 |
| 407633 | 1 | 14023 | 14042 | GCAGGCAGTCCTGGGTCATC | 71 | 40 |
| 407634 | 1 | 14032 | 14051 | GTGACTGCTGCAGGCAGTCC | 24 | 41 |
| 407635 | 1 | 14186 | 14205 | TGGCCCCAGCTGACGATGCC | 64 | 42 |
| 407636 | 1 | 14193 | 14212 | GCAGCCCTGGCCCCAGCTGA | 75 | 43 |
| 407637 | 1 | 14238 | 14257 | GTACTGGGAGACCCTGGTGT | 71 | 44 |
| 407638 | 1 | 14248 | 14267 | GCCACTCGATGTACTGGGAG | 0 | 45 |
| 407639 | 1 | 14254 | 14273 | TTTGCAGCCACTCGATGTAC | 76 | 46 |
| 407640 | 1 | 14263 | 14282 | GCATGAGCTTTTGCAGCCAC | 79 | 47 |
| 407641 | 1 | 14707 | 14726 | CCTGAGGCCAGCAGATCACG | 94 | 48 |
| 407642 | 1 | 14713 | 14732 | CAGCAGCCTGAGGCCAGCAG | 78 | 49 |
| 407643 | 1 | 15098 | 15117 | CACACATGGAGTCAGCATCG | 84 | 50 |
| 407644 | 1 | 15106 | 15125 | GAGGACAGCACACATGGAGT | 66 | 51 |
| 407645 | 1 | 15128 | 15147 | GAGAGCTAAACAACCGCCTT | 65 | 52 |
| 407646 | 1 | 15185 | 15204 | GGTGATGCTTCTGAATTGTC | 81 | 53 |
| 407647 | 1 | 15300 | 15319 | GCAGCCGTTTATTGTGAAGC | 83 | 54 |
| 407648 | 1 | 15388 | 15407 | GCATCTCAGAGGATGAGCAC | 8 | 55 |
| 407649 | 1 | 15430 | 15449 | GAGGGTTCATTTCAGTGATG | 24 | 56 |
| 407650 | 1 | 15436 | 15455 | CCATGTGAGGGTTCATTTCA | 39 | 57 |
| 407651 | 1 | 15482 | 15501 | AGCCTCAAACATCTATCAAA | 32 | 58 |
| 407652 | 1 | 15492 | 15511 | TGGGAGCTACAGCCTCAAAC | 30 | 59 |
| 407653 | 1 | 15546 | 15565 | AATATCATTGACAAGGGCTG | 21 | 60 |
| 407654 | 1 | 15630 | 15649 | CCACTGCAGCCAGGGCCTGG | 34 | 61 |
| 407655 | 1 | 15653 | 15672 | AGAGTGCAGCTTGCCAGGTC | 28 | 62 |
| 407656 | 1 | 15658 | 15677 | CAGCAAGAGTGCAGCTTGCC | 43 | 63 |
| 407657 | 1 | 15664 | 15683 | GGGACTCAGCAAGAGTGCAG | 26 | 64 |
| 407658 | 1 | 15749 | 15768 | GCTTGCCGGAGTCTGAGTGG | 16 | 65 |
| 407659 | 1 | 15778 | 15797 | GATGGCATCGAGTCCACTCT | 55 | 66 |
| 407660 | 1 | 15905 | 15924 | GCTCTGAAGTAGATGATGCC | 16 | 67 |
| 407661 | 1 | 15963 | 15982 | TTTACAAGAGCAGGGTGCCT | 47 | 68 |
| 407663 | 1 | 9112 | 9131 | TTGCAGGCAGGACTGGTGGT | 44 | 69 |
| 407664 | 1 | 5219 | 5238 | CAGGGCGAGGCAACCCCGTG | 70 | 70 |
| 407665 | 1 | 6001 | 6020 | GTTACGAAGACTGGGAAATG | 29 | 71 |

TABLE 1-continued

Inhibition of human Factor 7 mRNA levels by chimeric antisense oligonucleotides having 5-10-5 MOE wings and deoxy gap targeted to SEQ ID NO: 1, SEQ ID NO: 2, and SEQ ID NO: 3

| Oligo ID | Target SEQ ID NO | Target Start Site | Target Stop Site | Sequence (5' to 3') | % Inhibition | SEQ ID NO |
|---|---|---|---|---|---|---|
| 407666 | 1 | 8877 | 8896 | TCCCCAGGACATCTGGAACT | 52 | 72 |
| 407667 | 1 | 10897 | 10916 | GTGGCCATGCCCTGGGTCAG | 71 | 73 |
| 407668 | 1 | 12187 | 12206 | GAAGCCTTACCTGCCATGGA | 54 | 74 |
| 407669 | 1 | 12387 | 12406 | TAGACCCTCAGTGAGTGTCG | 57 | 75 |
| 407886 | 1 | 1173 | 1192 | GCAGAGGAGCCTGAGGGCCT | 72 | 76 |
| 407887 | 1 | 1201 | 1220 | CCAGGCAGCCCTGAAGCCCA | 78 | 77 |
| 407890 | 1 | 6080 | 6099 | CAGGGAGCCCGGCCGCAGCT | 60 | 78 |
| 407891 | 1 | 9176 | 9195 | CATGGACTTGAGGCACACTG | 66 | 79 |
| 407892 | 1 | 9187 | 9206 | CCCCATTCTGGCATGGACTT | 68 | 80 |
| 407893 | 1 | 9242 | 9261 | TCGAAGGCAGGGAGGCAGAA | 33 | 81 |
| 407894 | 1 | 9252 | 9271 | GTTCCGGCCCTCGAAGGCAG | 77 | 82 |
| 407895 | 1 | 10987 | 11006 | CACACAGATCAGCTGGTCAT | 72 | 83 |
| 407896 | 1 | 11029 | 11048 | CGTGTGGTCACTGCAGTACT | 73 | 84 |
| 407897 | 1 | 11039 | 11058 | GCTTGGTGCCCGTGTGGTCA | 77 | 85 |
| 407898 | 1 | 11075 | 11094 | CCAGCAGAGAGTACCCCTCG | 49 | 86 |
| 407899 | 1 | 11098 | 11117 | GGGTGTGCAGGACACCCCGT | 42 | 87 |
| 407900 | 1 | 12141 | 12160 | CCCCACAATTCGGCCTTGGG | 91 | 88 |
| 407901 | 1 | 12829 | 12848 | TGGTGTTGATCAGGGTCCCC | 89 | 89 |
| 407902 | 1 | 12837 | 12856 | CACCCAGATGGTGTTGATCA | 86 | 90 |
| 407903 | 1 | 12847 | 12866 | CCGCGGAGACCACCCAGATG | 98 | 91 |
| 407904 | 1 | 12858 | 12877 | GAAACAGTGGGCCGCGGAGA | 83 | 92 |
| 407905 | 1 | 12876 | 12895 | CCAGTTCTTGATTTTGTCGA | 40 | 93 |
| 407906 | 1 | 13847 | 13866 | ACCACGGGCTGGTGCAGGCG | 4 | 94 |
| 407907 | 1 | 13928 | 13947 | AATGAGAAGCGCACGAAGGC | 35 | 95 |
| 407908 | 1 | 13943 | 13962 | CCCCAGCCGCTGACCAATGA | 47 | 96 |
| 407909 | 1 | 14093 | 14112 | CCATCCGAGTAGCCGGCACA | 77 | 97 |
| 407910 | 1 | 14104 | 14123 | AGTCCTTGCTGCCATCCGAG | 86 | 98 |
| 407911 | 1 | 14115 | 14134 | CCCCTTGCAGGAGTCCTTGC | 74 | 99 |
| 407912 | 1 | 14149 | 14168 | CCCGGTAGTGGGTGGCATGT | 46 | 100 |
| 407913 | 1 | 14172 | 14191 | GATGCCCGTCAGGTACCACG | 74 | 101 |
| 407914 | 1 | 14181 | 14200 | CCAGCTGACGATGCCCGTCA | 82 | 102 |
| 407915 | 1 | 14198 | 14217 | GTTGCGCAGCCCTGGCCCA | 83 | 103 |
| 407916 | 1 | 14208 | 14227 | GTGGCCCACGGTTGCGCAGC | 53 | 104 |
| 407917 | 1 | 14218 | 14237 | ACACCCCAAAGTGGCCCACG | 70 | 105 |
| 407918 | 1 | 14226 | 14245 | CCTGGTGTACACCCCAAAGT | 72 | 106 |
| 407919 | 1 | 14243 | 14262 | TCGATGTACTGGGAGACCCT | 84 | 107 |

TABLE 1-continued

Inhibition of human Factor 7 mRNA levels by chimeric antisense oligonucleotides having 5-10-5 MOE wings and deoxy gap targeted to SEQ ID NO: 1, SEQ ID NO: 2, and SEQ ID NO: 3

| Oligo ID | Target SEQ ID NO | Target Start Site | Target Stop Site | Sequence (5' to 3') | % Inhibition | SEQ ID NO |
|---|---|---|---|---|---|---|
| 407920 | 1 | 14268 | 14287 | TGAGCGCATGAGCTTTTGCA | 65 | 108 |
| 407921 | 1 | 14331 | 14350 | CCACAGGCCAGGGCTGCTGG | 65 | 109 |
| 407922 | 1 | 14354 | 14373 | TCGACGCAGCCTTGGCTTTC | 82 | 110 |
| 407923 | 1 | 14363 | 14382 | CAGGACAGTTCGACGCAGCC | 76 | 111 |
| 407924 | 1 | 14373 | 14392 | GATTTGGTGCCAGGACAGTT | 68 | 112 |
| 407925 | 1 | 14383 | 14402 | GAATATATGGGATTTGGTGC | 64 | 113 |
| 407926 | 1 | 14633 | 14652 | CCAGGACAACCTTGGCACTC | 79 | 114 |
| 407927 | 1 | 14664 | 14683 | AGGTAAGGAGGCTCAGCTGG | 55 | 115 |
| 407928 | 1 | 14677 | 14696 | CTTGGCTGAAGGGAGGTAAG | 55 | 116 |
| 407929 | 1 | 14719 | 14738 | GCAGAGCAGCAGCCTGAGGC | 53 | 117 |
| 407930 | 1 | 14727 | 14746 | CAATGAAGGCAGAGCAGCAG | 70 | 118 |
| 407931 | 1 | 15111 | 15130 | CTTCAGAGGACAGCACACAT | 56 | 119 |
| 407932 | 1 | 15141 | 15160 | GAACCAGAAAAGTGAGAGCT | 55 | 120 |
| 407933 | 1 | 15154 | 15173 | TGATAATGGATAAGAACCAG | 58 | 121 |
| 407934 | 1 | 15166 | 15185 | CTGAAGTGAAGATGATAATG | 45 | 122 |
| 407935 | 1 | 15191 | 15210 | ATGCATGGTGATGCTTCTGA | 94 | 123 |
| 407936 | 1 | 15204 | 15223 | GGCATTCGCCACCATGCATG | 91 | 124 |
| 407937 | 1 | 15237 | 15256 | GAAGGGAGAAATACATTTGG | 59 | 125 |
| 407938 | 1 | 15245 | 15264 | CACCCAGCGAAGGGAGAAAT | 60 | 126 |
| 407939 | 1 | 15255 | 15274 | TGCAGCCCGGCACCCAGCGA | 93 | 127 |
| 407940 | 1 | 15288 | 15307 | TGTGAAGCTGGGAAGCAGGT | 62 | 128 |
| 407941 | 1 | 15305 | 15324 | GAGACGCAGCCGTTTATTGT | 65 | 129 |
| 407942 | 1 | 15320 | 15339 | CACAGGTGTGCGGAGGAGAC | 41 | 130 |
| 407943 | 1 | 15328 | 15347 | GCAGGCACCACAGGTGTGCG | 34 | 131 |
| 407944 | 1 | 15338 | 15357 | CCAGTGGGTGGCAGGCACCA | 59 | 132 |
| 407945 | 1 | 15351 | 15370 | AATCATGGGCAACCCAGTGG | 56 | 133 |
| 407946 | 1 | 15361 | 15380 | TCCAAAAATGAATCATGGGC | 5 | 134 |
| 407947 | 1 | 15393 | 15412 | AAAGAGCATCTCAGAGGATG | 26 | 135 |
| 407948 | 1 | 15403 | 15422 | TTGTGAAAGAAAAGAGCATC | 8 | 136 |
| 407949 | 1 | 15418 | 15437 | CAGTGATGTTGAAAATTGTG | 9 | 137 |
| 407950 | 1 | 15441 | 15460 | AGCTTCCATGTGAGGGTTCA | 58 | 138 |
| 407951 | 1 | 15464 | 15483 | AACAGCTTTTGTTTTTAAAA | 0 | 139 |
| 407952 | 1 | 15498 | 15517 | GGATCCTGGGAGCTACAGCC | 41 | 140 |
| 407953 | 1 | 15513 | 15532 | ACATCCAATTCCACAGGATC | 20 | 141 |
| 407954 | 1 | 15523 | 15542 | CAGGGAGAGAACATCCAATT | 39 | 142 |

TABLE 1-continued

Inhibition of human Factor 7 mRNA levels by chimeric
antisense oligonucleotides having 5-10-5 MOE wings
and deoxy gap targeted to SEQ ID NO: 1,
SEQ ID NO: 2, and SEQ ID NO: 3

| Oligo ID | Target SEQ ID NO | Target Start Site | Target Stop Site | Sequence (5' to 3') | % Inhibition | SEQ ID NO |
|---|---|---|---|---|---|---|
| 407955 | 1 | 15551 | 15570 | TGTGAAATATCATTGACAAG | 3 | 143 |
| 407956 | 1 | 15609 | 15628 | AACTTGCATTTAGTGATGCG | 19 | 144 |
| 407957 | 1 | 15617 | 15636 | GGCCTGGGAACTTGCATTTA | 52 | 145 |
| 407958 | 1 | 15754 | 15773 | GCCGTGCTTGCCGGAGTCTG | 58 | 146 |
| 407959 | 1 | 15783 | 15802 | GCAGGGATGGCATCGAGTCC | 0 | 147 |
| 407960 | 1 | 15800 | 15819 | GTGCCCAGGACGGCCCTGCA | 53 | 148 |
| 407961 | 1 | 15899 | 15918 | AAGTAGATGATGCCTGAGTG | 34 | 149 |
| 407962 | 1 | 15944 | 15963 | TTGGAAGCAGCCCACGGCTG | 41 | 150 |
| 407963 | 1 | 15957 | 15976 | AGAGCAGGGTGCCTTGGAAG | 33 | 151 |
| 407604 | 2 | 297 | 316 | CACACTGGTCCCCATCACTG | 34 | 152 |
| 407620 | 2 | 652 | 671 | AGGACCTGCCATGGACACTC | 79 | 153 |
| 407621 | 2 | 657 | 676 | ACAACAGGACCTGCCATGGA | 62 | 154 |
| 407622 | 2 | 663 | 682 | TCACCAACAACAGGACCTGC | 55 | 155 |
| 407627 | 2 | 773 | 792 | GCCCAGCACCGCGATCAGGT | 79 | 156 |
| 407888 | 2 | 102 | 121 | CGAAGACTGCAGCCAGGCAG | 34 | 157 |
| 407889 | 2 | 112 | 131 | TCCTGGGTTACGAAGACTGC | 54 | 158 |
| 407662 | 3 | 50 | 69 | TCCTGCAGCCAGGCAGCCCT | 86 | 159 |

Certain gapmers from Table 1 are 100% homologous to the rhesus monkey genomic sequence (nucleotides 691000 to 706000 of GENBANK Accession No. NW_00104507.1; incorporated herein as SEQ ID NO: 162) or the rhesus monkey mRNA sequence (GENKBANK Accession No. 3360_061_B; incorporated herein as SEQ ID NO: 163). Shown in Table 2 are the chimeric antisense oligonucleotides from Table 1, which are homologous with rhesus monkey. Gapmers are arranged by human target start site.

TABLE 2

Human/rhesus monkey cross-reactive chimeric
antisense oligonucleotides having 5-10-5 MOE
wings and deoxy gap

| ISIS No. | Human Target SEQ ID NO | Human Target Start Site | Human Target Stop Site | Sequence (5' to 3') | Rhesus monkey Target SEQ ID No. | Rhesus monkey Target Start Site | Rhesus monkey Target Stop Site | SEQ ID No. |
|---|---|---|---|---|---|---|---|---|
| 407597 | 1 | 1114 | 1133 | TGTTGACATTCCCCATGGGA | 160 | 537 | 556 | 9 |
| 407598 | 1 | 1147 | 1166 | CCATGATGAAATCTCTGCAG | 160 | 570 | 589 | 10 |
| 407599 | 1 | 1156 | 1175 | CCTGGGAGACCATGATGAAA | 160 | 579 | 598 | 11 |
| 407886 | 1 | 1173 | 1192 | GCAGAGGAGCCTGAGGGCCT | 160 | 596 | 615 | 76 |
| 407600 | 1 | 1190 | 1209 | TGAAGCCCAAGCAGAAGGCA | 160 | 613 | 632 | 12 |
| 407601 | 1 | 1196 | 1215 | CAGCCCTGAAGCCCAAGCAG | 160 | 619 | 638 | 13 |
| 407887 | 1 | 1201 | 1220 | CCAGGCAGCCCTGAAGCCCA | 160 | 624 | 643 | 77 |
| 407602 | 1 | 1207 | 1226 | CTGCAGCCAGGCAGCCCTGA | 160 | 630 | 649 | 14 |

TABLE 2-continued

Human/rhesus monkey cross-reactive chimeric antisense oligonucleotides having 5-10-5 MOE wings and deoxy gap

| ISIS No. | Human Target SEQ ID NO | Human Target Start Site | Human Target Stop Site | Sequence (5' to 3') | Rhesus monkey Target SEQ ID No. | Rhesus monkey Target Start Site | Rhesus monkey Target Stop Site | SEQ ID No. |
|---|---|---|---|---|---|---|---|---|
| 407594 | 1 | 1208 | 1227 | CCTGCAGCCAGGCAGCCCTG | 160 | 631 | 650 | 6 |
| 407595 | 1 | 2169 | 2188 | TCCTGAGGCCTTAGCGACCC | 160 | 1628 | 1647 | 7 |
| 407596 | 1 | 2206 | 2225 | GAGGCCCCGGCTTCCACGGC | 160 | 1666 | 1685 | 8 |
| 407664 | 1 | 5219 | 5238 | CAGGGCGAGGCAACCCCGTG | 160 | 3001 | 3020 | 70 |
| 407666 | 1 | 8877 | 8896 | TCCCCAGGACATCTGGAACT | 160 | 6444 | 6463 | 72 |
| 407603 | 1 | 9073 | 9092 | TAAGAAATCCAGAACAGCTT | 160 | 6637 | 6656 | 15 |
| 407663 | 1 | 9112 | 9131 | TTGCAGGCAGGACTGGTGGT | 160 | 6676 | 6695 | 69 |
| 407605 | 1 | 9169 | 9188 | TTGAGGCACACTGGTCCCCA | 160 | 6736 | 6755 | 16 |
| 407891 | 1 | 9176 | 9195 | CATGGACTTGAGGCACACTG | 160 | 6743 | 6762 | 79 |
| 407892 | 1 | 9187 | 9206 | CCCCATTCTGGCATGGACTT | 160 | 6754 | 6773 | 80 |
| 407606 | 1 | 9204 | 9223 | CTGGTCCTTGCAGGAGCCCC | 160 | 6771 | 6790 | 17 |
| 407607 | 1 | 9209 | 9228 | TGGAGCTGGTCCTTGCAGGA | 160 | 6776 | 6795 | 18 |
| 407608 | 1 | 9217 | 9236 | TATAGGACTGGAGCTGGTCC | 160 | 6784 | 6803 | 19 |
| 407609 | 1 | 9226 | 9245 | AGAAGCAGATATAGGACTGG | 160 | 6793 | 6812 | 20 |
| 407610 | 1 | 9234 | 9253 | AGGGAGGCAGAAGCAGATAT | 160 | 6801 | 6820 | 21 |
| 407893 | 1 | 9242 | 9261 | TCGAAGGCAGGGAGGCAGAA | 160 | 6809 | 6828 | 81 |
| 407894 | 1 | 9252 | 9271 | GTTCCGGCCCTCGAAGGCAG | 160 | 6819 | 6838 | 82 |
| 407611 | 1 | 9259 | 9278 | TCTCACAGTTCCGGCCCTCG | 160 | 6826 | 6845 | 22 |
| 407612 | 1 | 10982 | 11001 | AGATCAGCTGGTCATCCTTG | 160 | 8679 | 8698 | 23 |
| 407895 | 1 | 10987 | 11006 | CACACAGATCAGCTGGTCAT | 160 | 8684 | 8703 | 83 |
| 407613 | 1 | 11010 | 11029 | TGCTCACAGCCGCCGTTCTC | 160 | 8707 | 8726 | 24 |
| 407614 | 1 | 11018 | 11037 | TGCAGTACTGCTCACAGCCG | 160 | 8715 | 8734 | 25 |
| 407896 | 1 | 11029 | 11048 | CGTGTGGTCACTGCAGTACT | 160 | 8726 | 8745 | 84 |
| 407897 | 1 | 11039 | 11058 | GCTTGGTGCCCGTGTGGTCA | 160 | 8736 | 8755 | 85 |
| 407898 | 1 | 11075 | 11094 | CCAGCAGAGAGTACCCCTCG | 160 | 8772 | 8791 | 86 |
| 407615 | 1 | 11088 | 11107 | GACACCCCGTCTGCCAGCAG | 160 | 8785 | 8804 | 26 |
| 407616 | 1 | 11093 | 11112 | TGCAGGACACCCCGTCTGCC | 160 | 8790 | 8809 | 27 |
| 407899 | 1 | 11098 | 11117 | GGGTGTGCAGGACACCCCGT | 160 | 8795 | 8814 | 158 |
| 407617 | 1 | 12084 | 12103 | TCCACATGGATATTCAACTG | 160 | 9808 | 9827 | 28 |
| 407618 | 1 | 12091 | 12110 | GTATTTTTCCACATGGATAT | 160 | 9815 | 9834 | 29 |
| 407619 | 1 | 12098 | 12117 | AGAATAGGTATTTTTCCACA | 160 | 9822 | 9841 | 30 |
| 407900 | 1 | 12141 | 12160 | CCCCACAATTCGGCCTTGGG | 160 | 9865 | 9884 | 88 |
| 407668 | 1 | 12187 | 12206 | GAAGCCTTACCTGCCATGGA | 160 | 9911 | 9930 | 74 |
| 407669 | 1 | 12387 | 12406 | TAGACCCTCAGTGAGTGTCG | 160 | 10116 | 10135 | 75 |
| 407623 | 1 | 12795 | 12814 | TCCATTCACCAACAACAGGA | 160 | 10524 | 10543 | 31 |

TABLE 2-continued

Human/rhesus monkey cross-reactive chimeric antisense oligonucleotides having 5-10-5 MOE wings and deoxy gap

| ISIS No. | Human Target SEQ ID NO | Human Target Start Site | Human Target Stop Site | Sequence (5' to 3') | Rhesus monkey Target SEQ ID No. | Rhesus monkey Target Start Site | Rhesus monkey Target Stop Site | SEQ ID No. |
|---|---|---|---|---|---|---|---|---|
| 407901 | 1 | 12829 | 12848 | TGGTGTTGATCAGGGTCCCC | 160 | 10558 | 10577 | 89 |
| 407902 | 1 | 12837 | 12856 | CACCCAGATGGTGTTGATCA | 160 | 10566 | 10585 | 90 |
| 407624 | 1 | 12842 | 12861 | GAGACCACCCAGATGGTGTT | 160 | 10571 | 10590 | 32 |
| 407903 | 1 | 12847 | 12866 | CCGCGGAGACCACCCAGATG | 160 | 10576 | 10595 | 91 |
| 407904 | 1 | 12858 | 12877 | GAAACAGTGGGCCGCGGAGA | 160 | 10587 | 10606 | 92 |
| 407625 | 1 | 12863 | 12882 | TTGTCGAAACAGTGGGCCGC | 160 | 10592 | 10611 | 33 |
| 407626 | 1 | 12871 | 12890 | TCTTGATTTTGTCGAAACAG | 160 | 10600 | 10619 | 34 |
| 407905 | 1 | 12876 | 12895 | CCAGTTCTTGATTTTGTCGA | 160 | 10605 | 10624 | 93 |
| 407628 | 1 | 13777 | 13796 | TGATGACCTGCGCCACCCGC | 160 | 11499 | 11518 | 35 |
| 407906 | 1 | 13847 | 13866 | ACCACGGGCTGGTGCAGGCG | 160 | 11569 | 11588 | 94 |
| 407629 | 1 | 13856 | 13875 | TCAGTGAGGACCACGGGCTG | 160 | 11578 | 11597 | 36 |
| 407630 | 1 | 13863 | 13882 | CACATGGTCAGTGAGGACCA | 160 | 11585 | 11604 | 37 |
| 407631 | 1 | 13869 | 13888 | GGGCACCACATGGTCAGTGA | 160 | 11591 | 11610 | 38 |
| 407632 | 1 | 13888 | 13907 | TCCGTTCGGGCAGGCAGAGG | 160 | 11610 | 11629 | 39 |
| 407907 | 1 | 13928 | 13947 | AATGAGAAGCGCACGAAGGC | 160 | 11650 | 11669 | 95 |
| 407908 | 1 | 13943 | 13962 | CCCCAGCCGCTGACCAATGA | 160 | 11665 | 11684 | 96 |
| 403090 | 1 | 14017 | 14036 | AGTCCTGGGTCATCAGCCGG | 160 | 11739 | 11758 | 4 |
| 407633 | 1 | 14023 | 14042 | GCAGGCAGTCCTGGGTCATC | 160 | 11745 | 11764 | 40 |
| 407634 | 1 | 14032 | 14051 | GTGACTGCTGCAGGCAGTCC | 160 | 11754 | 11773 | 41 |
| 407909 | 1 | 14093 | 14112 | CCATCCGAGTAGCCGGCACA | 160 | 11815 | 11834 | 97 |
| 407910 | 1 | 14104 | 14123 | AGTCCTTGCTGCCATCCGAG | 160 | 11826 | 11845 | 98 |
| 407911 | 1 | 14115 | 14134 | CCCCTTGCAGGAGTCCTTGC | 160 | 11837 | 11856 | 99 |
| 407912 | 1 | 14149 | 14168 | CCCGGTAGTGGGTGGCATGT | 160 | 11871 | 11890 | 100 |
| 407913 | 1 | 14172 | 14191 | GATGCCCGTCAGGTACCACG | 160 | 11894 | 11913 | 101 |
| 407914 | 1 | 14181 | 14200 | CCAGCTGACGATGCCCGTCA | 160 | 11903 | 11922 | 102 |
| 407635 | 1 | 14186 | 14205 | TGGCCCCAGCTGACGATGCC | 160 | 11908 | 11927 | 42 |
| 407636 | 1 | 14193 | 14212 | GCAGCCCTGGCCCCAGCTGA | 160 | 11915 | 11934 | 43 |
| 407915 | 1 | 14198 | 14217 | GTTGCGCAGCCCTGGCCCCA | 160 | 11920 | 11939 | 103 |
| 407916 | 1 | 14208 | 14227 | GTGGCCCACGGTTGCGCAGC | 160 | 11930 | 11949 | 104 |
| 407917 | 1 | 14218 | 14237 | ACACCCCAAAGTGGCCCACG | 160 | 11940 | 11959 | 105 |
| 407918 | 1 | 14226 | 14245 | CCTGGTGTACACCCCAAAGT | 160 | 11948 | 11967 | 106 |
| 403093 | 1 | 14231 | 14250 | GAGACCCTGGTGTACACCCC | 160 | 11953 | 11972 | 5 |
| 407637 | 1 | 14238 | 14257 | GTACTGGGAGACCCTGGTGT | 160 | 11960 | 11979 | 44 |
| 407919 | 1 | 14243 | 14262 | TCGATGTACTGGGAGACCCT | 160 | 11965 | 11984 | 107 |
| 407638 | 1 | 14248 | 14267 | GCCACTCGATGTACTGGGAG | 160 | 11970 | 11989 | 45 |

TABLE 2-continued

Human/rhesus monkey cross-reactive chimeric antisense oligonucleotides having 5-10-5 MOE wings and deoxy gap

| ISIS No. | Human Target SEQ ID NO | Human Target Start Site | Human Target Stop Site | Sequence (5' to 3') | Rhesus monkey Target SEQ ID No. | Rhesus monkey Target Start Site | Rhesus monkey Target Stop Site | SEQ ID No. |
|---|---|---|---|---|---|---|---|---|
| 407639 | 1 | 14254 | 14273 | TTTGCAGCCACTCGATGTAC | 160 | 11976 | 11995 | 46 |
| 407640 | 1 | 14263 | 14282 | GCATGAGCTTTTGCAGCCAC | 160 | 11985 | 12004 | 47 |
| 407920 | 1 | 14268 | 14287 | TGAGCGCATGAGCTTTTGCA | 160 | 11990 | 12009 | 108 |
| 407922 | 1 | 14354 | 14373 | TCGACGCAGCCTTGGCTTTC | 160 | 12076 | 12095 | 110 |
| 407923 | 1 | 14363 | 14382 | CAGGACAGTTCGACGCAGCC | 160 | 12085 | 12104 | 111 |
| 407924 | 1 | 14373 | 14392 | GATTTGGTGCCAGGACAGTT | 160 | 12095 | 12114 | 112 |
| 407925 | 1 | 14383 | 14402 | GAATATATGGGATTTGGTGC | 160 | 12105 | 12124 | 113 |
| 407927 | 1 | 14664 | 14683 | AGGTAAGGAGGCTCAGCTGG | 160 | 12384 | 12403 | 115 |
| 407928 | 1 | 14677 | 14696 | CTTGGCTGAAGGGAGGTAAG | 160 | 12397 | 12416 | 116 |
| 407641 | 1 | 14707 | 14726 | CCTGAGGCCAGCAGATCACG | 160 | 12427 | 12446 | 48 |
| 407642 | 1 | 14713 | 14732 | CAGCAGCCTGAGGCCAGCAG | 160 | 12433 | 12452 | 49 |
| 407929 | 1 | 14719 | 14738 | GCAGAGCAGCAGCCTGAGGC | 160 | 12397 | 12416 | 117 |
| 407930 | 1 | 14727 | 14746 | CAATGAAGGCAGAGCAGCAG | 160 | 12447 | 12466 | 118 |
| 407643 | 1 | 15098 | 15117 | CACACATGGAGTCAGCATCG | 160 | 12815 | 12834 | 50 |
| 407644 | 1 | 15106 | 15125 | GAGGACAGCACACATGGAGT | 160 | 12823 | 12842 | 51 |
| 407931 | 1 | 15111 | 15130 | CTTCAGAGGACAGCACACAT | 160 | 12828 | 12847 | 119 |
| 407645 | 1 | 15128 | 15147 | GAGAGCTAAACAACCGCCTT | 160 | 12845 | 12864 | 52 |
| 407932 | 1 | 15141 | 15160 | GAACCAGAAAAGTGAGAGCT | 160 | 12858 | 12847 | 120 |
| 407933 | 1 | 15154 | 15173 | TGATAATGGATAAGAACCAG | 160 | 12871 | 12890 | 121 |
| 407934 | 1 | 15166 | 15185 | CTGAAGTGAAGATGATAATG | 160 | 12883 | 12902 | 122 |
| 407646 | 1 | 15185 | 15204 | GGTGATGCTTCTGAATTGTC | 160 | 12902 | 12921 | 53 |
| 407935 | 1 | 15191 | 15210 | ATGCATGGTGATGCTTCTGA | 160 | 12908 | 12927 | 123 |
| 407936 | 1 | 15204 | 15223 | GGCATTCGCCACCATGCATG | 160 | 12921 | 12940 | 124 |
| 407940 | 1 | 15288 | 15307 | TGTGAAGCTGGGAAGCAGGT | 160 | 12985 | 13004 | 128 |
| 407647 | 1 | 15300 | 15319 | GCAGCCGTTTATTGTGAAGC | 160 | 12997 | 13016 | 54 |
| 407941 | 1 | 15305 | 15324 | GAGACGCAGCCGTTTATTGT | 160 | 13002 | 13021 | 129 |
| 407942 | 1 | 15320 | 15339 | CACAGGTGTGCGGAGGAGAC | 160 | 13017 | 13036 | 130 |
| 407943 | 1 | 15328 | 15347 | GCAGGCACCACAGGTGTGCG | 160 | 13025 | 13044 | 131 |
| 407944 | 1 | 15338 | 15357 | CCAGTGGGTGGCAGGCACCA | 160 | 13035 | 13054 | 132 |
| 407648 | 1 | 15388 | 15407 | GCATCTCAGAGGATGAGCAC | 160 | 13085 | 13104 | 136 |
| 407947 | 1 | 15393 | 15412 | AAAGAGCATCTCAGAGGATG | 160 | 13090 | 13109 | 54 |
| 407948 | 1 | 15403 | 15422 | TTGTGAAAGAAAAGAGCATC | 160 | 13100 | 13119 | 55 |
| 407949 | 1 | 15418 | 15437 | CAGTGATGTTGAAAATTGTG | 160 | 13115 | 13134 | 57 |
| 407649 | 1 | 15430 | 15449 | GAGGGTTCATTTCAGTGATG | 160 | 13127 | 13146 | 56 |
| 407650 | 1 | 15436 | 15455 | CCATGTGAGGGTTCATTTCA | 160 | 13133 | 13152 | 57 |

TABLE 2-continued

Human/rhesus monkey cross-reactive chimeric antisense oligonucleotides having 5-10-5 MOE wings and deoxy gap

| ISIS No. | Human Target SEQ ID NO | Human Target Start Site | Human Target Stop Site | Sequence (5' to 3') | Rhesus monkey Target SEQ ID No. | Rhesus monkey Target Start Site | Rhesus monkey Target Stop Site | SEQ ID No. |
|---|---|---|---|---|---|---|---|---|
| 407950 | 1 | 15441 | 15460 | AGCTTCCATGTGAGGGTTCA | 160 | 13138 | 13157 | 138 |
| 407951 | 1 | 15464 | 15483 | AACAGCTTTTGTTTTTAAAA | 160 | 13163 | 13182 | 139 |
| 407651 | 1 | 15482 | 15501 | AGCCTCAAACATCTATCAAA | 160 | 13181 | 13200 | 58 |
| 407652 | 1 | 15492 | 15511 | TGGGAGCTACAGCCTCAAAC | 160 | 13191 | 13210 | 59 |
| 407952 | 1 | 15498 | 15517 | GGATCCTGGGAGCTACAGCC | 160 | 13197 | 13216 | 140 |
| 407953 | 1 | 15513 | 15532 | ACATCCAATTCCACAGGATC | 160 | 13212 | 13231 | 141 |
| 407954 | 1 | 15523 | 15542 | CAGGGAGAGAACATCCAATT | 160 | 13222 | 13241 | 142 |
| 407653 | 1 | 15546 | 15565 | AATATCATTGACAAGGGCTG | 160 | 13245 | 13264 | 60 |
| 407955 | 1 | 15551 | 15570 | TGTGAAATATCATTGACAAG | 160 | 13250 | 13269 | 143 |
| 407957 | 1 | 15617 | 15636 | GGCCTGGGAACTTGCATTTA | 160 | 13312 | 13331 | 145 |
| 407654 | 1 | 15630 | 15649 | CCACTGCAGCCAGGGCCTGG | 160 | 13325 | 13344 | 61 |
| 407655 | 1 | 15653 | 15672 | AGAGTGCAGCTTGCCAGGTC | 160 | 13348 | 13367 | 62 |
| 407656 | 1 | 15658 | 15677 | CAGCAAGAGTGCAGCTTGCC | 160 | 13353 | 13372 | 63 |
| 407657 | 1 | 15664 | 15683 | GGGACTCAGCAAGAGTGCAG | 160 | 13359 | 13378 | 64 |
| 407658 | 1 | 15749 | 15768 | GCTTGCCGGAGTCTGAGTGG | 160 | 13444 | 13463 | 65 |
| 407958 | 1 | 15754 | 15773 | GCCGTGCTTGCCGGAGTCTG | 160 | 13449 | 13468 | 146 |
| 407659 | 1 | 15778 | 15797 | GATGGCATCGAGTCCACTCT | 160 | 13473 | 13492 | 66 |
| 407959 | 1 | 15783 | 15802 | GCAGGGATGGCATCGAGTCC | 160 | 13478 | 13497 | 147 |
| 407960 | 1 | 15800 | 15819 | GTGCCCAGGACGGCCCTGCA | 160 | 13495 | 13514 | 148 |
| 407961 | 1 | 15899 | 15918 | AAGTAGATGATGCCTGAGTG | 160 | 13564 | 13583 | 149 |
| 407660 | 1 | 15905 | 15924 | GCTCTGAAGTAGATGATGCC | 160 | 13570 | 13589 | 67 |
| 407962 | 1 | 15944 | 15963 | TTGGAAGCAGCCCACGGCTG | 160 | 13609 | 13628 | 150 |
| 407963 | 1 | 15957 | 15976 | AGAGCAGGGTGCCTTGGAAG | 160 | 13622 | 13641 | 151 |
| 407661 | 1 | 15963 | 15982 | TTTACAAGAGCAGGGTGCCT | 160 | 13628 | 13647 | 68 |
| 407604 | 2 | 297 | 316 | CACACTGGTCCCCATCACTG | 160 | 6730 | 6749 | 152 |
| 407620 | 2 | 652 | 671 | AGGACCTGCCATGGACACTC | 160 | 9906 | 9925 | 153 |
| 407621 | 2 | 657 | 676 | ACAACAGGACCTGCCATGGA | 161 | 723 | 742 | 154 |
| 407622 | 2 | 663 | 682 | TCACCAACAACAGGACCTGC | 160 | 10519 | 10538 | 155 |
| 407627 | 2 | 773 | 792 | GCCCAGCACCGCGATCAGGT | 160 | 10629 | 10648 | 156 |
| 407662 | 3 | 50 | 69 | TCCTGCAGCCAGGCAGCCCT | 160 | 632 | 651 | 159 |

Example 2

Dose-Dependent Antisense Inhibition of Human Factor 7 in HepB3 Cells

Several antisense oligonucleotides from Example 1 (see Table 1) exhibiting at least 80% in vitro inhibition of human Factor 7 were tested at various doses in HepB3 cells. Cells were plated at a density of 4,000 cells per well and treated with lipofectin reagent with 3.125 nM, 6.25 nM, 12.5 nM, 25 nM, 50 nM, and 100 nM concentrations of antisense oligonucleotide, as indicated in Table 3. After a treatment period of approximately 16 hours, RNA was isolated from the cells and Factor 7 mRNA levels were measured by real-time RT-PCR, as described herein. Human Factor 7 primer probe set RTS 2927 (forward sequence: GGGACCCTGATCAACACCAT, incorporated herein as SEQ ID NO: 164; reverse sequence: CCAGTTCTTGATTTTGTCGAAACA, incorporated herein as SEQ ID NO: 165; probe sequence: TGGGTGGTCTC-CGCGGCCX, incorporated herein as SEQ ID NO: 166) was used to measure mRNA levels. Factor 7 mRNA levels were adjusted according to total RNA content as measured by RIBOGREEN®. Results are presented as percent inhibition of Factor 7, relative to untreated control cells. As illustrated in Table 3, Factor 7 mRNA levels were reduced in a dose-dependent manner.

TABLE 3

Dose-dependent antisense inhibition of human Factor 7 in HepB3 cells

| ISIS No. | 3.125 nM | 6.25 nM | 12.5 nM | 25.0 nM | 50.0 nM | 100.0 nM | SEQ ID No. |
|---|---|---|---|---|---|---|---|
| 407641 | 53 | 53 | 71 | 84 | 88 | 89 | 48 |
| 407606 | 20 | 0 | 49 | 55 | 83 | 84 | 17 |
| 407594 | 10 | 34 | 63 | 77 | 84 | 80 | 6 |
| 407662 | 0 | 35 | 58 | 74 | 81 | 83 | 166 |
| 407643 | 16 | 59 | 68 | 76 | 92 | 95 | 50 |
| 407935 | 57 | 76 | 78 | 89 | 90 | 89 | 123 |
| 407939 | 62 | 79 | 83 | 91 | 92 | 92 | 127 |
| 407900 | 52 | 58 | 80 | 87 | 94 | 91 | 88 |
| 407936 | 45 | 77 | 79 | 86 | 91 | 90 | 124 |
| 407910 | 31 | 44 | 69 | 68 | 82 | 89 | 98 |

Example 3

Antisense Inhibition of Human Factor 7 in HepB3 Cells

Antisense oligonucleotides targeted to a Factor 7 nucleic acid were designed and tested for their effects on Factor 7 mRNA in vitro. Certain antisense oligonucleotides from Table 3 were also retested for their effects on Factor 7 mRNA in vitro. Cultured HepB3 cells at a density of 4,000 cells per well were transfected using lipofectin reagent with 50 nM antisense oligonucleotide. After a treatment period of approximately 24 hours, RNA was isolated from the cells and Factor 7 mRNA levels were measured by real-time RT-PCR, as described herein. Human Factor 7 primer probe set RTS 2927 was used to measure mRNA levels. Factor 7 mRNA levels were adjusted according to total RNA content as measured by RIBOGREEN®. Results are presented as percent inhibition of Factor 7, relative to untreated control.

The chimeric antisense oligonucleotides in Table 4 were designed as 5-10-5 MOE gapmers. The gapmers are 20 nucleotides in length, wherein the central gap segment is comprised of ten 2'-deoxynucleotides and is flanked on both sides (in the 5' and 3' directions) by wings comprising five nucleotides each. Each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. The first seven listed gapmers in Table 4 are from Table 3 and are designated by an asterisk (*). "Human Target start site" indicates the 5'-most nucleotide to which the gapmer is targeted in the specified human gene sequence. "Human Target stop site" indicates the 3'-most nucleotide to which the gapmer is targeted in the specified human gene sequence. Each gapmer listed in Table 4 is targeted to SEQ ID NO: 1 (nucleotides 1255000 to 1273000 of GENBANK® Accession No. NT_027140.6), SEQ ID NO: 2 (GENBANK® Accession No. NM_019616.2), or SEQ ID NO: 167 (GENBANK® Accession No. NM_000131.3).

TABLE 4

Inhibition of human Factor 7 mRNA levels by chimeric antisense oligonucleotides having 5-10-5 MOE wings and deoxy gap targeted to SEQ ID NO: 1, SEQ ID NO: 2, and SEQ ID NO: 167

| ISIS No. | Human Target SEQ ID NO | Human Target Start Site | Human Target Stop Site | Sequence (5' to 3') | % Inhibition | SEQ ID No. |
|---|---|---|---|---|---|---|
| *407606 | 1 | 9204 | 9223 | CTGGTCCTTGCAGGAGCCCC | 57 | 17 |
| *407900 | 1 | 12141 | 12160 | CCCCACAATTCGGCCTTGGG | 78 | 88 |
| *407910 | 1 | 14104 | 14123 | AGTCCTTGCTGCCATCCGAG | 72 | 98 |
| *407641 | 1 | 14707 | 14726 | CCTGAGGCCAGCAGATCACG | 73 | 48 |
| *407643 | 1 | 15098 | 15117 | CACACATGGAGTCAGCATCG | 80 | 50 |
| *407935 | 1 | 15191 | 15210 | ATGCATGGTGATGCTTCTGA | 72 | 123 |
| *407939 | 1 | 15255 | 15274 | TGCAGCCCGGCACCCAGCGA | 76 | 127 |
| 416492 | 1 | 616 | 635 | GGATCATTCTGGCCCTGAGC | 13 | 168 |
| 416493 | 1 | 738 | 757 | TCTTGGGTGTGGATGTAAAT | 0 | 169 |
| 416494 | 1 | 803 | 822 | CAGATTTAAACTGCAGATGA | 0 | 170 |
| 416495 | 1 | 838 | 857 | TCTAGAATTCCAAACCCCTA | 0 | 171 |
| 416496 | 1 | 855 | 874 | CAACACTTCAAATACGATCT | 0 | 172 |

TABLE 4-continued

Inhibition of human Factor 7 mRNA levels by chimeric antisense oligonucleotides having 5-10-5 MOE wings and deoxy gap targeted to SEQ ID NO: 1, SEQ ID NO: 2, and SEQ ID NO: 167

| ISIS No. | Human Target SEQ ID NO | Human Target Start Site | Human Target Stop Site | Sequence (5' to 3') | % Inhibition | SEQ ID No. |
|---|---|---|---|---|---|---|
| 416497 | 1 | 883 | 902 | CGTGCAGGTGTTAAGGTGTG | 0 | 173 |
| 416498 | 1 | 994 | 1013 | GGCCAGTGGCCATGCATCCC | 5 | 174 |
| 416499 | 1 | 1011 | 1030 | GAGAGCTGCACCTGGCCGGC | 7 | 175 |
| 416500 | 1 | 1026 | 1045 | CTGAACACCCCAGCTGAGAG | 1 | 176 |
| 416424 | 1 | 1151 | 1170 | GAGACCATGATGAAATCTCT | 27 | 177 |
| 416425 | 1 | 1182 | 1201 | AAGCAGAAGGCAGAGGAGCC | 13 | 178 |
| 416426 | 1 | 1187 | 1206 | AGCCCAAGCAGAAGGCAGAG | 34 | 179 |
| 416427 | 1 | 1193 | 1212 | CCCTGAAGCCCAAGCAGAAG | 5 | 180 |
| 416501 | 1 | 1251 | 1270 | CTGCCCTTCCACCAAGTTTA | 18 | 181 |
| 416502 | 1 | 1437 | 1456 | GTTCTTTGAAAAATAATCCC | 22 | 182 |
| 416423 | 1 | 2179 | 2198 | GTGTTTCTCCTCCTGAGGCC | 51 | 183 |
| 416503 | 1 | 2311 | 2330 | TAGCCACCCCGCGGGCTGGC | 0 | 184 |
| 416504 | 1 | 2484 | 2503 | TCAGAAAAGCTCTCAAGAAC | 0 | 185 |
| 416505 | 1 | 2495 | 2514 | GCAGATTTGCATCAGAAAAG | 45 | 186 |
| 416506 | 1 | 4766 | 4785 | CTTTAAAATCAGTTTCACAC | 18 | 187 |
| 416507 | 1 | 4847 | 4866 | GGTTACTGAGCGCGGAAGAA | 73 | 188 |
| 416508 | 1 | 4873 | 4892 | CGAGTTCTGCAGGAGCGGCC | 67 | 189 |
| 416509 | 1 | 4880 | 4899 | AGGAGCCCGAGTTCTGCAGG | 56 | 190 |
| 416510 | 1 | 4916 | 4935 | GACGAGGCCTCAGGTGGACG | 30 | 191 |
| 416511 | 1 | 4926 | 4945 | TTGCTGGGAGGACGAGGCCT | 35 | 192 |
| 416512 | 1 | 4934 | 4953 | GACGACCTTTGCTGGGAGGA | 43 | 193 |
| 416429 | 1 | 6022 | 6041 | ACGCCGTGGGCTTCCTCCTG | 47 | 194 |
| 416430 | 1 | 6066 | 6085 | GCAGCTCCTCCAGGAACGCG | 52 | 195 |
| 416431 | 1 | 6079 | 6098 | AGGGAGCCCGGCCGCAGCTC | 25 | 196 |
| 416432 | 1 | 6108 | 6127 | AGCACTGCTCCTCCTTGCAC | 44 | 197 |
| 416513 | 1 | 6399 | 6418 | CTGATGTGAAAACCGGCATG | 37 | 198 |
| 416514 | 1 | 6406 | 6425 | GTATTTTCTGATGTGAAAAC | 8 | 199 |
| 416515 | 1 | 8547 | 8566 | TAGGCATGACCATCCTCAAT | 39 | 200 |
| 416516 | 1 | 8599 | 8618 | GTGAGAATACAACAGATGAG | 24 | 201 |
| 416517 | 1 | 8708 | 8727 | GGGTGCAGTAGCAGATGCAA | 23 | 202 |
| 416518 | 1 | 8855 | 8874 | GGGTGACCACACATTTCCTG | 55 | 203 |
| 416434 | 1 | 9076 | 9095 | CTGTAAGAAATCCAGAACAG | 0 | 204 |
| 416491 | 1 | 9120 | 9139 | GAGAAGGGTTGCAGGCAGGA | 2 | 205 |
| 416438 | 1 | 9194 | 9213 | CAGGAGCCCCCATTCTGGCA | 63 | 206 |
| 416439 | 1 | 9201 | 9220 | GTCCTTGCAGGAGCCCCCAT | 56 | 207 |

TABLE 4-continued

Inhibition of human Factor 7 mRNA levels by chimeric antisense oligonucleotides having 5-10-5 MOE wings and deoxy gap targeted to SEQ ID NO: 1, SEQ ID NO: 2, and SEQ ID NO: 167

| ISIS No. | Human Target SEQ ID NO | Human Target Start Site | Human Target Stop Site | Sequence (5' to 3') | % Inhibition | SEQ ID No. |
|---|---|---|---|---|---|---|
| 416440 | 1 | 9213 | 9232 | GGACTGGAGCTGGTCCTTGC | 44 | 208 |
| 416441 | 1 | 9220 | 9239 | AGATATAGGACTGGAGCTGG | 32 | 209 |
| 416442 | 1 | 9223 | 9242 | AGCAGATATAGGACTGGAGC | 57 | 210 |
| 416443 | 1 | 9231 | 9250 | GAGGCAGAAGCAGATATAGG | 17 | 211 |
| 416444 | 1 | 9255 | 9274 | ACAGTTCCGGCCCTCGAAGG | 24 | 212 |
| 416519 | 1 | 9290 | 9309 | AAATATGGGACCCAAAGTGG | 9 | 213 |
| 416520 | 1 | 9298 | 9317 | CCCTCTGCAAATATGGGACC | 14 | 214 |
| 416521 | 1 | 9362 | 9381 | CACCCCACCAGGTTGTGCAC | 36 | 215 |
| 416522 | 1 | 9515 | 9534 | GGCTGAGAATTGCCCAGGGC | 25 | 216 |
| 416523 | 1 | 9522 | 9541 | TCTCGAGGGCTGAGAATTGC | 18 | 217 |
| 416524 | 1 | 9665 | 9684 | TAATTTAATATTCAGATGGT | 0 | 218 |
| 416525 | 1 | 9725 | 9744 | TATGAGTCCTTCTAGTGAAT | 5 | 219 |
| 416526 | 1 | 9848 | 9867 | TGTCCACATGACCCCACAGG | 19 | 220 |
| 416527 | 1 | 9912 | 9931 | GAGCTTCCCAAGTTGGCAGT | 49 | 221 |
| 416528 | 1 | 9942 | 9961 | TGATAAAACCTCTGGACACC | 10 | 222 |
| 416529 | 1 | 9999 | 10018 | GGGCTGAGACTGAGGTCAGC | 18 | 223 |
| 416530 | 1 | 10166 | 10185 | AGGGTAGCCTTTGCCTTGGC | 35 | 224 |
| 416531 | 1 | 10317 | 10336 | AGATGACCAGCAGGAAGCCT | 19 | 225 |
| 416532 | 1 | 10323 | 10342 | GGACCCAGATGACCAGCAGG | 12 | 226 |
| 416533 | 1 | 10330 | 10349 | GCATTCTGGACCCAGATGAC | 41 | 227 |
| 416534 | 1 | 10377 | 10396 | ATGCACACCAGGGCTGCTGG | 32 | 228 |
| 416535 | 1 | 10382 | 10401 | GCAGGATGCACACCAGGGCT | 47 | 229 |
| 416536 | 1 | 10398 | 10417 | CGGGAAGGCCTGCCCTGCAG | 23 | 230 |
| 416537 | 1 | 10677 | 10696 | TGACCACTCTTCCGAGCAGC | 55 | 231 |
| 416538 | 1 | 10807 | 10826 | CGTGGACTGATCCAAAGGAC | 46 | 232 |
| 416539 | 1 | 10837 | 10856 | GACAGAGCCTGAGCTTGGCA | 53 | 233 |
| 416445 | 1 | 11013 | 11032 | TACTGCTCACAGCCGCCGTT | 57 | 234 |
| 416446 | 1 | 11024 | 11043 | GGTCACTGCAGTACTGCTCA | 64 | 235 |
| 416540 | 1 | 11143 | 11162 | GGACTGGTGTCATCTGGGAC | 38 | 236 |
| 416541 | 1 | 11259 | 11278 | CCACCCTTGGTGCCCAGATC | 53 | 237 |
| 416542 | 1 | 11297 | 11316 | CAGGGTGCCCATCCTAGTCA | 56 | 238 |
| 416543 | 1 | 11395 | 11414 | TCCTGCGAGTGGGAGTTGGA | 0 | 239 |
| 416544 | 1 | 11499 | 11518 | ATCCCATTTTCCCAGGAGCC | 58 | 240 |
| 416545 | 1 | 11505 | 11524 | AGAAACATCCCATTTTCCCA | 8 | 241 |
| 416546 | 1 | 11519 | 11538 | CCAGGCTGGTTTGGAGAAAC | 21 | 242 |

TABLE 4-continued

Inhibition of human Factor 7 mRNA levels by chimeric antisense oligonucleotides having 5-10-5 MOE wings and deoxy gap targeted to SEQ ID NO: 1, SEQ ID NO: 2, and SEQ ID NO: 167

| ISIS No. | Human Target SEQ ID NO | Human Target Start Site | Human Target Stop Site | Sequence (5' to 3') | % Inhibition | SEQ ID No. |
|---|---|---|---|---|---|---|
| 416547 | 1 | 11729 | 11748 | ATGAAATTCTACCTAAAGAT | 0 | 243 |
| 416548 | 1 | 11735 | 11754 | AGGTGAATGAAATTCTACCT | 29 | 244 |
| 416549 | 1 | 11838 | 11857 | GACAATGGTCAGGGCTGGTT | 68 | 245 |
| 416550 | 1 | 11852 | 11871 | TGGCTGGCTGAGGAGACAAT | 55 | 246 |
| 416551 | 1 | 12000 | 12019 | CAGAAACACCCATCCTCTGA | 19 | 247 |
| 416448 | 1 | 12088 | 12107 | TTTTTCCACATGGATATTCA | 34 | 248 |
| 416449 | 1 | 12094 | 12113 | TAGGTATTTTCCACATGGA | 68 | 249 |
| 416450 | 1 | 12122 | 12141 | GGTTTGCTGGCATTTCTTTT | 49 | 250 |
| 416451 | 1 | 12175 | 12194 | GCCATGGACACTCCCCTTTG | 75 | 251 |
| 416552 | 1 | 12398 | 12417 | TCTGCACAGGGTAGACCCTC | 46 | 252 |
| 416553 | 1 | 12403 | 12422 | GGTTCTCTGCACAGGGTAGA | 56 | 253 |
| 416554 | 1 | 12467 | 12486 | AAAGATCCCACCTCAAAGAG | 7 | 254 |
| 416555 | 1 | 12478 | 12497 | AAAGATCAGGCAAAGATCCC | 6 | 255 |
| 416556 | 1 | 12508 | 12527 | ATAGCTTTGATCCAATGCTC | 53 | 256 |
| 416557 | 1 | 12639 | 12658 | TCCCAGGCAAAGCTGCTCAG | 56 | 257 |
| 416453 | 1 | 12867 | 12886 | GATTTGTCGAAACAGTGGG | 45 | 258 |
| 416558 | 1 | 13159 | 13178 | TGACAGCACGAAGCCCAGAG | 19 | 259 |
| 416559 | 1 | 13638 | 13657 | GCCATTTCTAGGTCTGCAGG | 25 | 260 |
| 416455 | 1 | 13760 | 13779 | CGCCGGCTCTGCTCATCCCC | 72 | 261 |
| 416456 | 1 | 13770 | 13789 | CTGCGCCACCCGCCGGCTCT | 58 | 262 |
| 416457 | 1 | 13780 | 13799 | GGATGATGACCTGCGCCACC | 48 | 263 |
| 416458 | 1 | 13831 | 13850 | GGCGGAGCAGCGCGATGTCG | 29 | 264 |
| 416459 | 1 | 13859 | 13878 | TGGTCAGTGAGGACCACGGG | 23 | 265 |
| 416460 | 1 | 13866 | 13885 | CACCACATGGTCAGTGAGGA | 49 | 266 |
| 416461 | 1 | 13923 | 13942 | GAAGCGCACGAAGGCCAGCG | 43 | 267 |
| 416462 | 1 | 14020 | 14039 | GGCAGTCCTGGGTCATCAGC | 60 | 268 |
| 416463 | 1 | 14027 | 14046 | TGCTGCAGGCAGTCCTGGGT | 39 | 269 |
| 416464 | 1 | 14072 | 14091 | AACATGTACTCCGTGATATT | 53 | 270 |
| 416465 | 1 | 14122 | 14141 | CACTGTCCCCCTTGCAGGAG | 51 | 271 |
| 416466 | 1 | 14132 | 14151 | TGTGGGCCTCCACTGTCCCC | 57 | 272 |
| 416467 | 1 | 14189 | 14208 | CCCTGGCCCCAGCTGACGAT | 55 | 273 |
| 416468 | 1 | 14234 | 14253 | TGGGAGACCCTGGTGTACAC | 46 | 274 |
| 416469 | 1 | 14251 | 14270 | GCAGCCACTCGATGTACTGG | 55 | 275 |
| 416470 | 1 | 14257 | 14276 | GCTTTTGCAGCCACTCGATG | 39 | 276 |
| 416471 | 1 | 14260 | 14279 | TGAGCTTTTGCAGCCACTCG | 62 | 277 |

TABLE 4-continued

Inhibition of human Factor 7 mRNA levels by chimeric antisense oligonucleotides having 5-10-5 MOE wings and deoxy gap targeted to SEQ ID NO: 1, SEQ ID NO: 2, and SEQ ID NO: 167

| ISIS No. | Human Target SEQ ID NO | Human Target Start Site | Human Target Stop Site | Sequence (5' to 3') | % Inhibition | SEQ ID No. |
|---|---|---|---|---|---|---|
| 416472 | 1 | 14348 | 14367 | CAGCCTTGGCTTTCTCTCCA | 76 | 278 |
| 416473 | 1 | 14613 | 14632 | CCCTGCCCCTCTGTCCAGCG | 61 | 279 |
| 416474 | 1 | 14642 | 14661 | TGTCTGCCTCCAGGACAACC | 40 | 280 |
| 416475 | 1 | 14653 | 14672 | CTCAGCTGGGCTGTCTGCCT | 70 | 281 |
| 416476 | 1 | 14686 | 14705 | GCAGGTGGGCTTGGCTGAAG | 58 | 282 |
| 416477 | 1 | 14710 | 14729 | CAGCCTGAGGCCAGCAGATC | 74 | 283 |
| 416478 | 1 | 14735 | 14754 | GTCTCCAGCAATGAAGGCAG | 44 | 284 |
| 416479 | 1 | 15103 | 15122 | GACAGCACACATGGAGTCAG | 56 | 285 |
| 416480 | 1 | 15132 | 15151 | AAGTGAGAGCTAAACAACCG | 25 | 286 |
| 416481 | 1 | 15157 | 15176 | AGATGATAATGGATAAGAAC | 15 | 287 |
| 416482 | 1 | 15188 | 15207 | CATGGTGATGCTTCTGAATT | 64 | 288 |
| 416483 | 1 | 15433 | 15452 | TGTGAGGGTTCATTTCAGTG | 22 | 289 |
| 416484 | 1 | 15485 | 15504 | TACAGCCTCAAACATCTATC | 0 | 290 |
| 416485 | 1 | 15489 | 15508 | GAGCTACAGCCTCAAACATC | 7 | 291 |
| 416486 | 1 | 15540 | 15559 | ATTGACAAGGGCTGTGGCAG | 12 | 292 |
| 416487 | 1 | 15571 | 15590 | GCAGGTGCTCCCAGGGTCTC | 39 | 293 |
| 416488 | 1 | 15639 | 15658 | CAGGTCCTCCCACTGCAGCC | 41 | 294 |
| 416489 | 1 | 15650 | 15669 | GTGCAGCTTGCCAGGTCCTC | 38 | 295 |
| 416490 | 1 | 15661 | 15680 | ACTCAGCAAGAGTGCAGCTT | 33 | 296 |
| 416560 | 1 | 15973 | 15992 | TAAAACTTTATTTACAAGAG | 0 | 297 |
| 416561 | 1 | 15985 | 16004 | GGTGTGTTCCCATAAAACTT | 16 | 298 |
| 416562 | 1 | 16185 | 16204 | AAAGCAGAGCCAGCTCTGAC | 12 | 299 |
| 416563 | 1 | 16596 | 16615 | GCCTGCATTTCCCATTGGCA | 0 | 300 |
| 416564 | 1 | 16738 | 16757 | GCCACTCACAGAAAGCTGGA | 0 | 301 |
| 416565 | 1 | 16872 | 16891 | CAGGATGCTCATGGCAGACA | 0 | 302 |
| 416566 | 1 | 16911 | 16930 | GTTTGTATGGAGAGACCAAT | 0 | 303 |
| 416567 | 1 | 16977 | 16996 | TGGTGGCACCAGATGTCTGA | 2 | 304 |
| 416568 | 1 | 17112 | 17131 | CATTGTGCCTGGCACACAGG | 14 | 305 |
| 416569 | 1 | 17136 | 17155 | GCCTGGTGTGCACACATTGT | 12 | 306 |
| 416428 | 2 | 110 | 129 | CTGGGTTACGAAGACTGCAG | 11 | 307 |
| 416422 | 167 | 107 | 126 | AGCGACCCCGCCTGCAGCCA | 8 | 308 |
| 416433 | 167 | 341 | 360 | AGAAATCCAGAACAGCTTCG | 0 | 309 |
| 416435 | 167 | 353 | 372 | CCCATCACTGTAAGAAATCC | 3 | 310 |
| 416436 | 167 | 360 | 379 | ACTGGTCCCCATCACTGTAA | 27 | 311 |
| 416437 | 167 | 366 | 385 | AGGCACACTGGTCCCCATCA | 52 | 312 |

TABLE 4-continued

Inhibition of human Factor 7 mRNA levels by chimeric antisense oligonucleotides having 5-10-5 MOE wings and deoxy gap targeted to SEQ ID NO: 1, SEQ ID NO: 2, and SEQ ID NO: 167

| ISIS No. | Human Target SEQ ID NO | Human Target Start Site | Human Target Stop Site | Sequence (5' to 3') | % Inhibition | SEQ ID No. |
|---|---|---|---|---|---|---|
| 416447 | 167 | 616 | 635 | CATGGATATTCAACTGTGGG | 17 | 313 |
| 416452 | 167 | 726 | 745 | CCAACAACAGGACCTGCCAT | 19 | 314 |
| 416454 | 167 | 846 | 865 | CGTGCTCGCCCAGCACCGCG | 56 | 315 |

Certain gapmers from Table 4 are 100% homologous to the rhesus monkey genomic sequence (nucleotides 691000 to 706000 of GENBANK Accession No. NW_00104507.1; incorporated herein as SEQ ID NO: 162) or the rhesus monkey mRNA sequence (GENKBANK Accession No. 3360_061_B; incorporated herein as SEQ ID NO: 163). Shown in Table 5 are the chimeric antisense oligonucleotides from Table 4, which are homologous with rhesus monkey.

TABLE 5

Human/rhesus monkey cross-reactive chimeric antisense oligonucleotides having 5-10-5 MOE wings and deoxy gap

| ISIS No. | Human Target SEQ ID No. | Human Target Start Site | Human Target Stop Site | Sequence (5' to 3') | Rhesus Monkey Target SEQ ID No. | Rhesus Monkey Target Start Site | Rhesus Monkey Target Stop Site | SEQ ID No. |
|---|---|---|---|---|---|---|---|---|
| 407606 | 1 | 9204 | 9223 | CTGGTCCTTGCAGGAGCCCC | 162 | 6771 | 6790 | 17 |
| 407900 | 1 | 12141 | 12160 | CCCCACAATTCGGCCTTGGG | 162 | 9865 | 9884 | 88 |
| 407910 | 1 | 14104 | 14123 | AGTCCTTGCTGCCATCCGAG | 162 | 11826 | 11845 | 98 |
| 407641 | 1 | 14707 | 14726 | CCTGAGGCCAGCAGATCACG | 162 | 12427 | 12446 | 48 |
| 407643 | 1 | 15098 | 15117 | CACACATGGAGTCAGCATCG | 162 | 12815 | 12834 | 50 |
| 407935 | 1 | 15191 | 15210 | ATGCATGGTGATGCTTCTGA | 162 | 12908 | 12927 | 123 |
| 416492 | 1 | 616 | 635 | GGATCATTCTGGCCCTGAGC | 162 | 24 | 43 | 168 |
| 416493 | 1 | 738 | 757 | TCTTGGGTGTGGATGTAAAT | 162 | 149 | 168 | 169 |
| 416494 | 1 | 803 | 822 | CAGATTTAAACTGCAGATGA | 162 | 214 | 233 | 170 |
| 416495 | 1 | 838 | 857 | TCTAGAATTCCAAACCCCTA | 162 | 259 | 278 | 171 |
| 416496 | 1 | 855 | 874 | CAACACTTCAAATACGATCT | 162 | 276 | 295 | 172 |
| 416497 | 1 | 883 | 902 | CGTGCAGGTGTTAAGGTGTG | 162 | 306 | 325 | 173 |
| 416498 | 1 | 994 | 1013 | GGCCAGTGGCCATGCATCCC | 162 | 417 | 436 | 174 |
| 416499 | 1 | 1011 | 1030 | GAGAGCTGCACCTGGCCGGC | 162 | 434 | 453 | 175 |
| 416500 | 1 | 1026 | 1045 | CTGAACACCCCAGCTGAGAG | 162 | 449 | 468 | 176 |
| 416424 | 1 | 1151 | 1170 | GAGACCATGATGAAATCTCT | 162 | 574 | 593 | 177 |
| 416425 | 1 | 1182 | 1201 | AAGCAGAAGGCAGAGGAGCC | 162 | 605 | 624 | 178 |
| 416426 | 1 | 1187 | 1206 | AGCCCAAGCAGAAGGCAGAG | 162 | 610 | 629 | 179 |
| 416427 | 1 | 1193 | 1212 | CCCTGAAGCCCAAGCAGAAG | 162 | 616 | 635 | 180 |
| 416501 | 1 | 1251 | 1270 | CTGCCCTTCCACCAAGTTTA | 162 | 674 | 693 | 181 |
| 416502 | 1 | 1437 | 1456 | GTTCTTTGAAAAATAATCCC | 162 | 858 | 877 | 182 |
| 416423 | 1 | 2179 | 2198 | GTGTTTCTCCTCCTGAGGCC | 162 | 1638 | 1657 | 183 |
| 416503 | 1 | 2311 | 2330 | TAGCCACCCCGCGGGCTGGC | 162 | 1771 | 1790 | 184 |

TABLE 5-continued

Human/rhesus monkey cross-reactive chimeric antisense oligonucleotides having 5-10-5 MOE wings and deoxy gap

| ISIS No. | Human Target SEQ ID No. | Human Target Start Site | Human Target Stop Site | Sequence (5' to 3') | Rhesus Monkey Target SEQ ID No. | Rhesus Monkey Target Start Site | Rhesus Monkey Target Stop Site | SEQ ID No. |
|---|---|---|---|---|---|---|---|---|
| 416504 | 1 | 2484 | 2503 | TCAGAAAAGCTCTCAAGAAC | 162 | 1944 | 1963 | 185 |
| 416505 | 1 | 2495 | 2514 | GCAGATTTGCATCAGAAAAG | 162 | 1955 | 1974 | 186 |
| 416506 | 1 | 4766 | 4785 | CTTTAAAATCAGTTTCACAC | 162 | 2556 | 2575 | 187 |
| 416507 | 1 | 4847 | 4866 | GGTTACTGAGCGCGGAAGAA | 162 | 2637 | 2656 | 188 |
| 416508 | 1 | 4873 | 4892 | CGAGTTCTGCAGGAGCGGCC | 162 | 2663 | 2682 | 189 |
| 416509 | 1 | 4880 | 4899 | AGGAGCCCGAGTTCTGCAGG | 162 | 2670 | 2689 | 190 |
| 416510 | 1 | 4916 | 4935 | GACGAGGCCTCAGGTGGACG | 162 | 2706 | 2725 | 191 |
| 416511 | 1 | 4926 | 4945 | TTGCTGGGAGGACGAGGCCT | 162 | 2716 | 2735 | 192 |
| 416512 | 1 | 4934 | 4953 | GACGACCTTTGCTGGGAGGA | 162 | 2724 | 2743 | 193 |
| 416513 | 1 | 6399 | 6418 | CTGATGTGAAAACCGGCATG | 162 | 4144 | 4163 | 198 |
| 416514 | 1 | 6406 | 6425 | GTATTTTCTGATGTGAAAAC | 162 | 4151 | 4170 | 199 |
| 416515 | 1 | 8547 | 8566 | TAGGCATGACCATCCTCAAT | 162 | 6104 | 6123 | 200 |
| 416516 | 1 | 8599 | 8618 | GTGAGAATACAACAGATGAG | 162 | 6156 | 6175 | 201 |
| 416517 | 1 | 8708 | 8727 | GGGTGCAGTAGCAGATGCAA | 162 | 6265 | 6284 | 202 |
| 416518 | 1 | 8855 | 8874 | GGGTGACCACACATTTCCTG | 162 | 6422 | 6441 | 203 |
| 416434 | 1 | 9076 | 9095 | CTGTAAGAAATCCAGAACAG | 162 | 6640 | 6659 | 204 |
| 416491 | 1 | 9120 | 9139 | GAGAAGGGTTGCAGGCAGGA | 162 | 6684 | 6703 | 205 |
| 416438 | 1 | 9194 | 9213 | CAGGAGCCCCCATTCTGGCA | 162 | 6761 | 6780 | 206 |
| 416439 | 1 | 9201 | 9220 | GTCCTTGCAGGAGCCCCCAT | 162 | 6768 | 6787 | 207 |
| 416440 | 1 | 9213 | 9232 | GGACTGGAGCTGGTCCTTGC | 162 | 6780 | 6799 | 208 |
| 416441 | 1 | 9220 | 9239 | AGATATAGGACTGGAGCTGG | 162 | 6787 | 6806 | 209 |
| 416442 | 1 | 9223 | 9242 | AGCAGATATAGGACTGGAGC | 162 | 6790 | 6809 | 210 |
| 416443 | 1 | 9231 | 9250 | GAGGCAGAAGCAGATATAGG | 162 | 6798 | 6817 | 211 |
| 416444 | 1 | 9255 | 9274 | ACAGTTCCGGCCCTCGAAGG | 162 | 6822 | 6841 | 212 |
| 416519 | 1 | 9290 | 9309 | AAATATGGGACCCAAAGTGG | 162 | 6857 | 6876 | 213 |
| 416520 | 1 | 9298 | 9317 | CCCTCTGCAAATATGGGACC | 162 | 6865 | 6884 | 214 |
| 416521 | 1 | 9362 | 9381 | CACCCCACCAGGTTGTGCAC | 162 | 6906 | 6925 | 215 |
| 416522 | 1 | 9515 | 9534 | GGCTGAGAATTGCCCAGGGC | 162 | 7059 | 7078 | 216 |
| 416523 | 1 | 9522 | 9541 | TCTCGAGGGCTGAGAATTGC | 162 | 7066 | 7085 | 217 |
| 416524 | 1 | 9665 | 9684 | TAATTTAATATTCAGATGGT | 162 | 7239 | 7258 | 218 |
| 416525 | 1 | 9725 | 9744 | TATGAGTCCTTCTAGTGAAT | 162 | 7299 | 7318 | 219 |
| 416526 | 1 | 9848 | 9867 | TGTCCACATGACCCCACAGG | 162 | 7422 | 7441 | 220 |
| 416527 | 1 | 9912 | 9931 | GAGCTTCCCAAGTTGGCAGT | 162 | 7479 | 7498 | 221 |
| 416528 | 1 | 9942 | 9961 | TGATAAACCTCTGGACACC | 162 | 7509 | 7528 | 222 |
| 416529 | 1 | 9999 | 10018 | GGGCTGAGACTGAGGTCAGC | 162 | 7566 | 7585 | 223 |

TABLE 5-continued

Human/rhesus monkey cross-reactive chimeric antisense oligonucleotides having 5-10-5 MOE wings and deoxy gap

| ISIS No. | Human Target SEQ ID No. | Human Target Start Site | Human Target Stop Site | Sequence (5' to 3') | Rhesus Monkey Target SEQ ID No. | Rhesus Monkey Target Start Site | Rhesus Monkey Target Stop Site | SEQ ID No. |
|---|---|---|---|---|---|---|---|---|
| 416530 | 1 | 10166 | 10185 | AGGGTAGCCTTTGCCTTGGC | 162 | 7852 | 7871 | 224 |
| 416531 | 1 | 10317 | 10336 | AGATGACCAGCAGGAAGCCT | 162 | 8006 | 8025 | 225 |
| 416532 | 1 | 10323 | 10342 | GGACCCAGATGACCAGCAGG | 162 | 8012 | 8031 | 226 |
| 416533 | 1 | 10330 | 10349 | GCATTCTGGACCCAGATGAC | 162 | 8019 | 8038 | 227 |
| 416534 | 1 | 10377 | 10396 | ATGCACACCAGGGCTGCTGG | 162 | 8066 | 8085 | 228 |
| 416535 | 1 | 10382 | 10401 | GCAGGATGCACACCAGGGCT | 162 | 8071 | 8090 | 229 |
| 416536 | 1 | 10398 | 10417 | CGGGAAGGCCTGCCCTGCAG | 162 | 8087 | 8106 | 230 |
| 416537 | 1 | 10677 | 10696 | TGACCACTCTTCCGAGCAGC | 162 | 8376 | 8395 | 231 |
| 416538 | 1 | 10807 | 10826 | CGTGGACTGATCCAAAGGAC | 162 | 8505 | 8524 | 232 |
| 416539 | 1 | 10837 | 10856 | GACAGAGCCTGAGCTTGGCA | 162 | 8535 | 8554 | 233 |
| 416445 | 1 | 11013 | 11032 | TACTGCTCACAGCCGCCGTT | 162 | 8710 | 8729 | 234 |
| 416446 | 1 | 11024 | 11043 | GGTCACTGCAGTACTGCTCA | 162 | 8721 | 8740 | 235 |
| 416540 | 1 | 11143 | 11162 | GGACTGGTGTCATCTGGGAC | 162 | 8840 | 8859 | 236 |
| 416541 | 1 | 11259 | 11278 | CCACCCTTGGTGCCCAGATC | 162 | 8953 | 8972 | 237 |
| 416542 | 1 | 11297 | 11316 | CAGGGTGCCCATCCTAGTCA | 162 | 8991 | 9010 | 238 |
| 416543 | 1 | 11395 | 11414 | TCCTGCGAGTGGGAGTTGGA | 162 | 9089 | 9108 | 239 |
| 416544 | 1 | 11499 | 11518 | ATCCCATTTTCCCAGGAGCC | 162 | 9193 | 9212 | 240 |
| 416545 | 1 | 11505 | 11524 | AGAAACATCCCATTTTCCCA | 162 | 9199 | 9218 | 241 |
| 416546 | 1 | 11519 | 11538 | CCAGGCTGGTTTGGAGAAAC | 162 | 9213 | 9232 | 242 |
| 416547 | 1 | 11729 | 11748 | ATGAAATTCTACCTAAAGAT | 162 | 9434 | 9453 | 243 |
| 416548 | 1 | 11735 | 11754 | AGGTGAATGAAATTCTACCT | 162 | 9440 | 9459 | 244 |
| 416549 | 1 | 11838 | 11857 | GACAATGGTCAGGGCTGGTT | 162 | 9543 | 9562 | 245 |
| 416550 | 1 | 11852 | 11871 | TGGCTGGCTGAGGAGACAAT | 162 | 9557 | 9576 | 246 |
| 416551 | 1 | 12000 | 12019 | CAGAAACACCCATCCTCTGA | 162 | 9724 | 9743 | 247 |
| 416448 | 1 | 12088 | 12107 | TTTTTCCACATGGATATTCA | 162 | 9812 | 9831 | 248 |
| 416449 | 1 | 12094 | 12113 | TAGGTATTTTCCACATGGA | 162 | 9818 | 9837 | 249 |
| 416450 | 1 | 12122 | 12141 | GGTTTGCTGGCATTTCTTTT | 162 | 9846 | 9865 | 250 |
| 416451 | 1 | 12175 | 12194 | GCCATGGACACTCCCCTTTG | 162 | 9899 | 9918 | 251 |
| 416552 | 1 | 12398 | 12417 | TCTGCACAGGGTAGACCCTC | 162 | 10127 | 10146 | 252 |
| 416553 | 1 | 12403 | 12422 | GGTTCTCTGCACAGGGTAGA | 162 | 10132 | 10151 | 253 |
| 416554 | 1 | 12467 | 12486 | AAAGATCCCACCTCAAAGAG | 162 | 10196 | 10215 | 254 |
| 416555 | 1 | 12478 | 12497 | AAAGATCAGGCAAAGATCCC | 162 | 10207 | 10226 | 255 |
| 416556 | 1 | 12508 | 12527 | ATAGCTTTGATCCAATGCTC | 162 | 10237 | 10256 | 256 |
| 416557 | 1 | 12639 | 12658 | TCCCAGGCAAAGCTGCTCAG | 162 | 10368 | 10387 | 257 |
| 416453 | 1 | 12867 | 12886 | GATTTTGTCGAAACAGTGGG | 162 | 10596 | 10615 | 258 |
| 416558 | 1 | 13159 | 13178 | TGACAGCACGAAGCCCAGAG | 162 | 10880 | 10899 | 259 |

TABLE 5-continued

Human/rhesus monkey cross-reactive chimeric antisense oligonucleotides having 5-10-5 MOE wings and deoxy gap

| ISIS No. | Human Target SEQ ID No. | Human Target Start Site | Human Target Stop Site | Sequence (5' to 3') | Rhesus Monkey Target SEQ ID No. | Rhesus Monkey Target Start Site | Rhesus Monkey Target Stop Site | SEQ ID No. |
|---|---|---|---|---|---|---|---|---|
| 416559 | 1 | 13638 | 13657 | GCCATTTCTAGGTCTGCAGG | 162 | 11360 | 11379 | 260 |
| 416455 | 1 | 13760 | 13779 | CGCCGGCTCTGCTCATCCCC | 162 | 11482 | 11501 | 261 |
| 416456 | 1 | 13770 | 13789 | CTGCGCCACCCGCCGGCTCT | 162 | 11492 | 11511 | 262 |
| 416457 | 1 | 13780 | 13799 | GGATGATGACCTGCGCCACC | 162 | 11502 | 11521 | 263 |
| 416458 | 1 | 13831 | 13850 | GGCGGAGCAGCGCGATGTCG | 162 | 11553 | 11572 | 264 |
| 416459 | 1 | 13859 | 13878 | TGGTCAGTGAGGACCACGGG | 162 | 11581 | 11600 | 265 |
| 416460 | 1 | 13866 | 13885 | CACCACATGGTCAGTGAGGA | 162 | 11588 | 11607 | 266 |
| 416461 | 1 | 13923 | 13942 | GAAGCGCACGAAGGCCAGCG | 162 | 11645 | 11664 | 267 |
| 416462 | 1 | 14020 | 14039 | GGCAGTCCTGGGTCATCAGC | 162 | 11742 | 11761 | 268 |
| 416463 | 1 | 14027 | 14046 | TGCTGCAGGCAGTCCTGGGT | 162 | 11749 | 11768 | 269 |
| 416464 | 1 | 14072 | 14091 | AACATGTACTCCGTGATATT | 162 | 11794 | 11813 | 270 |
| 416465 | 1 | 14122 | 14141 | CACTGTCCCCCTTGCAGGAG | 162 | 11844 | 11863 | 271 |
| 416466 | 1 | 14132 | 14151 | TGTGGGCCTCCACTGTCCCC | 162 | 11854 | 11873 | 272 |
| 416467 | 1 | 14189 | 14208 | CCCTGGCCCCAGCTGACGAT | 162 | 11911 | 11930 | 273 |
| 416468 | 1 | 14234 | 14253 | TGGGAGACCCTGGTGTACAC | 162 | 11956 | 11975 | 274 |
| 416469 | 1 | 14251 | 14270 | GCAGCCACTCGATGTACTGG | 162 | 11973 | 11992 | 275 |
| 416470 | 1 | 14257 | 14276 | GCTTTTGCAGCCACTCGATG | 162 | 11979 | 11998 | 276 |
| 416471 | 1 | 14260 | 14279 | TGAGCTTTTGCAGCCACTCG | 162 | 11982 | 12001 | 277 |
| 416472 | 1 | 14348 | 14367 | CAGCCTTGGCTTTCTCTCCA | 162 | 12070 | 12089 | 278 |
| 416473 | 1 | 14613 | 14632 | CCCTGCCCCTCTGTCCAGCG | 162 | 12333 | 125352 | 279 |
| 416474 | 1 | 14642 | 14661 | TGTCTGCCTCCAGGACAACC | 162 | 12362 | 12381 | 280 |
| 416475 | 1 | 14653 | 14672 | CTCAGCTGGGCTGTCTGCCT | 162 | 12373 | 12392 | 281 |
| 416476 | 1 | 14686 | 14705 | GCAGGTGGGCTTGGCTGAAG | 162 | 12406 | 12425 | 282 |
| 416477 | 1 | 14710 | 14729 | CAGCCTGAGGCCAGCAGATC | 162 | 12430 | 12449 | 283 |
| 416478 | 1 | 14735 | 14754 | GTCTCCAGCAATGAAGGCAG | 162 | 12455 | 12474 | 284 |
| 416479 | 1 | 15103 | 15122 | GACAGCACACATGGAGTCAG | 162 | 12820 | 12839 | 285 |
| 416480 | 1 | 15132 | 15151 | AAGTGAGAGCTAAACAACCG | 162 | 12849 | 12868 | 286 |
| 416481 | 1 | 15157 | 15176 | AGATGATAATGGATAAGAAC | 162 | 12874 | 12893 | 287 |
| 416482 | 1 | 15188 | 15207 | CATGGTGATGCTTCTGAATT | 162 | 12905 | 12924 | 288 |
| 416483 | 1 | 15433 | 15452 | TGTGAGGGTTCATTTCAGTG | 162 | 13130 | 13149 | 289 |
| 416484 | 1 | 15485 | 15504 | TACAGCCTCAAACATCTATC | 162 | 13184 | 13203 | 290 |
| 416485 | 1 | 15489 | 15508 | GAGCTACAGCCTCAAACATC | 162 | 13188 | 13207 | 291 |
| 416486 | 1 | 15540 | 15559 | ATTGACAAGGGCTGTGGCAG | 162 | 13239 | 13258 | 292 |
| 416487 | 1 | 15571 | 15590 | GCAGGTGCTCCCAGGGTCTC | 162 | 13270 | 13289 | 293 |
| 416488 | 1 | 15639 | 15658 | CAGGTCCTCCCACTGCAGCC | 162 | 13334 | 13353 | 294 |

TABLE 5-continued

Human/rhesus monkey cross-reactive chimeric antisense oligonucleotides having 5-10-5 MOE wings and deoxy gap

| ISIS No. | Human Target SEQ ID No. | Human Target Start Site | Human Target Stop Site | Sequence (5' to 3') | Rhesus Target SEQ ID No. | Rhesus Monkey Target Start Site | Rhesus Monkey Target Stop Site | SEQ ID No. |
|---|---|---|---|---|---|---|---|---|
| 416489 | 1 | 15650 | 15669 | GTGCAGCTTGCCAGGTCCTC | 162 | 13345 | 13364 | 295 |
| 416490 | 1 | 15661 | 15680 | ACTCAGCAAGAGTGCAGCTT | 162 | 13356 | 13375 | 296 |
| 416560 | 1 | 15973 | 15992 | TAAAACTTTATTTACAAGAG | 162 | 13638 | 13657 | 297 |
| 416561 | 1 | 15985 | 16004 | GGTGTGTTCCCATAAAACTT | 162 | 13650 | 13669 | 298 |
| 416562 | 1 | 16185 | 16204 | AAAGCAGAGCCAGCTCTGAC | 162 | 13849 | 13868 | 299 |
| 416563 | 1 | 16596 | 16615 | GCCTGCATTTCCCATTGGCA | 162 | 13931 | 13950 | 300 |
| 416564 | 1 | 16738 | 16757 | GCCACTCACAGAAAGCTGGA | 162 | 14071 | 14090 | 301 |
| 416565 | 1 | 16872 | 16891 | CAGGATGCTCATGGCAGACA | 162 | 14205 | 14224 | 302 |
| 416566 | 1 | 16911 | 16930 | GTTTGTATGGAGAGACCAAT | 162 | 14244 | 14263 | 303 |
| 416567 | 1 | 16977 | 16996 | TGGTGGCACCAGATGTCTGA | 162 | 14310 | 14329 | 304 |
| 416568 | 1 | 17112 | 17131 | CATTGTGCCTGGCACACAGG | 162 | 14445 | 14464 | 305 |
| 416569 | 1 | 17136 | 17155 | GCCTGGTGTGCACACATTGT | 162 | 14469 | 14488 | 306 |
| 416422 | 167 | 107 | 126 | AGCGACCCCGCCTGCAGCCA | 163 | 107 | 126 | 308 |
| 416433 | 167 | 341 | 360 | AGAAATCCAGAACAGCTTCG | 163 | 341 | 360 | 309 |
| 416435 | 167 | 353 | 372 | CCCATCACTGTAAGAAATCC | 163 | 353 | 372 | 310 |
| 416436 | 167 | 360 | 379 | ACTGGTCCCCATCACTGTAA | 163 | 360 | 379 | 311 |
| 416437 | 167 | 366 | 385 | AGGCACACTGGTCCCCATCA | 163 | 366 | 385 | 312 |
| 416447 | 167 | 616 | 635 | CATGGATATTCAACTGTGGG | 163 | 616 | 635 | 313 |
| 416452 | 167 | 726 | 745 | CCAACAACAGGACCTGCCAT | 163 | 726 | 745 | 314 |
| 416454 | 167 | 846 | 865 | CGTGCTCGCCCAGCACCGCG | 163 | 846 | 865 | 315 |

Example 4

Antisense Inhibition of Human Factor 7 in HepB3 Cells

Antisense oligonucleotides targeted to a Factor 7 nucleic acid were designed and tested for their effects on Factor 7 mRNA in vitro. Cultured HepB3 cells at a density of 4,000 cells per well were transfected using lipofectin reagent with 50 nM antisense oligonucleotide. After a treatment period of approximately 24 hours, RNA was isolated from the cells and Factor 7 mRNA levels were measured by real-time RT-PCR, as described herein. Human Factor 7 primer probe set RTS 2927 was used to measure mRNA levels. Factor 7 mRNA levels were adjusted according to total RNA content as measured by RIBOGREEN®. Results are presented as percent inhibition of Factor 7, relative to untreated control.

The chimeric antisense oligonucleotides in Table 6 were designed as 5-10-5 MOE, 3-14-3 MOE, and 2-13-5 MOE gapmers. The 5-10-5 gapmers are 20 nucleotides in length, wherein the central gap segment is comprised of ten 2'-deoxy- nucleotides and is flanked on both sides (in the 5' and 3' directions) by wings comprising five nucleotides each. The 3-14-3 gapmers are 20 nucleotides in length, wherein the central gap segment is comprised of fourteen 2'-deoxynucle- otides and is flanked on both sides (in the 5' and 3' directions) by wings comprising three nucleotides each. The 2-13-5 gap- mers are 20 nucleotides in length, wherein the central gap segment is comprised of thirteen 2'-deoxynucleotides. The central gap is flanked on the 5' end with a wing comprising two nucleotides and on the 3' end with a wing comprising five nucleotides. For each of the motifs (5-10-5, 3-14-3, and 2-13- 5), each nucleotide in the 5' wing segment and each nucle- otide in the 3' wing segment has a 2'-MOE modification. The internucleoside linkages throughout each gapmer are phos- phorothioate (P=S) linkages. All cytidine residues through- out each gapmer are 5-methylcytidines. "Target start site" indicates the 5'-most nucleotide to which the gapmer is tar- geted. "Target stop site" indicates the 3'-most nucleotide to which the gapmer is targeted. Each gapmer listed in Table 6 is targeted to SEQ ID NO: 1 (nucleotides 1255000 to 1273000 of GENBANK Accession No. NT_027140.6).

TABLE 6

Inhibition of human Factor 7 mRNA levels by chimeric antisense oligonucleotides targeted to SEQ ID NO: 1

| ISIS No. | Target Start Site | Target Stop Site | Sequence (5' to 3') | Motif | % Inhibition | SEQ ID No. |
|---|---|---|---|---|---|---|
| 422117 | 4834 | 4853 | GGAAGAAGGGACGGAAGGTG | 5-10-5 | 1 | 316 |
| 422186 | 4834 | 4853 | GGAAGAAGGGACGGAAGGTG | 3-14-3 | 14 | 316 |
| 422263 | 4834 | 4853 | GGAAGAAGGGACGGAAGGTG | 2-13-5 | 19 | 316 |
| 422118 | 4835 | 4854 | CGGAAGAAGGGACGGAAGGT | 5-10-5 | 15 | 317 |
| 422187 | 4835 | 4854 | CGGAAGAAGGGACGGAAGGT | 3-14-3 | 28 | 317 |
| 422264 | 4835 | 4854 | CGGAAGAAGGGACGGAAGGT | 2-13-5 | 24 | 317 |
| 422119 | 4836 | 4855 | GCGGAAGAAGGGACGGAAGG | 5-10-5 | 39 | 318 |
| 422188 | 4836 | 4855 | GCGGAAGAAGGGACGGAAGG | 3-14-3 | 37 | 318 |
| 422265 | 4836 | 4855 | GCGGAAGAAGGGACGGAAGG | 2-13-5 | 34 | 318 |
| 422120 | 4837 | 4856 | CGCGGAAGAAGGGACGGAAG | 5-10-5 | 40 | 319 |
| 422189 | 4837 | 4856 | CGCGGAAGAAGGGACGGAAG | 3-14-3 | 0 | 319 |
| 422266 | 4837 | 4856 | CGCGGAAGAAGGGACGGAAG | 2-13-5 | 13 | 319 |
| 422121 | 4838 | 4857 | GCGCGGAAGAAGGGACGGAA | 5-10-5 | 43 | 320 |
| 422190 | 4838 | 4857 | GCGCGGAAGAAGGGACGGAA | 3-14-3 | 12 | 320 |
| 422267 | 4838 | 4857 | GCGCGGAAGAAGGGACGGAA | 2-13-5 | 38 | 320 |
| 422122 | 4839 | 4858 | AGCGCGGAAGAAGGGACGGA | 5-10-5 | 24 | 321 |
| 422191 | 4839 | 4858 | AGCGCGGAAGAAGGGACGGA | 3-14-3 | 27 | 321 |
| 422268 | 4839 | 4858 | AGCGCGGAAGAAGGGACGGA | 2-13-5 | 63 | 321 |
| 422123 | 4840 | 4859 | GAGCGCGGAAGAAGGGACGG | 5-10-5 | 16 | 322 |
| 422192 | 4840 | 4859 | GAGCGCGGAAGAAGGGACGG | 3-14-3 | 27 | 322 |
| 422269 | 4840 | 4859 | GAGCGCGGAAGAAGGGACGG | 2-13-5 | 27 | 322 |
| 422124 | 4841 | 4860 | TGAGCGCGGAAGAAGGGACG | 5-10-5 | 0 | 323 |
| 422193 | 4841 | 4860 | TGAGCGCGGAAGAAGGGACG | 3-14-3 | 6 | 323 |
| 422270 | 4841 | 4860 | TGAGCGCGGAAGAAGGGACG | 2-13-5 | 15 | 323 |
| 422125 | 4842 | 4861 | CTGAGCGCGGAAGAAGGGAC | 5-10-5 | 8 | 324 |
| 422194 | 4842 | 4861 | CTGAGCGCGGAAGAAGGGAC | 3-14-3 | 11 | 324 |
| 422271 | 4842 | 4861 | CTGAGCGCGGAAGAAGGGAC | 2-13-5 | 32 | 324 |
| 422126 | 4843 | 4862 | ACTGAGCGCGGAAGAAGGGA | 5-10-5 | 22 | 325 |
| 422195 | 4843 | 4862 | ACTGAGCGCGGAAGAAGGGA | 3-14-3 | 37 | 325 |
| 422272 | 4843 | 4862 | ACTGAGCGCGGAAGAAGGGA | 2-13-5 | 12 | 325 |
| 422127 | 4844 | 4863 | TACTGAGCGCGGAAGAAGGG | 5-10-5 | 17 | 326 |
| 422196 | 4844 | 4863 | TACTGAGCGCGGAAGAAGGG | 3-14-3 | 2 | 326 |
| 422273 | 4844 | 4863 | TACTGAGCGCGGAAGAAGGG | 2-13-5 | 0 | 326 |
| 422128 | 4845 | 4864 | TTACTGAGCGCGGAAGAAGG | 5-10-5 | 27 | 327 |
| 422197 | 4845 | 4864 | TTACTGAGCGCGGAAGAAGG | 3-14-3 | 26 | 327 |
| 422274 | 4845 | 4864 | TTACTGAGCGCGGAAGAAGG | 2-13-5 | 24 | 327 |
| 422129 | 4846 | 4865 | GTTACTGAGCGCGGAAGAAG | 5-10-5 | 45 | 328 |

TABLE 6-continued

Inhibition of human Factor 7 mRNA levels by chimeric antisense oligonucleotides targeted to SEQ ID NO: 1

| ISIS No. | Target Start Site | Target Stop Site | Sequence (5' to 3') | Motif | % Inhibition | SEQ ID No. |
|---|---|---|---|---|---|---|
| 422198 | 4846 | 4865 | GTTACTGAGCGCGGAAGAAG | 3-14-3 | 50 | 328 |
| 422275 | 4846 | 4865 | GTTACTGAGCGCGGAAGAAG | 2-13-5 | 42 | 328 |
| 422199 | 4847 | 4866 | GGTTACTGAGCGCGGAAGAA | 3-14-3 | 65 | 188 |
| 422276 | 4847 | 4866 | GGTTACTGAGCGCGGAAGAA | 2-13-5 | 66 | 188 |

Example 5

Dose-Dependent Antisense Inhibition of Human Coagulation Factor 7 in HepB3 Cells Gapmers (from Tables 1 through 6, above) exhibiting in vitro inhibition of Factor 7 were selected and tested at various doses in HepB3 cells. Cells were plated at a density of 4,000 cells per well and transfected using lipofectin reagent with 6.25 nM, 12.5 nM, 25.0 nM, 50.0 nM, and 100.0 nM concentrations of antisense oligonucleotide, as indicated in Table 7. After a treatment period of approximately 16 hours, RNA was isolated from the cells and Factor 7 mRNA levels were measured by real-time RT-PCR, as described herein. Human Factor 7 primer probe set RTS 2927 was used to measure mRNA levels. Factor 7 mRNA levels were adjusted according to total RNA content as measured by RIBOGREEN®. Results are presented as percent inhibition of Factor 7, relative to untreated control cells. As illustrated in Table 7, Factor 7 mRNA levels were reduced in a dose-dependent manner.

TABLE 7

Dose-dependent antisense inhibition of human Factor 7 in HepB3 cells

| ISIS No. | 6.25 nM | 12.5 nM | 25.0 nM | 50.0 nM | 100.0 nM | SEQ ID No. |
|---|---|---|---|---|---|---|
| 407643 | 36 | 49 | 70 | 83 | 93 | 50 |
| 407900 | 18 | 36 | 61 | 82 | 91 | 88 |
| 407935 | 38 | 53 | 70 | 82 | 86 | 123 |
| 407939 | 37 | 57 | 77 | 84 | 87 | 127 |
| 416438 | 11 | 33 | 56 | 75 | 82 | 206 |
| 416446 | 25 | 24 | 50 | 69 | 64 | 235 |
| 416449 | 19 | 33 | 45 | 65 | 85 | 249 |
| 416455 | 28 | 44 | 64 | 78 | 87 | 261 |
| 416472 | 16 | 44 | 64 | 80 | 88 | 278 |
| 416477 | 21 | 46 | 64 | 78 | 87 | 283 |
| 416507 | 30 | 53 | 70 | 77 | 72 | 188 |
| 416508 | 42 | 51 | 71 | 79 | 89 | 189 |
| 416549 | 38 | 44 | 63 | 73 | 78 | 245 |

Example 6

Antisense Inhibition of Human Factor 7 in HepB3 Cells by Oligonucleotides Designed by Microwalk Additional gapmers were designed based on the gapmers presented in Table 7. These gapmers were designed by creating gapmers shifted slightly upstream and downstream (i.e. "microwalk") of the original gapmers from Table 7. Gapmers were also created with various motifs, e.g. 5-10-5 MOE, 3-14-3 MOE, and 2-13-5 MOE. These gapmers were tested in vitro. Cultured HepB3 cells at a density of 4,000 cells per well were transfected using lipofectin reagent with 50 nM antisense oligonucleotide. After a treatment period of approximately 24 hours, RNA was isolated from the cells and Factor 7 mRNA levels were measured by real-time RT-PCR. Factor 7 mRNA levels were adjusted according to total RNA content, as measured by RIBOGREEN®. Results are presented as percent inhibition of Factor 7, relative to untreated control cells.

The in vitro inhibition data for the gapmers designed by microwalk was then compared with the in vitro inhibition data for the gapmers from Table 7, as indicated in Tables 8, 9, 10, 11, 12, and 13. The oligonucleotides are displayed according to the region on the human gene sequence to which they map.

The chimeric antisense oligonucleotides in Table 8 were designed as 5-10-5 MOE, 3-14-3 MOE, and 2-13-5 MOE gapmers. The first listed gapmer in Table 8 is the original gapmer (see Table 7) from which the remaining gapmers were designed via microwalk and is designated by an asterisk (*). The 5-10-5 gapmers are 20 nucleotides in length, wherein the central gap segment is comprised of ten 2'-deoxynucleotides and is flanked on both sides (in the 5' and 3' directions) by wings comprising five nucleotides each. The 3-14-3 gapmers are 20 nucleotides in length, wherein the central gap segment is comprised of fourteen 2'-deoxynucleotides and is flanked on both sides (in the 5' and 3' directions) by wings comprising three nucleotides each. The 2-13-5 gapmers are 20 nucleotides in length, wherein the central gap segment is comprised of thirteen 2'-deoxynucleotides. The central gap is flanked on the 5' end with a wing comprising two nucleotides and on the 3' end with a wing comprising five nucleotides. For each of the motifs (5-10-5, 3-14-3, and 2-13-5), each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. "Target start site" indicates the 5'-most nucleotide to which the gapmer is targeted. "Target stop site" indicates the 3'-most nucleotide to which the gapmer is targeted. Each gapmer listed in Table 8 is targeted to SEQ ID NO: 1 (nucleotides 1255000 to 1273000 of GENBANK Accession No. NT_027140.6).

As shown in Table 8, all of the 5-10-5 MOE gapmers, 3-14-3 MOE gapmers, and 2-13-5 MOE gapmers targeted to the target region beginning at target start site 4868 and ending at the target stop site 4899 (i.e. nucleobases 4868-4899) of SEQ ID NO: 1 inhibited Factor 7 mRNA by at least 48%.

Certain gapmers within the target region (i.e. nucleobases 4868-4899) inhibited Factor 7 mRNA expression by at least 40%, for example, ISIS numbers 416508, 422138, 422213, 422290, 422139, 422214, 422291, 422140, 422215, 422292, 422141, 422216, 422293, 422142, 422217, 422294, 422218, 422295, 422143, 422219, 422296, 422144, 422220, 422297, 422145, 422221, 422298, 422146, 422222, 422299, 422147, 422223, 422300, 422148, 422224, 422301, 416509, 422225, and 422302.

Certain gapmers within the target region (i.e. nucleobases 4868-4899) inhibited Factor 7 mRNA expression by at least 50%, for example, ISIS numbers 416508, 422138, 422213, 422290, 422139, 422214, 422291, 422140, 422215, 422292, 422141, 422216, 422293, 422142, 422217, 422294, 422218, 422295, 422143, 422219, 422296, 422144, 422220, 422297, 422145, 422221, 422298, 422146, 422222, 422299, 422147, 422300, 422148, 422224, 422301, 416509, 422225, and 422302.

Certain gapmers within the target region (i.e. nucleobases 4868-4899) inhibited Factor 7 mRNA expression by at least 60%, for example, ISIS numbers 416508, 422138, 422213, 422139, 422140, 422215, 422292, 422141, 422216, 422293, 422142, 422217, 422294, 422218, 422295, 422143, 422219, 422296, 422297, 422298, 422299, 422147, 422300, 422224, 422301, 416509, and 422302.

Certain gapmers within the target region (i.e. nucleobases 4868-4899) inhibited Factor 7 mRNA expression by at least 70%, for example, ISIS numbers 422138, 422140, 422215, 422292, 422142, 422217, 422294, 422218, 422295, 422143, and 422296.

TABLE 8

Inhibition of human Factor 7 mRNA levels by chimeric antisense oligonucleotides targeted to nucleobases 4868 to 4899 of SEQ ID NO: 1

| ISIS No. | Target Start Site | Target Stop Site | Sequence (5' to 3') | Motif | % Inhibition | SEQ ID NO |
|---|---|---|---|---|---|---|
| *416508 | 4873 | 4892 | CGAGTTCTGCAGGAGCGGCC | 5-10-5 | 67 | 189 |
| 422138 | 4868 | 4887 | TCTGCAGGAGCGGCCTAAAT | 5-10-5 | 70 | 329 |
| 422213 | 4868 | 4887 | TCTGCAGGAGCGGCCTAAAT | 3-14-3 | 67 | 329 |
| 422290 | 4868 | 4887 | TCTGCAGGAGCGGCCTAAAT | 2-13-5 | 50 | 329 |
| 422139 | 4869 | 4888 | TTCTGCAGGAGCGGCCTAAA | 5-10-5 | 66 | 330 |
| 422214 | 4869 | 4888 | TTCTGCAGGAGCGGCCTAAA | 3-14-3 | 60 | 330 |
| 422291 | 4869 | 4888 | TTCTGCAGGAGCGGCCTAAA | 2-13-5 | 53 | 330 |
| 422140 | 4870 | 4889 | GTTCTGCAGGAGCGGCCTAA | 5-10-5 | 74 | 331 |
| 422215 | 4870 | 4889 | GTTCTGCAGGAGCGGCCTAA | 3-14-3 | 73 | 331 |
| 422292 | 4870 | 4889 | GTTCTGCAGGAGCGGCCTAA | 2-13-5 | 75 | 331 |
| 422141 | 4871 | 4890 | AGTTCTGCAGGAGCGGCCTA | 5-10-5 | 64 | 332 |
| 422216 | 4871 | 4890 | AGTTCTGCAGGAGCGGCCTA | 3-14-3 | 68 | 332 |
| 422293 | 4871 | 4890 | AGTTCTGCAGGAGCGGCCTA | 2-13-5 | 69 | 332 |
| 422142 | 4872 | 4891 | GAGTTCTGCAGGAGCGGCCT | 5-10-5 | 73 | 333 |
| 422217 | 4872 | 4891 | GAGTTCTGCAGGAGCGGCCT | 3-14-3 | 75 | 333 |
| 422294 | 4872 | 4891 | GAGTTCTGCAGGAGCGGCCT | 2-13-5 | 78 | 333 |
| 422218 | 4873 | 4892 | CGAGTTCTGCAGGAGCGGCC | 3-1-4-3 | 70 | 189 |
| 422295 | 4873 | 4892 | CGAGTTCTGCAGGAGCGGCC | 2-13-5 | 74 | 189 |
| 422143 | 4874 | 4893 | CCGAGTTCTGCAGGAGCGGC | 5-10-5 | 70 | 334 |
| 422219 | 4874 | 4893 | CCGAGTTCTGCAGGAGCGGC | 3-14-3 | 65 | 334 |
| 422296 | 4874 | 4893 | CCGAGTTCTGCAGGAGCGGC | 2-13-5 | 74 | 334 |
| 422144 | 4875 | 4894 | CCCGAGTTCTGCAGGAGCGG | 5-10-5 | 58 | 335 |
| 422220 | 4875 | 4894 | CCCGAGTTCTGCAGGAGCGG | 3-1-4-3 | 59 | 335 |
| 422297 | 4875 | 4894 | CCCGAGTTCTGCAGGAGCGG | 2-13-5 | 63 | 335 |
| 422145 | 4876 | 4895 | GCCCGAGTTCTGCAGGAGCG | 5-10-5 | 57 | 336 |
| 422221 | 4876 | 4895 | GCCCGAGTTCTGCAGGAGCG | 3-1-4-3 | 59 | 336 |

TABLE 8-continued

Inhibition of human Factor 7 mRNA levels by chimeric antisense oligonucleotides targeted to nucleobases 4868 to 4899 of SEQ ID NO: 1

| ISIS No. | Target Start Site | Target Stop Site | Sequence (5' to 3') | Motif | % Inhibition | SEQ ID NO |
|---|---|---|---|---|---|---|
| 422298 | 4876 | 4895 | GCCCGAGTTCTGCAGGAGCG | 2-1-3-5 | 62 | 336 |
| 422146 | 4877 | 4896 | AGCCCGAGTTCTGCAGGAGC | 5-10-5 | 58 | 337 |
| 422222 | 4877 | 4896 | AGCCCGAGTTCTGCAGGAGC | 3-14-3 | 55 | 337 |
| 422299 | 4877 | 4896 | AGCCCGAGTTCTGCAGGAGC | 2-13-5 | 64 | 337 |
| 422147 | 4878 | 4897 | GAGCCCGAGTTCTGCAGGAG | 5-10-5 | 64 | 338 |
| 422223 | 4878 | 4897 | GAGCCCGAGTTCTGCAGGAG | 3-1-4-3 | 48 | 338 |
| 422300 | 4878 | 4897 | GAGCCCGAGTTCTGCAGGAG | 2-13-5 | 65 | 338 |
| 422148 | 4879 | 4898 | GGAGCCCGAGTTCTGCAGGA | 5-10-5 | 57 | 339 |
| 422224 | 4879 | 4898 | GGAGCCCGAGTTCTGCAGGA | 3-14-3 | 62 | 339 |
| 422301 | 4879 | 4898 | GGAGCCCGAGTTCTGCAGGA | 2-13-5 | 67 | 339 |
| 416509 | 4880 | 4899 | AGGAGCCCGAGTTCTGCAGG | 5-10-5 | 60 | 190 |
| 422225 | 4880 | 4899 | AGGAGCCCGAGTTCTGCAGG | 3-14-3 | 56 | 190 |
| 422302 | 4880 | 4899 | AGGAGCCCGAGTTCTGCAGG | 2-13-5 | 67 | 190 |

The chimeric antisense oligonucleotides in Table 9 were designed as 5-10-5 MOE, 3-14-3 MOE, and 2-13-5 MOE gapmers. The first listed gapmer in Table 9 is the original gapmer (see Table 7) from which the remaining gapmers were designed via microwalk and is designated by an asterisk (*). The 5-10-5 gapmers are 20 nucleotides in length, wherein the central gap segment is comprised of 10 2'-deoxynucleotides and is flanked on both sides (in the 5' and 3' directions) by wings comprising 5 nucleotides each. The 3-14-3 gapmers are 20 nucleotides in length, wherein the central gap segment is comprised of 14 2'-deoxynucleotides and is flanked on both sides (in the 5' and 3' directions) by wings comprising 3 nucleotides each. The 2-13-5 gapmers are 20 nucleotides in length, wherein the central gap segment is comprised of 13 2'-deoxynucleotides. The central gap is flanked on the 5' end with a wing comprising 2 nucleotides and on the 3' end with a wing comprising 5 nucleotides. For each of the motifs (5-10-5, 3-14-3, and 2-13-5), each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. "Target start site" indicates the 5'-most nucleotide to which the gapmer is targeted. "Target stop site" indicates the 3'-most nucleotide to which the gapmer is targeted. Each gapmer listed in Table 9 is targeted to SEQ ID NO: 1 (nucleotides 1255000 to 1273000 of GENBANK Accession No. NT_027140.6).

As shown in Table 9, most of the 5-10-5 MOE gapmers, 3-14-3 MOE gapmers, and 2-13-5 MOE gapmers targeted to the target region beginning at target start site 11830 and ending at the target stop site 11869 (i.e. nucleobases 11830-11869) of SEQ ID NO: 1 inhibited Factor 7 mRNA by at least 40%.

Certain gapmers within the target region (i.e. nucleobases 11830-11869) inhibited Factor 7 mRNA expression by at least 20%, for example, ISIS numbers 416549, 422154, 422231, 422089, 422155, 422232, 422090, 422156, 422233, 422091, 422157, 422234, 422092, 422158, 422235, 422093, 422159, 422236, 422094, 422160, 422237, 422095, 422161, 422238, 422162, 422239, 422096, 422163, 422240, 422097, 422164, 422241, 422098, 422165, 422242, 422099, 422166, 422243, 422100, 422167, 422244, 422101, 422168, 422245, 422102, 422169, 422246, 422103, 422170, 422247, 422104, 422171, 422248, 422105, 422172, 422249, 422106, 422173, 422250, 422107, 422174, and 422251.

Certain gapmers within the target region (i.e. nucleobases 11830-11869) inhibited Factor 7 mRNA expression by at least 30%, for example, ISIS numbers 416549, 422154, 422155, 422232, 422090, 422156, 422233, 422091, 422157, 422234, 422092, 422158, 422235, 422093, 422159, 422236, 422094, 422160, 422237, 422095, 422161, 422238, 422162, 422239, 422096, 422163, 422240, 422097, 422164, 422241, 422098, 422165, 422242, 422099, 422166, 422243, 422100, 422167, 422244, 422101, 422168, 422102, 422169, 422246, 422103, 422247, 422104, 422171, 422248, 422105, 422172, 422249, 422106, 422173, 422250, 422107, 422174, and 422251.

Certain gapmers within the target region (i.e. nucleobases 11830-11869) inhibited Factor 7 mRNA expression by at least 40%, for example, ISIS numbers 416549, 422232, 422090, 422233, 422091, 422157, 422234, 422158, 422235, 422093, 422159, 422236, 422094, 422160, 422237, 422095, 422161, 422238, 422162, 422239, 422096, 422163, 422240, 422097, 422164, 422241, 422098, 422165, 422242, 422099, 422166, 422243, 422100, 422167, 422244, 422101, 422102, 422169, 422246, 422104, 422171, 422248, 422105, 422249, 422173, 422250, and 422174.

Certain gapmers within the target region (i.e. nucleobases 11830-11869) inhibited Factor 7 mRNA expression by at least 50%, for example, ISIS numbers 416549, 422234, 422235, 422237, 422095, 422161, 422238, 422162, 422239, 422096, 422163, 422240, 422097, 422164, 422241, 422098, 422165, 422242, 422166, 422243, 422100, 422167, 422244, 422102, 422169, 422104, 422171, 422248, 422105, 422249, 422173, 422250, and 422174.

Certain gapmers within the target region (i.e. nucleobases 11830-11869) inhibited Factor 7 mRNA expression by at least 60%, for example, ISIS numbers 416549, 422234, 422095, 422238, 422239, 422096, 422240, 422164, 422241, 422242, 422166, 422243, 422102, 422171, 422248, and 422105.

Certain gapmers within the target region (i.e. nucleobases 11830-11869) inhibited Factor 7 mRNA expression by at least 70%, for example, ISIS number 422096.

TABLE 9

Inhibition of human Factor 7 mRNA levels by chimeric antisense oligonucleotides targeted to nucleobases 11830 to 11869 of SEQ ID NO: 1

| Oligo ID | Target Start Site | Target Stop Site | Sequence (5' to 3') | Motif | % Inhibition | SEQ ID NO |
|---|---|---|---|---|---|---|
| *416549 | 11838 | 11857 | GACAATGGTCAGGGCTGGTT | 5-10-5 | 69 | 245 |
| 422088 | 11830 | 11849 | TCAGGGCTGGTTTTGGAGGA | 5-10-5 | 8 | 340 |
| 422154 | 11830 | 11849 | TCAGGGCTGGTTTTGGAGGA | 3-14-3 | 31 | 340 |
| 422231 | 11830 | 11849 | TCAGGGCTGGTTTTGGAGGA | 2-13-5 | 22 | 340 |
| 422089 | 11831 | 11850 | GTCAGGGCTGGTTTTGGAGG | 5-10-5 | 22 | 341 |
| 422155 | 11831 | 11850 | GTCAGGGCTGGTTTTGGAGG | 3-1-4-3 | 34 | 341 |
| 422232 | 11831 | 11850 | GTCAGGGCTGGTTTTGGAGG | 2-13-5 | 41 | 341 |
| 422090 | 11832 | 11851 | GGTCAGGGCTGGTTTTGGAG | 5-10-5 | 42 | 342 |
| 422156 | 11832 | 11851 | GGTCAGGGCTGGTTTTGGAG | 3-1-4-3 | 38 | 342 |
| 422233 | 11832 | 11851 | GGTCAGGGCTGGTTTTGGAG | 2-13-5 | 46 | 342 |
| 422091 | 11833 | 11852 | TGGTCAGGGCTGGTTTTGGA | 5-10-5 | 42 | 343 |
| 422157 | 11833 | 11852 | TGGTCAGGGCTGGTTTTGGA | 3-14-3 | 49 | 343 |
| 422234 | 11833 | 11852 | TGGTCAGGGCTGGTTTTGGA | 2-13-5 | 62 | 343 |
| 422092 | 11834 | 11853 | ATGGTCAGGGCTGGTTTTGG | 5-10-5 | 36 | 344 |
| 422158 | 11834 | 11853 | ATGGTCAGGGCTGGTTTTGG | 3-14-3 | 49 | 344 |
| 422235 | 11834 | 11853 | ATGGTCAGGGCTGGTTTTGG | 2-13-5 | 50 | 344 |
| 422093 | 11835 | 11854 | AATGGTCAGGGCTGGTTTTG | 5-10-5 | 42 | 345 |
| 422159 | 11835 | 11854 | AATGGTCAGGGCTGGTTTTG | 3-14-3 | 45 | 345 |
| 422236 | 11835 | 11854 | AATGGTCAGGGCTGGTTTTG | 2-1-3-5 | 44 | 345 |
| 422094 | 11836 | 11855 | CAATGGTCAGGGCTGGTTTT | 5-10-5 | 48 | 346 |
| 422160 | 11836 | 11855 | CAATGGTCAGGGCTGGTTTT | 3-14-3 | 42 | 346 |
| 422237 | 11836 | 11855 | CAATGGTCAGGGCTGGTTTT | 2-13-5 | 50 | 346 |
| 422095 | 11837 | 11856 | ACAATGGTCAGGGCTGGTTT | 5-10-5 | 60 | 347 |
| 422161 | 11837 | 11856 | ACAATGGTCAGGGCTGGTTT | 3-14-3 | 53 | 347 |
| 422238 | 11837 | 11856 | ACAATGGTCAGGGCTGGTTT | 2-13-5 | 64 | 347 |
| 422162 | 11838 | 11857 | GACAATGGTCAGGGCTGGTT | 3-14-3 | 59 | 245 |
| 422239 | 11838 | 11857 | GACAATGGTCAGGGCTGGTT | 2-13-5 | 67 | 245 |
| 422096 | 11839 | 11858 | AGACAATGGTCAGGGCTGGT | 5-10-5 | 76 | 348 |
| 422163 | 11839 | 11858 | AGACAATGGTCAGGGCTGGT | 3-14-3 | 56 | 348 |
| 422240 | 11839 | 11858 | AGACAATGGTCAGGGCTGGT | 2-13-5 | 66 | 348 |
| 422097 | 11840 | 11859 | GAGACAATGGTCAGGGCTGG | 5-10-5 | 59 | 349 |
| 422164 | 11840 | 11859 | GAGACAATGGTCAGGGCTGG | 3-14-3 | 64 | 349 |

TABLE 9-continued

Inhibition of human Factor 7 mRNA levels by chimeric antisense oligonucleotides targeted to nucleobases 11830 to 11869 of SEQ ID NO: 1

| Oligo ID | Target Start Site | Target Stop Site | Sequence (5' to 3') | Motif | % Inhibition | SEQ ID NO |
|---|---|---|---|---|---|---|
| 422241 | 11840 | 11859 | GAGACAATGGTCAGGGCTGG | 2-13-5 | 61 | 349 |
| 422098 | 11841 | 11860 | GGAGACAATGGTCAGGGCTG | 5-10-5 | 53 | 350 |
| 422165 | 11841 | 11860 | GGAGACAATGGTCAGGGCTG | 3-14-3 | 57 | 350 |
| 422242 | 11841 | 11860 | GGAGACAATGGTCAGGGCTG | 2-13-5 | 64 | 350 |
| 422099 | 11842 | 11861 | AGGAGACAATGGTCAGGGCT | 5-10-5 | 48 | 351 |
| 422166 | 11842 | 11861 | AGGAGACAATGGTCAGGGCT | 3-14-3 | 63 | 351 |
| 422243 | 11842 | 11861 | AGGAGACAATGGTCAGGGCT | 2-13-5 | 62 | 351 |
| 422100 | 11843 | 11862 | GAGGAGACAATGGTCAGGGC | 5-10-5 | 59 | 352 |
| 422167 | 11843 | 11862 | GAGGAGACAATGGTCAGGGC | 3-14-3 | 53 | 352 |
| 422244 | 11843 | 11862 | GAGGAGACAATGGTCAGGGC | 2-13-5 | 55 | 352 |
| 422101 | 11844 | 11863 | TGAGGAGACAATGGTCAGGG | 5-10-5 | 42 | 353 |
| 422168 | 11844 | 11863 | TGAGGAGACAATGGTCAGGG | 3-1-4-3 | 30 | 353 |
| 422245 | 11844 | 11863 | TGAGGAGACAATGGTCAGGG | 2-13-5 | 24 | 353 |
| 422102 | 11845 | 11864 | CTGAGGAGACAATGGTCAGG | 5-10-5 | 62 | 354 |
| 422169 | 11845 | 11864 | CTGAGGAGACAATGGTCAGG | 3-14-3 | 56 | 354 |
| 422246 | 11845 | 11864 | CTGAGGAGACAATGGTCAGG | 2-13-5 | 46 | 354 |
| 422103 | 11846 | 11865 | GCTGAGGAGACAATGGTCAG | 5-10-5 | 38 | 355 |
| 422170 | 11846 | 11865 | GCTGAGGAGACAATGGTCAG | 3-14-3 | 28 | 355 |
| 422247 | 11846 | 11865 | GCTGAGGAGACAATGGTCAG | 2-13-5 | 36 | 355 |
| 422104 | 11847 | 11866 | GGCTGAGGAGACAATGGTCA | 5-10-5 | 59 | 356 |
| 422171 | 11847 | 11866 | GGCTGAGGAGACAATGGTCA | 3-14-3 | 61 | 356 |
| 422248 | 11847 | 11866 | GGCTGAGGAGACAATGGTCA | 2-13-5 | 60 | 356 |
| 422105 | 11848 | 11867 | TGGCTGAGGAGACAATGGTC | 5-10-5 | 60 | 357 |
| 422172 | 11848 | 11867 | TGGCTGAGGAGACAATGGTC | 3-14-3 | 39 | 357 |
| 422249 | 11848 | 11867 | TGGCTGAGGAGACAATGGTC | 2-13-5 | 52 | 357 |
| 422106 | 11849 | 11868 | CTGGCTGAGGAGACAATGGT | 5-10-5 | 32 | 358 |
| 422173 | 11849 | 11868 | CTGGCTGAGGAGACAATGGT | 3-14-3 | 51 | 358 |
| 422250 | 11849 | 11868 | CTGGCTGAGGAGACAATGGT | 2-1-3-5 | 54 | 358 |
| 422107 | 11850 | 11869 | GCTGGCTGAGGAGACAATGG | 5-10-5 | 36 | 359 |
| 422174 | 11850 | 11869 | GCTGGCTGAGGAGACAATGG | 3-14-3 | 55 | 359 |
| 422251 | 11850 | 11869 | GCTGGCTGAGGAGACAATGG | 2-13-5 | 36 | 359 |

The chimeric antisense oligonucleotides in Table 10 were designed as 5-10-5 MOE, 3-14-3 MOE, and 2-13-5 MOE gapmers. The first listed gapmer in Table 10 is the original gapmer (see Table 7) from which the remaining gapmers were designed via microwalk and is designated by an asterisk (*). The 5-10-5 gapmers are 20 nucleotides in length, wherein the central gap segment is comprised of 10 2'-deoxynucleotides and is flanked on both sides (in the 5' and 3' directions) by wings comprising 5 nucleotides each. The 3-14-3 gapmers are 20 nucleotides in length, wherein the central gap segment is comprised of 14 2'-deoxynucleotides and is flanked on both sides (in the 5' and 3' directions) by wings comprising 3 nucleotides each. The 2-13-5 gapmers are 20 nucleotides in length, wherein the central gap segment is comprised of 13

2'-deoxynucleotides. The central gap is flanked on the 5' end with a wing comprising 2 nucleotides and on the 3' end with a wing comprising 5 nucleotides. For each of the motifs (5-10-5, 3-14-3, and 2-13-5), each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. "Target start site" indicates the 5'-most nucleotide to which the gapmer is targeted. "Target stop site" indicates the 3'-most nucleotide to which the gapmer is targeted. Each gapmer listed in Table 10 is targeted to SEQ ID NO: 1 (nucleotides 1255000 to 1273000 of GENBANK Accession No. NT_027140.6).

As shown in Table 10, most of the 5-10-5 MOE gapmers, 3-14-3 MOE gapmers, and 2-13-5 MOE gapmers targeted to the target region beginning at target start site 13760 and ending at the target stop site 13789 (i.e. nucleobases 13760-13789) of SEQ ID NO: 1 inhibited Factor 7 mRNA by at least 30%.

Certain gapmers within the target region (i.e. nucleobases 13760-13789) inhibited Factor 7 mRNA expression by at least 20%, for example, ISIS numbers 416455, 422175, 422252, 422108, 422176, 422253, 422109, 422177, 422254, 422110, 422178, 422255, 422111, 422179, 422256, 422112, 422180, 422257, 422113, 422181, 422258, 422114, 422259, 422115, 422183, 422260, 422116, 422184, 422261, 416456, and 422185.

Certain gapmers within the target region (i.e. nucleobases 13760-13789) inhibited Factor 7 mRNA expression by at least 30%, for example, ISIS numbers 416455, 422175, 422252, 422108, 422176, 422253, 422109, 422177, 422254, 422110, 422178, 422255, 422111, 422179, 422112, 422180, 422257, 422113, 422181, 422258, 422114, 422259, 422115, 422183, 422260, 422116, 422184, 422261, 416456, and 422185.

Certain gapmers within the target region (i.e. nucleobases 13760-13789) inhibited Factor 7 mRNA expression by at least 40%, for example, ISIS numbers 416455, 422175, 422252, 422108, 422176, 422253, 422109, 422177, 422254, 422110, 422179, 422112, 422180, 422257, 422113, 422181, 422258, 422114, 422259, 422115, 422183, 422260, 422116, 422184, 422261, 416456, and 422185.

Certain gapmers within the target region (i.e. nucleobases 13760-13789) inhibited Factor 7 mRNA expression by at least 50%, for example, ISIS numbers 416455, 422175, 422252, 422108, 422176, 422253, 422109, 422177, 422254, 422110, 422112, 422180, 422257, 422113, 422181, 422258, 422114, 422259, 422115, 422183, 422260, 422116, 422184, 422261, and 416456.

Certain gapmers within the target region (i.e. nucleobases 13760-13789) inhibited Factor 7 mRNA expression by at least 60%, for example, ISIS numbers 422175, 422252, 422108, 422253, 422109, 422177, 422112, 422257, 422113, 422181, 422258, 422259, 422115, 422183, and 422261.

Certain gapmers within the target region (i.e. nucleobases 13760-13789) inhibited Factor 7 mRNA expression by at least 70%, for example, ISIS numbers 422252, 422177, 422183, and 422261.

TABLE 10

Inhibition of human Factor 7 mRNA levels by chimeric antisense oligonucleotides targeted to nucleobases 13760 to 13789 of SEQ ID NO: 1

| ISIS No. | Target Start Site | Target Stop Site | Sequence (5' to 3') | Motif | % Inhibition | SEQ ID NO |
|---|---|---|---|---|---|---|
| *416455 | 13760 | 13779 | CGCCGGCTCTGCTCATCCCC | 5-10-5 | 51 | 261 |
| 422175 | 13760 | 13779 | CGCCGGCTCTGCTCATCCCC | 3-14-3 | 69 | 261 |
| 422252 | 13760 | 13779 | CGCCGGCTCTGCTCATCCCC | 2-13-5 | 70 | 261 |
| 422108 | 13761 | 13780 | CCGCCGGCTCTGCTCATCCC | 5-10-5 | 69 | 360 |
| 422176 | 13761 | 13780 | CCGCCGGCTCTGCTCATCCC | 3-14-3 | 52 | 360 |
| 422253 | 13761 | 13780 | CCGCCGGCTCTGCTCATCCC | 2-13-5 | 61 | 360 |
| 422109 | 13762 | 13781 | CCCGCCGGCTCTGCTCATCC | 5-10-5 | 68 | 361 |
| 422177 | 13762 | 13781 | CCCGCCGGCTCTGCTCATCC | 3-14-3 | 74 | 361 |
| 422254 | 13762 | 13781 | CCCGCCGGCTCTGCTCATCC | 2-13-5 | 42 | 361 |
| 422110 | 13763 | 13782 | ACCCGCCGGCTCTGCTCATC | 5-10-5 | 53 | 362 |
| 422178 | 13763 | 13782 | ACCCGCCGGCTCTGCTCATC | 3-14-3 | 37 | 362 |
| 422255 | 13763 | 13782 | ACCCGCCGGCTCTGCTCATC | 2-13-5 | 30 | 362 |
| 422111 | 13764 | 13783 | CACCCGCCGGCTCTGCTCAT | 5-10-5 | 37 | 363 |
| 422179 | 13764 | 13783 | CACCCGCCGGCTCTGCTCAT | 3-14-3 | 43 | 363 |
| 422256 | 13764 | 13783 | CACCCGCCGGCTCTGCTCAT | 2-13-5 | 29 | 363 |
| 422112 | 13765 | 13784 | CCACCCGCCGGCTCTGCTCA | 5-10-5 | 61 | 364 |
| 422180 | 13765 | 13784 | CCACCCGCCGGCTCTGCTCA | 3-14-3 | 54 | 364 |

TABLE 10-continued

Inhibition of human Factor 7 mRNA levels by chimeric antisense oligonucleotides targeted to nucleobases 13760 to 13789 of SEQ ID NO: 1

| ISIS No. | Target Start Site | Target Stop Site | Sequence (5' to 3') | Motif | % Inhibition | SEQ ID NO |
|---|---|---|---|---|---|---|
| 422257 | 13765 | 13784 | CCACCCGCCGGCTCTGCTCA | 2-13-5 | 65 | 364 |
| 422113 | 13766 | 13785 | GCCACCCGCCGGCTCTGCTC | 5-10-5 | 68 | 365 |
| 422181 | 13766 | 13785 | GCCACCCGCCGGCTCTGCTC | 3-14-3 | 66 | 365 |
| 422258 | 13766 | 13785 | GCCACCCGCCGGCTCTGCTC | 2-13-5 | 66 | 365 |
| 422114 | 13767 | 13786 | CGCCACCCGCCGGCTCTGCT | 5-10-5 | 50 | 366 |
| 422182 | 13767 | 13786 | CGCCACCCGCCGGCTCTGCT | 3-14-3 | 11 | 366 |
| 422259 | 13767 | 13786 | CGCCACCCGCCGGCTCTGCT | 2-13-5 | 61 | 366 |
| 422115 | 13768 | 13787 | GCGCCACCCGCCGGCTCTGC | 5-10-5 | 66 | 367 |
| 422183 | 13768 | 13787 | GCGCCACCCGCCGGCTCTGC | 3-14-3 | 79 | 367 |
| 422260 | 13768 | 13787 | GCGCCACCCGCCGGCTCTGC | 2-13-5 | 56 | 367 |
| 422116 | 13769 | 13788 | TGCGCCACCCGCCGGCTCTG | 5-10-5 | 52 | 368 |
| 422184 | 13769 | 13788 | TGCGCCACCCGCCGGCTCTG | 3-14-3 | 55 | 368 |
| 422261 | 13769 | 13788 | TGCGCCACCCGCCGGCTCTG | 2-13-5 | 47 | 368 |
| 416456 | 13770 | 13789 | CTGCGCCACCCGCCGGCTCT | 5-10-5 | 50 | 262 |
| 422185 | 13770 | 13789 | CTGCGCCACCCGCCGGCTCT | 3-14-3 | 48 | 262 |
| 422262 | 13770 | 13789 | CTGCGCCACCCGCCGGCTCT | 2-13-5 | 0 | 262 |

The chimeric antisense oligonucleotides in Table 11 were designed as 5-10-5 MOE, 3-14-3 MOE, and 2-13-5 MOE gapmers. The first listed gapmer in Table 11 is the original gapmer (see Table 7) from which the remaining gapmers were designed via microwalk and is designated by an asterisk (*). The 5-10-5 gapmers are 20 nucleotides in length, wherein the central gap segment is comprised of 10 2'-deoxynucleotides and is flanked on both sides (in the 5' and 3' directions) by wings comprising 5 nucleotides each. The 3-14-3 gapmers are 20 nucleotides in length, wherein the central gap segment is comprised of 14 2'-deoxynucleotides and is flanked on both sides (in the 5' and 3' directions) by wings comprising 3 nucleotides each. The 2-13-5 gapmers are 20 nucleotides in length, wherein the central gap segment is comprised of 13 2'-deoxynucleotides. The central gap is flanked on the 5' end with a wing comprising 2 nucleotides and on the 3' end with a wing comprising 5 nucleotides. For each of the motifs (5-10-5, 3-14-3, and 2-13-5), each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. "Target start site" indicates the 5'-most nucleotide to which the gapmer is targeted. "Target stop site" indicates the 3'-most nucleotide to which the gapmer is targeted. Each gapmer listed in Table 11 is targeted to SEQ ID NO: 1 (nucleotides 1255000 to 1273000 of GENBANK Accession No. NT_027140.6).

As shown in Table 11, all of the 5-10-5 MOE gapmers, 3-14-3 MOE gapmers, and 2-13-5 MOE gapmers targeted to the target region beginning at target start site 14707 and ending at the target stop site 14732 (i.e. nucleobases 14707-14732) of SEQ ID NO: 1 inhibited Factor 7 mRNA by at least 48%.

Certain gapmers within the target region (i.e. nucleobases 14707-14732) inhibited Factor 7 mRNA expression by at least 40%, for example, ISIS numbers 416477, 407641, 422200, 422277, 422130, 422201, 422278, 422131, 422202, 422279, 422203, 422280, 422132, 422204, 422281, 422133, 422205, 422282, 407642, 422206, and 422283.

Certain gapmers within the target region (i.e. nucleobases 14707-14732) inhibited Factor 7 mRNA expression by at least 50%, for example, ISIS numbers 416477, 407641, 422200, 422277, 422130, 422201, 422278, 422131, 422279, 422203, 422280, 422132, 422204, 422281, 422133, 422205, 407642, 422206, and 422283.

Certain gapmers within the target region (i.e. nucleobases 14707-14732) inhibited Factor 7 mRNA expression by at least 60%, for example, ISIS numbers 416477, 407641, 422130, 422201, 422278, 422131, 422204, 422133, 422205, 407642, and 422206.

Certain gapmers within the target region (i.e. nucleobases 14707-14732) inhibited Factor 7 mRNA expression by at least 70%, for example, ISIS numbers 416477, 422130, 422201, and 422204.

TABLE 11

Inhibition of human Factor 7 mRNA levels by chimeric antisense oligonucleotides targeted to nucleobases 14707 to 14732 of SEQ ID NO: 1

| ISIS No. | Target Start Site | Target Stop Site | Sequence (5' to 3') | Motif | % Inhibition | SEQ ID NO |
|---|---|---|---|---|---|---|
| *416477 | 14710 | 14729 | CAGCCTGAGGCCAGCAGATC | 5-10-5 | 71 | 283 |
| 407641 | 14707 | 14726 | CCTGAGGCCAGCAGATCACG | 5-10-5 | 68 | 48 |
| 422200 | 14707 | 14726 | CCTGAGGCCAGCAGATCACG | 3-14-3 | 58 | 48 |
| 422277 | 14707 | 14726 | CCTGAGGCCAGCAGATCACG | 2-13-5 | 56 | 48 |
| 422130 | 14708 | 14727 | GCCTGAGGCCAGCAGATCAC | 5-10-5 | 79 | 369 |
| 422201 | 14708 | 14727 | GCCTGAGGCCAGCAGATCAC | 3-14-3 | 71 | 369 |
| 422278 | 14708 | 14727 | GCCTGAGGCCAGCAGATCAC | 2-13-5 | 64 | 369 |
| 422131 | 14709 | 14728 | AGCCTGAGGCCAGCAGATCA | 5-10-5 | 68 | 370 |
| 422202 | 14709 | 14728 | AGCCTGAGGCCAGCAGATCA | 3-14-3 | 49 | 370 |
| 422279 | 14709 | 14728 | AGCCTGAGGCCAGCAGATCA | 2-13-5 | 56 | 370 |
| 422203 | 14710 | 14729 | CAGCCTGAGGCCAGCAGATC | 3-14-3 | 52 | 283 |
| 422280 | 14710 | 14729 | CAGCCTGAGGCCAGCAGATC | 2-13-5 | 52 | 283 |
| 422132 | 14711 | 14730 | GCAGCCTGAGGCCAGCAGAT | 5-10-5 | 54 | 371 |
| 422204 | 14711 | 14730 | GCAGCCTGAGGCCAGCAGAT | 3-14-3 | 72 | 371 |
| 422281 | 14711 | 14730 | GCAGCCTGAGGCCAGCAGAT | 2-13-5 | 57 | 371 |
| 422133 | 14712 | 14731 | AGCAGCCTGAGGCCAGCAGA | 5-10-5 | 65 | 372 |
| 422205 | 14712 | 14731 | AGCAGCCTGAGGCCAGCAGA | 3-14-3 | 63 | 372 |
| 422282 | 14712 | 14731 | AGCAGCCTGAGGCCAGCAGA | 2-13-5 | 48 | 372 |
| 407642 | 14713 | 14732 | CAGCAGCCTGAGGCCAGCAG | 5-10-5 | 63 | 49 |
| 422206 | 14713 | 14732 | CAGCAGCCTGAGGCCAGCAG | 3-14-3 | 65 | 49 |
| 422283 | 14713 | 14732 | CAGCAGCCTGAGGCCAGCAG | 2-13-5 | 50 | 49 |

The chimeric antisense oligonucleotides in Table 12 were designed as 5-10-5 MOE, 3-14-3 MOE, and 2-13-5 MOE gapmers. The first listed gapmer in Table 12 is the original gapmer (see Table 7) from which the remaining gapmers were designed via microwalk and is designated by an asterisk (*). The 5-10-5 gapmers are 20 nucleotides in length, wherein the central gap segment is comprised of 10 2'-deoxynucleotides and is flanked on both sides (in the 5' and 3' directions) by wings comprising 5 nucleotides each. The 3-14-3 gapmers are 20 nucleotides in length, wherein the central gap segment is comprised of 14 2'-deoxynucleotides and is flanked on both sides (in the 5' and 3' directions) by wings comprising 3 nucleotides each. The 2-13-5 gapmers are 20 nucleotides in length, wherein the central gap segment is comprised of 13 2'-deoxynucleotides. The central gap is flanked on the 5' end with a wing comprising 2 nucleotides and on the 3' end with a wing comprising 5 nucleotides. For each of the motifs (5-10-5, 3-14-3, and 2-13-5), each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. "Target start site" indicates the 5'-most nucleotide to which the gapmer is targeted. "Target stop site" indicates the 3'-most nucleotide to which the gapmer is targeted. Each gapmer listed in Table 12 is targeted to SEQ ID NO: 1 (nucleotides 1255000 to 1273000 of GENBANK Accession No. NT_027140.6).

As shown in Table 12, all of the 5-10-5 MOE gapmers, 3-14-3 MOE gapmers, and 2-13-5 MOE gapmers targeted to the target region beginning at target start site 15098 and ending at the target stop site 15122 (i.e. nucleobases 15098-15122) of SEQ ID NO: 1 inhibited Factor 7 mRNA by at least 25%.

Certain gapmers within the target region (i.e. nucleobases 15098-15122) inhibited Factor 7 mRNA expression by at least 20%, for example, ISIS numbers 407643, 422207, 422284, 422134, 422208, 422285, 422135, 422209, 422286, 422136, 422210, 422287, 422137, 422211, 422288, 416479, 422212, and 422289.

Certain gapmers within the target region (i.e. nucleobases 15098-15122) inhibited Factor 7 mRNA expression by at least 30%, for example, ISIS numbers 407643, 422207, 422284, 422134, 422208, 422285, 422135, 422209, 422286, 422136, 422287, 422137, 422211, 422288, 416479, 422212, and 422289.

Certain gapmers within the target region (i.e. nucleobases 15098-15122) inhibited Factor 7 mRNA expression by at least 40%, for example, ISIS numbers 407643, 422207, 422284, 422134, 422208, 422135, 422209, 422286, 422136, 422287, 422137, 422211, 422288, and 416479.

Certain gapmers within the target region (i.e. nucleobases 15098-15122) inhibited Factor 7 mRNA expression by at least 50%, for example, ISIS numbers 407643, 422134, 422208, 422135, 422286, and 422136.

Certain gapmers within the target region (i.e. nucleobases 15098-15122) inhibited Factor 7 mRNA expression by at least 60%, for example, ISIS numbers 407643 and 422134.

a wing comprising 5 nucleotides. For each of the motifs (5-10-5, 3-14-3, and 2-13-5), each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. "Target start site" indicates the 5'-most nucleotide to which the gapmer is targeted. "Target stop site" indicates the 3'-most nucleotide to which the gapmer is targeted. Each gapmer listed in Table 13 is targeted to SEQ ID NO: 1 (nucleotides 1255000 to 1273000 of GENBANK Accession No. NT_027140.6).

TABLE 12

Inhibition of human Factor 7 mRNA levels by chimeric antisense oligonucleotides targeted to nucleobases 15098 to 15122 of SEQ ID NO: 1

| Oligo ID | Target Start Site | Target Stop Site | Sequence (5' to 3') | Motif | % Inhibition | SEQ ID NO |
|---|---|---|---|---|---|---|
| *407643 | 15098 | 15117 | CACACATGGAGTCAGCATCG | 5-10-5 | 69 | 50 |
| 422207 | 15098 | 15117 | CACACATGGAGTCAGCATCG | 3-14-3 | 41 | 50 |
| 422284 | 15098 | 15117 | CACACATGGAGTCAGCATCG | 2-13-5 | 43 | 50 |
| 422134 | 15099 | 15118 | GCACACATGGAGTCAGCATC | 5-10-5 | 67 | 373 |
| 422208 | 15099 | 15118 | GCACACATGGAGTCAGCATC | 3-14-3 | 56 | 373 |
| 422285 | 15099 | 15118 | GCACACATGGAGTCAGCATC | 2-13-5 | 39 | 373 |
| 422135 | 15100 | 15119 | AGCACACATGGAGTCAGCAT | 5-10-5 | 53 | 374 |
| 422209 | 15100 | 15119 | AGCACACATGGAGTCAGCAT | 3-14-3 | 47 | 374 |
| 422286 | 15100 | 15119 | AGCACACATGGAGTCAGCAT | 2-13-5 | 53 | 374 |
| 422136 | 15101 | 15120 | CAGCACACATGGAGTCAGCA | 5-10-5 | 57 | 375 |
| 422210 | 15101 | 15120 | CAGCACACATGGAGTCAGCA | 3-14-3 | 25 | 375 |
| 422287 | 15101 | 15120 | CAGCACACATGGAGTCAGCA | 2-13-5 | 41 | 375 |
| 422137 | 15102 | 15121 | ACAGCACACATGGAGTCAGC | 5-10-5 | 45 | 376 |
| 422211 | 15102 | 15121 | ACAGCACACATGGAGTCAGC | 3-14-3 | 42 | 376 |
| 422288 | 15102 | 15121 | ACAGCACACATGGAGTCAGC | 2-13-5 | 44 | 376 |
| 416479 | 15103 | 15122 | GACAGCACACATGGAGTCAG | 5-10-5 | 47 | 285 |
| 422212 | 15103 | 15122 | GACAGCACACATGGAGTCAG | 3-14-3 | 30 | 285 |
| 422289 | 15103 | 15122 | GACAGCACACATGGAGTCAG | 2-13-5 | 34 | 285 |

The chimeric antisense oligonucleotides in Table 13 were designed as 5-10-5 MOE, 3-14-3 MOE, and 2-13-5 MOE gapmers. The first listed gapmer in Table 13 is the original gapmer (see Table 7) from which the remaining gapmers were designed via microwalk and is designated by an asterisk (*). The 5-10-5 gapmers are 20 nucleotides in length, wherein the central gap segment is comprised of 10 2'-deoxynucleotides and is flanked on both sides (in the 5' and 3' directions) by wings comprising 5 nucleotides each. The 3-14-3 gapmers are 20 nucleotides in length, wherein the central gap segment is comprised of 14 2'-deoxynucleotides and is flanked on both sides (in the 5' and 3' directions) by wings comprising 3 nucleotides each. The 2-13-5 gapmers are 20 nucleotides in length, wherein the central gap segment is comprised of 13 2'-deoxynucleotides. The central gap is flanked on the 5' end with a wing comprising 2 nucleotides and on the 3' end with As shown in Table 13, all of the 5-10-5 MOE gapmers, 3-14-3 MOE gapmers, and 2-13-5 MOE gapmers targeted to the target region beginning at target start site 15188 and ending at the target stop site 15211 (i.e. nucleobases 15188-15211) of SEQ ID NO: 1 inhibited Factor 7 mRNA by at least 41%.

Certain gapmers within the target region (i.e. nucleobases 15188-15211) inhibited Factor 7 mRNA expression by at least 40%, for example, ISIS numbers 407935, 416482, 422149, 422226, 422085, 422150, 422227, 422086, 422151, 422228, 422152, 422229, 422087, 422153, and 422230.

Certain gapmers within the target region (i.e. nucleobases 15188-15211) inhibited Factor 7 mRNA expression by at least 50%, for example, ISIS numbers 407935, 416482, 422149, 422085, 422150, 422227, 422086, 422151, 422228, 422152, 422229, 422087, 422153, and 422230.

Certain gapmers within the target region (i.e. nucleobases 15188-15211) inhibited Factor 7 mRNA expression by at least 60%, for example, ISIS numbers 407935, 416482, 422149, 422085, 422150, 422227, 422086, 422151, 422228, 422152, 422229, 422087, 422153, and 422230.

Certain gapmers within the target region (i.e. nucleobases 15188-15211) inhibited Factor 7 mRNA expression by at least 70%, for example, ISIS numbers 407935, 422085, 422150, 422086, 422228, 422152, 422229, and 422087.

Certain gapmers within the target region (i.e. nucleobases 15188-15211) inhibited Factor 7 mRNA expression by at least 80%, for example, ISIS numbers 422086 and 422087.

TABLE 13

Inhibition of human Factor 7 mRNA levels by chimeric antisense oligonucleotides targeted to nucleobases 15188 to 15211 of SEQ ID NO: 1

| Oligo ID | Target Start Site | Target Stop Site | Sequence (5' to 3') | Motif | % Inhibition | SEQ ID NO |
|---|---|---|---|---|---|---|
| *407935 | 15191 | 15210 | ATGCATGGTGATGCTTCTGA | 5-10-5 | 79 | 123 |
| 416482 | 15188 | 15207 | CATGGTGATGCTTCTGAATT | 5-10-5 | 64 | 288 |
| 422149 | 15188 | 15207 | CATGGTGATGCTTCTGAATT | 3-14-3 | 61 | 288 |
| 422226 | 15188 | 15207 | CATGGTGATGCTTCTGAATT | 2-13-5 | 41 | 288 |
| 422085 | 15189 | 15208 | GCATGGTGATGCTTCTGAAT | 5-10-5 | 70 | 377 |
| 422150 | 15189 | 15208 | GCATGGTGATGCTTCTGAAT | 3-14-3 | 74 | 377 |
| 422227 | 15189 | 15208 | GCATGGTGATGCTTCTGAAT | 2-13-5 | 67 | 377 |
| 422086 | 15190 | 15209 | TGCATGGTGATGCTTCTGAA | 5-10-5 | 81 | 378 |
| 422151 | 15190 | 15209 | TGCATGGTGATGCTTCTGAA | 3-14-3 | 68 | 378 |
| 422228 | 15190 | 15209 | TGCATGGTGATGCTTCTGAA | 2-13-5 | 73 | 378 |
| 422152 | 15191 | 15210 | ATGCATGGTGATGCTTCTGA | 3-14-3 | 74 | 123 |
| 422229 | 15191 | 15210 | ATGCATGGTGATGCTTCTGA | 2-13-5 | 71 | 123 |
| 422087 | 15192 | 15211 | CATGCATGGTGATGCTTCTG | 5-10-5 | 83 | 379 |
| 422153 | 15192 | 15211 | CATGCATGGTGATGCTTCTG | 3-14-3 | 67 | 379 |
| 422230 | 15192 | 15211 | CATGCATGGTGATGCTTCTG | 2-13-5 | 65 | 379 |

Example 7

Dose Response Antisense Inhibition of Human Factor 7 in HepB3 Cells

Gapmers from Examples 5 and 6 (see Tables 7, 8, 9, 10, 11, 12, and 13), exhibiting in vitro inhibition of human Factor 7, were tested at various doses in HepB3 cells. Cells were plated at a density of 4,000 cells per well and transfected using lipofectin reagent with 3.125 nM, 6.25 nM, 12.5 nM, 25 nM, 50 nM, and 100 nM concentrations of antisense oligonucleotide, as specified in Table 14. After a treatment period of approximately 16 hours, RNA was isolated from the cells and Factor 7 mRNA levels were measured by quantitative real-time PCR. Human Factor 7 primer probe set RTS 2927 was used to measure mRNA levels. Factor 7 mRNA levels were adjusted according to total RNA content, as measured by RIBOGREEN®. Results are presented as percent inhibition of Factor 7, relative to untreated control cells. As illustrated in Table 14, Factor 7 mRNA levels were reduced in a dose-dependent manner.

TABLE 14

Dose-dependent antisense inhibition of human Factor 7 in HepB3 cells via transfection of oligonucleotides with lipofectin

| ISIS No. | 3.125 nM | 6.25 nM | 12.5 nM | 25 nM | 50 nM | 100 nM | SEQ ID NO |
|---|---|---|---|---|---|---|---|
| 407935 | 19 | 39 | 58 | 70 | 85 | 87 | 123 |
| 407939 | 17 | 35 | 57 | 75 | 80 | 83 | 127 |
| 422086 | 8 | 26 | 46 | 65 | 83 | 90 | 378 |
| 422087 | 14 | 24 | 51 | 73 | 83 | 90 | 379 |
| 422096 | 17 | 23 | 43 | 60 | 68 | 82 | 348 |
| 422150 | 9 | 23 | 38 | 59 | 79 | 87 | 377 |
| 422152 | 18 | 29 | 47 | 67 | 83 | 89 | 123 |
| 422177 | 12 | 24 | 44 | 64 | 81 | 88 | 361 |
| 422183 | 28 | 37 | 56 | 78 | 84 | 88 | 367 |
| 422228 | 17 | 25 | 43 | 60 | 78 | 90 | 378 |
| 422229 | 21 | 32 | 53 | 72 | 86 | 92 | 123 |
| 422130 | 4 | 15 | 34 | 59 | 77 | 85 | 369 |
| 422140 | 18 | 35 | 49 | 64 | 74 | 74 | 331 |
| 422142 | 16 | 34 | 51 | 66 | 72 | 68 | 333 |
| 422215 | 13 | 30 | 54 | 65 | 84 | 82 | 331 |
| 422217 | 8 | 18 | 45 | 63 | 79 | 83 | 333 |
| 422252 | 18 | 17 | 45 | 61 | 77 | 87 | 261 |

TABLE 14-continued

Dose-dependent antisense inhibition of human Factor 7 in HepB3 cells via transfection of oligonucleotides with lipofectin

| ISIS No. | 3.125 nM | 6.25 M | 12.5 nM | 25 nM | 50 nM | 100 nM | SEQ ID NO |
|---|---|---|---|---|---|---|---|
| 422292 | 13 | 21 | 44 | 63 | 81 | 83 | 331 |
| 422294 | 9 | 21 | 32 | 61 | 77 | 84 | 333 |
| 422295 | 17 | 22 | 44 | 64 | 80 | 85 | 189 |
| 422296 | 21 | 27 | 39 | 67 | 78 | 82 | 334 |

The gapmers were also transfected via electroporation and their dose-dependent inhibition of human Factor 7 mRNA was measured. Cells were plated at a density of 20,000 cells per well and transfected via electroporation with 3.125 µM, 6.25 µM, 12.5 µM, 25 µM, 50 µM, and 100 µM concentrations of antisense oligonucleotide, as specified in Table 15. After a treatment period of approximately 16 hours, RNA was isolated from the cells and Factor 7 mRNA levels were measured by quantitative real-time PCR. Human Factor 7 primer probe set RTS 2927 was used to measure mRNA levels. Factor 7 mRNA levels were adjusted according to total RNA content, as measured by RIBOGREEN®. Results are presented as percent inhibition of Factor 7, relative to untreated control cells. As illustrated in Table 15, Factor 7 mRNA levels were reduced in a dose-dependent manner.

TABLE 15

Dose-dependent antisense inhibition of human Factor 7 in HepB3 cells via transfection of oligonucleotides with electroporation

| ISIS No. | 3.125 µM | 6.25 µM | 12.5 µM | 25 µM | 50 µM | 100 µM | SEQ ID No. |
|---|---|---|---|---|---|---|---|
| 407935 | 37 | 47 | 67 | 73 | 80 | 87 | 123 |
| 407939 | 18 | 28 | 42 | 56 | 68 | 82 | 127 |
| 422086 | 20 | 34 | 44 | 63 | 75 | 84 | 378 |
| 422087 | 22 | 26 | 48 | 57 | 72 | 80 | 379 |
| 422096 | 26 | 30 | 46 | 50 | 62 | 85 | 348 |
| 422150 | 17 | 20 | 40 | 54 | 68 | 83 | 377 |
| 422152 | 14 | 22 | 32 | 44 | 65 | 76 | 123 |
| 422177 | 3 | 10 | 29 | 21 | 31 | 63 | 361 |
| 422183 | 16 | 28 | 37 | 44 | 59 | 71 | 367 |
| 422228 | 18 | 33 | 40 | 47 | 71 | 83 | 378 |
| 422229 | 21 | 30 | 33 | 44 | 65 | 77 | 123 |
| 422130 | 28 | 29 | 59 | 61 | 73 | 86 | 369 |
| 422140 | 29 | 34 | 51 | 64 | 69 | 77 | 331 |
| 422142 | 26 | 47 | 63 | 67 | 77 | 78 | 333 |
| 422215 | 11 | 9 | 31 | 50 | 68 | 84 | 331 |
| 422217 | 15 | 19 | 29 | 55 | 61 | 83 | 333 |
| 422252 | 23 | 12 | 26 | 38 | 58 | 80 | 261 |
| 422292 | 36 | 25 | 47 | 59 | 75 | 86 | 331 |
| 422295 | 10 | 8 | 37 | 58 | 68 | 80 | 189 |
| 422296 | 62 | 40 | 56 | 56 | 82 | 84 | 334 |

Example 8

Selection and Confirmation of Effective Dose-Dependent Antisense Inhibition of Human Factor 7 in HepB3 Cells Gapmers exhibiting in vitro inhibition of human Factor 7 in Example 7 were selected and tested at various doses in HepB3 cells. Cells were plated at a density of 20,000 cells per well and transfected via electroporation with 3.125 µM, 6.25 µM, 12.5 µM, 25 µM, 50 µM, and 100 µM concentrations of antisense oligonucleotide, as specified in Table 16. After a treatment period of approximately 16 hours, RNA was isolated from the cells and human Factor 7 mRNA levels were measured by quantitative real-time PCR. Human Factor 7 primer probe set RTS 2927 was used to measure mRNA levels. Factor 7 mRNA levels were adjusted according to total RNA content, as measured by RIBOGREEN®. Results are presented as percent inhibition of Factor 7, relative to untreated control cells. As illustrated in Table 16, Factor 7 mRNA levels were reduced in a dose-dependent manner.

TABLE 16

Dose-dependent antisense inhibition of human Factor 7 in HepB3 cells via transfection of oligonucleotides with electroporation

| ISIS No. | 3.125 µM | 6.25 µM | 12.5 µM | 25 µM | 50 µM | 100 µM | SEQ ID NO: |
|---|---|---|---|---|---|---|---|
| 407935 | 63 | 79 | 84 | 90 | 90 | 91 | 123 |
| 407939 | 35 | 60 | 60 | 73 | 81 | 83 | 127 |
| 422086 | 25 | 48 | 74 | 82 | 86 | 90 | 378 |
| 422087 | 19 | 38 | 66 | 75 | 80 | 87 | 379 |
| 422130 | 14 | 24 | 61 | 68 | 82 | 88 | 369 |
| 422142 | 34 | 47 | 62 | 67 | 65 | 65 | 333 |
| 422150 | 0 | 31 | 53 | 67 | 77 | 86 | 377 |
| 422183 | 2 | 3 | 24 | 50 | 64 | 71 | 367 |
| 422229 | 30 | 45 | 67 | 79 | 90 | 92 | 123 |
| 422292 | 31 | 40 | 68 | 75 | 82 | 83 | 331 |
| 422296 | 47 | 44 | 70 | 78 | 80 | 82 | 334 |

Example 9

Antisense Inhibition of Human Factor 7 with Short (14-mer) Oligonucleotides

Short antisense oligonucleotides (shortmers) were designed to target a Factor 7 nucleic acid. The shortmers in Table 17 were designed as 2-10-2 MOE gapmers. The gapmers are 14 nucleotides in length, wherein the central gap segment is comprised of 10 2'-deoxynucleotides and is flanked on both sides (in the 5' and 3' directions) by wings comprising 2 nucleotides each. Each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines.

Shortmers were evaluated for their ability to reduce human Factor 7 mRNA in HepB3 cells and compared with one 5-10-5 chimeric oligonucleotide from Table 16, ISIS 407939. HepB3 cells at a density of 20,000 cells per well in a 96-well plate were transfected using electroporation with 1,000 nM of antisense oligonucleotide. After a treatment period of approximately 24 hours, RNA was isolated from the cells and Factor 7 mRNA levels were measured by real-time RT-PCR, as described herein. Factor 7 mRNA levels were adjusted according to total RNA content as measured by RIBOGREEN®. Results are presented in Table 17 as percent inhibition of Factor 7 mRNA, relative to untreated control cells. ISIS 407939 is the first oligonucleotide in Table 17 to which the shortmers were compared, and is marked by an asterisk (*).

Each gapmer listed in Table 17 is targeted to human gene sequences, SEQ ID NO: 1 (nucleotides 1255000 to 1273000 of GENBANK Accession No. NT_027140.6) or SEQ ID NO: 2 (GENBANK Accession No. NM_019616.2). "Target start site" indicates the 5'-most nucleotide to which the gapmer is targeted in the human gene sequence. "Target stop site" indicates the 3'-most nucleotide to which the gapmer is targeted in the human gene sequence.

TABLE 17

Inhibition of human Factor 7 mRNA levels by chimeric antisense oligonucleotides having 2-10-2 MOE wings and deoxy gap targeted to SEQ ID NO: 1 or SEQ ID NO: 2

| ISIS No. | Human Target SEQ ID NO: | Human Target Start Site | Human Target Stop Site | Sequence (5' to 3') | % inhibition | SEQ ID NO |
|---|---|---|---|---|---|---|
| *407939 | 1 | 15255 | 15274 | TGCAGCCCGGCACCCAGCGA | 81 | 127 |
| 435758 | 1 | 610 | 623 | CCCTGAGCTGGGCA | 4 | 380 |
| 435759 | 1 | 657 | 670 | GAGCCACAGAGCCT | 11 | 381 |
| 435760 | 1 | 744 | 757 | TCTTGGGTGTGGAT | 17 | 382 |
| 435761 | 1 | 796 | 809 | CAGATGAAAACTTG | 5 | 383 |
| 435762 | 1 | 885 | 898 | CAGGTGTTAAGGTG | 0 | 384 |
| 435763 | 1 | 945 | 958 | AGGAGAAAGGTCAG | 2 | 385 |
| 435764 | 1 | 1018 | 1031 | TGAGAGCTGCACCT | 8 | 386 |
| 435765 | 1 | 1092 | 1105 | CAAAGTTCTCTGCC | 1 | 387 |
| 435634 | 1 | 1147 | 1160 | TGAAATCTCTGCAG | 5 | 388 |
| 435635 | 1 | 1152 | 1165 | CATGATGAAATCTC | 0 | 389 |
| 435636 | 1 | 1157 | 1170 | GAGACCATGATGAA | 13 | 390 |
| 435637 | 1 | 1196 | 1209 | TGAAGCCCAAGCAG | 11 | 391 |
| 435638 | 1 | 1201 | 1214 | AGCCCTGAAGCCCA | 55 | 392 |
| 435766 | 1 | 1217 | 1230 | GCACCTGCAGCCAG | 51 | 393 |
| 435767 | 1 | 1248 | 1261 | CACCAAGTTTATGG | 0 | 394 |
| 435768 | 1 | 1384 | 1397 | GCCTGGATGCTGGT | 75 | 395 |
| 435769 | 1 | 1442 | 1455 | TTCTTTGAAAAATA | 0 | 396 |
| 435770 | 1 | 1529 | 1542 | CTCTGAGAGGCCCC | 81 | 397 |
| 435771 | 1 | 2130 | 2143 | GTCATAAGGCCATG | 13 | 398 |
| 435772 | 1 | 2233 | 2246 | GCAGTCCCTGCTCA | 42 | 399 |
| 435773 | 1 | 2348 | 2361 | CAGGGAACACCCTC | 57 | 400 |
| 435774 | 1 | 2390 | 2403 | GTCCCAGGGAAGGC | 17 | 401 |
| 435775 | 1 | 2439 | 2452 | TCTGGAAGGAACAG | 25 | 402 |
| 435777 | 1 | 4713 | 4726 | CTGAGGATGCAGGC | 53 | 403 |
| 435778 | 1 | 4817 | 4830 | GCTACTGGGCCACG | 49 | 404 |
| 435779 | 1 | 4847 | 4860 | TGAGCGCGGAAGAA | 50 | 405 |
| 435780 | 1 | 4945 | 4958 | GGAGGGACGACCTT | 28 | 406 |
| 435781 | 1 | 5124 | 5137 | ACCACGCGGTGGTG | 0 | 407 |
| 435782 | 1 | 5209 | 5222 | CGTGCGCTCAGCTC | 36 | 408 |
| 435783 | 1 | 6396 | 6409 | AAACCGGCATGCGC | 49 | 409 |
| 435784 | 1 | 6433 | 6446 | CCTAAGTGTGCTTT | 17 | 410 |
| 435785 | 1 | 6540 | 6553 | AGCTTCTCACCACG | 46 | 411 |
| 435787 | 1 | 8481 | 8494 | GAGTGTGAGGCTTC | 34 | 412 |
| 435789 | 1 | 8518 | 8531 | CATGTTAGCCTTTG | 3 | 413 |
| 435790 | 1 | 8548 | 8561 | ATGACCATCCTCAA | 1 | 414 |

TABLE 17-continued

Inhibition of human Factor 7 mRNA levels by chimeric antisense oligonucleotides having 2-10-2 MOE wings and deoxy gap targeted to SEQ ID NO: 1 or SEQ ID NO: 2

| ISIS No. | Human Target SEQ ID NO: | Human Target Start Site | Human Target Stop Site | Sequence (5' to 3') | % inhibition | SEQ ID NO |
|---|---|---|---|---|---|---|
| 435791 | 1 | 8590 | 8603 | ATGAGAAATGCTTT | 0 | 415 |
| 435792 | 1 | 8651 | 8664 | TGCTGAAGAAACTG | 9 | 416 |
| 435793 | 1 | 8711 | 8724 | TGCAGTAGCAGATG | 27 | 417 |
| 435794 | 1 | 8776 | 8789 | GAGGTACACAGGCT | 26 | 418 |
| 435795 | 1 | 8828 | 8841 | ACACCCGAGGTTCA | 66 | 419 |
| 435796 | 1 | 8858 | 8871 | TGACCACACATTTC | 30 | 420 |
| 435797 | 1 | 8895 | 8908 | AATCTTGGCCCCTC | 16 | 421 |
| 435798 | 1 | 8933 | 8946 | AGCCAGACTTTCCT | 54 | 422 |
| 435639 | 1 | 9072 | 9085 | TCCAGAACAGCTTC | 31 | 423 |
| 435640 | 1 | 9081 | 9094 | TGTAAGAAATCCAG | 2 | 424 |
| 435799 | 1 | 9165 | 9178 | CTGGTCCCCATCTG | 33 | 425 |
| 435642 | 1 | 9168 | 9181 | ACACTGGTCCCCAT | 60 | 426 |
| 435478 | 1 | 9173 | 9186 | GAGGCACACTGGTC | 43 | 427 |
| 435643 | 1 | 9204 | 9217 | CTTGCAGGAGCCCC | 51 | 428 |
| 435644 | 1 | 9209 | 9222 | TGGTCCTTGCAGGA | 30 | 429 |
| 435645 | 1 | 9214 | 9227 | GGAGCTGGTCCTTG | 44 | 430 |
| 435646 | 1 | 9221 | 9234 | TAGGACTGGAGCTG | 13 | 431 |
| 435647 | 1 | 9226 | 9239 | AGATATAGGACTGG | 0 | 432 |
| 435648 | 1 | 9231 | 9244 | GAAGCAGATATAGG | 0 | 433 |
| 435649 | 1 | 9236 | 9249 | AGGCAGAAGCAGAT | 21 | 434 |
| 435650 | 1 | 9255 | 9268 | CCGGCCCTCGAAGG | 6 | 435 |
| 435651 | 1 | 9261 | 9274 | ACAGTTCCGGCCCT | 71 | 436 |
| 435800 | 1 | 9289 | 9302 | GGACCCAAAGTGGG | 0 | 437 |
| 435801 | 1 | 9339 | 9352 | CGGTTGGCCAGGCC | 38 | 438 |
| 435802 | 1 | 9420 | 9433 | GTCACCTAGACCAA | 61 | 439 |
| 435803 | 1 | 9517 | 9530 | GAGAATTGCCCAGG | 0 | 440 |
| 435804 | 1 | 9549 | 9562 | CAGGGACTCTCAGC | 26 | 441 |
| 435805 | 1 | 9716 | 9729 | TGAATTACTGAACC | 0 | 442 |
| 435806 | 1 | 9846 | 9859 | TGACCCCACAGGGA | 7 | 443 |
| 435807 | 1 | 9902 | 9915 | CAGTACTTCCCACG | 35 | 444 |
| 435808 | 1 | 9939 | 9952 | CTCTGGACACCGGG | 66 | 445 |
| 435809 | 1 | 10062 | 10075 | CTGACAATGTGATG | 5 | 446 |
| 435810 | 1 | 10114 | 10127 | CTGAGGGAATGTTG | 1 | 447 |
| 435811 | 1 | 10203 | 10216 | GTGGTCAAGGATGA | 27 | 448 |
| 435812 | 1 | 10355 | 10368 | GCTGAGCAGAGATC | 35 | 449 |

TABLE 17-continued

Inhibition of human Factor 7 mRNA levels by chimeric
antisense oligonucleotides having 2-10-2 MOE wings
and deoxy gap targeted to SEQ ID NO: 1 or SEQ ID NO: 2

| ISIS No. | Human Target SEQ ID NO: | Human Target Start Site | Human Target Stop Site | Sequence (5' to 3') | % inhibition | SEQ ID NO |
|---|---|---|---|---|---|---|
| 435813 | 1 | 10385 | 10398 | GGATGCACACCAGG | 55 | 450 |
| 435814 | 1 | 10584 | 10597 | TGACGAGAGGACCA | 31 | 451 |
| 435815 | 1 | 10677 | 10690 | CTCTTCCGAGCAGC | 59 | 452 |
| 435816 | 1 | 10803 | 10816 | TCCAAAGGACAAGG | 4 | 453 |
| 435817 | 1 | 10835 | 10848 | CTGAGCTTGGCACC | 39 | 454 |
| 435818 | 1 | 10978 | 10991 | GTCATCCTTGTCTG | 43 | 455 |
| 435652 | 1 | 10981 | 10994 | CTGGTCATCCTTGT | 48 | 456 |
| 435653 | 1 | 10986 | 10999 | ATCAGCTGGTCATC | 32 | 457 |
| 435654 | 1 | 11005 | 11018 | GCCGTTCTCGTTCA | 71 | 458 |
| 435655 | 1 | 11011 | 11024 | ACAGCCGCCGTTCT | 49 | 459 |
| 435656 | 1 | 11018 | 11031 | ACTGCTCACAGCCG | 58 | 460 |
| 435657 | 1 | 11023 | 11036 | GCAGTACTGCTCAC | 69 | 461 |
| 435658 | 1 | 11028 | 11041 | TCACTGCAGTACTG | 60 | 462 |
| 435659 | 1 | 11070 | 11083 | TACCCCTCGTGGCA | 18 | 463 |
| 435660 | 1 | 11088 | 11101 | CCGTCTGCCAGCAG | 58 | 464 |
| 435661 | 1 | 11095 | 11108 | GGACACCCCGTCTG | 18 | 465 |
| 435819 | 1 | 11181 | 11194 | TTTGTCCAGTAAGA | 1 | 466 |
| 435820 | 1 | 11294 | 11307 | CATCCTAGTCACTG | 19 | 467 |
| 435821 | 1 | 11454 | 11467 | AGTCAGTACAGACA | 0 | 468 |
| 435822 | 1 | 11494 | 11507 | CCAGGAGCCTTTAC | 37 | 469 |
| 435823 | 1 | 11622 | 11635 | TGAGTCCCAGGCTG | 41 | 470 |
| 435824 | 1 | 11724 | 11737 | CCTAAAGATGAATC | 21 | 471 |
| 435776 | 1 | 11732 | 11745 | GGGACACTCACACT | 51 | 472 |
| 435825 | 1 | 11830 | 11843 | CTGGTTTTGGAGGA | 0 | 473 |
| 435826 | 1 | 11861 | 11874 | AAGTGGCTGGCTGA | 27 | 474 |
| 435827 | 1 | 12057 | 12070 | TCAGAAAGATGCAG | 5 | 475 |
| 435662 | 1 | 12084 | 12097 | TGGATATTCAACTG | 19 | 476 |
| 435663 | 1 | 12089 | 12102 | CCACATGGATATTC | 50 | 477 |
| 435664 | 1 | 12094 | 12107 | TTTTTCCACATGGA | 4 | 478 |
| 435665 | 1 | 12099 | 12112 | AGGTATTTTTCCAC | 0 | 479 |
| 435666 | 1 | 12128 | 12141 | GGTTTGCTGGCATT | 71 | 480 |
| 435667 | 1 | 12141 | 12154 | AATTCGGCCTTGGG | 16 | 481 |
| 435479 | 1 | 12173 | 12186 | CACTCCCCTTTGGG | 9 | 482 |
| 435668 | 1 | 12182 | 12195 | TGCCATGGACACTC | 75 | 483 |
| 435828 | 1 | 12277 | 12290 | GACCTGCCCATTTT | 0 | 484 |
| 435829 | 1 | 12396 | 12409 | GGGTAGACCCTCAG | 18 | 485 |

TABLE 17-continued

Inhibition of human Factor 7 mRNA levels by chimeric antisense oligonucleotides having 2-10-2 MOE wings and deoxy gap targeted to SEQ ID NO: 1 or SEQ ID NO: 2

| ISIS No. | Human Target SEQ ID NO: | Human Target Start Site | Human Target Stop Site | Sequence (5' to 3') | % inhibition | SEQ ID NO |
|---|---|---|---|---|---|---|
| 435830 | 1 | 12493 | 12506 | TGATTTTGCAAAGA | 0 | 486 |
| 435831 | 1 | 12523 | 12536 | GATCTTCACATAGC | 51 | 487 |
| 435832 | 1 | 12632 | 12645 | TGCTCAGACCTGGC | 70 | 488 |
| 435671 | 1 | 12796 | 12809 | TCACCAACAACAGG | 28 | 489 |
| 435672 | 1 | 12842 | 12855 | ACCCAGATGGTGTT | 12 | 490 |
| 435673 | 1 | 12847 | 12860 | AGACCACCCAGATG | 34 | 491 |
| 435674 | 1 | 12863 | 12876 | AAACAGTGGGCCGC | 34 | 492 |
| 435675 | 1 | 12868 | 12881 | TGTCGAAACAGTGG | 24 | 493 |
| 435676 | 1 | 12873 | 12886 | GATTTGTCGAAAC | 11 | 494 |
| 435833 | 1 | 13133 | 13146 | AGACACTTGAGAGC | 24 | 495 |
| 435834 | 1 | 13165 | 13178 | TGACAGCACGAAGC | 20 | 496 |
| 435835 | 1 | 13264 | 13277 | TTATTTGGGCATGG | 7 | 497 |
| 435836 | 1 | 13637 | 13650 | CTAGGTCTGCAGGG | 41 | 498 |
| 435837 | 1 | 13725 | 13738 | CTCGCCTGGAAGGA | 37 | 499 |
| 435678 | 1 | 13733 | 13746 | AGGTCGTGCTCGCC | 67 | 500 |
| 435679 | 1 | 13738 | 13751 | CGCTGAGGTCGTGC | 62 | 501 |
| 435680 | 1 | 13743 | 13756 | GTGCTCGCTGAGGT | 52 | 502 |
| 435681 | 1 | 13781 | 13794 | ATGACCTGCGCCAC | 40 | 503 |
| 435682 | 1 | 13786 | 13799 | GGATGATGACCTGC | 36 | 504 |
| 435683 | 1 | 13823 | 13836 | ATGTCGTGGTTGGT | 3 | 505 |
| 435684 | 1 | 13832 | 13845 | AGCAGCGCGATGTC | 56 | 506 |
| 435685 | 1 | 13856 | 13869 | AGGACCACGGGCTG | 40 | 507 |
| 435686 | 1 | 13861 | 13874 | CAGTGAGGACCACG | 31 | 508 |
| 435687 | 1 | 13866 | 13879 | ATGGTCAGTGAGGA | 7 | 509 |
| 435688 | 1 | 13871 | 13884 | ACCACATGGTCAGT | 0 | 510 |
| 435689 | 1 | 13890 | 13903 | TTCGGGCAGGCAGA | 23 | 511 |
| 435690 | 1 | 13895 | 13908 | GTCCGTTCGGGCAG | 55 | 512 |
| 435691 | 1 | 13946 | 13959 | CAGCCGCTGACCAA | 25 | 513 |
| 435692 | 1 | 13964 | 13977 | CGGTCCAGCAGCTG | 32 | 514 |
| 435480 | 1 | 14016 | 14029 | GGTCATCAGCCGGG | 53 | 515 |
| 435481 | 1 | 14017 | 14030 | GGGTCATCAGCCGG | 50 | 516 |
| 435482 | 1 | 14018 | 14031 | TGGGTCATCAGCCG | 62 | 517 |
| 435483 | 1 | 14019 | 14032 | CTGGGTCATCAGCC | 82 | 518 |
| 435484 | 1 | 14020 | 14033 | CCTGGGTCATCAGC | 45 | 519 |
| 435485 | 1 | 14021 | 14034 | TCCTGGGTCATCAG | 34 | 520 |

TABLE 17-continued

Inhibition of human Factor 7 mRNA levels by chimeric antisense oligonucleotides having 2-10-2 MOE wings and deoxy gap targeted to SEQ ID NO: 1 or SEQ ID NO: 2

| ISIS No. | Human Target SEQ ID NO: | Human Target Start Site | Human Target Stop Site | Sequence (5' to 3') | % inhibition | SEQ ID NO |
|---|---|---|---|---|---|---|
| 435486 | 1 | 14022 | 14035 | GTCCTGGGTCATCA | 64 | 521 |
| 435487 | 1 | 14023 | 14036 | AGTCCTGGGTCATC | 36 | 522 |
| 435488 | 1 | 14024 | 14037 | CAGTCCTGGGTCAT | 17 | 523 |
| 435693 | 1 | 14026 | 14039 | GGCAGTCCTGGGTC | 43 | 524 |
| 435694 | 1 | 14031 | 14044 | CTGCAGGCAGTCCT | 39 | 525 |
| 435695 | 1 | 14036 | 14049 | GACTGCTGCAGGCA | 48 | 526 |
| 435696 | 1 | 14081 | 14094 | CAGAACATGTACTC | 10 | 527 |
| 435697 | 1 | 14092 | 14105 | AGTAGCCGGCACAG | 53 | 528 |
| 435698 | 1 | 14119 | 14132 | CCTTGCAGGAGTCC | 61 | 529 |
| 435551 | 1 | 14144 | 14157 | GTGGCATGTGGGCC |  | 530 |
| 435699 | 1 | 14190 | 14203 | GCCCCAGCTGACGA | 48 | 531 |
| 435489 | 1 | 14231 | 14244 | CTGGTGTACACCCC | 72 | 532 |
| 435490 | 1 | 14232 | 14245 | CCTGGTGTACACCC | 49 | 533 |
| 435491 | 1 | 14233 | 14246 | CCCTGGTGTACACC | 61 | 534 |
| 435492 | 1 | 14234 | 14247 | ACCCTGGTGTACAC | 45 | 535 |
| 435493 | 1 | 14235 | 14248 | GACCCTGGTGTACA | 58 | 536 |
| 435494 | 1 | 14236 | 14249 | AGACCCTGGTGTAC | 47 | 537 |
| 435495 | 1 | 14237 | 14250 | GAGACCCTGGTGTA | 27 | 538 |
| 435496 | 1 | 14238 | 14251 | GGAGACCCTGGTGT | 47 | 539 |
| 435497 | 1 | 14239 | 14252 | GGGAGACCCTGGTG | 27 | 540 |
| 435498 | 1 | 14240 | 14253 | TGGGAGACCCTGGT | 37 | 541 |
| 435499 | 1 | 14241 | 14254 | CTGGGAGACCCTGG | 59 | 542 |
| 435500 | 1 | 14242 | 14255 | ACTGGGAGACCCTG | 49 | 543 |
| 435501 | 1 | 14243 | 14256 | TACTGGGAGACCCT | 51 | 544 |
| 435502 | 1 | 14244 | 14257 | GTACTGGGAGACCC | 69 | 545 |
| 435503 | 1 | 14245 | 14258 | TGTACTGGGAGACC | 17 | 546 |
| 435504 | 1 | 14246 | 14259 | ATGTACTGGGAGAC | 8 | 547 |
| 435714 | 1 | 14251 | 14264 | ACTCGATGTACTGG | 3 | 548 |
| 435715 | 1 | 14256 | 14269 | CAGCCACTCGATGT | 35 | 549 |
| 435716 | 1 | 14261 | 14274 | TTTTGCAGCCACTC | 22 | 550 |
| 435717 | 1 | 14266 | 14279 | TGAGCTTTTGCAGC | 0 | 551 |
| 435718 | 1 | 14303 | 14316 | GCTCGCAGGAGGAC | 26 | 552 |
| 435719 | 1 | 14354 | 14367 | CAGCCTTGGCTTTC | 50 | 553 |
| 435720 | 1 | 14662 | 14675 | AGGCTCAGCTGGGC | 16 | 554 |
| 435721 | 1 | 14667 | 14680 | TAAGGAGGCTCAGC | 12 | 555 |
| 435722 | 1 | 14687 | 14700 | TGGGCTTGGCTGAA | 50 | 556 |

TABLE 17-continued

Inhibition of human Factor 7 mRNA levels by chimeric antisense oligonucleotides having 2-10-2 MOE wings and deoxy gap targeted to SEQ ID NO: 1 or SEQ ID NO: 2

| ISIS No. | Human Target SEQ ID NO: | Human Target Start Site | Human Target Stop Site | Sequence (5' to 3') | % inhibition | SEQ ID NO |
|---|---|---|---|---|---|---|
| 435723 | 1 | 14707 | 14720 | GCCAGCAGATCACG | 68 | 557 |
| 435724 | 1 | 14712 | 14725 | CTGAGGCCAGCAGA | 52 | 558 |
| 435725 | 1 | 14717 | 14730 | GCAGCCTGAGGCCA | 79 | 559 |
| 435726 | 1 | 14734 | 14747 | GCAATGAAGGCAGA | 26 | 560 |
| 435727 | 1 | 15098 | 15111 | TGGAGTCAGCATCG | 73 | 561 |
| 435728 | 1 | 15103 | 15116 | ACACATGGAGTCAG | 16 | 562 |
| 435729 | 1 | 15108 | 15121 | ACAGCACACATGGA | 30 | 563 |
| 435730 | 1 | 15128 | 15141 | TAAACAACCGCCTT | 49 | 564 |
| 435731 | 1 | 15136 | 15149 | GTGAGAGCTAAACA | 11 | 565 |
| 435732 | 1 | 15141 | 15154 | GAAAAGTGAGAGCT | 0 | 566 |
| 435733 | 1 | 15181 | 15194 | CTGAATTGTCTGAA | 5 | 567 |
| 435734 | 1 | 15187 | 15200 | ATGCTTCTGAATTG | 16 | 568 |
| 435735 | 1 | 15192 | 15205 | TGGTGATGCTTCTG | 81 | 569 |
| 435736 | 1 | 15197 | 15210 | ATGCATGGTGATGC | 50 | 570 |
| 435737 | 1 | 15262 | 15275 | GTGCAGCCCGGCAC | 70 | 571 |
| 435738 | 1 | 15388 | 15401 | CAGAGGATGAGCAC | 16 | 572 |
| 435739 | 1 | 15393 | 15406 | CATCTCAGAGGATG | 5 | 573 |
| 435740 | 1 | 15430 | 15443 | TCATTTCAGTGATG | 0 | 574 |
| 435741 | 1 | 15435 | 15448 | AGGGTTCATTTCAG | 6 | 575 |
| 435742 | 1 | 15440 | 15453 | ATGTGAGGGTTCAT | 11 | 576 |
| 435743 | 1 | 15487 | 15500 | GCCTCAAACATCTA | 40 | 577 |
| 435744 | 1 | 15492 | 15505 | CTACAGCCTCAAAC | 19 | 578 |
| 435745 | 1 | 15497 | 15510 | GGGAGCTACAGCCT | 0 | 579 |
| 435746 | 1 | 15546 | 15559 | ATTGACAAGGGCTG | 32 | 580 |
| 435747 | 1 | 15551 | 15564 | ATATCATTGACAAG | 0 | 581 |
| 435748 | 1 | 15569 | 15582 | TCCCAGGGTCTCTG | 18 | 582 |
| 435749 | 1 | 15630 | 15643 | CAGCCAGGGCCTGG | 29 | 583 |
| 435750 | 1 | 15635 | 15648 | CACTGCAGCCAGGG | 14 | 584 |
| 435751 | 1 | 15650 | 15663 | CTTGCCAGGTCCTC | 28 | 585 |
| 435752 | 1 | 15655 | 15668 | TGCAGCTTGCCAGG | 12 | 586 |
| 435753 | 1 | 15660 | 15673 | AAGAGTGCAGCTTG | 9 | 587 |
| 435754 | 1 | 15665 | 15678 | TCAGCAAGAGTGCA | 16 | 588 |
| 435755 | 1 | 15670 | 15683 | GGGACTCAGCAAGA | 0 | 589 |
| 435756 | 1 | 15805 | 15818 | TGCCCAGGACGGCC | 20 | 590 |
| 435757 | 1 | 15895 | 15908 | TGCCTGAGTGCCCC | 51 | 591 |

TABLE 17-continued

Inhibition of human Factor 7 mRNA levels by chimeric
antisense oligonucleotides having 2-10-2 MOE wings
and deoxy gap targeted to SEQ ID NO: 1 or SEQ ID NO: 2

| ISIS No. | Human Target SEQ ID NO: | Human Target Start Site | Human Target Stop Site | Sequence (5' to 3') | % inhibition | SEQ ID NO |
|---|---|---|---|---|---|---|
| 435838 | 1 | 16009 | 16022 | TCCATGGACACTAA | 29 | 592 |
| 435839 | 1 | 16051 | 16064 | GGTCAGCTGGTCTG | 14 | 593 |
| 435840 | 1 | 16163 | 16176 | GGGCCCGCCACTGG | 0 | 594 |
| 435841 | 1 | 16205 | 16218 | CTCGGACAAAAGAG | 1 | 595 |
| 435842 | 1 | 16596 | 16609 | ATTTCCCATTGGCA | 0 | 596 |
| 435843 | 1 | 16730 | 16743 | GCTGGAGCTGAGCC | 0 | 597 |
| 435844 | 1 | 16773 | 16786 | TGGCCAGTGGCCTC | 30 | 598 |
| 435845 | 1 | 16872 | 16885 | GCTCATGGCAGACA | 21 | 599 |
| 435846 | 1 | 16910 | 16923 | TGGAGAGACCAATG | 7 | 600 |
| 435847 | 1 | 17139 | 17152 | TGGTGTGCACACAT | 36 | 601 |
| 435848 | 1 | 17207 | 17220 | TGGCCACTGCCTCA | 32 | 602 |
| 435849 | 1 | 17250 | 17263 | TGCCGTAGTGGCCG | 31 | 603 |
| 435850 | 1 | 17280 | 17293 | CTTGGCCAGTGTGG | 15 | 604 |
| 435851 | 1 | 17588 | 17601 | ACAGGCCAGGCTGG | 0 | 605 |
| 435786 | 1 | 48751 | 48764 | AGGTGACCCGTGAG | 68 | 606 |
| 435788 | 1 | 127793 | 127806 | CCTGTGAGTGTGAG | 20 | 607 |
| 435641 | 2 | 297 | 310 | GGTCCCCATCACTG | 51 | 608 |
| 435669 | 2 | 657 | 670 | GGACCTGCCATGGA | 36 | 609 |
| 435670 | 2 | 662 | 675 | CAACAGGACCTGCC | 47 | 610 |
| 435677 | 2 | 785 | 798 | GTGCTCGCCCAGCA | 60 | 611 |

Example 10

Antisense Inhibition of Murine Factor 7 In Vitro

Chimeric antisense oligonucleotides were designed as 5-10-5 MOE wings and deoxy gap were designed to target murine Factor 7 (nucleotides 10024000 to 10037000 of GEN-BANK Accession No. NT_039455.6; incorporated herein as SEQ ID NO: 160). The gapmers are 20 nucleotides in length, wherein the central gap segment is comprised of 10 2'-deoxynucleotides and is flanked on both sides (in the 5' and 3' directions) by wings comprising 5 nucleotides each. Each nucleotide in each wing segment has a 2'-MOE modification. The internucleoside linkages throughout each gapmer are phosphorothioate (P=S) linkages. All cytidine residues throughout each gapmer are 5'methylcytidines. The antisense oligonucleotides were evaluated for their ability to reduce murine Factor 7 mRNA in primary mouse hepatocytes. The antisense oligonucleotides were evaluated for their ability to reduce Factor 7 mRNA in primary mouse hepatocytes.

Primary mouse hepatocytes were treated with 6.25 nM, 12.5 nM, 25 nM, 50 nM, 100 nM, and 200 nM of antisense oligonucleotides for a period of approximately 24 hours. RNA was isolated from the cells and Factor 7 mRNA levels were measured by quantitative real-time PCR, as described herein. Murine Factor 7 primer probe set RTS 2855 (forward sequence AATGAGGAACAGTGCTCCTTTGA, SEQ ID NO: 612; reverse sequence TGTAAACAATCCAGAACTGCTTGGT, SEQ ID NO: 613; probe sequence CCCGGGAGATCTTCAAGAGCCCX, SEQ ID NO: 614) was used to measure mRNA levels. Factor 7 mRNA levels were adjusted according to total RNA content as measured by RIBOGREEN®. Certain murine antisense oligonucleotides reduced Factor 7 mRNA levels in a dose-dependent manner.

Example 11

Antisense Inhibition of Murine Factor 7 In Vivo

Four antisense oligonucleotides showing significant dose-dependent inhibition from the in vitro study (see Example 10) were evaluated for their ability to reduce Factor 7 mRNA in vivo. The antisense oligonucleotides are targeted to murine Factor 7 mRNA (nucleotides 10024000 to 10037000 of GEN-BANK Accession No. NT_039455.6; SEQ ID NO: 160). Target start sites for the four of the antisense oligonucleotides are as follows: 11326, 11336, 11613, and 11766.

Treatment

BALB/c mice were treated with ISIS 403102 (CCATA-GAACAGCTTCACAGG, target site 11336, incorporated herein as SEQ ID NO: 161). BALB/c mice were injected subcutaneously with 5 mg/kg, 10 mg/kg, 25 mg/kg, or 50 mg/kg of ISIS 403102 twice a week for 3 weeks. A control group of mice was injected subcutaneously with PBS twice a week for 3 weeks. After the treatment period, whole liver was collected for RNA and protein analysis, and plasma was collected for clotting analysis (PT/aPTT).

RNA Analysis

RNA was extracted from liver tissue for real-time RT-PCR analysis of Factor 7. As shown in Table 18, ISIS 403102 achieved a dose-dependent reduction of murine Factor 7 over the PBS control. Results are presented as percent inhibition of Factor 7, relative to the control.

TABLE 18

Dose-dependent antisense inhibition of murine
Factor 7 mRNA in BALB/c mice

| mg/kg | % inhibition |
|---|---|
| 5 | 64 |
| 10 | 84 |
| 25 | 96 |
| 50 | 99 |

Protein Analysis

Plasma Factor 7 protein was measured using a Factor 7 chromogenic assay (Hyphen BioMed). As shown in Table 19, ISIS 403102 achieved a dose-dependent reduction of murine Factor 7 protein over the PBS control. Results are presented as percent inhibition of Factor 7, relative to control.

TABLE 19

Dose-dependent antisense inhibition of
murine Factor 7 protein in BALB/c mice

| mg/kg | % inhibition |
|---|---|
| 5 | 71 |
| 10 | 88 |
| 25 | 99 |
| 50 | 99 |

Clotting Analysis

Prothrombin Time (PT) and Activated Partial Thromboplastin Time (aPTT) were measured using platelet poor plasma (PPP) from mice treated with ISIS 403102. PT and aPTT values provided in Table 20 are reported as International Normalized Ratio (INR) values. INR values for PT and aPTT were determined by dividing the PT or aPTT value for the experimental group by the PT or aPTT for the PBS treated group. This ratio was then raised to the power of the International Sensitivity Index (ISI) of the tissue factor used. As shown in Table 20, PT was significantly prolonged in mice treated with ISIS 403102 compared to the control. aPTT was slightly prolonged in mice treated with ISIS 403102. These data suggest that ISIS 403102 has a greater affect on the extrinsic pathway of blood coagulation than the intrinsic pathway of blood coagulation.

TABLE 20

Effect of ISIS 403102 on PT and aPTT in BALB/c mice

| mg/kg | PT INR | aPTT INR |
|---|---|---|
| 5 | 1.09 | 1.05 |
| 10 | 1.33 | 1.04 |
| 25 | 2.33 | 1.09 |
| 50 | 4.37 | 1.16 |

Example 12

Single Dose Pharmacokinetic Assay of ISIS 403102

Treatment

The half-life and duration of action of ISIS 403102 in mice was evaluated. A group of 27 BALB/c mice was injected with 50 mg/kg of ISIS 403102. Three mice from the group were sacrificed at days 1, 2, 3, 4, 6, 8, 12, 24, and 56 after the single dose of ISIS 403102 was administered. A control group of 3 mice was injected with a single dose of PBS, and mice in this group were sacrificed on day 1. Mice in all groups were sacrificed by cervical dislocation following anesthesia with 150 mg/kg ketamine mixed with 10 mg/kg xylazine administered by intraperitoneal injection. Liver was harvested for RNA analysis and plasma was collected for clotting analysis (PT and aPTT).

RNA Analysis

RNA was extracted from liver tissue for real-time RT-PCR analysis of Factor 7. Results are presented as percent inhibition of Factor 7, relative to PBS control. As shown in Table 21, treatment with ISIS 403102 resulted in 92% inhibition of Factor 7 mRNA by day 4 after which the effect of ISIS 403102 gradually decreased and was reduced to 11% by day 24. By day 56, Factor 7 mRNA levels in ISIS 403102 treated mice are equal to that of the PBS control. Results are presented as percent inhibition of Factor 7, relative to control. These data show that the peak effect of a single dose of 50 mg/kg of ISIS 403102 occurs on about day 4 and duration of action lasts for at least 24 days.

TABLE 21

Antisense inhibition of murine Factor 7
mRNA in BALB/c mice in a single dose
pharmacokinetic study

| Days | % Inhibition |
|---|---|
| 1 | 61 |
| 2 | 87 |
| 3 | 92 |
| 4 | 92 |
| 6 | 86 |
| 8 | 80 |
| 12 | 72 |
| 24 | 11 |
| 56 | 0 |

PT and aPTT Assay

Prothrombin Time (PT) and Activated Partial Thromboplastin Time (aPTT) were measured using platelet poor plasma (PPP) from mice treated with ISIS 403102. PT and aPTT values provided in Table 22 are reported as International Normalized Ratio (INR) values. INR values for PT and aPTT were determined by dividing the PT or aPTT value for the experimental group (i.e. 50 mg/kg treatment with ISIS 403102) by the PT or aPTT for the PBS treated group. This ratio was then raised to the power of the International Sensitivity Index (ISI) of the tissue factor used.

As shown in Table 22, PT increased from 1.11 on day 1 to 1.97 on day 4. PT decreased gradually after day 4 until PT reached 1.10 on day 56. aPTT increased from 1.00 to 1.24 on day 4. aPTT decreased gradually after day 4 until aPTT reached 0.97 on day 56. Consistent with the mRNA expression data (above), these data show that the peak effect of a single dose of 50 mg/kg of ISIS 403102 occurs on about day 4 and duration of action lasts at least 24 days.

TABLE 22

PT and aPTT analysis in BALB/c mice in a single dose pharmacokinetic study

| Days | PT INR | aPTT INR |
|---|---|---|
| 1 | 1.11 | 1.00 |
| 2 | 1.64 | 1.05 |
| 3 | 1.81 | 1.24 |
| 4 | 1.97 | 1.15 |
| 6 | 1.59 | 1.23 |
| 8 | 1.55 | 1.18 |
| 12 | 1.30 | 1.18 |
| 24 | 1.12 | 1.02 |
| 56 | 1.10 | 0.97 |

Example 13

Multiple Dose Pharmacokinetic Assay of ISIS 403102

Treatment

The duration of action of multiple doses of ISIS 403102 on antisense inhibition of murine Factor 7 and clotting time was evaluated. In a first group of mice, 25 mg/kg of ISIS 403102 was injected subcutaneously as a single dose. Mice from the first group were sacrificed on days 1 and 3 after the single dose. In a second group of mice, 25 mg/kg of ISIS 403102 was administered subcutaneously twice a week for 1 week. Mice from the second group were sacrificed on day 3 after the last dose of ISIS 403102 was administered. In a third group of mice, 25 mg/kg of ISIS 403102 was administered subcutaneously twice a week for 2 weeks. Mice from the third group were sacrificed on day 3 after the last dose of ISIS 403102 was administered. In a fourth group of mice, 25 mg/kg of ISIS 403102 was administered subcutaneously twice a week for 3 weeks. Mice from the fourth group were sacrificed on days 2, 7, 14, 28, 42, and 56 after the last dose of ISIS 403102 was administered. A control group of 3 mice was injected with PBS in a single dose. Mice from the control group were sacrificed 1 day later. Mice in all groups were sacrificed by cervical dislocation following anesthesia with 150 mg/kg ketamine mixed with 10 mg/kg xylazine administered by intraperitoneal injection. Liver was harvested for RNA analysis and plasma was collected for clotting analysis (PT and aPTT) for mice in all groups.

RNA Analysis

RNA was extracted from liver tissue for quantitative RT-PCR analysis of Factor 7. Results are presented as percent inhibition of Factor 7, relative to PBS control. As shown in Table 23, a single dose treatment of ISIS 403102 resulted in inhibition of Factor 7 as early as day 1. Inhibition increased through day 3 in the single dose treatment group. Two doses of ISIS 403102 resulted in increased inhibition on day 3 as compared to one dose of ISIS 403102. Inhibition increased through day 3 in the 2 dose treatment group. Four doses of ISIS 403102 resulted in increased inhibition in comparison to the 2 dose treatment group on day 3.

Six doses of ISIS 403102 resulted in increased inhibition on day 7 as compared to 6 doses of ISIS 403102 on day 2. In mice treated with 6 doses of ISIS 403102, Factor 7 inhibition declined progressively on days 14, 28, 42, and 56.

TABLE 23

Dose-dependent reduction of Factor 7 mRNA in a multiple dose pharmacokinetic study

| No. of doses | Days after last dose | % inhibition |
|---|---|---|
| 1 | 1 | 44 |
| 1 | 3 | 74 |
| 2 | 3 | 86 |
| 4 | 3 | 91 |
| 6 | 2 | 83 |
| 6 | 7 | 88 |
| 6 | 14 | 64 |
| 6 | 28 | 33 |
| 6 | 42 | 5 |
| 6 | 56 | 11 |

PT and aPTT Assay

Prothrombin Time (PT) and Activated Partial Thromboplastin Time (aPTT) were measured using platelet poor plasma (PPP) from mice treated with ISIS 403102. PT and aPTT values provided in Table 24 are reported as International Normalized Ratio (INR) values. INR values for PT and aPTT were determined by dividing the PT or aPTT value for the experimental group (i.e. 50 mg/kg treatment with ISIS 403102) by the PT or aPTT for the PBS treated group. This ratio was then raised to the power of the International Sensitivity Index (ISI) of the tissue factor used.

As shown in Table 24, PT was increased on day 3 in mice treated with a single dose of ISIS 403102 in comparison to mice treated with a single dose of ISIS 403102 on day 1. On day 3, PT increased in mice treated with 2 doses of ISIS 403102 over mice treated with a single dose of ISIS 403102. PT increased in mice treated with 4 doses of ISIS 403102 over those mice treated with 2 doses of ISIS 403102 on day 3. PT decreased in mice receiving 6 doses of ISIS 403102 from day 7 to day 56.

aPTT was slightly increased on day 3 in mice treated with a single dose of ISIS 403102 in comparison to mice treated with a single dose of ISIS 403102 on day 1. On day 3, aPTT increased in mice treated with 2 doses of ISIS 403102 over mice treated with a single dose of ISIS 403102. aPTT increased in mice treated with 4 doses of ISIS 403102 over those mice treated with 2 doses of ISIS 403102 on day 3. aPTT decreased in mice receiving 6 doses of ISIS 403102 from day 7 to day 56.

TABLE 24

PT and aPTT analysis in BALB/c mice in a multiple dose pharmacokinetic study

| No. of doses | Days after last dose | PT INR | aPTT INR |
|---|---|---|---|
| 1 | 1 | 1.04 | 1.08 |
| 1 | 3 | 1.20 | 1.10 |
| 2 | 3 | 1.43 | 1.29 |
| 4 | 3 | 2.13 | 1.53 |
| 6 | 2 | 1.64 | 1.62 |
| 6 | 7 | 2.08 | 1.67 |
| 6 | 14 | 1.37 | 1.25 |
| 6 | 28 | 0.96 | 0.90 |

TABLE 24-continued

PT and aPTT analysis in BALB/c mice in a
multiple dose pharmacokinetic study

| No. of doses | Days after last dose | PT INR | aPTT INR |
|---|---|---|---|
| 6 | 42 | 1.00 | 1.00 |
| 6 | 56 | 0.99 | 0.98 |

Example 14

In Vivo Effect of Antisense Inhibition of Factor 7 with ISIS 403102 in the $FeCl_3$ Induced Venous Thrombosis (VT) Model Treatment Three groups of BALB/c mice were injected with 25 mg/kg, 37.5 mg/kg, or 50 mg/kg of ISIS 403102, administered subcutaneously twice a week for 3 weeks. Two control groups of BALB/c mice were treated with PBS, administered subcutaneously twice a week for 3 weeks. Thrombus formation was induced with $FeCl_3$ in half of the mice while the rest of the mice were assayed for tail bleeding. Two days after receiving the last dose of ISIS 403102 or PBS, mice were anesthetized with 150 mg/kg ketamine mixed with 10 mg/kg xylazine administered by intraperitoneal injection. Thrombus formation was induced with $FeCl_3$ in all groups of the VT mice except the first control group.

In mice undergoing $FeCl_3$ treatment, thrombus formation was induced by applying a piece of filter paper (2×4 mm) pre-saturated with 10% $FeCl_3$ solution directly on the vena cava. After 3 minutes of exposure, the filter paper was removed. Thirty minutes after the filter paper application, a fixed length of the vein containing the thrombus was dissected out for platelet analysis. Liver was collected for RNA analysis.

RNA Analysis

RNA was extracted from liver tissue for real-time RT-PCR analysis of Factor 7. Results are presented as percent inhibition of Factor 7, relative to PBS control. As shown in Table 25, treatment with ISIS 403102 resulted in significant dose-dependent reduction of Factor 7 mRNA in comparison to the PBS control. These data show that antisense oligonucleotides can be used to inhibit expression of Factor 7.

TABLE 25

Dose-dependent reduction of Factor 7 mRNA
in the $FeCl_3$ induced venous thrombosis model

| mg/kg | % inhibition |
|---|---|
| 25 | 24 |
| 37.5 | 74 |
| 50 | 69 |

Quantification of Platelet Composition

Real-time RT-PCR quantification of platelet factor-4 (PF-4) was used to quantify platelets in the vena cava as a measure of thrombus formation. Results are presented as a percentage of PF-4 in ISIS 403102, as compared to the two PBS-treated control groups. As shown in Table 26, treatment with ISIS 403102 resulted in a reduction of PF-4 in comparison to the PBS control. Therefore, antisense oligonucleotides are useful for inhibiting thrombus and clot formation.

TABLE 26

Analysis of thrombus formation by real-time
RT-PCR quantification of PF-4 in the $FeCl_3$
induced venous thrombosis model

|  | mg/kg | PF-4 |
|---|---|---|
| PBS − $FeCl_3$ |  | 0 |
| PBS + $FeCl_3$ |  | 100 |
| ISIS 403102 | 25 | 34 |
|  | 37.5 | 24 |
|  | 50 | 24 |

Tail Bleeding Assay

Mice not receiving treatment with $FeCl_3$ solution were evaluated in a tail bleeding chamber. Mice were placed into the bleeding chamber two days after the final treatment of ISIS 403102 or PBS. Mice were anesthetized in the chamber with isofluorane and a small piece of tail (approximately 4 mm from the tip) was cut with sterile scissors. The cut tail was immediately placed in a 15 mL Falcon tube filled with approximately 10 mL of 0.9% NaCl buffer solution warmed to 37° C. The blood was collected over the course of 40 minutes. The saline filled tubes were weighed both before and after bleeding. The results are provided in Table 27.

Treatment with 25 mg/kg and 37.5 mg/kg ISIS 403102 caused a slight decrease in the amount of bleeding in comparison to PBS treated mice. Bleeding was the same in mice treated with 50 mg/kg ISIS 403102 and mice treated with PBS. These data suggest that treatment with ISIS 403102 does not increase hemorrhagic potential.

TABLE 27

Tail bleeding assay

|  | Mg/kg | Blood (g) |
|---|---|---|
| PBS |  | 0.10 |
| 403102 | 25 | 0.06 |
|  | 37.5 | 0.06 |
|  | 50 | 0.10 |

Example 15

In Vivo Antisense Inhibition of Murine Factor 7 by ISIS 403102 Compared to Warfarin Treatment ISIS 403102 and warfarin (Coumadin®) were evaluated in BALB/c mice. Four groups of BALB/c mice were treated with 5 mg/kg, 10 mg/kg, 20 mg/kg, or 40 mg/kg of ISIS 403102, administered subcutaneously twice a week for 3 weeks. Two days after receiving the last dose of ISIS 403102, mice were anesthetized with 150 mg/kg ketamine mixed with 10 mg/kg xylazine administered by intraperitoneal injection. A fifth group of BALB/c mice was treated with 3 mg/kg of warfarin, administered intraperioneally daily for 6 days. Four hours after the last dose of warfarin, mice were sacrificed. A control group of BALB/c mice were treated with PBS, administered subcutaneously twice a week for 3 weeks. Two days after the last dose of PBS, mice were anesthetized with 150 mg/kg ketamine mixed with 10 mg/kg xylazine administered by intraperitoneal injection. Thrombus formation was induced with $FeCl_3$ in groups of mice except the first control group.

In mice undergoing $FeCl_3$ treatment, thrombus formation was induced by applying a piece of filter paper (2×4 mm)

pre-saturated with 10% FeCl₃ solution directly on the vena cava. After 3 minutes of exposure, the filter paper was removed. Thirty minutes after the filter paper application, a fixed length of the vein containing the thrombus was dissected out for platelet analysis. Liver was collected for RNA analysis.

RNA Analysis

RNA was extracted from liver tissue for real-time RT-PCR analysis of Factor 7. Results are presented as percent inhibition of Factor 7, relative to PBS control. As shown in Table 28, treatment with ISIS 403102 resulted in significant dose-dependent reduction of Factor 7 mRNA in comparison to the PBS control. Conversely, treatment with warfarin did not result in significant reduction of Factor 7 as compared to the PBS control.

TABLE 28

Dose-dependent reduction of Factor 7 mRNA in the FeCl₃ induced venous thrombosis model

|  | mg/kg | % inhibition |
|---|---|---|
| PBS − FeCl₃ |  | 0 |
| PBS + FeCl₃ |  | 0 |
| Warfarin | 3 | 10 |
| ISIS 403102 | 5 | 59 |
|  | 10 | 84 |
|  | 20 | 95 |
|  | 40 | 99 |

Example 16

Effect of Dose-Dependent Antisense Inhibition of Murine Factor 7 on the FeCl₃ Induced Venous Thrombosis (VT) Model Compared to Warfarin Treatment ISIS 403102 and warfarin (Coumadin®) were evaluated in BALB/c mice. Four groups of BALB/c mice were treated with 5 mg/kg, 10 mg/kg, 20 mg/kg, or 40 mg/kg of ISIS 403102, administered subcutaneously twice a week for 3 weeks. Two days after receiving the last dose of ISIS 403102, mice were anesthetized with 150 mg/kg ketamine mixed with 10 mg/kg xylazine administered by intraperitoneal injection. Six additional groups of BALB/c mice was treated with 0.5 mg/kg, 1 mg/kg, 2 mg·kg, 3 mg/kg, 4 mg/kg, or 5 mg/kg of warfarin, administered intraperioneally daily for 6 days. Four hours after the last dose of warfarin, mice were sacrificed. A control group of BALB/c mice were treated with PBS, administered subcutaneously twice a week for 3 weeks. Two days after the last dose of PBS, mice were anesthetized with 150 mg/kg ketamine mixed with 10 mg/kg xylazine administered by intraperitoneal injection. Thrombus formation was induced with FeCl₃ in groups of mice except the first control group.

In mice undergoing FeCl₃ treatment, thrombus formation was induced by applying a piece of filter paper (2×4 mm) pre-saturated with 10% FeCl₃ solution directly on the vena cava. After 3 minutes of exposure, the filter paper was removed. Thirty minutes after the filter paper application, a fixed length of the vein containing the thrombus was dissected out for platelet analysis. Liver was collected for RNA analysis.

Quantification of Platelet Composition

Real-time RT-PCR quantification of platelet factor-4 (PF-4) was used to quantify platelets in the vena cava as a measure of thrombus formation. Results are presented as a percentage of PF-4 in ISIS 403102 or warfarin treated mice, as compared to the two PBS-treated control groups. As shown in Table 29, treatment with ISIS 403102 resulted in a dose-dependent reduction of PF-4 in comparison to the PBS control for dosages of 5 mg/kg and higher. Treatment with warfarin resulted in a reduction of PF-4 in comparison to the PBS control at a dose of 1 mg/kg and higher. Therefore, ISIS antisense oligonucleotides are useful for inhibiting thrombus and clot formation.

TABLE 29

Analysis of thrombus formation by real-time RT-PCR quantification of PF-4 in the FeCl₃ induced venous thrombosis model

|  | mg/kg | PF-4 |
|---|---|---|
| PBS − FeCl₃ |  | 0 |
| PBS + FeCl₃ |  | 100 |
| Warfarin | 0.5 | 165 |
|  | 1 | 63 |
|  | 2 | 47 |
|  | 3 | 35 |
|  | 4 | 22 |
|  | 5 | 0 |
| ISIS 403102 | 1 | 120 |
|  | 3 | 112 |
|  | 5 | 69 |
|  | 10 | 22 |
|  | 20 | 41 |
|  | 40 | 38 |

Example 17

Effect of Antisense Inhibition of Murine Factor 7 in a Tail Bleeding Assay Compared to Warfarin Treatment Tail-bleeding was measured to observe whether treatment with ISIS 403102 or warfarin causes internal hemorrhage in mice. ISIS 403102 and warfarin (Coumadin®) were evaluated in the tail bleeding assay. Six groups of BALB/c mice were treated with 1.25 mg/kg, 2.5 mg/kg, 5 mg/kg, 10 mg/kg, 20 mg/kg, or 40 mg/kg of ISIS 403102, administered subcutaneously twice a week for 3 weeks. An additional 6 groups of BALB/c mice were treated with 0.5 mg/kg, 1 mg/kg, 2 mg/kg, 3 mg/kg, 4 mg/kg, and 5 mg/kg of warfarin, administered intraperioneally daily for 6 days. A separate control group of BALB/c mice was treated with PBS, administered subcutaneously twice a week for 3 weeks.

Tail-Bleeding Assay

Two days after the final treatment of ISIS 403102, warfarin, or PBS, mice were placed in a tail bleeding chamber. Mice were anesthetized in the chamber with isofluorane and a small piece of tail (approximately 4 mm from the tip) was cut with sterile scissors. The cut tail was immediately placed in a 15 mL Falcon tube filled with approximately 10 mL of 0.9% NaCl buffer solution warmed to 37° C. The blood was collected over the course of 40 minutes. The saline filled tubes were weighed both before and after bleeding. The results are provided in Table 30.

Treatment with ISIS 403102 did not significantly affect bleeding as compared to PBS control mice. However, warfarin did increase bleeding in mice as compared to the PBS control mice. Increased doses of warfarin correlated positively with increased blood loss. These data suggest that the hemorrhagic potential of ISIS 403102 is low, especially in comparison to warfarin.

TABLE 30

Tail bleeding assay in the FeCl$_3$ induced venous thrombosis model

| Treatment | Dose in mg/kg | Blood (g) |
|---|---|---|
| PBS | 0 | 0.06 |
| Warfarin | 0.5 | 0.16 |
|  | 1 | 0.28 |
|  | 2 | 0.58 |
|  | 3 | 0.78 |
|  | 4 | 0.66 |
|  | 5 | 0.93 |
| ISIS 404071 | 1.25 | 0.03 |
|  | 2.5 | 0.03 |
|  | 5 | 0.03 |
|  | 10 | 0.09 |
|  | 20 | 0.09 |
|  | 40 | 0.09 |

Example 18

Effect of Antisense Inhibition of Murine Factor 7 in the Tail Bleeding Assay Compared to Apixaban Treatment ISIS 403102 and Apixaban were evaluated in BALB/c mice. In a first group of BALB/c mice, 40 mg/kg of ISIS 403102 was administered subcutaneously twice a week for 3 weeks. An additional 3 groups of BALB/c mice were treated with 5 mg/kg and 10 mg/kg of Apixaban, administered in a single intraperitoneal dose, and 10 mg/kg of Apixaban administered as a single subcutaneous dose. A control group of BALB/c mice was treated with PBS, administered subcutaneously twice a week for 3 weeks.

Tail-Bleeding Assay

Two days after the final treatment of ISIS 403102 or PBS, mice were placed in a tail bleeding chamber. Mice from the groups treated with Apixaban were analyzed 30 minutes after the single dose. Mice were anesthetized in the chamber with isofluorane and a small piece of tail (approximately 4 mm from the tip) was cut with sterile scissors. The cut tail was immediately placed in a 15 mL Falcon tube filled with approximately 10 mL of 0.9% NaCl buffer solution warmed to 37° C. The blood was collected over the course of 40 minutes. The saline filled tubes were weighed before and after bleeding. The results are provided in Table 31.

Mice treated with ISIS 403102 had less bleeding than PBS treated mice. Mice treated with 5 mg/kg of apixaban by intraperitoneal injection had the same amount of bleeding as PBS treated mice. Mice treated with 10 mg/kg of apixaban by intraperitoneal injection had increased bleeding as compared to the PBS treated mice. Mice treated with 10 mg/kg of apixaban by subcutaneous injection had less bleeding than PBS mice. These data suggest that the hemorrhagic potential of ISIS 403102 is low.

TABLE 31

Tail bleeding assay in BALB/c mice

|  | mg/kg | Blood (g) |
|---|---|---|
| PBS |  | 0.22 |
| ISIS 403102 | 40 (s.c.) | 0.10 |
| Apixaban | 5 (i.p.) | 0.22 |
|  | 10 (i.p.) | 0.58 |
|  | 10 (s.c.) | 0.04 |

Example 19

In Vivo Effect of Antisense Inhibition of Murine Factor 7 on Cancer Metastasis

The effect of inhibition of Factor 7 with ISIS 403102 on the formation of tissue factor-Factor 7 complex and its role in extravasation of cancer cells during metastasis will be evaluated. Two groups of severe combined immunodeficiency (SCID) mice will be treated with ISIS 403102, injected at a dose of 20 mg/kg twice a week for 3 weeks. A control group of mice will be injected with PBS twice a week for 3 weeks. Two days after the last dose of ISIS 403102 or PBS, one of the ISIS 403102 treated groups and the control group will be injected intravenously with 50×10$^6$ MDA-MB-231 breast carcinoma cells.

Two weeks after the injection with MDA-MB-231 breast carcinoma cells, mice will be sacrificed. The lungs will be harvested and real-time RT-PCR analysis of human GAPDH mRNA levels performed. The results will be normalized with mouse cyclophilin A mRNA levels. Human GAPDH levels will in the group treated with ISIS 403102 and MDA-MB-231 breast carcinoma cells group will be compared to human GAPDH levels in the other two groups of mice. This experiment is designed to assess the effect of inhibition of Factor 7 on the development of metastasis in the lungs.

Example 20

In Vivo Effect of Antisense Inhibition of Murine Factor 7 on Liver Fibrosis

The effect of inhibition of Factor 7 with ISIS 403102 on experimental liver fibrosis will be evaluated in the carbon tetrachloride liver injury model.

Treatment

In a first group of BALB/c mice, 20 mg/kg ISIS 403102 will be injected subcutaneously twice a week for 8 weeks. In a second group of mice, PBS will be injected subcutaneously twice a week for 8 weeks. Two weeks after the first treatment with ISIS 403102 or PBS, both groups of mice will be dosed intraperitoneally with 5 µl of carbon tetrachloride (CCl$_4$) dissolved in 95 µl of mineral oil twice a week for 5 weeks. A third group of mice will be injected with 100 µl mineral oil alone. Mice will be sacrificed by cervical dislocation following anesthesia with isofluorane. Liver tissue will be harvested from all mice. Real-time RT-PCR will be used to determine the expression of fibrosis related genes, including, collagen type 1, α-smooth muscle actin, matrix metalloproteinase (MMP) 3, TGF-β, Timp1 and Timp2 (MMP inhibitors). The levels in the experimental group will be compared to the levels in the control mice to assess the effect of inhibition of Factor 7 on the development of liver fibrosis.

Example 21

In Vivo Effect of Antisense Inhibition of Murine Factor 7 on Collagen-Induced Arthritis The effect of inhibition of Factor 7 with ISIS 403102 on the formation of tissue factor-Factor 7 complex and its role in fibrin accumulation in the joints leading to joint inflammation and rheumatoid arthritis will be evaluated in a collagen-induced arthritis model.

Treatment

In a first group of DBA/1J mice, 20 mg/kg of ISIS 403102 will be injected subcutaneously twice a week for 8 weeks.

Two groups of mice will be injected with PBS twice a week for 8 weeks. Two weeks after the first treatment of ISIS 403102, type II bovine collagen (Chondrex) will be mixed with complete Freund's adjuvant, homogenized on ice and the emulsion, containing 100 μg of collagen, will be injected subcutaneously in the experimental group and the first control group. A booster injection containing 100 μg collagen type II in incomplete Freund's adjuvant will be injected subcutaneously 7 days after the first collagen injection in both these groups.

Mice in all groups will be examined each day from day 18 after the first collagen injection for the visual appearance of arthritis in peripheral joints. The clinical severity of arthritis will be scored as follows: 1 point for each swollen digit except the thumb (maximum, 4), 1 point for the tarsal or carpal joint, and 1 point for the metatarsal or metacarpal joint with a maximum score of 6 for a hindpaw and 5 for a forepaw. Each paw will be graded individually, the cumulative clinical arthritic score per mouse reaching a maximum of 22 points. Arthritis in the experimental groups will be compared to the control group to assess the effect of inhibition of Factor 7 on the development of arthritis in the joints.

Six weeks after the initial injection of collagen, the maximal level of arthritis will be induced. After mice are anesthetized with isofluorane and plasma is collected, the mice will be sacrificed by cervical dislocation. Livers will be harvested for RNA analysis of Factor 7 mRNA. Plasma collected from all three groups will be analyzed for clotting time (PT and aPTT). The measurement of thrombin-antithrombin (TAT) complexes in the plasma will also be performed by ELISA. The results in the experimental groups will be compared to the control group to assess the effect of inhibition of Factor 7 on the clotting time and formation of TAT complexes.

The invention claimed is:

1. A compound comprising a single-stranded modified antisense oligonucleotide consisting of 12 to 30 linked nucleosides targeted to a human Factor 7 nucleic acid, wherein the oligonucleotide has a sequence that is least 90% complementary to SEQ ID NO: 1 as measured over the entirety of said oligonucleotide, and wherein the oligonucleotide comprises:
   a gap segment consisting of linked deoxynucleosides;
   a 5' wing segment consisting of linked nucleosides;
   a 3' wing segment consisting of linked nucleosides;
   wherein the gap segment is positioned immediately adjacent to and between the 5' wing segment and the 3' wing segment and wherein each nucleoside of each wing segment comprises a modified sugar.

2. The compound of claim 1, wherein the oligonucleotide comprises:
   a gap segment consisting of ten linked deoxynucleosides;
   a 5' wing segment consisting of five linked nucleosides;
   a 3' wing segment consisting of five linked nucleosides;
   wherein the gap segment is positioned immediately adjacent to and between the 5' wing segment and the 3' wing segment, wherein each nucleoside of each wing segment comprises a 2'-O-methoxyethyl sugar, wherein each cytosine in said oligonucleotide is a 5-methylcytosine, and wherein each internucleoside linkage of said oligonucleotide is a phosphorothioate linkage.

3. The compound of claim 2, wherein the oligonucleotide consists of 20 linked nucleosides.

4. A composition comprising the compound of claim 1 and a pharmaceutically acceptable carrier or diluent.

5. The compound of claim 1, wherein the oligonucleotide has a sequence that is 100% complementary to SEQ ID NO: 1 as measured over the entirety of said oligonucleotide.

6. The compound of claim 1, wherein the oligonucleotide comprises at least one modified internucleoside linkage.

7. The compound of claim 6, wherein the modified internucleoside linkage is a phosphorothioate linkage.

8. The compound of claim 1, wherein the modified sugar is a 2'-O-methoxyethyl sugar or a bicyclic sugar.

9. The compound of claim 1, wherein the oligonucleotide comprises at least one modified nucleobase.

10. The compound of claim 9, wherein the modified nucleobase is a 5-methylcytosine.

11. A composition comprising a compound comprising a single-stranded modified antisense oligonucleotide consisting of 12 to 30 linked nucleosides targeted to a human Factor 7 nucleic acid, wherein the oligonucleotide has a sequence that is least 90% complementary to SEQ ID NO: 1 as measured over the entirety of said oligonucleotide, wherein the oligonucleotide comprises at least one modification selected from the group consisting of a modified internucleoside linkage, a modified sugar, and a modified nucleobase, a pharmaceutically acceptable carrier or diluent and a therapeutic agent selected from the group consisting of aspirin, clopidogrel, dipyridamole, heparin, lepirudin, ticlopidine, warfarin, apixaban, rivaroxaban, and lovenox.

12. A method comprising identifying an animal having a disease or condition associated with Factor 7 and administering to the animal a therapeutically effective amount of the compound comprising a single-stranded modified antisense oligonucleotide consisting of 12 to 30 linked nucleosides targeted to a human Factor 7 nucleic acid, wherein the oligonucleotide has a sequence that is least 90% complementary to SEQ ID NO: 1 as measured over the entirety of said oligonucleotide, wherein the oligonucleotide comprises at least one modification selected from the group consisting of a modified internucleoside linkage, a modified sugar, and a modified nucleobase such that expression of Factor 7 is inhibited.

13. The method of claim 12, wherein the disease or condition is selected from the group consisting of a thromboembolic complication, a hyperproliferative disorder, and an inflammatory condition.

14. The method of claim 13, wherein the thromboembolic complication is thrombosis, embolism, thromboembolism, deep vein thrombosis, pulmonary embolism, myocardial infarction, or stroke.

15. The method of claim 12, wherein the animal is a human.

16. The method of claim 12, comprising co-administering the compound and a therapeutic agent selected from the group consisting of aspirin, clopidogrel, dipyridamole, heparin, lepirudin, ticlopidine, warfarin, apixaban, rivaroxaban, and lovenox.

17. The method of claim 16, wherein the compound and the therapeutic agent are administered concomitantly.

18. The method of claim 12, wherein the oligonucleotide has a sequence that is 100% complementary to SEQ ID NO: 1 as measured over the entirety of said oligonucleotide.

19. The method of claim 12, wherein the oligonucleotide comprises at least one modified internucleoside linkage.

20. The method of claim 19, wherein the modified internucleoside linkage is a phosphorothioate linkage.

21. The method of claim 12, wherein the oligonucleotide comprises at least one modified sugar.

22. The method of claim 21, wherein the modified sugar is a 2'-O-methoxyethyl sugar or a bicyclic sugar.

23. The method of claim 12, wherein the oligonucleotide comprises at least one modified nucleobase.

24. The method of claim 23, wherein the modified nucleobase is a 5-methylcytosine.

25. The method of claim 12, wherein the oligonucleotide comprises:
   a gap segment consisting of linked deoxynucleosides;
   a 5' wing segment consisting of linked nucleosides;
   a 3' wing segment consisting of linked nucleosides;
   wherein the gap segment is positioned immediately adjacent to and between the 5' wing segment and the 3' wing segment and wherein each nucleoside of each wing segment comprises a modified sugar.

26. The method of claim 12, wherein the oligonucleotide comprises:

a gap segment consisting of ten linked deoxynucleosides;
a 5' wing segment consisting of five linked nucleosides;
a 3' wing segment consisting of five linked nucleosides;
wherein the gap segment is positioned immediately adjacent to and between the 5' wing segment and the 3' wing segment, wherein each nucleoside of each wing segment comprises a 2'-O-methoxyethyl sugar, wherein each cytosine in said oligonucleotide is a 5-methylcytosine, and wherein each internucleoside linkage of said oligonucleotide is a phosphorothioate linkage.

27. The method of claim 26, wherein the oligonucleotide consists of 20 linked nucleosides.

* * * * *

SEQUENCE LISTING

```
<160> NUMBER OF SEQ ID NOS: 614

<210> SEQ ID NO 1
<211> LENGTH: 18001
<212> TYPE: DNA
<213> ORGANISM: H. Sapiens

<400> SEQUENCE: 1
gaagtcatca gcaatgcaac tgttcacatg gaggatactc cctgcttgag gggtcagaca        60
ggcctgctgg gcaacccagg aggcttggat gaccgtctac cccagtgttt ttgggatgga       120
aagttccaca ttctgagaac cctcagtccc tgggcaacct ggggtggtta gtcaccacag       180
cttgtggctt gggcccatga cagcaggtag aaatgacgtg gactgccgcc agccgggcac       240
agtggctcac gcctgtaatc ccagcacttt gggaggctga ggcatgtgga tcacttgagg       300
tcaggagttc gaaaccagcc tggtcaacac ggtgaaaccc catctctgct aaaaaaaaaa       360
aatatatata tataaattag ccaggcatgg tgacgtgcac ctgtggtccc agctactcag       420
gaggctgagg cacaagaatc acttgaaccc gggaggtgga ggttgcagtg agattgcacc       480
agtgcactct ccagcctggc aacagagcaa gactctgtct caaacaaaca aaacaaaaca       540
aacaaaaaga cgtaagatgt ggaccgctgg agaatggggg tgctgcctgc agtcaaaacg       600
gagtgggggt gcccagctca gggccagaat gatcctattc ccggcacttc tcagtgaggc       660
tctgtggctc acctaagaaa ccagcctccc ttgcaggcaa cggcctagct ggcctggtct       720
ggaggctctc ttcaaatatt tacatccaca cccaagatac agtcttgaga tttgactcgc       780
atgattgcta tgggacaagt tttcatctgc agtttaaatc tgtttcccaa cttacattag       840
gggtttggaa ttctagatcg tatttgaagt gttggtgcca cacacacctt aacacctgca       900
cgctggcaac aaaaccgtcc gctctgcagc acagctgggg tcacctgacc tttctcctgt       960 ccccccact tgagctcagt ggctgggcag caggggatgc atggccactg gccggccagg      1020
tgcagctctc agctggggtg ttcagaggac gcctgtgtcc tccctcccc catccctctg      1080 tcaccttgg aggcagagaa ctttgcccgt cagtccatg gggaatgtca acaggcaggg      1140
gcagcactgc agagatttca tcatggtctc ccaggccctc aggctcctct gccttctgct      1200
tgggcttcag ggctgcctgg ctgcaggtgc gtccggggag gttttctcca taaacttggt      1260
ggaagggcag tgggcaaatc caggagccag ccgggcttc ccaaacccg cccttgctcc      1320 ggacaccccc atccaccagg agggtttct ggcggctcct gttcaatttc ttccttcta       1380 gaaaccagca tccaggcaca ggaggggagg cccttcttgg tgcccaggc tttggcggga      1440
```

```
ttattttttca aagaacttta ggagtgggtg gtgctttcct ggcccccatg ggcccctgcc    1500
tgtgaggtcg gacaagcgca gggagtctgg ggcctctcag agtgcaggaa gtgcgcacag    1560
ggtgctccca ggctggggag cacaggtagg ggacggtgcg tgggggatgg cgcctggggc    1620
atgggggatg gggtgtggga aacggcatgt ggggcgtagg ggatgggtg tggaggatcg     1680 ggggtgggga tggcgtgtgg ggtgtggggg atgggccgtg ggggggtggg gcctgggaaa    1740
cagcatgtgg ggcatggggt gtgggggtga ggtgtgggaa agtgtgtggg gtgtggggga    1800
tggggcatgg aaagggcgtg tggggtgcag gggatggggc atggaggtgt gggggatggg    1860
gtgtgtgggg tgtcggggat ggggcatgtg gggtgtgggg gatggggcat ggaaagggcg    1920
tgtggggtgc agaggatggg gcatgggggg gtggggatgg cgagtggggc tggggcctgg    1980
gaatggtgag tggggcatgg ggatggcgag taggggggtgt ggcgtgagga tggctagtgg   2040
ggcgtgggga tggcgtgtgg ggatggcgag tggggggtgg gctgtgaggg acagtgcctg    2100
ggatgtgggg ctgcagccct agctcacagc atggccttat gaccccggcc accttcctgc    2160
cccaggcggg gtcgctaagg cctcaggagg agaaacacgg gacatgccgt ggaagccggg    2220
gcctcacaga ggtgagcagg gactgccact ggttttgtcc tggggcccag tgggggccaa    2280
catcacctcc ttcccctccc atggcaaaga gccagcccgc ggggtggcta ctgcagtgcc    2340
ccccaaggag ggtgttccct gctcgagagg aagtgaccgc tccagcttgg ccttccctgg    2400
gactggggtg caggcgattt tatcttcttt gctccattct gttccttcca gataatcgtg    2460
tgttcttcat caggttttcc tcagttcttg agagcttttc tgatgcaaat ctgctttcac    2520
cccagggcgg tcaccggctc tgctcacacc agcctccaag ggtgtgggtg tcccgggagt    2580
gtgggtgtcc cggggcgtg ggtgtcccag gagtgtgggt gtcccggggg cgtgggtgtc     2640
ccgggagtgt gggtgtcccg gggcgtggg tgtcccggga gtgtgggtgt cccggaggcg     2700
agggtgtccc gggagtgtgg gtgtcccggg ggagtgggtg tcccgggagt gtgggtgtcc    2760
cggaggcgag ggtgtcccgg gagtgtgggt gtccggggg cgtgggtgtc ccggagtgt      2820 gggtgtcccg ggggagtggg tgtcccggga gtgtgggtgt cccggaggcg agggtgtccc    2880
gggagtgtgg gtgtcccggg ggagtgggtg tcccgggagt gtgggtgtcc cggaggcgag    2940
ggtgtcccgg gagtgtgggt gtccggggg cgtgggtgtc ccggagcgt gggtgtcccg      3000 ggggcgtggg tgtcccggga gtgtgggtgt cccgggggcg tgggtgtccc gggagtgtgg    3060
gtgtcccggg ggcgtgggtg tcccgggagt gtgggtgtcc cggagtgtg gtgttccgg      3120 aggcgagggt gtcccgggag tgtcgtgtc cggggggcgt gggtgtcccg ggggcgtggg     3180
tgtcccgggg gcgtgggtgt tccggaggcg agggtatccc agaagtgtga gtgtcccagg    3240
ggcgtgggtg tccgggggt gtgggtgtcc cgggggcgtg ggtgtccggg gagtgtgggt     3300
gttccggagg tgagggtgtc ccggagtgt gggtgttccg gaggcgaggg tgtcccggga     3360
gtgtgggtgt ccggggggcg tgggtgtccc gggagtgtgg gtgttccgga ggtgagggtg    3420
tcccgggagt gtgggtgttc cggaggcgag ggtgtcccgg gagtgtgggt gtcccagggg    3480
cgtgggtgtc ccgggagtgt gggtgttccg gaggcgaggg tgtcccggga gtgtgggtgt    3540
tccgggagcg agggtgtccc gggagtgtgg gtgtcccggg ggcgtgggtg tcccgggggt    3600
tgtgggtgtc ccgggagtgt gggtgttccg gaggcgaggg tgtcccggga gtgtgggtgt    3660
tccgggagcg agggtgtccc gggagtgtgg gtgtcccggg ggtgtgggtg tcccggggggt   3720 gtgggtgtcc cgggagtgtg ggtgtcccgg gggagtgggt gtcccgggag tgtgggtgtt    3780
```

```
ccggaggcga gggtgtccca ggagcgtggg tgtcccggag gcgagggtgt cccgggagcg    3840
tgggtgtccc gggggcgtgg gtgtcccggg agtgtgggtg tcccggggga gtgggtgtcc    3900
cgggagtgtg ggtgtcccgg aggcgagggt gtcccaggag tgtgggtgtc cgggggcgt     3960
gggtgtcccg ggagtgtggg tgttccagag gcgagggtat cccagaagtg tgagtgtccc    4020
gggggtgtgg gtgtcccggg ggtcgtgggt gtcccggagg tgtgggtgtt ccagaggcga    4080
gggtgtcccg ggagtgtggg tgtcccaggg gtgtgggtgt cccgggggcg tgggtgtccc    4140
gggagtgtgg gtgtcccggg ggagtgggtg tcccgggagt gtgggtgttc cggaggcgag    4200
ggtgtcccgg gagtgtgggt gttcggagg cgagggtgtc ccgggagcgt gggtgtcccg     4260
ggggcgtggg tgtcccggga gcgtgggtgt cccaggggtg tgggtgtccc ggggcgtgg     4320
gtgtcccggg agtgtgggtg tcccgggga gtggatgtcc cggagtgtg gtgttccgg      4380
aggcgagggt gtcccgggag tgtgggtgtt ccggaggcga gggtgtcccg ggagtgtggg    4440
tgtcccgggg gcgtgggtgt cccgggagtg tgggtgtccc ggggcgtgg gtatcccaga    4500
agtgtgagtg tccagggggc gtgggtgtcc gggggcgtg gtgtcccgg gggtgtgggt    4560
gtcccggggg tcgtgggtgt cccgggagcg tgggtgtcgg ggactgcagg gacatgggcc    4620
tccctccca ctcctgccgc ccagggcacc tcctgtgagg actcggagtc cgtgagttcc     4680
cacctccttg agcccgattc tttggtgtcc ccgcctgcat cctcagcctc cttccaaacc    4740
agaccagttc tctaggggcg tcgacgtgtg aaactgattt taaagaaaac aggcagtggc    4800
ctttctctcg gccccacgtg gcccagtagc gctcaccttc cgtccctct ccgcgctca     4860
gtaaccaatt taggccgctc ctgcagaact cgggctcctg cccaccggcc cacagcgtcc    4920
acctgaggcc tcgtcctccc agcaaaggtc gtccctccgg aacgcgcctc ctgcggcctc    4980
tccagagccc ctcccgcgcg tcctctcagc ccgctcgcc tcctcccggg gcctccctct    5040
cccgcctgcc cccaggcccg tctccccctcg cgggctgagg caggttcggg cagcacggcc    5100
gccccggggc ggggtcact ctccaccacc gcgtggtgcc cacagctcac ggcgctcccg     5160
ggtgacggtc ccctcggctg tagggcgtcc tgaagagcgg cctgctcgga gctgagcgca    5220
cgggggttgcc tcgccctggg cgtctctggc cctcaccagc cccgtcttcc catgggcaaa    5280
acggcggtcc tgtttgtcca caagtaaccg tcggggttac ggaggggcca ggagctgcgg    5340
cgggggggctg tgctctcagg accgccccca ggaggatccg cgcgaggtct ggagctctca    5400
ggggtcgcgg gggacagagg ggccccaagc ggaggcgggg aaggcggcag aagcccagga    5460
ccgccaagag ctggcgagga agccggggc tcgctgtcgg gggagccggg caggggccgc    5520
gcctcggacc aggacggagg cctggggaag gcggatctgg ccgccggaga cgcggtgcgg    5580
gtggagacga gggatttgga tttccgcggg cggctgtacg gatttccacg cgcggttcac    5640
gtgggcccca gggggttgcc cggcacccgg ggccgcgccg ccttctcctc gccggcatcg    5700
acccgcagcc tcacgtttac gcggcggcgc ccgcagcccc cttcggcccg gcttccgcgc    5760
gtgccccga gcgcgccctc gggatcagcc cccggaagca gagaggccag gccgggaagg    5820
atgggcgacg ggggtggctg acccgggagc acggcaggga ggacacccag ccaggcccgc    5880
gagcagcgcc gctcccctcc tccaggacgg gcggaaacct gcgatgcccc cgccgcgtgg    5940
gccgtggggc ggtctccgag gcactgggcg gggcacgcgg tgggcgcttc acggaactcg    6000
catttcccag tcttcgtaac ccaggaggaa gcccacggcg tcctgcaccg gcgccggcgc    6060
gccaacgcgt tcctgaggga gctgcggccg ggctccctgg agagggagtg caaggaggag    6120
cagtgctcct tcgaggaggc ccgggagatc ttcaaggacg cggagaggac ggtgagccca    6180
```

```
gcctcggggc gccccgcgcc gcggacactg caggcggcgg tgaaccaggc cgcgtggggc    6240
cgcctgcgtc tctttggctg cggctgtggg cggcgaacac gcagcggcgc ccgcgcggcg    6300
ctttctgcgg gggtcgcttt ccgcccgggg tgactccgct ttcctgggcg atgcccccca    6360
cccccaggca cgcgctctcc ccgtgcggcc gcaccgcgca tgccggtttt cacatcagaa    6420
aatacgattt gcaaagcaca cttagggtgt ccccttaac ttcccaaggg agtcccccca     6480
gtccccgaag ggtccagggc agcctgcgca tcgcagacgc gcgcggctcg cagaagggac    6540
gtggtgagaa gctggcccac agcatgccac cagcggcacc tcctcagggc acgtgtcggg    6600
gagaaacaac acttagggac ctgggacttt ctccagctca cgctcacggg tcacctcaca    6660
ctccaagatc acctcaaaga ggacacctca cacagggcac acttcacact cacaggtcac    6720
ctcacactca caggacacct cacactcaca gggcacactt cacactcacg ggtcacctca    6780
cactccaaga tcacctcaaa gaggacacct cacacagggc acacttcaca ctcacaggtc    6840
acctcacact cacaggacac ctcacactca cagggcacac ttcacactca cgggtcacct    6900
cacactccaa gatcacctca agaggacac ctcacacagg gcacacttca cactcacggg    6960
tcacctcaca ctcacaggac acctcacaca agacacctca cacggggcac acttcacact    7020
cacaggtcac ctcacaccca caggacacct cacacagggc acacttcaca ctcacgggtc    7080
acctcacact cacaggacac ctcacacaag acacctcaca cggggcacac ttcacactca    7140
caggtcacct cacacccaca ggacacctca cacagggcac acttcacact cacgggtcac    7200
ctcacactca caggacacct cacactcagg gcgcacttca cactcacggg tcacctcaca    7260
cccacaggac acctcacaga ggtcacctca cacaggacac ctcacactca gggtgcactt    7320
caaacccaca ggtcatttca cctcacactc acaggacacc tcacacaaga taccacacgg    7380
ggcacacttc acactcacag gtcacctcac actcacagga cacctcacag aggtcacctc    7440
acacggggca cacttcacac tcacaggtca cctcacaccc acaggacacc tcacagaggt    7500
cacctcacac ccacaggaca cctcacacag gacacctcac agaggtcacc tcacacccac    7560
aggacacctc acactcatag gtcacctcag tcttacagga caactcacac tcacaggtca    7620
ccttactctc acaggacacc tcacactcac aggtcacctt actctcacag gacacctcac    7680
tctcacagga cacctcacac agggcacact tcactcccac aggtcaccat acctcacaca    7740
gatcacctca tactcacaga tcacttcatt ctcacaggat acctcacact cagggcacac    7800
ttcacactca caggtcacac ctcacacaga tcatctcatt ctcacaggac acctccctct    7860
cacaggtcac ctcacactca caggacacct cacagaggtc acctcacacc cacaggacac    7920
ctcacagagg tcacctcaca cggggcacac ttcacactca ggtcacctca cacccacagg    7980
acacctcaca gaggtcacct cacacccaca ggacaactca cagaggtcac ctcacacagg    8040
acacctcaca aggtcacctc acacccaca ggacacctca cactcatagg tcacctcagt     8100
cttacaggac aactcacact cacaggtcac cttactctca caggcaccct cacactcaca    8160
ggtcacctta ctctcacagg cacctcaca cagggcacac ttcactccca caggtcacca     8220
tacctcacac agatcacctc atactcacag atcacttcat tctcacagga tacctcacac    8280
tcagggcaca cttcacactc acaggtcaca cctcacacag atcatctcat tctcacagga    8340
cacctccctc tcacaggtca ccttacactc atctcacact cacaggtcgc cacacctcac    8400
actcacagga tgcctcacac tcacagaacc acatctcata tgcacaagac acctcacact    8460
caggacacct catgctcaaa gaagcctcac actcacagga ggtccagctg tctgaggcaa    8520
```

```
aggctaacat gacccttcc agacaaattg aggatggtca tgcctagcat ttttatacac    8580
ctagttttga aagcatttct catctgttgt attctcacag caccccgtga gtttaagttc    8640
aggtggccaa cagtttcttc agcaatcact tttttctgtg gagtgctttt gctgtttgtg    8700
gaatatttg catctgctac tgcaccctct ccccgtatgt gtggccaccc tgtcagaggt     8760
ggagctgtgg ctcagagcct gtgtacctcg tcccaggtcc acagctcagc gacagaagag    8820
tcagggttga acctcgggtg ttctgacttg ggagcaggaa atgtgtggtc acccatagtt    8880
ccagatgtcc tggggagggg ccaagattag aagaaaccta cctcagctcc agaggaaagt    8940
ctggcttcct gagcccaccc cgccagaccc aggtccaagt cccccaaccc cagttcatgg    9000
tgtgtccagt gcttaccgtt gggtgctctg gtgaaggtgc atctcacgag gcttgctctc    9060
ttgttccttc agaagctgtt ctggatttct acagtggtg agtggatgat caccaccagt     9120
cctgcctgca acccttctca gcttactgac accagcccac tccacagatg gggaccagtg    9180
tgcctcaagt ccatgccaga atgggggctc ctgcaaggac cagctccagt cctatatctg    9240
cttctgcctc cctgccttcg agggccgaa ctgtgagacg cgtaaggccc cactttgggt     9300
cccatatttg cagagggccc tggggagctg gtggaggtgg cctggccaac cgggctgcag    9360
ggtgcacaac ctggtggggt gtgtaggccg ggcattcagg gctcagcccc agttggaaat    9420
tggtctaggt gaccttgaaa tcccttccag tctgaggtct ttgacaggga cccaaggttc    9480
tgattatcag actcagtggc cccttgggct cccggccctg gcaattctc agccctcgag      9540
atggcccagc tgagagtccc tgtgtccctg tcccacttcc acatcccacc acgcaggacc    9600
gcttggtaaa cttccccttc tctactttcc attacaaagg tttgaggggt ttgttttttt    9660
tttaaccatc tgaatattaa attatcacaa agtttgaggc ccccaacctc ccttgggttc    9720
agtaattcac tagaaggact catagaatcc actgaagtgg atacactcac aggtaccgtt    9780
tattacagca aaggatgcag gcttaagtct gcagagggac caggcacaag cttcccttg     9840
tcctctccct gtggggtcat gtggacagtc cttaattctc ccagaatgac gtgtgacgag    9900
acgtgggaag tactgccaac ttgggaagct ctacgagccc cggtgtccag aggttttatc    9960
agggctcaat cacatagacc cagctgacca cccgcatggc tgacctcagt ctcagccct     10020
ccagaggcta cgccgatagt gcggcccaag gccccaccat acatcacatt gtcagctaga    10080
ccatccagca tggctcaagg cccaggtaaa caccaacatt ccctcaggca agaccttcca    10140
agggcttagc ggtcatttcc caggagccaa ggcaaaggct acccttctc tggcacagca      10200
gttcatcctt gaccacccaa gaccacattc ttacactgaa tgagctctcc tgtgcagcag    10260
ccatttctt ctctaagcag aagagagccc agcaagctgg aggaggctga agagagaggc     10320
ttcctgctgg tcatctgggt ccagaatgcc tggagatctc tgctcagccc tggtgcccag    10380
cagccctggt gtgcatcctg cagggcaggc cttcccgccg gagtcctgga cttgctcagg    10440
gccactcccc ttgcccatgt caaccaaagt caggctgccg gttctgcttc ttctgtctga    10500
gcccatgacc agtgctggga ctaactgtcc ccaggcgggc tcacggtggt acgaggccag    10560
cttggagaac tgtctcagct ctctggtcct ctcgtcagtt gggtctctga ttggaaagtc    10620
ccttggacac ttttaccatc cccattggac tttcactttc cccaggctc ccatcagctg      10680
ctcggaagag tggtcaccct ggaggccact gcccaccagc caggcacccc ccaaatgcaa    10740
ccgcagccag cactgccagc cactggcaag gctgttcaga catgtggctc ctctgatcca    10800
cgccttgtcc tttggatcag tccacggagc aggtggtgcc aagctcaggc tctgtcaccc    10860
acagctcagt gccaccttcc aggcagaaca ccactgctga cccagggcat ggccaccccg    10920
```

-continued

```
ggggctggct ctcgctgacc cccagaagcc cctctcaggg tgtccccttc ctgtccccag    10980
acaaggatga ccagctgatc tgtgtgaacg agaacggcgg ctgtgagcag tactgcagtg    11040
accacacggg caccaagcgc tcctgtcggt gccacgaggg gtactctctg ctggcagacg    11100
gggtgtcctg cacacccaca ggtgaccagg cttcatgtcc cagtcccaga tgacaccagt    11160
ccctgtccca ctacggatta tcttactgga caaagacgg gtgggagtgg cttcacatct    11220
actgagcact aactatgcac tgaccaattg tgaggtggga tctgggcacc aagggtggca    11280
caggccagag cgacagtgac taggatgggc accctgggg caatccctga atggcctcag    11340
gcccctgcc aattctaggc agaccagggg agccaagcaa ggcactatct cacgtccaac     11400
tcccactcgc aggacctccg ccagggttca tgaatctact tcggcacagc caatgtctgt    11460
actgactgct gcccactctg cattccaaaa ctcgtaaagg ctcctgggaa aatgggatgt    11520
ttctccaaac cagcctggaa cgaatgggct gcacttccaa aagcagggac accccacacc    11580
cactgtgtct caaagaggcg gacgtgccca ccctggccac acagcctggg actcagcctg    11640
ccacctcctc gggcttcctt tctggcccaa gaccttgatt gaagcagatc aaaactaagc    11700
atgggatcaa acaacacag tttgattcat ctttaggtag aatttcattc accttctact     11760
aaagtcaaac aacacatctt ctccctgaaa agtgagcaga gggcggtttt aagacgtaag    11820
ccctctgttt cctccaaaac cagccctgac cattgtctcc tcagccagcc acttcttcaa    11880
gggcctctca tggccgggcc ccaccagtca ggcccagccg aggccctgcc ttccaccacc    11940
cctgggccct gggagctcct gctcctgggg gcctcccata gcctcggcct caaggcctct    12000
cagaggatgg gtgtttctga atctttccta gtggcacgtt catccctcac aaatctctgc    12060
atctttctga cttttgtttt acacagttga atatccatgt ggaaaaatac ctattctaga    12120
aaaagaaat gccagcaaac cccaaggccg aattgtgggg ggcaaggtgt gccccaaagg     12180
ggagtgtcca tggcaggtaa ggcttcccct ggcttcagga ttccaagccc tgagggtctt    12240
gaagcctttt gaatgtgaac aacagctctg gaagggaaaa tgggcaggtc agccccaagc    12300
ccaccaggct ccaagtcagc acacctagca cctccagctc gcggcacccc catgctttta    12360
gtggggcaag gaaggagaaa agaaaacgac actcactgag gtctaccct gtgcagagaa     12420
ccctgcgaga tgccccatcc gagttgtcac gtcgtcctca cggttactct ttgaggtggg    12480
atctttgcct gatctttgca aaatcaggag cattggatca aagctatgtg aagatcctgt    12540
gaggtgaaca gtgaaatctc acagcgacat ttgtattctt gggccgtgcc caagagcacg    12600
tctcggctag agaggggcac agcctcccag agccaggtct gagcagcttt gcctggaggg    12660
gatctgcaaa gaccccagga tttcagaaag aaattgtgca atgccagagg ttccttggca    12720
tgcccgggag ggcgagtcat cagagaaaca atgacagcaa tgtgacttcc acacctcctg    12780
tcccccgcc caggtcctgt tgttggtgaa tggagctcag ttgtgtgggg gaccctgat     12840
caacaccatc tgggtggtct ccgcggccca ctgtttcgac aaaatcaaga actgaggaa     12900
cctgatcgcg gtgctgggtg gtaccactc tcccctgtcc gaccgcggtg ctgggtgggt    12960
gccactcttc cctgtccgac cgcggtgctg ggtgggtgcc actctcccct gtccgaccgc    13020
ggtgctgggt gggtgccact ctcccctgtc cgaccgcggt gctgggtggg tgccactctc    13080
cgctgtccga ccgcggtgct gggtgggtac cactctcccc tgtctgaccg cagctctcaa    13140
gtgtctcagg ggctgtggct ctgggcttcg tgctgtcact tccacagaca gacagacatc    13200
cccaaaaggg gagcaaccat gctgggcacg actgctgtgg ccaccgtgct ctcagccact    13260
```

```
ttcccatgcc caaataaaac gataaaagac tgggggcttc tgcccatcct gcctcacttg   13320
accaagagcc cagaagagga tgcgacaccc agggcctcat ggaccaccg gctggcaggg    13380
gttctgctca ctgggtttat gggtgagacg agcactccca ggagggccac tgggccggga   13440
agaactgtgg agaatcgggg cacgccctgt cctcccagct gccagggcac agcatccctt   13500
ccccacctca acacccagac cccagattca ccccagttca cttgtcccca cacgagccac   13560
aggctgccac ctggggcagg ctggcccac cttggggtta gatgcaggtc cccttgcccc    13620
agaaggagac tgcagcccct gcagacctag aaatggccac agcccatccc catgcaccag   13680
ggggtgaggt ggcaggtggt ggaaagggcc tgagggggc ttcttccttc caggcgagca    13740
cgacctcagc gagcacgacg gggatgagca gagccggcgg gtggcgcagg tcatcatccc   13800
cagcacgtac gtcccgggca ccaccaacca cgacatcgcg ctgctccgcc tgcaccagcc   13860
cgtggtcctc actgaccatg tggtgcccct ctgcctgccc gaacggacgt tctctgagag   13920
gacgctggcc ttcgtgcgct tctcattggt cagcggctgg ggccagctgc tggaccgtgg   13980
cgccacggcc ctggagctca tggtcctcaa cgtgccccgg ctgatgaccc aggactgcct   14040
gcagcagtca cggaaggtgg agactcccc aaatatcacg gagtacatgt tctgtgccgg    14100
ctactcggat ggcagcaagg actcctgcaa ggggacagt ggaggccac atgccaccca     14160
ctaccggggc acgtggtacc tgacgggcat cgtcagctgg ggccagggct gcgcaaccgt   14220
gggccacttt ggggtgtaca ccagggtctc ccagtacatc gagtggctgc aaaagctcat   14280
gcgctcagag ccacgcccag gagtcctcct gcgagcccca tttccctagc ccagcagccc   14340
tggcctgtgg agagaaagcc aaggctgcgt cgaactgtcc tggcaccaaa tcccatatat   14400
tcttctgcag ttaatggggt agaggagggc atgggaggga gggagaggtg gggagggaga   14460
cagagacaga aacagagaga gacagagaca gagagagact gagggagaga ctctgaggac   14520
atggagagag actcaaagag actccaagat tcaaagagac taatagagac acagagatgg   14580
aatagaaaag atgagaggca gaggcagaca ggcgctggac agaggggcag gggagtgcca   14640
aggttgtcct ggaggcagac agcccagctg agcctcctta cctcccttca gccaagccca   14700
cctgcacgtg atctgctggc ctcaggctgc tgctctgcct tcattgctgg agacagtaga   14760
ggcatgaaca cacatggatg cacacacaca cacgccaatg cacacacaca gagatatgca   14820
cacacacgga tgcacacaca gatggtcaca cagagatacg caaacacacc gatgcacacg   14880
cacatagaga tatgcacaca cagatgcaca cacagatata cacatggatg cacgcacatg   14940
ccaatgcacg cacacatcag tgcacacgga tgcacagaga tatgcacaca ccgatgtgcg   15000
cacacacaga tatgcacaca catggatgag cacacacaca ccaatgcgca cacacaccga   15060
tgtacacaca cagatgcaca cacagatgca cacacaccga tgctgactcc atgtgtgctg   15120
tcctctgaag gcggttgttt agctctcact tttctggttc ttatccatta tcatcttcac   15180
ttcagacaat tcagaagcat caccatgcat ggtggcgaat gccccaaac tctcccccaa    15240
atgtatttct cccttcgctg ggtgccgggc tgcacagact attccccacc tgcttcccag   15300
cttcacaata aacggctgcg tctcctccgc acacctgtgg tgcctgccac ccactgggtt   15360
gcccatgatt catttttgga gccccggtg ctcatcctct gagatgctct tttcttttcac   15420
aattttcaac atcactgaaa tgaaccctca catggaagct atttttttaaa aacaaaagct   15480
gtttgataga tgtttgaggc tgtagctccc aggatcctgt ggaattggat gttctctccc   15540
tgccacagcc cttgtcaatg atatttcaca gagaccctgg gagcacctgc tcaagagtca   15600
gggacacacg catcactaaa tgcaagttcc caggccctgg ctgcagtggg aggacctggc   15660
```

```
aagctgcact cttgctgagt ccccagggtg gtggaagaag aatgagaaac acatgaacag   15720
agaaatgggg aggtgacaaa cagtgccccc actcagactc cggcaagcac ggctcagaga   15780
gtggactcga tgccatccct gcagggccgt cctgggcacc actggcactc acagcagcaa   15840
ggtgggcacc attggcactc acagcagcaa ggcaggcacc agcaacccac ctcggggca   15900 ctcaggcatc atctacttca gagcagacag ggtctatgaa ctacagccgt gggctgcttc   15960
caaggcaccc tgctcttgta aataaagttt tatgggaaca cacccatatt agtgtccatg   16020
gagtggccgt ggcagagacg tccagccgga cagaccagct gacccgccaa gcccagcatg   16080
gttagtgtca ggacctctgc tgaagatgct tgctgaccct ggccagaccc cggttcctaa   16140 tgcccctaa acgggacggg agccagtggc gggccctgat ccaggtcaga gctggctctg   16200
cttctctttt tgtccgagtg accatgcctc agtttcctca tgtgtaaaac aggagcccac   16260
cgtgatgctt atggtgggat gagatcagca tggatggaac aaggccctgg aagggcccat   16320
gccatggtca tcgacagcaa agccactctg cagacagatg cttcagtgaa ttggtagaaa   16380
attctgcaac cagaatgccc ggggctcctg agggcctaag cccagcccag ggttctggaa   16440
gccactctga cttcttggga gtggaagttg gcaggactct tcctgggaag aagcggaggg   16500
tggggatgag aggacagttc aggagcccac ccagacccac aggaggaaac tagggagtc   16560 atgcggggtc ctggtggagc gccagcctcc cttcctgcca atgggaaatg caggcgccca   16620
cctcatggtg ctgccggagg aggggcccg ggactcccca gaggcttcgc tgaagggcct   16680
gggcgccccc aaaggctaca tgtttcatat gggacgtgcc acctgccacg gctcagctcc   16740
agctttctgt gagtggcgag atagaatacg gggaggccac tggccatggg cctgggacag   16800
ggtgggatga ggcggcaggc ttgggccacc aaagccagca tcgccaccca gcattgatga   16860
caaagactgc gtgtctgcca tgagcatcct gctgttggtg cacacaccgc attggtctct   16920
ccatacaaac atgcctagag gcgatgtcag agggtggaga ccaggagagg caggagtcag   16980
acatctggtg ccaccaggaa ggcccttctc agaggaccag gctgtgcgtg gtgcccgccg   17040
tgggaggcca gcctggcgtt ggcatccagc atcatcagtt tgtgcagtcg ggtgggctc   17100 agtgagtgcc tcctgtgtgc caggcacaat gacgcacaat gtgtgcacac caggctcatg   17160
tgcaggtggc tgcgagacag ggcgacccat caaggcagat gcaccatgag gcagtggcca   17220
gtgctgtggg tgttaggggc attgctcccc ggccactacg gcatagcagg cagtgatcgc   17280
cacactggcc aagctttaga ccatttattc cagagacccc agaggcaaaa agcccggctg   17340
cacctcccag tgactcccac agccattgag cagagacact caggaccttg tgatgggagg   17400
tttctgcact ggagaacgag cccagaagcc ctctcagcct cggaacagtg tggccagtgg   17460
tgggcaggtc aggaggggct tcagacacag cctgtccctc cagatggtca cgggaaggtc   17520
actccccaca gaagtacgtt ttggggccat gcgggcacag aaggtttggg ggtgggtggg   17580
gcaggtgcca gcctggcctg tgggaggcca tggtgcagat gccaagcccc ccgtgaca   17640 tgagaccacc tgataccacc cagagagtgg ctgtgagcgg aagggcccgc ccagaaacaa   17700
gcagggcctt ggggcagaag tcctgggctc agatcccacg ctcactgcca gcggcctcgg   17760
ctcaggcttc tgcgctctct aaacttagtt ttctcttctg gaaaaatgat ggggaaaatg   17820
atatttgtat gtgaggactg agagttaaat gtaaacatct ggaaactaca aaatgagcac   17880
gaaatgatgt ttttattctt agaacagaaa gtccccacac ccgcgccct ggtgactgat   17940 gaggatgagg ttctgcgggg cctctctggc cgcccagctc tgcctgggga aggtggggcc   18000
``` a                                                                                18001

<210> SEQ ID NO 2
<211> LENGTH: 3075
<212> TYPE: DNA
<213> ORGANISM: H. Sapiens

<400> SEQUENCE: 2

| | | | | | |
|---|---|---|---|---|---|
| agtcccatgg | ggaatgtcaa | caggcagggg | cagcactgca | gagatttcat | catggtctcc |   60 |
| caggccctca | ggctcctctg | ccttctgctt | gggcttcagg | gctgcctggc | tgcagtcttc |  120 |
| gtaacccagg | aggaagccca | cggcgtcctg | caccggcgcc | ggcgcgccaa | cgcgttcctg |  180 |
| gaggagctgc | ggccgggctc | cctggagagg | gagtgcaagg | aggagcagtg | ctccttcgag |  240 |
| gaggcccggg | agatcttcaa | ggacgcggag | aggacgaagc | tgttctggat | ttcttacagt |  300 |
| gatggggacc | agtgtgcctc | aagtccatgc | cagaatgggg | gctcctgcaa | ggaccagctc |  360 |
| cagtcctata | tctgcttctg | cctccctgcc | ttcgagggcc | ggaactgtga | gacgcacaag |  420 |
| gatgaccagc | tgatctgtgt | gaacgagaac | ggcggctgtg | agcagtactg | cagtgaccac |  480 |
| acgggcacca | agcgctcctg | tcggtgccac | gagggggtact | ctctgctggc | agacggggtg |  540 |
| tcctgcacac | ccacagttga | atatccatgt | ggaaaaatac | ctattctaga | aaaagaaat |  600 |
| gccagcaaac | cccaaggccg | aattgtgggg | ggcaaggtgt | gccccaaagg | ggagtgtcca |  660 |
| tggcaggtcc | tgttgttggt | gaatggagct | cagttgtgtg | ggggaccct | gatcaacacc |  720 |
| atctgggtgg | tctccgcggc | ccactgtttc | gacaaaatca | agaactggag | gaacctgatc |  780 |
| gcggtgctgg | gcgagcacga | cctcagcgag | cacgacgggg | atgagcagag | ccggcgggtg |  840 |
| gcgcaggtca | tcatccccag | cacgtacgtc | ccgggcacca | ccaaccacga | catcgcgctg |  900 |
| ctccgcctgc | accagcccgt | ggtcctcact | gaccatgtgg | tgcccctctg | cctgcccgaa |  960 |
| cggacgttct | ctgagaggac | gctggccttc | gtgcgcttct | cattggtcag | cggctggggc | 1020 |
| cagctgctgg | accgtggcgc | cacggccctg | gagctcatgg | tcctcaacgt | gccccggctg | 1080 |
| atgacccagg | actgcctgca | gcagtcacgg | aaggtgggag | actccccaaa | tatcacggag | 1140 |
| tacatgttct | gtgccggcta | ctcggatggc | agcaaggact | cctgcaaggg | ggacagtgga | 1200 |
| ggcccacatg | ccacccacta | ccggggcacg | tggtacctga | cgggcatcgt | cagctggggc | 1260 |
| cagggctgcg | caaccgtggg | ccactttggg | gtgtacacca | gggtctccca | gtacatcgag | 1320 |
| tggctgcaaa | agctcatgcg | ctcagagcca | cgcccaggag | tcctcctgcg | agccccattt | 1380 |
| ccctagccca | gcagccctgg | cctgtggaga | gaaagccaag | gctgcgtcga | actgtcctgg | 1440 |
| caccaaatcc | catatattct | tctgcagtta | atggggtaga | ggagggcatg | ggagggagg | 1500 |
| agaggtgggg | agggagacag | agacagaaac | agagagagac | agagacagag | agagactgag | 1560 |
| ggagagactc | tgaggacatg | gagagagact | caaagagact | ccaagattca | aagagactaa | 1620 |
| tagagacaca | gagatggaat | agaaaagatg | agaggcagag | gcagacaggc | gctggacaga | 1680 |
| ggggcagggg | agtgccaagg | ttgtcctgga | ggcagacagc | ccagctgagc | ctccttacct | 1740 |
| cccttcagcc | aagcccacct | gcacgtgatc | tgctggcctc | aggctgctgc | tctgccttca | 1800 |
| ttgctggaga | cagtagaggc | atgaacacac | atggatgcac | acacacacac | gccaatgcac | 1860 |
| acacacagag | atatgcacac | acggatgcac | acacagat | ggtcacacag | agatacgcaa | 1920 |
| acacaccgat | gcacacgcac | atagagatat | gcacacacag | atgcacacac | agatatacac | 1980 |
| atggatgcac | gcacatgcca | atgcacgcac | acatcagtgc | acacggatgc | acagagatat | 2040 |
| gcacacaccg | atgtgcgcac | acacagatat | gcacacacat | ggatgagcac | acacacacca | 2100 |

```
atgcgcacac acaccgatgt acacacacag atgcacacac agatgcacac acaccgatgc    2160
tgactccatg tgtgctgtcc tctgaaggcg gttgtttagc tctcactttt ctggttctta    2220
tccattatca tcttcacttc agacaattca gaagcatcac catgcatggt ggcgaatgcc    2280
cccaaactct cccccaaatg tatttctccc ttcgctgggt gccgggctgc acagactatt    2340
ccccacctgc ttcccagctt cacaataaac ggctgcgtct cctccgcaca cctgtggtgc    2400
ctgccaccca ctgggttgcc catgattcat ttttggagcc cccggtgctc atcctctgag    2460
atgctctttt ctttcacaat tttcaacatc actgaaatga accctcacat ggaagctatt    2520
ttttaaaaac aaaagctgtt tgatagatgt ttgaggctgt agctcccagg atcctgtgga    2580
attggatgtt ctctccctgc cacagccctt gtcaatgata tttcacagag accctgggag    2640
cacctgctca agagtcaggg acacacgcat cactaaatgc aagttcccag gccctggctg    2700
cagtgggagg acctggcaag ctgcactctt gctgagtccc cagggtggtg aagaagaat     2760 gagaaacaca tgaacagaga atgggggagg tgacaaacag tgcccccact cagactccgg    2820
caagcacggc tcagagagtg gactcgatgc catccctgca gggccgtcct gggcaccact    2880
ggcactcaca gcagcaaggt gggcaccatt ggcactcaca gcagcaaggc aggcaccagc    2940
aacccacctc gggggcactc aggcatcatc tacttcagag cagacagggt ctatgaacta    3000
cagccgtggg ctgcttccaa ggcaccctgc tcttgtaaat aaagttttat gggaacacaa    3060
aaaaaaaaaa aaaaa                                                     3075

<210> SEQ ID NO 3
<211> LENGTH: 564
<212> TYPE: DNA
<213> ORGANISM: H. Sapiens
<220> FEATURE:
<223> OTHER INFORMATION: Synthetic Oligonucleotide

<400> SEQUENCE: 3
atcatggtct cccaggccct caggctcctc tgccttctgc ttgggcttca gggctgcctg      60
gctgcaggag gaagcccacg gcgtcctgca ccggcgccgg cgcgccaacg cgttcctgga     120
ggagctgcgg ccgggctccc tggagaggga gtgcaaggag gagcagtgct ccttcgagga    180
ggcccgggag atcttcaagg acgcggagag gacgtggtga gtggatgatc accaccagtc    240
ctgcctgcaa cccttctcag cttactgaca ccagcccact ccacagatgg ggaccagtgt    300
gcctcaagtc catgccagaa tggggctcc tgcaaggacc agctccagtc ctatatctgc     360
ttctgcctcc ctgccttcga gggccggaac tgtgagacgc acaaggatga ccagctgatc    420
tgtgtgaacg agaacggcgg ctgtgagcag tactgcagtg accacacggg caccaagcgc    480
tcctgtcggt gccacgaggg gtactctctg ctggcagacg gggtgtcctg cacacccaca    540
gttgaatatc catgtggaaa aata                                            564

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
```
agtcctgggt catcagccgg                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
gagaccctgg tgtacacccc                                          20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
cctgcagcca ggcagccctg                                          20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
tcctgaggcc ttagcgaccc                                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
gaggccccgg cttccacggc                                          20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
tgttgacatt ccccatggga                                          20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
ccatgatgaa atctctgcag                                          20

<210> SEQ ID NO 11
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 11
cctgggagac catgatgaaa                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
tgaagcccaa gcagaaggca                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
cagccctgaa gcccaagcag                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
ctgcagccag gcagccctga                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
taagaaatcc agaacagctt                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
ttgaggcaca ctggtcccca                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
ctggtccttg caggagcccc                                              20
```

```
<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
tggagctggt ccttgcagga                                                 20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
tataggactg gagctggtcc                                                 20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
agaagcagat ataggactgg                                                 20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
agggaggcag aagcagatat                                                 20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
tctcacagtt ccggccctcg                                                 20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
agatcagctg gtcatccttg                                                 20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 24
tgctcacagc cgccgttctc                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
tgcagtactg ctcacagccg                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
gacaccccgt ctgccagcag                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
tgcaggacac cccgtctgcc                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
tccacatgga tattcaactg                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29 gtattttttcc acatggatat                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
agaataggta tttttccaca                                               20

<210> SEQ ID NO 31
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
tccattcacc aacaacagga                                                  20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
gagaccaccc agatggtgtt                                                  20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
ttgtcgaaac agtgggccgc                                                  20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
tcttgatttt gtcgaaacag                                                  20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
tgatgacctg cgccacccgc                                                  20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
tcagtgagga ccacgggctg                                                  20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
```
cacatggtca gtgaggacca                                                                20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
gggcaccaca tggtcagtga                                                                20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
tccgttcggg caggcagagg                                                                20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
gcaggcagtc ctgggtcatc                                                                20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
gtgactgctg caggcagtcc                                                                20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
tggccccagc tgacgatgcc                                                                20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
gcagccctgg ccccagctga                                                                20

<210> SEQ ID NO 44
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 44
gtactgggag accctggtgt                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 45
gccactcgat gtactgggag                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
tttgcagcca ctcgatgtac                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
gcatgagctt ttgcagccac                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
cctgaggcca gcagatcacg                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
cagcagcctg aggccagcag                                               20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
cacacatgga gtcagcatcg                                               20
```

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
gaggacagca cacatggagt                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
gagagctaaa caaccgcctt                                               20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
ggtgatgctt ctgaattgtc                                               20

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 54
gcagccgttt attgtgaagc                                               20

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 55
gcatctcaga ggatgagcac                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 56
gagggttcat ttcagtgatg                                               20

<210> SEQ ID NO 57
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 57
ccatgtgagg gttcatttca                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 58
agcctcaaac atctatcaaa                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
tgggagctac agcctcaaac                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
aatatcattg acaagggctg                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 61
ccactgcagc cagggcctgg                                               20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 62
agagtgcagc ttgccaggtc                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 63
cagcaagagt gcagcttgcc                                               20

```
<210> SEQ ID NO 64
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 64
gggactcagc aagagtgcag                                               20

<210> SEQ ID NO 65
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 65
gcttgccgga gtctgagtgg                                               20

<210> SEQ ID NO 66
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 66
gatggcatcg agtccactct                                               20

<210> SEQ ID NO 67
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 67
gctctgaagt agatgatgcc                                               20

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 68
tttacaagag cagggtgcct                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 69
ttgcaggcag gactggtggt                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 70
cagggcgagg caacccgtg                                            20

<210> SEQ ID NO 71
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 71
gttacgaaga ctgggaaatg                                           20

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 72
tccccaggac atctggaact                                           20

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
gtggccatgc cctgggtcag                                           20

<210> SEQ ID NO 74
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 74
gaagccttac ctgccatgga                                           20

<210> SEQ ID NO 75
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 75
tagaccctca gtgagtgtcg                                           20

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76
gcagaggagc ctgagggcct                                           20

<210> SEQ ID NO 77
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 77
ccaggcagcc ctgaagccca                                              20

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 78
cagggagccc ggccgcagct                                              20

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
catggacttg aggcacactg                                              20

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 80
ccccattctg gcatggactt                                              20

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 81
tcgaaggcag ggaggcagaa                                              20

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
gttccggccc tcgaaggcag                                              20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
```
cacacagatc agctggtcat                                          20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 84
cgtgtggtca ctgcagtact                                          20

<210> SEQ ID NO 85
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 85
gcttggtgcc cgtgtggtca                                          20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
ccagcagaga gtaccctcg                                           20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 87
gggtgtgcag gacaccccgt                                          20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
ccccacaatt cggccttggg                                          20

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 89
tggtgttgat cagggtcccc                                          20

<210> SEQ ID NO 90
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 90
cacccagatg gtgttgatca                                               20

<210> SEQ ID NO 91
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 91
ccgcggagac cacccagatg                                               20

<210> SEQ ID NO 92
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 92
gaaacagtgg gccgcggaga                                               20

<210> SEQ ID NO 93
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 93
ccagttcttg attttgtcga                                               20

<210> SEQ ID NO 94
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 94
accacgggct ggtgcaggcg                                               20

<210> SEQ ID NO 95
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 95
aatgagaagc gcacgaaggc                                               20

<210> SEQ ID NO 96
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 96
ccccagccgc tgaccaatga                                               20
```

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 97
ccatccgagt agccggcaca                                               20

<210> SEQ ID NO 98
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 98
agtccttgct gccatccgag                                               20

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
ccccttgcag gagtccttgc                                               20

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 100
cccggtagtg ggtggcatgt                                               20

<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 101
gatgcccgtc aggtaccacg                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 102
ccagctgacg atgcccgtca                                               20

<210> SEQ ID NO 103
<211> LENGTH: 20
<212> TYPE: DNA
<213> ORGANISM: Artificial Sequence
<220> FEATURE:
<223> OTHER INFORMATION: Synthetic Oligonucleotide -continued

<400> SEQUENCE: 103
gttgcgcagc cctggcccca                                              20

<210> SEQ ID NO 104
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 104
gtggcccacg gttgcgcagc                                              20

<210> SEQ ID NO 105
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 105
acaccccaaa gtggcccacg                                              20

<210> SEQ ID NO 106
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 106
cctggtgtac accccaaagt                                              20

<210> SEQ ID NO 107
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 107
tcgatgtact gggagaccct                                              20

<210> SEQ ID NO 108
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 108
tgagcgcatg agcttttgca                                              20

<210> SEQ ID NO 109
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 109
ccacaggcca gggctgctgg                                              20

<210> SEQ ID NO 110

<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 110
tcgacgcagc cttggctttc                                                      20

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 111
caggacagtt cgacgcagcc                                                      20

<210> SEQ ID NO 112
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 112
gatttggtgc caggacagtt                                                      20

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 113
gaatatatgg gatttggtgc                                                      20

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 114
ccaggacaac cttggcactc                                                      20

<210> SEQ ID NO 115
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 115
aggtaaggag gctcagctgg                                                      20

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 116

-continued cttggctgaa gggaggtaag                          20

<210> SEQ ID NO 117
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 117
gcagagcagc agcctgaggc                          20

<210> SEQ ID NO 118
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 118
caatgaaggc agagcagcag                          20

<210> SEQ ID NO 119
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 119
cttcagagga cagcacacat                          20

<210> SEQ ID NO 120
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 120
gaaccagaaa agtgagagct                          20

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
tgataatgga taagaaccag                          20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 122
ctgaagtgaa gatgataatg                          20

<210> SEQ ID NO 123
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 123
atgcatggtg atgcttctga                                               20

<210> SEQ ID NO 124
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 124
ggcattcgcc accatgcatg                                               20

<210> SEQ ID NO 125
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 125
gaagggagaa atacatttgg                                               20

<210> SEQ ID NO 126
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 126
cacccagcga agggagaaat                                               20

<210> SEQ ID NO 127
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 127
tgcagcccgg cacccagcga                                               20

<210> SEQ ID NO 128
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 128
tgtgaagctg ggaagcaggt                                               20

<210> SEQ ID NO 129
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 129
gagacgcagc cgtttattgt                                               20
```

<210> SEQ ID NO 130
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 130
cacaggtgtg cggaggagac                                              20

<210> SEQ ID NO 131
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 131
gcaggcacca caggtgtgcg                                              20

<210> SEQ ID NO 132
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 132
ccagtgggtg gcaggcacca                                              20

<210> SEQ ID NO 133
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 133
aatcatgggc aacccagtgg                                              20

<210> SEQ ID NO 134
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 134
tccaaaaatg aatcatgggc                                              20

<210> SEQ ID NO 135
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 135
aaagagcatc tcagaggatg                                              20

<210> SEQ ID NO 136
<211> LENGTH: 20
<212> TYPE: DNA
<213> ORGANISM: Artificial Sequence
<220> FEATURE:

```
<223> OTHER INFORMATION: Synthetic Oligonucleotide

<400> SEQUENCE: 136
ttgtgaaaga aaagagcatc                                              20

<210> SEQ ID NO 137
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 137
cagtgatgtt gaaaattgtg                                              20

<210> SEQ ID NO 138
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 138
agcttccatg tgagggttca                                              20

<210> SEQ ID NO 139
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 139
aacagctttt gttttaaaa                                               20

<210> SEQ ID NO 140
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 140
ggatcctggg agctacagcc                                              20

<210> SEQ ID NO 141
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 141
acatccaatt ccacaggatc                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 142
cagggagaga acatccaatt                                              20
```

```
<210> SEQ ID NO 143
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 143
tgtgaaatat cattgacaag                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 144
aacttgcatt tagtgatgcg                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 145
ggcctgggaa cttgcattta                                              20

<210> SEQ ID NO 146
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 146
gccgtgcttg ccggagtctg                                              20

<210> SEQ ID NO 147
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 147
gcagggatgg catcgagtcc                                              20

<210> SEQ ID NO 148
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 148
gtgcccagga cggccctgca                                              20

<210> SEQ ID NO 149
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 149
aagtagatga tgcctgagtg                                               20

<210> SEQ ID NO 150
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 150
ttggaagcag cccacggctg                                               20

<210> SEQ ID NO 151
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 151
agagcagggt gccttggaag                                               20

<210> SEQ ID NO 152
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 152
cacactggtc cccatcactg                                               20

<210> SEQ ID NO 153
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 153
aggacctgcc atggacactc                                               20

<210> SEQ ID NO 154
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 154
acaacaggac ctgccatgga                                               20

<210> SEQ ID NO 155
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 155
tcaccaacaa caggacctgc                                               20

<210> SEQ ID NO 156
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 156
gcccagcacc gcgatcaggt                                                    20

<210> SEQ ID NO 157
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 157
cgaagactgc agccaggcag                                                    20

<210> SEQ ID NO 158
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 158
tcctgggtta cgaagactgc                                                    20

<210> SEQ ID NO 159
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 159
tcctgcagcc aggcagccct                                                    20

<210> SEQ ID NO 160
<211> LENGTH: 13001
<212> TYPE: DNA
<213> ORGANISM: Mus musculus

<400> SEQUENCE: 160
gtagagtcct cgaggctaat acacagagca aaacagaccc agagaagaca cagacccaga         60
gcaagacagg gatccagagc aagatacaga tccagagcaa gacacagatc cagagcaaga        120
cacaaatcca gagcaagaca cagatccaga gcaagacaga tccagaggaa ataaaagtga        180
tactgacctt tctgattcag atcagctctc tagttcttaa acttcaagtt actggtggca        240
ttgccactgg tccccaacct tgcagggtgt cagaacccac aggcatcatc aaactctgtg        300
attaggactg ctccaaagat tctgcttccc catggagtga gggagcctgc atctgtgtag        360
gtgtcatgga tgatgtgagt gtgaaggtgt agcgtgcatg tatacaaggg tgtgcatagg        420
ctgtgtgtgg agtgtgtgca taggtgtaag aatggtatgc aactgtgcaa agacagtgtg        480
catgtgtaca agtccataag gaagtgtgag cataatgtat gtgtgtgtcc ccaggtaatt        540
ctgagcccac tgtcacttac gggtctctca tgtgtgtcac atgtacaagg gtgaggctga        600
catgtagcag catgctgagg gttccagtcc tgttctgcag actgtggggg agcccttggg        660
gagctggctg gggatgaggc ttagtgcttc ctatcccaga gaaggggcaa atggtccctg        720
agcacataca aggaatatcc acataagaag gactcccgga tcccagaaga agcctgttta        780
```

```
tctttcctga aaggtaagt ggggaggagt ccaaaagacg acagacagt gaccccatgc      840
tatccctcca tgtgtctgca ctatgtatgt acagtgctaa tggtacccat ggtacaggtg    900
tgaaaagaag accaagcaaa caaggcccct gcaggtccaa atgggatcct tgacgcctga    960
gacgcaggag ccagccaagg cacgtgccac agggaggtcg ccatctgctg aagaacttta   1020
gccagagccc aagcaccagg cgggctcagc atctgtcctc tgaagcaact ccaattgttc   1080
tgctgctcca gaaagctaaa tacacagttc ctggaactca atagggaaga gaatcctgag   1140
accaggtcca gcctcacata agagagctgg gatgaatggc tgccatctcc tctcatgtcc   1200
ctggagttac cctgtcacga gagcattgga ttttactggg tgaaatttga cctctatccc   1260
agaagaagca actggggtcc caagtgtgaa gggaccccag gagtcaaagg tgcccctggg   1320
gtacaccatg ctggcaaaga ttaaagtccc tgactagaga gggagaggta ctgtagtgtc   1380
ccacaaatga ggtctgactc ccaaaagagt ggtccagcct tgtactgccc cctccctgaa   1440
aagaacattt tcctcagagg gtccaactga agcccacagt gtagtctagg aggctgcatg   1500
accataaacc gagtgtcctt gggctagatc cagtttttac acagaaagtt tcacgtgctg   1560
agaaaccttg ttgatctcag gcaacccagt gtccacaact ccacctggag cctgggccag   1620
aggacacaaa gggacaagtc atgggccacc tgccgatagc tgtttccaca gtgtgggaag   1680
aggaggggca gggcagccct tgagagccat tgacggctgc acagcccagg tctgccctac   1740
aggtcttttc caggtcataa gcccataccc tgtgctttaa caatgtcatc actgtgaata   1800
tggacatcca tcggtgggtg agctctgttc acacctccgg tctgagccca cattgcctgc   1860
cttagctttc ctctttccct ggatgtacaa gtgccagaga cataagtggc agcctccaac   1920
cggcctccat gcttccagcc aatgctccag cttttctccac ccctctcccc tcccccctga  1980
cctttgccct cccggcagca tctgacagt caccagccag aagccacagt ctcatcatgg    2040
ttccacaggc gcatgggctg ctgcttctct gctttctgct ccagctccag ggacctctag   2100
ggactgcagg tatatatgtc tgtctgtccg ggagggttt ctctgtgcat ggagttgctg    2160
ctctttgcag aggcagctgg gacatcaaca ggaaccccct catgagcagc acttgatg     2220
tgtgtccctg acaaaagcag atagcatctg gatgcttgcc acccggaaat aggcagctct   2280
tcacaggggt gggatctttg ctgtcgtcc tccagagacg ttttagaagt agggtgcttt    2340
cctgccctct atggacacag acacttgcct gtgaaattag agcctgggg tcactcagta    2400
cagagctctg tggcaagggg tcagatgtgt cagaacagcc acagggcaac tgcactagag   2460
ggctcgctca ctgccttggc tctacatcca catccacagc ccctcccacc aagtccccca   2520
ccacatacat acatgtgtgc ctctaaggcc ttggggagaa aagctcgtag ttatgaatca   2580
caagttgcag tcttacagaa agagatgctg ccaggaacat tcccatgcat agtgacatgg   2640
gtggtcgagc cagtactgtc ccccttggaa gcccatggca catagggatt gcagtggatt   2700
ctcctgtgga actgagtgac aacaggagca atggctttcc caagttctct gcagtggtat   2760
ggaagacctt ggggtcaggt ttgctttgga tctccaggag attggctgaa gtaaatttac   2820
cttctcctaa gggcccaccc cttacacaat cacttgctgt agaagtgtat gtgtcccagt   2880
ggctggtggc atatggatcc ttctctgcct ggtgaaggac attgattggt ccagttggac   2940
agtgtctcca tcctctctag gaacaccaga gagtgttcct cggcccttcc tcttccctct   3000
ctctgtccct tcccaaaatg gtttatctga cttccactct tgtccttcca agggaccctc   3060
ctctggggtg taccaacgtc ctcctggtaa gcagagccac ctttcaaccc cacctagacc   3120
cagctcctcc cagtaaggcc ctctgagcct cctctgcata gggaaagcct gtctctgtta   3180
```

```
gccctcctcc tgaatacatt ggatgctatt gggtcttcca taactgcctt ccttcaaggc    3240
tcttcttccc atctcagtta cacgtcttcc cgtccacaga tatcccaggc acacagttta    3300
tgtgacacag ttgtcatatg aggactttga gggcctcaac accatccttg gtttccaccc    3360
ctgactacct ttaggtgatt taaacatctg caccccatct ccacacccac tcctgggatt    3420
cagacccaaa tctttgcttt tccaaagcca agtgtggaac actgtcttct agtttctgtc    3480
gaggtcactg acattcaagg tcgtgtggta gaggctgcat ctgaaacact tccaatgtag    3540
aaaatcacag gactcagaac cccaggtgag gcagctgtgg ccatggtacc cagggctaat    3600
gctatgttat ggtaagatct gaagcccag ggctatgact tgagattctt cgattgactc     3660
cctggacaca ggatagagga cacagatggg agaagagagg gagatttaaa tatatgtttg    3720
tgcacacatt ttatgagtac ccaagaaagg ggttgcacaa tgtgtgatta actgtctctt    3780
tgtggcttgg tgtcacatgt aaacctcgtg ttcactggcc tcacaggaga ccacaccatt    3840
tggcaatctc gttactaccg atgtgtcatt tcgtgacctt ttgtaagctc tccaagcatc    3900
ttctcattat aaattcctaa gagagatata ggagaaatgc caaatcacat ggatatggta    3960
aactttcatc tcatctaata aatatgtcac catatacttc tacataatac tgtgccatgt    4020
tctctgtcac catcaatgaa agacacaccc attttcttaa agatatatt tatttaatgt     4080 atatgagtac accgtagctg tcttcagaca cacctgaaga gggcatcaga tcccattaca    4140
gatggttgtg aaccacaatg tggttgctgg gaattgaact caggacctct ggaagagcaa    4200
tcagtgctct taaccgctga gccatctctc cagcacaaca catccaattt taaattcagc    4260
tgtgcctggt ctgtgtcatt ccctgtgacc ttcagcccac agaagatggt aagccattga    4320
cggaaacaac ctatgcacct tccgttcctt gaggtgaaca ggaactcttt ggtccccacc    4380
aaagagtgga atggaaaaag attaatgtgg atcagttgtt cccatcactg cgggagatgg    4440
gtgtttctgc cactgagaga tctggtgtgg gtggttttca tgggctgacc cagtgtggtt    4500
tccttcactc actggaatga tccagtgtgg ctgtttccat tcctgatggg accaagagtg    4560
ggtggcttct gagcagcttg agggaagctg ccaggagcac atgagacctt ctgtttctca    4620
gttttcataa cccaggagga agcacatggt gtcctacaca ggcaaaggcg tgccaactca    4680
ctcctggagg agctttggcc cggctctctg gagagagagt gcaatgagga acagtgctcc    4740
tttgaggagg cccgggagat cttcaagagc cctgagagga ccgtgagtgc cccatctcgt    4800
gcctgctctt gtgtaacaca ctgagactgg aaggaagtga gctggggatt gtgagggtca    4860
cacctatgtc tctggatctg tctcccctc actgcggagg ctgccactca gtactcatag     4920
atggacagga accctgacac acacaggttt ctctctcaac catgccacaa gcagttttac    4980
aagaaataca actcataaac tacactggct gtgtctccta ttttcccaga ggggaatccc    5040
ttattcctta cgggctgccc atgaagtaaa cctgagaggg aaaattcacc tcaagaaggc    5100
aggacacaca cacacacaca cacacacaca cacacacaca cacacgcagg cctcactgga    5160
aacgtgtgag gaacaccaag gcttcctctg ccacacttgg ccatgtgcac agatttgcct    5220
ccactcctga gttactcttt tttatgtttg tttgtttgtt tgtggtttgt tgttttttt     5280 ttttttgag acagggtttt gctatgtagc ccaggctgac ctccaattct tcatcttcat    5340
tgcctcccaa ttattggaat tataagtatg tgctaccccg cctggccctg tggtttcatt    5400
ttgtaaaaga tacatattta tacatcactg agcatgttcc tgtctggtta gacatctcac    5460
tctggagggt tttcccagca agggtgtgtc aggataagac aaggctttaa gacggggtcc    5520
```

-continued

```
actgtgtttc attttgtcat catctctgga aaaaatagtc agtcacagct tcagggcgg    5580 ttgtgagggg ctggttgttc gttctccaag ggcttttctt ctcaccagcc ttggctcata    5640
tcacacctca cactcacagg aggctcccct cacactcata ggaggctccc ctcacactca    5700
caggaggatc acctcacact tacaggaagc tcacctcaca ctcataggag gatcaccttg    5760
cactcacagg aagctcacct cacactcaca ggaagctcac ctcacactcg cagaacacct    5820
ctctctctct caaaagagac ctcacattcg cagaagtcct cacacaggaa tttcacatgt    5880
actggagaat ttacacccac agaacacctc acagaggaac cctcattccc acaggatagc    5940
tcacaaaccc aaagaatgtt ccacacagga aattacaccg cacacttctc tcacaagtgc    6000
cctcacactc actcagagca actcacacag ggagcctgga gaagctgctt tcctcactga    6060
ctggagcaac cacctgacag aaataactgg aggaaagaca ggtttattct ggttggtcgt    6120
tcaggagtca gggaaggcgt gacagtcaca gcgcatccag tcaggaggta gagagtaagg    6180
gatgctggtg ttgagctcac tatctcctct ttattcagac cagaactccc atgggatgac    6240
acctcccaca tttagaggtc cagcccagaa ctggagaaag caggatcagg gtcagaactc    6300
tggtgcgctc acttgggaaa ggcaattgtg tggcgactta aatatctcta gaaagggcgt    6360
agagaaacat caacctcaga taatccctcc tcgtctccag aggaacgcta tcttcccaag    6420
ccccacacag atgcccaggt caggagcccc agccatagct cctgagctcc ctccgtggac    6480
actaagtgct acttctcatg accgtgcctc acatggcttc ttcttccctc tcagaagcag    6540
ttctggattg tttacagtgg tgagtaggtg aaagccatct gtgcccctcc cccacacccc    6600
ttctttgcag cacactaatg tcagctcacc cacagatggg gaccagtgtg cctcgaatcc    6660
atgtcagaac ggaggtacct gccaggatca tctcaagtct tacgtctgct tctgcctcct    6720
agactttgag ggtcggaact gtgagaaaag tgagaccaac ttcttgcctc cgtttgcaat    6780
ggatggagtc gggagggaag ggcctgggtg actggttcca gagaataaca gcctcatcga    6840
gtaaggagag ggtgtccagg ccagcctcgg cccctgaagg aaattgatct gggagacatt    6900
aagtatttct tttaaaccca tggcctttga tttatgagtc taagattctg ggtctcagac    6960
tcgctgtctg tcccttttga ctccttgccc tgagaattct gctgaactgg agagatttag    7020
gggagggagg gtccatctct gtccccacca ggtaagtcag ctaggtaaac ttcttctcct    7080
ctgctggttt aaaggtataa agtatttatt catctttgaa atatcaatta ttgttatgct    7140
tggagaccac caaactgctc tgggctcaac ggttcactac tggactccat agagttcact    7200
gacagcagag atacacatga gtattttatt acaccaacgt ttgccatggc cagaagcagg    7260 cttttctgttg ttctcttctg tgagctcaca tagacagctc agttcttcta gaatgcatgt    7320
aaagtgctgt gcagtatcac caatagaaag tcacttaacc ccgggcctag gtgtgagaga    7380
cctgtctcca gccccctccgg tcccaaatcc caccatcaat caaacctttg gttagccatc    7440
tggtatggcc caaggcccca gacaagtggc agtattccag ttgggggatg cccacgaggt    7500
cacctcttca gacaggacaa aagtgtcctt tctgcagacc aaggactcct tattgcccaa    7560
gtgggttctt cctggtatca gctgcctccg gttctcatca gaaagaggcc agagagagta    7620 aaggggggaag gggagaaggg ctcactaaca gtcactgatc catggaggcc tgtaaggttt    7680
ggtgatcagt gactgtgaat gacaggacag tcctctatac taaaatgaac tgaccaccct    7740
cgcctgcaaa tggccagtgc tggagccaag ggcctagatg gctcacatgg tcatgagggt    7800 tgcccccaaga gtaacttctc cctttgacat gtccgtgggc cagttcccca ttctattgag    7860
aacatttcct ttccttggaa atgtttgctt accacctcca gaacccttca catcttctca    7920
```

-continued

```
ttagagcctt ggaaggaaga tgtcatcaca caccagccta gcaccctcca agatttctca    7980
gacttgtgac tcccaaatcc agctctccat cccgccagat cagtccatag ggcaggtgac    8040
gcaagctcag ccttaatagc ccacagctac atgccatatt ccaagggggac aagagcaacc   8100 accaccatgg cccgtctgcc gaccttgcag agacctctca ggttgtcttc tccttttctc    8160
aggcaagaat gagcagctga tctgtgcaaa tgaaaatggt gactgtgacc agtactgcag    8220
ggaccatgta gggaccaagc gtacctgtag ctgtcatgag gactacacgc tacagccaga    8280
tgaggtgtcc tgcaaaccaa aggtaatag actgtgggga ctggagctgt cttaggctct      8340
gaagaggcag tcacctgtgt gggcctgtgg caagttatca gctccatgat gtgtaacaag    8400
gtcagacctc tgcttatcaa gtacctggta gatgctgact gacttgaggt gaaagggtag    8460
agacttgaag gacacctgac ctgagagctg ttagtctgga accctgggcc agcatcctgc    8520
actgcctcaa gtatcctgac cattgaagcc ggccaggagt ggatgaggag gtcctacacc    8580
aactcttatg tcccacttag agtctctgag acataatcgg gagtcacata ggcacacctg    8640
gcatctgtat ccactgctgc agttaacaac ataagatgac ctattattat tattattatt    8700
attattatta ttattatatg catgtgggca gtattacaga tgatgacagt cctgaaggga    8760
tcagagaatg tcagctcccc tgggcactga cgttacaggc agttgtgagc tgcttgttgt    8820
gggtgctggg atccactctt gcccctgct ctgaaaacat atctccacaa gaagactatt     8880
cgagctctgc ttccgaaggc ggaggcttcc ccggaagagg atgggctca gtctgtctca     8940 tgaagctgga aagttggaag cccacagctc agtgttcttt cttacccgaa gccttcgcag    9000
tgggtggcgc ccgagtctgc cttaaggacc ctgtcttcct gtgctggtgg cccatgctta    9060
cacagatcgt cactttcttc atagcgaacc agaacgacac gttctccctg tgaggctctg    9120
gcagacccca gctctagaaa gcaggtcctc agctgtcccc acaccgttgt ctgcctcctc    9180
tcctagccgc tgcacaaggc cctccctgcc cactctagaa gtaagcccca agttcctctg    9240
tcctgaggcc tctcactgcc cccagcagga gccatggcag cagccaactg cttctcatcc    9300
cacagtcacc ttcgcctctg caccctgctc tctctgactt ctgtttcata cagttgagta    9360
cccgtgtggg agaatacctg ttgtagaaaa aagaaactcc agcagccgcc aaggccgcat    9420
tgtgggaggc aacgtgtgcc ccaaagggga gtgtccatgg caggtaatgc tctccgtcca    9480
gggaaaacct ctctctccag ctccggctcc cctgacatta gggtttctac tctgggtat     9540 ggaagttttg agttgggtta catttataca gaagagacat gggccagcct ccatccccct    9600 atccctccc ccacactctt gtccagaaa agggaaagaa agcaggtatt ggggcccatc      9660
ccatgaaaac ccatgccagg cccacagttg ccttgcacaa gtcacttgaa gagctgtagt    9720
tgcacctcat catccatgca ccccacccctt ctgcaccccct gttgtctacc agagccagca   9780
gatctagggc tgctctaccc tgctggggga atccccaaag ggatggtggg caggaattgt    9840
gtcaagtcag ctgcttcctt gggggcaagg agaccataaa agtagcatgg ctctctttgt    9900
ctgtgtgccc ccgcccaggc tgtgctgaaa atcaatgggt tattgctgtg tggggccgtc    9960
ctgctggacg ccagatggat agtgaccgca gcccactgct tcgataatat ccgctactgg    10020
ggaaacatca cagtggtgat gggtaggtat ggccatccc tggcctctgg cctgagggca     10080
ttttcagatt aagattggct cagaggctga gagccaatgg cctgacaatg tctctaacca    10140
ggtgatatct tcaagagtgg cactggagat gaccccacttg tcctctgggc cccctcctg    10200 tcagagaata ggaaactggg gggctactct gtccaccttg ccctactcag attgggtgtc    10260
```

```
aaggacccca ttcactcctg caggctctgc ccattcacaa ccttccctcc agaactgcag   10320
tggaccctgg gccaggcttc tcctgagacc ctggcaagga gtcaaatcct cagacaccag   10380
aggctgaact gaccacagcc ctatccacat actctaggtt agagaagcaa gacaaacaag   10440
agctctgtgt ggggacatgg ccacacatgg taggatacgt gccatgagac atggtaggat   10500
atgtgccatg aggcatggta ggatatgtgc catgaggcat ggtaggatat gtgccatgag   10560
gcatggtagg atatgtgcca tgaggcatgg taggatatgt gccatgaggc atggtaggat   10620
acgtgccatg aggcatggta ggatatgtgc catgagtggc gtggtaggat atgtgccatg   10680
agtggcgtgg tgtcctccca ggtgaacatg acttcagtga aaggatgggg gatgagcaag   10740
tacgacgggt gacacaggtc atcatgcccg acaagtacat ccgcggcaag atcaaccacg   10800
acattgccct gctccgcctt caccggcctg tgaccttcac tgactacgtg gtgcccctgt   10860
gtctgcctga aaagtccttc tccgagaaca ccctagccag aatccgcttc tcaagggtca   10920
gtggctgggg ccagctactg gaccgtggtg ccacagccct ggaactcatg tccatcgagg   10980
tgccccggct gatgacccag gactgtctgg agcacgccaa gcacagctct aacacccca   11040 aaatcacaga gaacatgttc tgcgctggct acatggatgg taccaaggac gcctgcaagg   11100
gtgacagcgg tggcccacat gccacgcact accatgcac atggtatctg acaggtgtgg   11160
tcagctgggg ggagggctgt gcagctattg gtcacattgg ggtgtacacc agggtctccc   11220
agtacataga ctggctggtc agacacatgg actccaagct ccaggttggg gttttccgac   11280
tcccactact gtagctcctt ggatagccca acccgtccca agaaggaagc tacggcctgt   11340
gaagctgttc tatggacttt cctgctattc ttgtgtaagg gaagagaatg agataaagag   11400
agagtgaaga aagcagaggg ggaggtaaat gagagaggct gggaaggggg aaacagaaag   11460
cagggccggg ggaagagtct aagttagaga ctcacaaaga aactcaagag gggctgggca   11520
gtgcagtcac agtcaggcag ctgaggggca gggtgtccct gagggaggcg aggctcaggc   11580
cttgctcccg tctccccgta gctgcctcct gtctgcatgc attcggtctg cagtactaca   11640
cagtaggtat gcacatgagc acgtaggaca cgtgaatgtg ccgcatgcat gtgcgtgcct   11700
gtgtgtccat cattggcact gttgctcact tgtgcttcct gtgagcaccc tgtcttggtt   11760
tcaattaaat gagaaacatg gtctccacgt gtagggtcat gcttccgggt tgcctaaggg   11820
agtgtttctg aagtacagtg tgcacccctg ccatggactg tttccccctg gcagggaccg   11880
gctgatttca gcacaccttg gggataccctg ctgttaccct gggttgtcct taagtccctg   11940
agtggagcct ctgatgtcaa gtcacataca catcggcggg gctgctcttc ctgggaaaag   12000
gaaggggaag gtggactaga gtcaaagagt aagctgagag ggcttgatca agtgcgtcat   12060
ggccttagtt tccccaatca ctagtaggta ggcaggcatc catctcacag agccaatctg   12120
agttgccacc aagggcccctt gggaggcctt actgagaatc tagctccctg aagactgacg   12180
tgctcagtat gggttgtgct tattctccag tcagcatgtc ctttctgggg gtggggccat   12240
agagagggga ggcgacaaag ggaggacccc ctcaagccag ctttagtgtt tgtccctagt   12300
cccagaccac aggtctgctg tgagtacctc acagactcag tgtaggctca gtgacacagt   12360
acacgggcat catcaggcag ggcagcgatc aggcaccaga ctcctgccaa cagccaccag   12420
agcaccgcgc acatttccca agttctgtta tgtctgccac agcctaggaa atgacagtga   12480
cttccctcct ggtgagatgc cagcatcagc ctcaacatct gatgtcacgg gtgtgtgtgt   12540
ttgtcaggta cccacagcac gccaaggccc tctcagcact ggtaacagtg ataagccaag   12600
tgtcatcacc gtactctctg gctacgtgca tgcagccaca gtcatgagcc attgcctaac   12660
```

```
caaactccag tacagtgagc atgagaagcc tattgctgct cactaattag caggcatggt   12720
gcgcatgctc cgcagactca aaatagctc tgccagatga agctttgaag gaggaagggc   12780
tcagcatgta aaggtggag tcagggtgag cactgcctcc tcacaggcca aagttaggga   12840 gtttgttgt tgttgctgct gggactgctc ctgcagttct ctaggacac cggagcatgg    12900 gcctgtagcc ccaattacat gtacacacac actctcagaa gagtcaaatg gccacagcat  12960
gtgagaggag ctgtttccac atctatagct ctcagatggc t                      13001
```

<210> SEQ ID NO 161
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 161

```
ccatagaaca gcttcacagg                                                 20
```

<210> SEQ ID NO 162
<211> LENGTH: 15001
<212> TYPE: DNA
<213> ORGANISM: Macaca mulatta
<220> FEATURE:
<221> NAME/KEY: misc_feature
<222> LOCATION: (3049)...(4102)
<223> OTHER INFORMATION: n = A,T,C or G

<400> SEQUENCE: 162

```
tcaaaacaga gtggggctgc ccagctcagg gccagaatga tcctattccc agcacttctc    60
agtcaggctc tgtggctcaa ctaagaaacc ggcctcccett gcagacaatg gcctagctgg   120
cctggtctcc tggaggctct cttcaaatat ttacatccac acccaagata tgctctccag   180
aattgactcg cattattgct atgggccaag ttttcatctg cagtttaaat ctgtttccca   240
acctacgttc ctatgtccta ggggtttgga attctagatc gtatttgaag tgttggtgtc   300
acacacacac cttaacacct gcacgctggc aacaaaacca tccgctttgc agcacaactg   360
gggccgcctg acctttctcc tgtcctccct gcttgagctc agcagctggg cagcagggga   420
tgcatggcca ctggccggcc aggtgcagct ctcagctggg gtgttcagag gacgcctctg   480
tccccccctc ccccatccct ctgtcgccct tggaggcaga aactttgcc cgccagtccc    540 atgcggaatg tcaacaggca gaggcagcgc tgcagagatt tcatcatggt ctctcgagcc   600
ctcgggctcc tctgccttct gcttgggctt cagggctgtc tggctgcagg tgcgtccggg   660
gagattttcc ccataaactt ggtggaaggg cagtgggcaa atccaggagc cgacccgggc   720
ttcccaaacc gtccttgctc tggacacccc cattccaccag gagggttttc tggtggctcc   780
tgttcaattg ttttccttcc agaaaccagc atccaggcac aggaggggag gcccttctta   840
gtagcccagg cttggtggg attatttttc aaagaacttt aggagtgggt ggtgctttct    900
tggcccccat gggcccctgc ctgttaggtt ggacaagcac agggagtcgg gggcctctca    960
gagtatggga ggtgctcaca ggctgctccc aggctgggga ggacaagtgt gtgggggatg   1020
gtgcctgggg catgggggat ggggtgtgga ggatgggggt tggggatggc atgtggggtg   1080
tggaggatgg gccatgaggg ggtgggtcct gggaaacggt atgtggggta tgagggatgg   1140 ggcgtgggggt gcgggagggg gtgtgggaa agtgtgtggg gtgtgggga tgggatgtgg    1200 gaagtggcat gtggagtgca aggaatgggg catggaggtg ttgagcatgg ggtgtgtcgg   1260
```

```
gtgtgtgggg tgtgggggag ggggaatgga aagggtgtgt ggtgtgtggg ggatggggtg    1320 agggatggc gtgggaggtg gggcatgggg atggcaggtg tggcgtgggg atggcgagta    1380
gggggtgggg cgtggggatg gtgactgtgg ggtggggatg gcgagtgggg ctggggcctg    1440
ggaatggtga gtggggtggg gatggcgagt acagggtgtg gcatggggat ggcgaatggg    1500
gcatgaggat ggcgtgtggg gatggcgagc aggggggtgg gctgtgaggg acagtgcctg    1560
agatgtgggg ctgcagcccc agctcacaca tggccttatg accccagcca ccttcctgcc    1620
ccaggcgggg tcgctgaggc tcaggagga gaaaacacag gacctgctgt ggaagccagg    1680
gcctcacaga ggtgagcagg gactgccact ggtttagtcc cggggcccag tgggggccaa    1740
catcacctcc ttggcctccc atggcaagga gccagcccgc ggggtggcta ctgcactgcc    1800
ccccaaggag ggtgttccct gctcaagagg aagtgaccgc tccagttcag ccttccctgg    1860
gactggggtg caggtgacct tatcttcttt gttaaatcct gttccttcca gacaatcctg    1920
tgttattcat caggtttgcc tcagttcttg agagcttttc tgatgcaaat ctgctttcat    1980
cccagggcgg taggggctca gctcacgcca gcctccaggg gtgtgggtgt cctagaagtg    2040
tgggtgtccc gggggcgtgg gtgtccctgg agtgtgggtg tcctggggc atgggtgtcc    2100 cagagcgtgg gtgtccctgg agtgtgggtg tcccaggggc gtgggtgtcc cggaggcatg    2160
ggtgtcccgg ggcgtgggtg tcccggggcg tgggtgtccc aggggcgtgg gtgtcccgga    2220
agtgtgggtg tcccggggcg tgggtggctt ggggcatgg gtgtcccggg ggcgtgggtg    2280
gcttgggggc gtgggtgtcc cggggtgtg ggtgtcccgg gagcgggtgt cccgggagtg    2340
tgagtgtcct gggggtgtgg gtgtcccggg agtgtgagtg tcccaggggc ctggatgtcg    2400
ggggactgca gggacaccct tcccactcct gctgcccggg gcacctcccc tgaggactcc    2460
gcctccaaga gctcccacct cctggattct ttggtgaccc ccgcctgcat cctcagcctc    2520
cttccaaacc agaccggttc tctagggacg tggacgtgtg aaactgattt taaaggaaac    2580
agacggtggc gtttctctgg gccccacgtg gcccagtagc gcccaccttc cgtcccttct    2640
tccgcgctca gtaaccgatt taggccgctc ctgcagaact cgggctcctg cccacctacc    2700
acctgcgtcc acctgaggcc tcgtcctccc agcaaaggtc gtccctcccg aacgcgcctc    2760
ctgcggcctc tccagagccc ctcccgcgcg tcctctcggc ctcctcccgg gcctccctct    2820
cccgcctgcc ccacggcccg gccagtctcc cctcgcgggc tgaggcgggt tcaggcagcg    2880
cggccgcccc gggggtcact cctcgtccac caccgcgtgg tgcccacagc tcacagctcc    2940
cgggagacgg tccctcagc tgcagggcgt cctgaagaac ggcctgctca gagctgagcg    3000
cacgggcttg cctcgccctg ggcgcccttg gccctcgccg accccgttnn nnnnnnnnn    3060 nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnn nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn nnnnnnnnnn nnnnnnnnnn nnnnnnnnnn nnnnnnnnnn    3600
nnnnnnnnnn nnnnnnnnnn nnnnnnnnnn nnnnnnnnnn nnnnnnnnnn nnnnnnnnnn    3660
```

| | |
|---|---|
| nnnnnnnnnn nnnnnnnnnn nnnnnnnnnn nnnnnnnnnn nnnnnnnnnn nnnnnnnnnn | 3720 |
| nnnnnnnnnn nnnnnnnnnn nnnnnnnnnn nnnnnnnnnn nnnnnnnnnn nnnnnnnnnn | 3780 |
| nnnnnnnnnn nnnnnnnnnn nnnnnnnnnn nnnnnnnnnn nnnnnnnnnn nnnnnnnnnn | 3840 |
| nnnnnnnnnn nnnnnnnnnn nnnnnnnnnn nnnnnnnnnn nnnnnnnnnn nnnnnnnnnn | 3900 |
| nnnnnnnnnn nnnnnnnnnn nnnnnnnnnn nnnnnnnnnn nnnnnnnnnn nnnnnnnnnn | 3960 |
| nnnnnnnnnn nnnnnnnnnn nnnnnnnnnn nnnnnnnnnn nnnnnnnnnn nnnnnnnnnn | 4020 |
| nnnnnnnnnn nnnnnnnnnn nnnnnnnnnn nnnnnnnnnn nnnnnnnnnn nnnnnnnnnn | 4080 |
| nnnnnnnnnn nnnnnnnnnn nnaccctacc aggcacacgc tctccctacg cggccactcc | 4140 |
| gcgcatgccg gttttcacat cagaaaatac gatttgaaaa gcacacttag ggtgtcccc | 4200 |
| ttaacttcct aagggaggcc ccccaatccc ataaggatcc ggggcagtct gcgcatcacg | 4260 |
| gatgcgcggc tcacagaagg acgtggtga gaagctggcc tggggagct gctcgcggcc | 4320 |
| cacaccatgc caccagcggc acctccgcag ggcacatgtc ggggagaaaa aacatgtggg | 4380 |
| gacctggggc tttctccacc tcacactcac gggtcacctc acacaggaca cctcacactc | 4440 |
| agggtgcact tcaaactcac aggtcattac acctcacaca ggacgcctca cacaagacac | 4500 |
| ctcacatggt gcacttcaca ctcacaggtc acctcacatt cgacacctca cactgagcac | 4560 |
| acttcacact cgggacacct cacactcagg gtgcacttca aactcacagg tcattacacc | 4620 |
| tcacacagga cgcctcacac aagacacctc acagggca cacttcacac tcacgggtca | 4680 |
| cctcacattc gacacctaac acagatcacc tcactcagag gacacctcac actgggcaca | 4740 |
| cttcacactc aggacacctc acactcaggg tgcacttcag actcacaggt catgacacct | 4800 |
| cacacagatc acctcactct tataggacac ttcacactca cagatcacct cactctcaca | 4860 |
| ggacacttcg gacaggacac acttcacaca ggccacctca ggttatgtca aactcacagg | 4920 |
| tccctcaca cagtcacctc acacagtgta cacttcacac tcacaggtcc cctcacacag | 4980 |
| gtcacctcac acagtcacct cacacagtgt acacttcaca ctcacaggtc ccctcacaca | 5040 |
| ggacacctca cacagtcacc tcacacagt cacacttcac acaggtcccc tcacacagtc | 5100 |
| acctcacaca caggcacac ttcacactca caggtcccct cacacaggtc acctcacaca | 5160 |
| agatgcactt cacactcatg ggtcccatca cacacaggac acctcacact cgtcacctca | 5220 |
| cacatgttac atcaaactct caggtcccct cacacagtca cctcacacac agggcacact | 5280 |
| tcacattcgc aggtcacctc acaccaggcc cacgactctc acaggtcacc cacctcaca | 5340 |
| cacatcagct cacatagatc atctcaccct cacaggacat ccatcacact caccaggtcac | 5400 |
| gtcacactca tacctcaccc acaggtcacc tcacacaaat caccttgctc acacagatca | 5460 |
| cctcacacgc agggcacact tcacactcac aggttccctc acacaggaca cctcacactc | 5520 |
| acagatcacc tcaacaccga tcacctcaca caggggacac ttcattctca caggtcacct | 5580 |
| cacataggac atctcacaca caggtcacct cactcacaga tcacttcaca cagggcacac | 5640 |
| ttcactcaca gatcacacct cacctcccgc tcacagatca cctcactctc acagggcacc | 5700 |
| tcactctcac aggacacctc atacagggca cacttcactc ccacaggtca ccatacctca | 5760 |
| cacagatcag atcacttcat tctcacagga tacctcacac tcagggcaca cttcacactc | 5820 |
| acaggtcacc tcacacaagg cacccttcac acaggtcacc acacctcaca cagatcatct | 5880 |
| cactctcaca ggacccctca cactcagatt atctcacact caggtcacca cacctcacac | 5940 |
| tcttaggatg tctcacgcag gatgcctcac agtcacagag aaccacatct catatgcaca | 6000 |

```
agacacttca cattcacagg acacctcatg ctcacaggaa gcctcacact cacaggaagt    6060
ccagctgtct gagacaaagg ctaacatgac cctttccggg caaattgagg atggtcatgc    6120
ctagcatttt tatccaccta gttttcaaag catttctcat ctgttgtatt ctcacagcac    6180
cctgtgagtt taagtttagg tggccaacag tttcttcagc aatcactttt ttctgtggag    6240
tgcttttgct gtttgtggaa gattttgcat ctgctactgc accctctccc ggtgtcagcc    6300
ggtgtgtgtg gccaccctgt cagagatgga gctgtggctc aaagcctgtg tacctcatcc    6360
caggtccaca gctcagcgac agaagagtca gggctgaacc tcgggtgttc tgacctggga    6420
gcaggaaatg tgtggtcacc catagtttca gaagtcctgg ggaggggcca agattggaag    6480
aaatctacct cagctctgca ggaaagtctg gcttcctgag cccaccccgc caggcccagg    6540
tccaagttcc ccaaccccag ctcgtggttt gtccagtgct caccgttggg tgcactggtg    6600
aaggtgctca cgaggctttc tcttttgttc cctcagaagc tgttctggat ttcttacagt    6660
ggtgagtaga tgatcgccac caatcctgcc tgcaacccct ctcctcagcg tactgacgcc    6720
agcccattcc acagatgggg accagtgtgc ctcaaatccg tgccagaatg ggggctcctg    6780
caaggaccag ctccagtcct atatctgctt ctgcctccct tccttcgagg gccggaactg    6840
tgagaagagt gaggccccac tttgggtccc atatttgcag agggcctggc caaccgggtt    6900
gcagggtgca caacctggtg gggtgtgtgg accgggcatt ctgagctcag ccccagttgg    6960
aatttggtct aggtgacctt gaagtccctt ctagtctgag gtctttgaca gggacccaag    7020
gttctaattc tcagactcag tggccccttg ggctcccggc cctgggcaat tctcagccct    7080
cgagatggcc cagctgagag tccctgtgtc cctgtcccac ttccacgtcc caccaggcag    7140
caccgcttgg taaacttccc cttctctact ttccattaca aaggtttgag gtgttttttg    7200
ttttgtttgt ttgtttttgg ttttgttttg ttttgtttac catctgaata ttaaattatt    7260
gcaaagtttg aggcccccaa cttcccttag gttcagtaat tcactagaag gactcataga    7320
acccactgaa gtggatacac tcacagttac catttattac agcaaaggaa gctgacttaa    7380
gtctgcagag gaaccgggca caaacttccc attgtcccct ccctgtgggg tcatgtggac    7440
acttctccca gaaagacgtg tgatgagacg tgggaagtac tgccaacttg gaagctcta    7500 tgagccccgg tgtccagagg ttttatcagg gctcaatcac acagacccag ctgaccaccc    7560
acacggctga cctcagtctc agcccctcca gaggccaagc caatagtgtg cccgaggcc    7620 ctgccatcat cacattgtca gctagaccat ccagcatggc ccaaggtccg ggtaaacacc    7680
aacattccct cagggcttag cgatcacttc ccaggaaatg tgtggtcacc cttccaaggg    7740
cttagcgatc acttcccagg aaatgtgtgg tcacccttcc aagggcttag cgatcacttc    7800
ccaggaaatg tgtggtcacc cttccaaggg cttagtgatc acttcccagg agccaaggca    7860
aaggctaccc tttccctggg aacagcagct catccttgac cacccaaggt ggttcattct    7920
cacactgaac gagctctccg gcacagcagc cactttcttc tctaagtaga agagagccca    7980
gcaaggtggg gcaggctgaa gagagaggct tcctgctggt catctgggtc cagaatgcct    8040
ggggatctct gctcagccct ggtgcccagc agccctggtg tgcatcctgc agggcaggcc    8100
ttcccgccgg agtcctggac ttactcaggg ccactgccct tgcccacatc aatcaaagtc    8160
gggctgccgg ttctgctgct tctgtctgag cccatggcca gtgctgggac tgactgtccc    8220
taggcgggct cgcggtggca tgaggccagc ttggagaact gtctcagcgc tctggtcctc    8280
tcgtcagttg agtctctgat tggaagtccc ttggatactt ttaccatccc tacgggactt    8340
tcactttccc ccaggctccc ctcagcttcc catcagctgc tcggaagagt ggtcaccctg    8400
```

```
gaggccactg cccaccagcc aggcaccccc ccaaatgcaa ctgcagccag cgctgccccc   8460
gactggcaag gctgttcaga cgtgactcct ctgatccagg ccttgtcctt tggatcagtc   8520
cacggagcag gcggtgccaa gctcaggctc tgtcgcccac agctcagtgc cccttccagg   8580
cagaacgccg ctgctgactt agggcatggc atccccgggg gctggctctc actgaccaa    8640 agaggcccct ctcagggtat ccccttcctg tccgcagaca aggatgacca gctgatctgc   8700
gtgaacgaga cgcgcggctg tgagcagtac tgcagtgacc acgcgggtgc caagcgctcc   8760
tgttggtgcc acgaggggta ctcgctgctg gcagacgggg tgtcctgcat gcccacaggt   8820
gaccaggctt catgtcccag tcccagatga caccagtccc tgtcccacta cggattctct   8880
tactggacaa agacgggtg ggggtggctt cacatctgag caccaaccat gcgctgacca    8940
accgtgaggc aggatctggg caccaagggt ggcacaggcc agagcgacag tgactaggat   9000
gggcaccctg ggggcagtcc ctgaatggcc tcaggccccc tacccatgct aggcagacca   9060
ggggagccaa gcaaggctct atctcacgtc caactcccac tcgcaggacc tccgctgggg   9120
ttcgtgaatc taccttggca caggcagtgt ctgtactgac tgctgcccgc tctgaattcc   9180
aaaacttgta aaggctcctg ggaaaatggg atgtttctcc aaaccagcct ggaacaaatg   9240
ggctgcactt ccaaaggcag ggacacccca cgcccactgt gtctcgaaga ggtggacgtg   9300
cccaccctgg ccacacagcc tgggactcag cccaccacct cctcaggttt tctttctggc   9360
ccacgacctt gattggagca gatcaaaact aagcgtggga tcaaaacaac agagttgttt   9420
gtgacgttga ttcatcttta ggtagaattt cattcacctt ttactaaagt caagcaacac   9480
attttccccc tgaaaagtga gcagagggca atattaagac gtaagccctc catctcctcc   9540
aaaaccagcc ctgaccattg tctcctcagc cagccacttc cgcaagggcc tctcatggcc   9600
cagccccacc agtcaggccc agccccacca gtcaggccca gccgaggccc tgctttccac   9660
catccctggg ccctggcagc tcctgctcct gggggcctcc catagcctcg gcctcaaggc   9720
ctctcagagg atgggtgttt ctgaatcttt cctagtggct cgttcatcct tcacaaattt   9780
ctgcatcttt ctgactttg ttttacacag ttgaatatcc atgtggaaaa atacctattc     9840
tggaaaaaag aaatgccagc aaaccccaag gccgaattgt cggggcagg gtgtgcccca    9900 aaggggagtg tccatggcag gtaaggcttc ccttggcttc aggattctaa gccctgaggg   9960
tcttggagcc ttttgaatgt gagctgaaca acagttctgg aagggaaaat gggcaggtca  10020
gccccaaggc caccaggctc caagtcagcc cacctagaac ctctagctcg ctgcaccccc  10080
atgctttcag tggggcaagg aaggagaaaa gaaggcgaca ctcgctgagg gtctaccctg  10140
tgcagagaac cctgcgagat gcccctcccg agttgtcacg tcgtcctcac tgttactctt  10200
tgaggtggga tctttgcctg atctttgcaa aatcaggagc attggatcaa agctatgtga  10260
agatcccgtg aggtgaacag tgaaatctca cagcgacgtt tgtattgttg ggctgtgccc  10320
aagagcacgt ctcggctaga gaggggcgca gcctcccaga gccaggtctg agcagctttg  10380
cctgggaggg atctgcaaag accccaggat ttcagaaaca aattgtgcaa tgccagaggt  10440
cccttggcgt gccgggagg gcgagtcatc agagaaacaa tgacagtaat gtgacttcca    10500
tgcctcctgt cccccgccc aggtcctgtt gttggtgaat ggagctcagc tgtgtggagg    10560
gaccctgata aacaccatct gggtggtctc tgcggcccac tgtttcgaca aaatcaagag  10620
ctggaggaac ttgaccgcgg tgctgggtag gtgccgctct ccctgtgtg accgcggtgc    10680 tgggtaggtg ccgctctccc ctgtgtgacc gcggtgctgg gtaggtacca ctctcctctg  10740
```

```
accgcgttgc tgggtgggta ctgctctccc atctgactgc tgtgctggtt acgcgccgtt   10800
ctcccgtctg acgatggtgc tgagtaggcg ccactctccc ctgtctgacc acggctctca   10860
agtgtctcag gggccgcagc tctgggcttc gtgctgtcac ttccacagac agacagacat   10920
ctccaaaagg ggagcaactg tgctaggcat gactgctgtg ccaccgtcc tctcagccac    10980 tttcccatgc ccaaataaaa tggtaaaaga caggggttct gcccatcctg cctcacctgg   11040
ccaagagccc ataggaggat gcaacttcca gggcttcatg ggaccactgg gtggcaggga   11100
ctgtgctcac tgggtttaca ggtgagatga acattcccag gagggcactt ggctgggaag   11160
aactgtggag aatcagggca cccctgccc cccagctgc caggtcgcag cacccccttcc    11220 ccacctcaac gcccaggccc cagattcacc ccagttcaca cgtccccatg tgagccacag   11280
gctgccacct gcggcaggct ggccaggtca ccttggggtt ggatgcaggc cccctcacc    11340 ccaaaaggag actgcagccc ctgcagacct agaaatggcc acagcccgtc cccatgcacc   11400
agggggccag gcagcaggta gtgggatggg cctgagcaag gctccctcct tccaggcgag   11460
cacgacctca gcgagcacga aggggatgag cagagccggc gggtgcgca ggtcatcatc    11520 cccagcacgt atgtcctggg cgccaccaac cacgacatcg cgctgctccg cctgcagcag   11580
cccgtggtcc tcactgacca tgtggtgccc ctctgcctgc ccgaacggac gttctccgag   11640
aggacgctgg ccttcgtgcg cttctcgttg gtcagcggct ggggtcagct gctggaccgt   11700
ggtgccacag ccctggagct catggccctc aacgtgcccc ggctgatgac ccaggactgc   11760
ctgcagcagt cacagaaggc agaagcctcc ccgaatatca cggagtacat gttctgtgcc   11820
ggctactcgg acggcagcag ggactcctgc aaggggggaca gtggaggccc acacgccacc   11880
cgctaccggg gcacgtggta cctgacaggc atcgtcagct ggggccaggg ctgcgcggcc   11940
gtgggccact cggggtgta caccagggtc tcccagtaca tcgagtggct gcaaaagctc   12000
atgcactcag agccacgccc aggcgtcctc ctgcgagccc catttcccta gcctagcagc   12060 cctgcccct ggagagaaag ccaaggctgt gtagaactgt tctggcacaa aatcccatcg    12120
attcttctgc agttcatggg gtagaggagg gcatgggagg gagggagagg tggggaggga   12180
gacagagaca gaaacagaga gacaaagaga caggagaga ctgagggaga ggttctgagg    12240
acatggagag actcaaagag actccaagat tcaaagagcc taatagagac acagagaagg   12300
aatcgaaaag atgagatgca gaggcagaca ggcgctggac agaggggcag gggaatgctg   12360
cggttgtcct ggaggcagac agcccagctg agcctcctta tctctcttca gccaagccca   12420 cctgccgtg atctgctggc ctcaggctgc tgttctgcct tcattgctgg agacactaga    12480
ggcatgtaca cacgtggatg catacacaca caccaatgca cacacacaga gatatgcaca   12540 cacacgatg cacacacaga gggtcacaca gagatatgca aacacactga cacacacata    12600
cagagatatg cacatacaca gatgcatata cacagatatg cgcacacacg gatgcgtgca   12660
caccacacca atgcacacac acactaatgc acccacacgg atgcagagag atatgcacac   12720
accgatgtgc acatacacag atatgcacac acatggatga gtgcacacac accaatgtac   12780
acacacagat atgcacacac ggatgcacac acaccgatgc tgactccatg tgtgctgtcc   12840
tccaaaggcg gttgtttagc tctcactttt ctcgttctta tccattatca tcttcatttc   12900
agacaattca gaagcatcac catgcatgtt ggcaaatgcc ccaaactctc ccccaaatgt   12960
gccgggctgc acaggccgtt ccccaccggc ttcccaactt cacaataaat ggctgcatct   13020
cctccgcacg cctgtgggc ctgccaccca ccgtgtagcc tgtgattcat tttcagagcc    13080
tccagtgctc atcctctgag atgcttttt ctttcacagt tttcagcatc actgaaatga    13140
```

```
acctcacat ggcagctgtt cttttaaaa acaaaagctc tttgatagat gtttgaggct    13200
gtagctccca ggaccctgtg gaattggttg ttctctccct gccacagccc ttgtcaatga    13260
tatttcgcag agaccctggg agcacctgct tgagaatcag ggacatacca ctaaatgcag    13320
gttcccaggc cctggctgca gtgggaggac ctggcaagct gcactcttgc tgagtcccca    13380
gggtggtggg ggaagaatga gaaacacatg agcagagaaa tggggaggtg acagacactg    13440
cccgcactca gactccagca agcatggctc agagagcgga ctcaacgcca tccctgtagg    13500
gccgtcctgg gcaccagtgg cgctcacagc agcaaggcag gcaccagcaa cccacctcgg    13560
gggcactcag gcaacatcta ctttagagca gacagggtcc gtgaactaca gctgagggct    13620
gcttctaagc cacccggctc ttgtaaataa agttttatgg gaacacaccc acgttagtgt    13680
ccatggagtg gccgtgacag agatgtctag ccagacagac cagctgacct gccaagccca    13740
gcatgattag tgtcaggacc tctgccgaag atgctggctg accctggcca gaccccagtt    13800
cctaatgccc ccacacaggg acgggggcca gtggcgggcc ctgatcaggt cagagctggc    13860
tctgctttct cttttgtccg agtgactggg gagtcatgcg gggtcctggt ggggtgccag    13920
cctcccttct tgccaatggg aaatgcaggc acccacctca cggtgctgct gaaggagggg    13980
gcccgggact ctccagaaac tttgctgaag ggcctgggca ccctcgaagg ctacatttct    14040
tatgggacgt gccacctgcc atggctcagc tccagctttc tgtgagtggc gagatagaat    14100
acagggaggc cactggccat gggcctgcga cagggtgggg cgaggcagca ggctcgggcc    14160
tccaaagcca gcatcaccac ccagcgttga tgaaaaagac tgcatgtctg ccatgagcat    14220
cctgctgctg gtgcacacac cacattggtc tctccataca aacgtgccta gaggcgatgt    14280
cggagtgtgg agaccacgag aggcaggagt cagacatctg gtgccaccag gaaggcccct    14340
ctcagaggac tgggctgtgc gtggtgccca ccgtgggagg ctaccctggc gttggcaccc    14400
agtgccatca gtttgtgtag tcgggtgggg cccagtgagc acctcctgtg tgccaggcac    14460
aatgacgcac aatgtgtgca caccaggccc aggtgcaggt ggctgcgaga cgggcaacac    14520
atcaaggcag acacaccgtg aggcagtggc cagcactgtg ggttttaggg gcgttgctcc    14580
ggccactacg gcatagcagg tagtgattgc cacactggcc aagttttaga ccatttattc    14640
cagggacccc agaagcaaaa atcctggctg cacctcccgg tgactccac agccattgag    14700
tggagacgct cagggacctg gtgacaggag gtttctgtgc tggacaatga gcccagaagc    14760
cctctcagcc ttggaacagt gtggccagtg gtgggcaggt caggaggggt ttcagacaga    14820
gcctgtccct ccagatggtc aggggagggc tactccccac agaagtacat gttgggacca    14880
tgtgggcaca gaaggtttgg gggtgggtgg ggcaggtacc agcctggcct gtgggagacc    14940
gtggtgcaga tgccaagccc ccccgtgaca tcagaccacc tgacaccacc cagagaatgg    15000
c                                                                     15001
```

<210> SEQ ID NO 163
<211> LENGTH: 3068
<212> TYPE: DNA
<213> ORGANISM: Macaca mulatta
<220> FEATURE:
<221> NAME/KEY: misc_feature
<222> LOCATION: (182)...(342)
<223> OTHER INFORMATION: n = A,T,C or G

<400> SEQUENCE: 163

```
agtcccatgc ggaatgtcaa caggcagagg cagcgctgca gagatttcat catggtctct    60
```

```
cgagccctcg ggctcctctg ccttctgctt gggcttcagg gctgtctggc tgcaggcggg      120
gtcgctgagg cctcaggagg agaaacacag gacctgctgt ggaagccagg gcctcacaga      180
gnnnnnnnnn nnnnnnnnnn nnnnnnnnnn nnnnnnnnnn nnnnnnnnnn nnnnnnnnnn      240
nnnnnnnnnn nnnnnnnnnn nnnnnnnnnn nnnnnnnnnn nnnnnnnnnn nnnnnnnnnn      300
nnnnnnnnnn nnnnnnnnnn nnnnnnnnnn nnnnnnnnnn nnaagctgtt ctggatttct      360
tacagtgatg gggaccagtg tgcctcaaat ccgtgccaga atgggggctc ctgcaaggac      420
cagctccagt cctatatctg cttctgcctc ccttccttcg agggccggaa ctgtgagaag      480
aacaaggatg accagctgat ctgcgtgaac gagaacggcg gctgtgagca gtactgcagt      540
gaccacgcgg gtgccaagcg ctcctgttgg tgccacgagg ggtactcgct gctggcagac      600
ggggtgtcct gcatgccacc agttgaatat ccatgtggaa aaataccat tctggaaaaa      660
agaaatgcca gcaaacccca aggccgaatt gtcggggca gggtgtgccc caaggggag       720
tgtccatggc aggtcctgtt gttggtgaat ggagctcagc tgtgtggagg gaccctgata      780
aacaccatct gggtggtctc tgcggcccac tgtttcgaca aaatcaagag ctggaggaac      840
ttgaccgcgg tgctgggcga gcacgacctc agcgagcacg aaggggatga gcagagccgg      900
cgggtggcgc aggtcatcat ccccagcacg tatgtcctgg gcgccaccaa ccacgacatc      960
gcgctgctcc gcctgcagca gcccgtggtc tcactgacc atgtggtgcc cctctgcctg     1020
cccgaacgga cgttctccga gaggacgctg gccttcgtgc gcttctcgtt ggtcagcggc     1080
tggggtcagc tgctggaccg tggtgccaca gccctggagc tcatggccct caacgtgccc     1140
cggctgatga cccaggactg cctgcagcag tcacagaagg cagaagcctc cccgaatatc     1200
acggagtaca tgttctgtgc cggctactcg gacggcagca gggactcctg caaggggac      1260
agtggaggcc cacacgccac ccgctaccgg ggcacgtggt acctgacagg catcgtcagc     1320
tggggccagg gctgcgcggc cgtgggccac ttcgggtgt acaccagggt ctcccagtac     1380
atcgagtggc tgcaaaagct catgcactca gagccacgcc caggcgtcct cctgcgagcc     1440
ccatttccct agcctagcag ccctgccccc tggagagaaa gccaaggctg tgtagaactg     1500
ttctggcaca aaatcccatc gattcttctg cagttcatgg ggtagaggag ggcatgggag     1560
ggagggagag gtggggaggg agacagagac agaaacagag agacaaagag acagggagag     1620
actgagggag aggttctgag gacatggaga gactcaaaga gactccaaga ttcaaagagc     1680
ctaatagaga cacagagaag gaatcgaaaa gatgagatgc agaggcagac aggcgctgga     1740
cagagggggca ggggaatgct gcggttgtcc tggaggcaga cagcccagct gagcctcctt     1800
atctctcttc agccaagccc acctgcccgt gatctgctgg cctcaggctg ctgttctgcc     1860
ttcattgctg gagacactag aggcatgtac acacgtggat gcatacacac acaccaatgc     1920
acacacacag agatatgcac acacacggat gcacacacag agggtcacac agagatatgc     1980
aaacacactg acacacacat acagagatat gcacatacac agatgcatat acacagatat     2040
gcgcacacac ggatgcgtgc acaccacacc aatgcacaca cacactaatg cacccacacg     2100
gatgcagaga gatatgcaca caccgatgtg cacatacaca gatatgcaca cacatggatg     2160
agtgcacaca caccaatgta cacacacaga tatgcacaca cggatgcaca cacaccgatg     2220
ctgactccat gtgtgctgtc ctccaaggc ggttgtttag ctctcactt tctcgttctt       2280
atccattatc atcttcattt cagacaattc agaagcatca ccatgcatgt tggcaaatgc     2340
cccaaactct ccccccaaatg tgccgggctg cacaggccgt tccccaccgg cttcccaact     2400
tcacaataaa tggctgcatc tcctccgcac gcctgtgggg cctgccaccc accgtgtagc     2460
```

```
ctgtgattca ttttcagagc ctccagtgct catcctctga gatgcttttt tctttcacag    2520
ttttcagcat cactgaaatg aaccctcaca tggcagctgt tcttttttaaa aacaaaagct   2580 ctttgataga tgtttgaggc tgtagctccc aggaccctgt ggaattggtt gttctctccc    2640
tgccacagcc cttgtcaatg atatttcgca gagaccctgg gagcacctgc ttgagaatca    2700
gggacatacc actaaatgca ggttcccagg ccctggctgc agtgggagga cctggcaagc    2760
tgcactcttg ctgagtcccc agggtggtgg gggaagaatg agaaacacat gagcagagaa    2820
atggggaggt gacagacact gcccgcactc agactccagc aagcatggct cagagagcgg    2880
actcaacgcc atccctgtag ggccgtcctg gcaccagtg gcgctcacag cagcaaggca     2940
ggcaccagca acccacctcg ggggcactca ggcaacatct actttagagc agacagggtc    3000
cgtgaactac agctgagggc tgcttctaag ccacccggct cttgtaaata aagttttatg    3060
ggaacaca                                                              3068

<210> SEQ ID NO 164
<211> LENGTH: 20
<212> TYPE: DNA
<213> ORGANISM: Artificial Sequence
<220> FEATURE:
<223> OTHER INFORMATION: Primer

<400> SEQUENCE: 164
gggaccctga tcaacaccat                                                   20

<210> SEQ ID NO 165
<211> LENGTH: 24
<212> TYPE: DNA
<213> ORGANISM: Artificial Sequence
<220> FEATURE:
<223> OTHER INFORMATION: Primer

<400> SEQUENCE: 165
ccagttcttg attttgtcga aaca                                              24

<210> SEQ ID NO 166
<211> LENGTH: 18
<212> TYPE: DNA
<213> ORGANISM: Artificial Sequence
<220> FEATURE:
<223> OTHER INFORMATION: Probe

<400> SEQUENCE: 166
tgggtggtct ccgcggcc                                                     18

<210> SEQ ID NO 167
<211> LENGTH: 3141
<212> TYPE: DNA
<213> ORGANISM: H. Sapiens

<400> SEQUENCE: 167
agtcccatgg ggaatgtcaa caggcagggg cagcactgca gagatttcat catggtctcc      60
caggccctca ggctcctctg ccttctgctt gggcttcagg gctgcctggc tgcaggcggg     120
gtcgctaagg cctcaggagg agaaacacg gacatgccgt ggaagccggg gcctcacaga      180
gtcttcgtaa cccaggagga agcccacggc gtcctgcacc ggcgccggcg cgccaacgcg     240
ttcctggagg agctgcggcc gggctccctg gagagggagt gcaaggagga gcagtgctcc     300
ttcgaggagg cccgggagat cttcaaggac gcggagagga cgaagctgtt ctggattct     360
```

```
tacagtgatg gggaccagtg tgcctcaagt ccatgccaga atgggggctc ctgcaaggac      420
cagctccagt cctatatctg cttctgcctc cctgccttcg agggccggaa ctgtgagacg      480
cacaaggatg accagctgat ctgtgtgaac gagaacggcg gctgtgagca gtactgcagt     540
gaccacacgg gcaccaagcg ctcctgtcgg tgccacgagg ggtactctct gctggcagac     600
ggggtgtcct gcacccccac agttgaatat ccatgtggaa aaataccctat tctagaaaaa    660
agaaatgcca gcaaacccca aggccgaatt gtgggggca aggtgtgccc caaaggggag      720
tgtccatggc aggtcctgtt gttggtgaat ggagctcagt tgtgtggggg gaccctgatc    780
aacaccatct gggtggtctc cgcggcccac tgtttcgaca aaatcaagaa ctggaggaac    840
ctgatcgcgg tgctgggcga gcacgacctc agcgagcacg acggggatga gcagagccgg    900
cgggtggcgc aggtcatcat ccccagcacg tacgtcccgg gcaccaccaa ccacgacatc    960
gcgctgctcc gcctgcacca gcccgtggtc ctcactgacc atgtggtgcc cctctgcctg   1020
cccgaacgga cgttctctga gaggacgctg gccttcgtgc gcttctcatt ggtcagcggc   1080
tggggccagc tgctggaccg tggcgccacg gccctggagc tcatggtcct caacgtgccc   1140
cggctgatga cccaggactg cctgcagcag tcacggaagg tgggagactc cccaaatatc   1200
acggagtaca tgttctgtgc cggctactcg gatggcagca aggactcctg caaggggac    1260
agtggaggcc cacatgccac ccactaccgg ggcacgtggt acctgacggg catcgtcagc   1320
tggggccagg gctgcgcaac cgtgggccac tttggggtgt acaccagggt ctcccagtac   1380
atcgagtggc tgcaaaagct catgcgctca gagccacgcc caggagtcct cctgcgagcc   1440
ccatttcccct agcccagcag ccctggcctg tggagagaaa gccaaggctg cgtcgaactg   1500
tcctggcacc aaatcccata tattcttctg cagttaatgg ggtagaggag ggcatgggag   1560
ggagggagag gtggggaggg agacagagac agaaacagag agagacagag acagagagag   1620
actgagggag agactctgag gacatggaga gagactcaaa gagactccaa gattcaaaga   1680
gactaataga gacacagaga tggaatagaa aagatgagag gcagaggcag acaggcgctg   1740
gacagagggg caggggagtg ccaaggttgt cctggaggca gacagcccag ctgagcctcc   1800
ttacctccct tcagccaagc ccacctgcac gtgatctgct ggcctcaggc tgctgctctg   1860
ccttcattgc tggagacagt agaggcatga acacacatgg atgcacacac acacgccca    1920
atgcacacac acagagatat gcacacacac ggatgcacac acagatggtc acacagagat   1980
acgcaaacac accgatgcac acgcacatag agatatgcac acagatgcac acacagat     2040
atacacatgg atgcacgcac atgccaatgc acgcacacat cagtgcacac ggatgcacag   2100
agatatgcac acaccgatgt gcgcacacac agatatgcac acatggat gagcacacac     2160
acaccaatgc gcacacacac cgatgtacac acacagatgc acacagat gcacacacac     2220
cgatgctgac tccatgtgtg ctgtcctctg aaggcggttg tttagctctc acttttctgg   2280
ttcttatcca ttatcatctt cacttcagac aattcagaag catcaccatg catggtggcg   2340
aatgccccca aactctcccc caaatgtatt tctcccttcg ctgggtgccg ggctgcacag   2400
actattcccc acctgcttcc cagcttcaca ataaacggct gcgtctcctc cgcacacctg   2460
tggtgcctgc cacccactgg gttgccatg attcatttt ggagccccg gtgctcatcc      2520
tctgagatgc tcttttcttt cacaattttc aacatcactg aaatgaaccc tcacatggaa   2580
gctattttt aaaacaaaa gctgtttgat agatgtttga ggctgtagct cccaggatcc     2640
tgtgaattg gatgttctct ccctgccaca gcccttgtca atgatatttc acagagaccc    2700
tgggagcacc tgctcaagag tcagggacac acgcatcact aaatgcaagt tcccaggccc   2760
```

```
tggctgcagt gggaggacct ggcaagctgc actcttgctg agtccccagg gtggtggaag    2820
aagaatgaga aacacatgaa cagagaaatg gggaggtgac aaacagtgcc cccactcaga    2880
ctccggcaag cacggctcag agagtggact cgatgccatc cctgcagggc cgtcctgggc    2940
accactggca ctcacagcag caaggtgggc accattggca ctcacagcag caaggcaggc    3000
accagcaacc cacctcgggg gcactcaggc atcatctact tcagagcaga cagggtctat    3060
gaactacagc cgtgggctgc ttccaaggca ccctgctctt gtaaataaag ttttatggga    3120
acacaaaaaa aaaaaaaaaa a                                              3141
```

<210> SEQ ID NO 168
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 168
ggatcattct ggccctgagc    20

<210> SEQ ID NO 169
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 169
tcttgggtgt ggatgtaaat    20

<210> SEQ ID NO 170
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 170
cagatttaaa ctgcagatga    20

<210> SEQ ID NO 171
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 171
tctagaattc caaacccta    20

<210> SEQ ID NO 172
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 172
caacacttca aatacgatct    20

<210> SEQ ID NO 173
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 173
cgtgcaggtg ttaaggtgtg                                              20

<210> SEQ ID NO 174
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 174
ggccagtggc catgcatccc                                              20

<210> SEQ ID NO 175
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 175
gagagctgca cctggccggc                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 176
ctgaacaccc cagctgagag                                              20

<210> SEQ ID NO 177
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 177
gagaccatga tgaaatctct                                              20

<210> SEQ ID NO 178
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 178
aagcagaagg cagaggagcc                                              20

<210> SEQ ID NO 179
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 179
agcccaagca gaaggcagag                                              20
```

```
<210> SEQ ID NO 180
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 180
ccctgaagcc caagcagaag                                                  20

<210> SEQ ID NO 181
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 181
ctgcccttcc accaagttta                                                  20

<210> SEQ ID NO 182
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 182
gttctttgaa aaataatccc                                                  20

<210> SEQ ID NO 183
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 183
gtgtttctcc tcctgaggcc                                                  20

<210> SEQ ID NO 184
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 184
tagccacccc gcgggctggc                                                  20

<210> SEQ ID NO 185
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 185
tcagaaaagc tctcaagaac                                                  20

<210> SEQ ID NO 186
<211> LENGTH: 20
<212> TYPE: DNA
<213> ORGANISM: Artificial Sequence
<220> FEATURE:
```

<223> OTHER INFORMATION: Synthetic Oligonucleotide

<400> SEQUENCE: 186
gcagatttgc atcagaaaag                                            20

<210> SEQ ID NO 187
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 187
ctttaaaatc agtttcacac                                            20

<210> SEQ ID NO 188
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 188
ggttactgag cgcggaagaa                                            20

<210> SEQ ID NO 189
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 189
cgagttctgc aggagcggcc                                            20

<210> SEQ ID NO 190
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 190
aggagcccga gttctgcagg                                            20

<210> SEQ ID NO 191
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 191
gacgaggcct caggtggacg                                            20

<210> SEQ ID NO 192
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 192
ttgctgggag gacgaggcct                                            20

```
<210> SEQ ID NO 193
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 193
gacgaccttt gctgggagga                                                   20

<210> SEQ ID NO 194
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 194
acgccgtggg cttcctcctg                                                   20

<210> SEQ ID NO 195
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 195
gcagctcctc caggaacgcg                                                   20

<210> SEQ ID NO 196
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 196
agggagcccg gccgcagctc                                                   20

<210> SEQ ID NO 197
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 197
agcactgctc ctccttgcac                                                   20

<210> SEQ ID NO 198
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 198
ctgatgtgaa aaccggcatg                                                   20

<210> SEQ ID NO 199
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 199
gtattttctg atgtgaaaac                                              20

<210> SEQ ID NO 200
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 200
taggcatgac catcctcaat                                              20

<210> SEQ ID NO 201
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 201
gtgagaatac aacagatgag                                              20

<210> SEQ ID NO 202
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 202
gggtgcagta gcagatgcaa                                              20

<210> SEQ ID NO 203
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 203
gggtgaccac acatttcctg                                              20

<210> SEQ ID NO 204
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 204
ctgtaagaaa tccagaacag                                              20

<210> SEQ ID NO 205
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 205
gagaagggtt gcaggcagga                                              20

<210> SEQ ID NO 206
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 206
caggagcccc cattctggca                                               20

<210> SEQ ID NO 207
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 207
gtccttgcag gagcccccat                                               20

<210> SEQ ID NO 208
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 208
ggactggagc tggtccttgc                                               20

<210> SEQ ID NO 209
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 209
agatatagga ctggagctgg                                               20

<210> SEQ ID NO 210
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 210
agcagatata ggactggagc                                               20

<210> SEQ ID NO 211
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 211
gaggcagaag cagatatagg                                               20

<210> SEQ ID NO 212
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 212
```
acagttccgg ccctcgaagg                                               20

<210> SEQ ID NO 213
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 213
aaatatggga cccaaagtgg                                               20

<210> SEQ ID NO 214
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 214
ccctctgcaa atatgggacc                                               20

<210> SEQ ID NO 215
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 215
caccccacca ggttgtgcac                                               20

<210> SEQ ID NO 216
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 216
ggctgagaat tgcccagggc                                               20

<210> SEQ ID NO 217
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 217
tctcgagggc tgagaattgc                                               20

<210> SEQ ID NO 218
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 218
taatttaata ttcagatggt                                               20

<210> SEQ ID NO 219
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 219
tatgagtcct tctagtgaat        20

<210> SEQ ID NO 220
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 220
tgtccacatg accccacagg        20

<210> SEQ ID NO 221
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 221
gagcttccca agttggcagt        20

<210> SEQ ID NO 222
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 222
tgataaaacc tctggacacc        20

<210> SEQ ID NO 223
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 223
gggctgagac tgaggtcagc        20

<210> SEQ ID NO 224
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 224
agggtagcct ttgccttggc        20

<210> SEQ ID NO 225
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 225
agatgaccag caggaagcct        20

<210> SEQ ID NO 226
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 226
ggacccagat gaccagcagg                                               20

<210> SEQ ID NO 227
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 227
gcattctgga cccagatgac                                               20

<210> SEQ ID NO 228
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 228
atgcacacca gggctgctgg                                               20

<210> SEQ ID NO 229
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 229
gcaggatgca caccagggct                                               20

<210> SEQ ID NO 230
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 230
cgggaaggcc tgccctgcag                                               20

<210> SEQ ID NO 231
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 231
tgaccactct tccgagcagc                                               20

<210> SEQ ID NO 232
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 232
cgtggactga tccaaaggac                                              20

<210> SEQ ID NO 233
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 233
gacagagcct gagcttggca                                              20

<210> SEQ ID NO 234
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 234
tactgctcac agccgccgtt                                              20

<210> SEQ ID NO 235
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 235
ggtcactgca gtactgctca                                              20

<210> SEQ ID NO 236
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 236
ggactggtgt catctgggac                                              20

<210> SEQ ID NO 237
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 237
ccacccttgg tgcccagatc                                              20

<210> SEQ ID NO 238
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 238
cagggtgccc atcctagtca                                              20

<210> SEQ ID NO 239
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 239
tcctgcgagt gggagttgga                                            20

<210> SEQ ID NO 240
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 240
atcccatttt cccaggagcc                                            20

<210> SEQ ID NO 241
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 241
agaaacatcc cattttccca                                            20

<210> SEQ ID NO 242
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 242
ccaggctggt ttggagaaac                                            20

<210> SEQ ID NO 243
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 243
atgaaattct acctaaagat                                            20

<210> SEQ ID NO 244
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 244
aggtgaatga aattctacct                                            20

<210> SEQ ID NO 245
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 245
```

```
gacaatggtc agggctggtt                                              20

<210> SEQ ID NO 246
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 246
tggctggctg aggagacaat                                              20

<210> SEQ ID NO 247
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 247
cagaaacacc catcctctga                                              20

<210> SEQ ID NO 248
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 248
tttttccaca tggatattca                                              20

<210> SEQ ID NO 249
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 249
taggtatttt tccacatgga                                              20

<210> SEQ ID NO 250
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 250
ggtttgctgg catttctttt                                              20

<210> SEQ ID NO 251
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 251
gccatggaca ctccccttttg                                             20

<210> SEQ ID NO 252
<211> LENGTH: 20
<212> TYPE: DNA
```

```
<213> ORGANISM: Artificial Sequence
<220> FEATURE:
<223> OTHER INFORMATION: Synthetic Oligonucleotide

<400> SEQUENCE: 252
tctgcacagg gtagaccctc                                               20

<210> SEQ ID NO 253
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 253
ggttctctgc acagggtaga                                               20

<210> SEQ ID NO 254
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 254
aaagatccca cctcaaagag                                               20

<210> SEQ ID NO 255
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 255
aaagatcagg caaagatccc                                               20

<210> SEQ ID NO 256
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 256
atagctttga tccaatgctc                                               20

<210> SEQ ID NO 257
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 257
tcccaggcaa agctgctcag                                               20

<210> SEQ ID NO 258
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 258
gattttgtcg aaacagtggg                                               20
```

<210> SEQ ID NO 259
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 259
tgacagcacg aagcccagag                                         20

<210> SEQ ID NO 260
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 260
gccatttcta ggtctgcagg                                         20

<210> SEQ ID NO 261
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 261
cgccggctct gctcatcccc                                         20

<210> SEQ ID NO 262
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 262
ctgcgccacc cgccggctct                                         20

<210> SEQ ID NO 263
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 263
ggatgatgac ctgcgccacc                                         20

<210> SEQ ID NO 264
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 264
ggcggagcag cgcgatgtcg                                         20

<210> SEQ ID NO 265
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 265
tggtcagtga ggaccacggg                                        20

<210> SEQ ID NO 266
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 266
caccacatgg tcagtgagga                                        20

<210> SEQ ID NO 267
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 267
gaagcgcacg aaggccagcg                                        20

<210> SEQ ID NO 268
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 268
ggcagtcctg ggtcatcagc                                        20

<210> SEQ ID NO 269
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 269
tgctgcaggc agtcctgggt                                        20

<210> SEQ ID NO 270
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 270
aacatgtact ccgtgatatt                                        20

<210> SEQ ID NO 271
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 271
cactgtcccc cttgcaggag                                        20

```
<210> SEQ ID NO 272
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 272
tgtgggcctc cactgtcccc                                               20

<210> SEQ ID NO 273
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 273
ccctggcccc agctgacgat                                               20

<210> SEQ ID NO 274
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 274
tgggagaccc tggtgtacac                                               20

<210> SEQ ID NO 275
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 275
gcagccactc gatgtactgg                                               20

<210> SEQ ID NO 276
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 276
gcttttgcag ccactcgatg                                               20

<210> SEQ ID NO 277
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 277
tgagcttttg cagccactcg                                               20

<210> SEQ ID NO 278
<211> LENGTH: 20
<212> TYPE: DNA
<213> ORGANISM: Artificial Sequence
<220> FEATURE:
<223> OTHER INFORMATION: Synthetic Oligonucleotide
```

-continued

<400> SEQUENCE: 278
cagccttggc tttctctcca					20

<210> SEQ ID NO 279
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 279 ccctgccct ctgtccagcg					20

<210> SEQ ID NO 280
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 280
tgtctgcctc caggacaacc					20

<210> SEQ ID NO 281
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 281
ctcagctggg ctgtctgcct					20

<210> SEQ ID NO 282
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 282
gcaggtgggc ttggctgaag					20

<210> SEQ ID NO 283
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 283
cagcctgagg ccagcagatc					20

<210> SEQ ID NO 284
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 284
gtctccagca atgaaggcag					20

<210> SEQ ID NO 285
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 285
gacagcacac atggagtcag                                                   20

<210> SEQ ID NO 286
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 286
aagtgagagc taaacaaccg                                                   20

<210> SEQ ID NO 287
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 287
agatgataat ggataagaac                                                   20

<210> SEQ ID NO 288
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 288
catggtgatg cttctgaatt                                                   20

<210> SEQ ID NO 289
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 289
tgtgagggtt catttcagtg                                                   20

<210> SEQ ID NO 290
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 290
tacagcctca aacatctatc                                                   20

<210> SEQ ID NO 291
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 291
```
gagctacagc ctcaaacatc                                              20

<210> SEQ ID NO 292
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 292
attgacaagg gctgtggcag                                              20

<210> SEQ ID NO 293
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 293
gcaggtgctc ccagggtctc                                              20

<210> SEQ ID NO 294
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 294
caggtcctcc cactgcagcc                                              20

<210> SEQ ID NO 295
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 295
gtgcagcttg ccaggtcctc                                              20

<210> SEQ ID NO 296
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 296
actcagcaag agtgcagctt                                              20

<210> SEQ ID NO 297
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 297
taaaacttta tttacaagag                                              20

<210> SEQ ID NO 298
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 298
ggtgtgttcc cataaaactt                                              20

<210> SEQ ID NO 299
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 299
aaagcagagc cagctctgac                                              20

<210> SEQ ID NO 300
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 300
gcctgcattt cccattggca                                              20

<210> SEQ ID NO 301
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 301
gccactcaca gaaagctgga                                              20

<210> SEQ ID NO 302
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 302
caggatgctc atggcagaca                                              20

<210> SEQ ID NO 303
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 303
gtttgtatgg agagaccaat                                              20

<210> SEQ ID NO 304
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 304
tggtggcacc agatgtctga                                              20
```

```
<210> SEQ ID NO 305
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 305
cattgtgcct ggcacacagg                                               20

<210> SEQ ID NO 306
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 306
gcctggtgtg cacacattgt                                               20

<210> SEQ ID NO 307
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 307
ctgggttacg aagactgcag                                               20

<210> SEQ ID NO 308
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 308
agcgaccccg cctgcagcca                                               20

<210> SEQ ID NO 309
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 309
agaaatccag aacagcttcg                                               20

<210> SEQ ID NO 310
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 310
cccatcactg taagaaatcc                                               20

<210> SEQ ID NO 311
<211> LENGTH: 20
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 311
actggtcccc atcactgtaa                                              20

<210> SEQ ID NO 312
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 312
aggcacactg gtccccatca                                              20

<210> SEQ ID NO 313
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 313
catggatatt caactgtggg                                              20

<210> SEQ ID NO 314
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 314
ccaacaacag gacctgccat                                              20

<210> SEQ ID NO 315
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 315
cgtgctcgcc cagcaccgcg                                              20

<210> SEQ ID NO 316
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 316
ggaagaaggg acggaaggtg                                              20

<210> SEQ ID NO 317
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 317
cggaagaagg gacggaaggt                                              20

<210> SEQ ID NO 318
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 318
gcggaagaag ggacggaagg                                         20

<210> SEQ ID NO 319
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 319
cgcggaagaa gggacggaag                                         20

<210> SEQ ID NO 320
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 320
gcgcggaaga agggacggaa                                         20

<210> SEQ ID NO 321
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 321
agcgcggaag aagggacgga                                         20

<210> SEQ ID NO 322
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 322
gagcgcggaa gaagggacgg                                         20

<210> SEQ ID NO 323
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 323
tgagcgcgga agaagggacg                                         20

<210> SEQ ID NO 324
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 324
```

```
ctgagcgcgg aagaagggac                                              20

<210> SEQ ID NO 325
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 325
actgagcgcg gaagaaggga                                              20

<210> SEQ ID NO 326
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 326
tactgagcgc ggaagaaggg                                              20

<210> SEQ ID NO 327
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 327
ttactgagcg cggaagaagg                                              20

<210> SEQ ID NO 328
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 328
gttactgagc gcggaagaag                                              20

<210> SEQ ID NO 329
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 329
tctgcaggag cggcctaaat                                              20

<210> SEQ ID NO 330
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 330
ttctgcagga gcggcctaaa                                              20

<210> SEQ ID NO 331
<211> LENGTH: 20
<212> TYPE: DNA
```

```
<213> ORGANISM: Artificial Sequence
<220> FEATURE:
<223> OTHER INFORMATION: Synthetic Oligonucleotide

<400> SEQUENCE: 331
gttctgcagg agcggcctaa                                               20

<210> SEQ ID NO 332
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 332
agttctgcag gagcggccta                                               20

<210> SEQ ID NO 333
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 333
gagttctgca ggagcggcct                                               20

<210> SEQ ID NO 334
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 334
ccgagttctg caggagcggc                                               20

<210> SEQ ID NO 335
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 335
cccgagttct gcaggagcgg                                               20

<210> SEQ ID NO 336
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 336
gcccgagttc tgcaggagcg                                               20

<210> SEQ ID NO 337
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 337
agcccgagtt ctgcaggagc                                               20
```

<210> SEQ ID NO 338
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 338
gagcccgagt tctgcaggag                                              20

<210> SEQ ID NO 339
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 339
ggagcccgag ttctgcagga                                              20

<210> SEQ ID NO 340
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 340
tcagggctgg ttttggagga                                              20

<210> SEQ ID NO 341
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 341
gtcagggctg gttttggagg                                              20

<210> SEQ ID NO 342
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 342
ggtcagggct ggttttggag                                              20

<210> SEQ ID NO 343
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 343
tggtcagggc tggttttgga                                              20

<210> SEQ ID NO 344
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 344
atggtcaggg ctggttttgg                                         20

<210> SEQ ID NO 345
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 345
aatggtcagg gctggttttg                                         20

<210> SEQ ID NO 346
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 346
caatggtcag ggctggtttt                                         20

<210> SEQ ID NO 347
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 347
acaatggtca gggctggttt                                         20

<210> SEQ ID NO 348
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 348
agacaatggt cagggctggt                                         20

<210> SEQ ID NO 349
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 349
gagacaatgg tcagggctgg                                         20

<210> SEQ ID NO 350
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 350
ggagacaatg gtcagggctg                                         20

<210> SEQ ID NO 351
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 351
aggagacaat ggtcagggct                                           20

<210> SEQ ID NO 352
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 352
gaggagacaa tggtcagggc                                           20

<210> SEQ ID NO 353
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 353
tgaggagaca atggtcaggg                                           20

<210> SEQ ID NO 354
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 354
ctgaggagac aatggtcagg                                           20

<210> SEQ ID NO 355
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 355
gctgaggaga caatggtcag                                           20

<210> SEQ ID NO 356
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 356
ggctgaggag acaatggtca                                           20

<210> SEQ ID NO 357
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 357
tggctgagga gacaatggtc                                          20

<210> SEQ ID NO 358
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 358
ctggctgagg agacaatggt                                          20

<210> SEQ ID NO 359
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 359
gctggctgag gagacaatgg                                          20

<210> SEQ ID NO 360
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 360
ccgccggctc tgctcatccc                                          20

<210> SEQ ID NO 361
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 361
cccgccggct ctgctcatcc                                          20

<210> SEQ ID NO 362
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 362
acccgccggc tctgctcatc                                          20

<210> SEQ ID NO 363
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 363
cacccgccgg ctctgctcat                                          20

<210> SEQ ID NO 364
<211> LENGTH: 20

<210> SEQ ID NO 365
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 364
ccacccgccg gctctgctca                                              20

<210> SEQ ID NO 365
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 365
gccacccgcc ggctctgctc                                              20

<210> SEQ ID NO 366
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 366
cgccacccgc cggctctgct                                              20

<210> SEQ ID NO 367
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 367
gcgccacccg ccggctctgc                                              20

<210> SEQ ID NO 368
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 368
tgcgccaccc gccggctctg                                              20

<210> SEQ ID NO 369
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 369
gcctgaggcc agcagatcac                                              20

<210> SEQ ID NO 370
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 370

```
agcctgaggc cagcagatca                                               20

<210> SEQ ID NO 371
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 371
gcagcctgag gccagcagat                                               20

<210> SEQ ID NO 372
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 372
agcagcctga ggccagcaga                                               20

<210> SEQ ID NO 373
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 373
gcacacatgg agtcagcatc                                               20

<210> SEQ ID NO 374
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 374
agcacacatg gagtcagcat                                               20

<210> SEQ ID NO 375
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 375
cagcacacat ggagtcagca                                               20

<210> SEQ ID NO 376
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 376
acagcacaca tggagtcagc                                               20

<210> SEQ ID NO 377
<211> LENGTH: 20
<212> TYPE: DNA
<213> ORGANISM: Artificial Sequence
```

<220> FEATURE:
<223> OTHER INFORMATION: Synthetic Oligonucleotide

<400> SEQUENCE: 377
gcatggtgat gcttctgaat                                               20

<210> SEQ ID NO 378
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 378
tgcatggtga tgcttctgaa                                               20

<210> SEQ ID NO 379
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 379
catgcatggt gatgcttctg                                               20

<210> SEQ ID NO 380
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 380
ccctgagctg ggca                                                     14

<210> SEQ ID NO 381
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 381
gagccacaga gcct                                                     14

<210> SEQ ID NO 382
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 382
tcttgggtgt ggat                                                     14

<210> SEQ ID NO 383
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 383
cagatgaaaa cttg                                                     14

<210> SEQ ID NO 384
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 384
caggtgttaa ggtg                                                       14

<210> SEQ ID NO 385
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 385
aggagaaagg tcag                                                       14

<210> SEQ ID NO 386
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 386
tgagagctgc acct                                                       14

<210> SEQ ID NO 387
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 387
caaagttctc tgcc                                                       14

<210> SEQ ID NO 388
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 388
tgaaatctct gcag                                                       14

<210> SEQ ID NO 389
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 389
catgatgaaa tctc                                                       14

<210> SEQ ID NO 390
<211> LENGTH: 14
<212> TYPE: DNA
<213> ORGANISM: Artificial Sequence
<220> FEATURE:
<223> OTHER INFORMATION: Synthetic Oligonucleotide -continued

```
<400> SEQUENCE: 390
gagaccatga tgaa                                                    14

<210> SEQ ID NO 391
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 391
tgaagcccaa gcag                                                    14

<210> SEQ ID NO 392
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 392
agccctgaag ccca                                                    14

<210> SEQ ID NO 393
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 393
gcacctgcag ccag                                                    14

<210> SEQ ID NO 394
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 394
caccaagttt atgg                                                    14

<210> SEQ ID NO 395
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 395
gcctggatgc tggt                                                    14

<210> SEQ ID NO 396
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 396
ttctttgaaa aata                                                    14

<210> SEQ ID NO 397
```

```
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 397
ctctgagagg cccc                                                    14

<210> SEQ ID NO 398
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 398
gtcataaggc catg                                                    14

<210> SEQ ID NO 399
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 399
gcagtccctg ctca                                                    14

<210> SEQ ID NO 400
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 400
cagggaacac cctc                                                    14

<210> SEQ ID NO 401
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 401
gtcccaggga aggc                                                    14

<210> SEQ ID NO 402
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 402
tctggaagga acag                                                    14

<210> SEQ ID NO 403
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 403
```
ctgaggatgc aggc				14

<210> SEQ ID NO 404
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 404
gctactgggc cacg				14

<210> SEQ ID NO 405
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 405
tgagcgcgga agaa				14

<210> SEQ ID NO 406
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 406
ggagggacga cctt				14

<210> SEQ ID NO 407
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 407
accacgcggt ggtg				14

<210> SEQ ID NO 408
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 408
cgtgcgctca gctc				14

<210> SEQ ID NO 409
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 409
aaaccggcat gcgc				14

<210> SEQ ID NO 410
<211> LENGTH: 14
<212> TYPE: DNA

```
<213> ORGANISM: Artificial Sequence
<220> FEATURE:
<223> OTHER INFORMATION: Synthetic Oligonucleotide

<400> SEQUENCE: 410
cctaagtgtg cttt                                                        14

<210> SEQ ID NO 411
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 411
agcttctcac cacg                                                        14

<210> SEQ ID NO 412
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 412
gagtgtgagg cttc                                                        14

<210> SEQ ID NO 413
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 413
catgttagcc tttg                                                        14

<210> SEQ ID NO 414
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 414
atgaccatcc tcaa                                                        14

<210> SEQ ID NO 415
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 415
atgagaaatg cttt                                                        14

<210> SEQ ID NO 416
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 416
tgctgaagaa actg                                                        14
```

```
<210> SEQ ID NO 417
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 417
tgcagtagca gatg                                                        14

<210> SEQ ID NO 418
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 418
gaggtacaca ggct                                                        14

<210> SEQ ID NO 419
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 419
acacccgagg ttca                                                        14

<210> SEQ ID NO 420
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 420
tgaccacaca tttc                                                        14

<210> SEQ ID NO 421
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 421
aatcttggcc cctc                                                        14

<210> SEQ ID NO 422
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 422
agccagactt tcct                                                        14

<210> SEQ ID NO 423
<211> LENGTH: 14
<212> TYPE: DNA
<213> ORGANISM: Artificial Sequence
<220> FEATURE:
```

<223> OTHER INFORMATION: Synthetic Oligonucleotide

<400> SEQUENCE: 423
tccagaacag cttc                                                                14

<210> SEQ ID NO 424
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 424
tgtaagaaat ccag                                                                14

<210> SEQ ID NO 425
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 425
ctggtcccca tctg                                                                14

<210> SEQ ID NO 426
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 426
acactggtcc ccat                                                                14

<210> SEQ ID NO 427
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 427
gaggcacact ggtc                                                                14

<210> SEQ ID NO 428
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 428
cttgcaggag cccc                                                                14

<210> SEQ ID NO 429
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 429
tggtccttgc agga                                                                14

```
<210> SEQ ID NO 430
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 430
ggagctggtc cttg                                                          14

<210> SEQ ID NO 431
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 431
taggactgga gctg                                                          14

<210> SEQ ID NO 432
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 432
agatatagga ctgg                                                          14

<210> SEQ ID NO 433
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 433
gaagcagata tagg                                                          14

<210> SEQ ID NO 434
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 434
aggcagaagc agat                                                          14

<210> SEQ ID NO 435
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 435
ccggccctcg aagg                                                          14

<210> SEQ ID NO 436
<211> LENGTH: 14
<212> TYPE: DNA
<213> ORGANISM: Artificial Sequence
<220> FEATURE:
<223> OTHER INFORMATION: Synthetic Oligonucleotide
```

<400> SEQUENCE: 436
acagttccgg ccct					14

<210> SEQ ID NO 437
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 437
ggacccaaag tggg					14

<210> SEQ ID NO 438
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 438
cggttggcca ggcc					14

<210> SEQ ID NO 439
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 439
gtcacctaga ccaa					14

<210> SEQ ID NO 440
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 440
gagaattgcc cagg					14

<210> SEQ ID NO 441
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 441
cagggactct cagc					14

<210> SEQ ID NO 442
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 442
tgaattactg aacc					14

<210> SEQ ID NO 443
<211> LENGTH: 14

```
<212> TYPE: DNA
<213> ORGANISM: Artificial Sequence
<220> FEATURE:
<223> OTHER INFORMATION: Synthetic Oligonucleotide

<400> SEQUENCE: 443 tgacccaca ggga                                                          14

<210> SEQ ID NO 444
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 444
cagtacttcc cacg                                                         14

<210> SEQ ID NO 445
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 445
ctctggacac cggg                                                         14

<210> SEQ ID NO 446
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 446
ctgacaatgt gatg                                                         14

<210> SEQ ID NO 447
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 447
ctgagggaat gttg                                                         14

<210> SEQ ID NO 448
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 448
gtggtcaagg atga                                                         14

<210> SEQ ID NO 449
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 449
```
gctgagcaga gatc 14

<210> SEQ ID NO 450
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 450
ggatgcacac cagg 14

<210> SEQ ID NO 451
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 451
tgacgagagg acca 14

<210> SEQ ID NO 452
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 452
ctcttccgag cagc 14

<210> SEQ ID NO 453
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 453
tccaaaggac aagg 14

<210> SEQ ID NO 454
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 454
ctgagcttgg cacc 14

<210> SEQ ID NO 455
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 455
gtcatccttg tctg 14

<210> SEQ ID NO 456
<211> LENGTH: 14
<212> TYPE: DNA
<213> ORGANISM: Artificial Sequence

```
<220> FEATURE:
<223> OTHER INFORMATION: Synthetic Oligonucleotide

<400> SEQUENCE: 456
ctggtcatcc ttgt                                                    14

<210> SEQ ID NO 457
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 457
atcagctggt catc                                                    14

<210> SEQ ID NO 458
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 458
gccgttctcg ttca                                                    14

<210> SEQ ID NO 459
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 459
acagccgccg ttct                                                    14

<210> SEQ ID NO 460
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 460
actgctcaca gccg                                                    14

<210> SEQ ID NO 461
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 461
gcagtactgc tcac                                                    14

<210> SEQ ID NO 462
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 462
tcactgcagt actg                                                    14
```

```
<210> SEQ ID NO 463
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 463
tacccctcgt ggca                                                        14

<210> SEQ ID NO 464
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 464
ccgtctgcca gcag                                                        14

<210> SEQ ID NO 465
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 465
ggacaccccg tctg                                                        14

<210> SEQ ID NO 466
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 466
tttgtccagt aaga                                                        14

<210> SEQ ID NO 467
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 467
catcctagtc actg                                                        14

<210> SEQ ID NO 468
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 468
agtcagtaca gaca                                                        14

<210> SEQ ID NO 469
<211> LENGTH: 14
<212> TYPE: DNA
<213> ORGANISM: Artificial Sequence
<220> FEATURE:
<223> OTHER INFORMATION: Synthetic Oligonucleotide
```

```
<400> SEQUENCE: 469
ccaggagcct ttac                                                        14

<210> SEQ ID NO 470
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 470
tgagtcccag gctg                                                        14

<210> SEQ ID NO 471
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 471
cctaaagatg aatc                                                        14

<210> SEQ ID NO 472
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 472
gggacactca cact                                                        14

<210> SEQ ID NO 473
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 473
ctggttttgg agga                                                        14

<210> SEQ ID NO 474
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 474
aagtggctgg ctga                                                        14

<210> SEQ ID NO 475
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 475
tcagaaagat gcag                                                        14

<210> SEQ ID NO 476
```

```
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 476
tggatattca actg                                                       14

<210> SEQ ID NO 477
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 477
ccacatggat attc                                                       14

<210> SEQ ID NO 478
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 478
tttttccaca tgga                                                       14

<210> SEQ ID NO 479
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 479 aggtatttttt ccac                                                      14

<210> SEQ ID NO 480
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 480
ggtttgctgg catt                                                       14

<210> SEQ ID NO 481
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 481
aattcggcct tggg                                                       14

<210> SEQ ID NO 482
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 482
```
cactcccctt tggg                                                    14

<210> SEQ ID NO 483
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 483
tgccatggac actc                                                    14

<210> SEQ ID NO 484
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 484
gacctgccca tttt                                                    14

<210> SEQ ID NO 485
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 485
gggtagaccc tcag                                                    14

<210> SEQ ID NO 486
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 486
tgattttgca aaga                                                    14

<210> SEQ ID NO 487
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 487
gatcttcaca tagc                                                    14

<210> SEQ ID NO 488
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 488
tgctcagacc tggc                                                    14

<210> SEQ ID NO 489
<211> LENGTH: 14
<212> TYPE: DNA

```
<213> ORGANISM: Artificial Sequence
<220> FEATURE:
<223> OTHER INFORMATION: Synthetic Oligonucleotide

<400> SEQUENCE: 489
tcaccaacaa cagg                                                        14

<210> SEQ ID NO 490
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 490
acccagatgg tgtt                                                        14

<210> SEQ ID NO 491
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 491
agaccaccca gatg                                                        14

<210> SEQ ID NO 492
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 492
aaacagtggg ccgc                                                        14

<210> SEQ ID NO 493
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 493
tgtcgaaaca gtgg                                                        14

<210> SEQ ID NO 494
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 494
gattttgtcg aaac                                                        14

<210> SEQ ID NO 495
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 495
agacacttga gagc                                                        14
```

<210> SEQ ID NO 496
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 496
tgacagcacg aagc                                                         14

<210> SEQ ID NO 497
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 497
ttatttgggc atgg                                                         14

<210> SEQ ID NO 498
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 498
ctaggtctgc aggg                                                         14

<210> SEQ ID NO 499
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 499
ctcgcctgga agga                                                         14

<210> SEQ ID NO 500
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 500
aggtcgtgct cgcc                                                         14

<210> SEQ ID NO 501
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 501
cgctgaggtc gtgc                                                         14

<210> SEQ ID NO 502
<211> LENGTH: 14
<212> TYPE: DNA
<213> ORGANISM: Artificial Sequence
<220> FEATURE:

<223> OTHER INFORMATION: Synthetic Oligonucleotide

<400> SEQUENCE: 502
gtgctcgctg aggt					14

<210> SEQ ID NO 503
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 503
atgacctgcg ccac					14

<210> SEQ ID NO 504
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 504
ggatgatgac ctgc					14

<210> SEQ ID NO 505
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 505
atgtcgtggt tggt					14

<210> SEQ ID NO 506
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 506
agcagcgcga tgtc					14

<210> SEQ ID NO 507
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 507
aggaccacgg gctg					14

<210> SEQ ID NO 508
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 508
cagtgaggac cacg					14

```
<210> SEQ ID NO 509
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 509
atggtcagtg agga                                                         14

<210> SEQ ID NO 510
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 510
accacatggt cagt                                                         14

<210> SEQ ID NO 511
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 511
ttcgggcagg caga                                                         14

<210> SEQ ID NO 512
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 512
gtccgttcgg gcag                                                         14

<210> SEQ ID NO 513
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 513
cagccgctga ccaa                                                         14

<210> SEQ ID NO 514
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 514
cggtccagca gctg                                                         14

<210> SEQ ID NO 515
<211> LENGTH: 14
<212> TYPE: DNA
<213> ORGANISM: Artificial Sequence
<220> FEATURE:
<223> OTHER INFORMATION: Synthetic Oligonucleotide
```

```
<400> SEQUENCE: 515
ggtcatcagc cggg                                                    14

<210> SEQ ID NO 516
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 516
gggtcatcag ccgg                                                    14

<210> SEQ ID NO 517
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 517
tgggtcatca gccg                                                    14

<210> SEQ ID NO 518
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 518
ctgggtcatc agcc                                                    14

<210> SEQ ID NO 519
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 519
cctgggtcat cagc                                                    14

<210> SEQ ID NO 520
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 520
tcctgggtca tcag                                                    14

<210> SEQ ID NO 521
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 521
gtcctgggtc atca                                                    14

<210> SEQ ID NO 522
<211> LENGTH: 14
```

```
<212> TYPE: DNA
<213> ORGANISM: Artificial Sequence
<220> FEATURE:
<223> OTHER INFORMATION: Synthetic Oligonucleotide

<400> SEQUENCE: 522
agtcctgggt catc                                                          14

<210> SEQ ID NO 523
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 523
cagtcctggg tcat                                                          14

<210> SEQ ID NO 524
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 524
ggcagtcctg ggtc                                                          14

<210> SEQ ID NO 525
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 525
ctgcaggcag tcct                                                          14

<210> SEQ ID NO 526
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 526
gactgctgca ggca                                                          14

<210> SEQ ID NO 527
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 527
cagaacatgt actc                                                          14

<210> SEQ ID NO 528
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 528
```
agtagccggc acag                                               14

<210> SEQ ID NO 529
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 529
ccttgcagga gtcc                                               14

<210> SEQ ID NO 530
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 530
gtggcatgtg ggcc                                               14

<210> SEQ ID NO 531
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 531
gccccagctg acga                                               14

<210> SEQ ID NO 532
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 532
ctggtgtaca cccc                                               14

<210> SEQ ID NO 533
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 533
cctggtgtac accc                                               14

<210> SEQ ID NO 534
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 534
ccctggtgta cacc                                               14

<210> SEQ ID NO 535
<211> LENGTH: 14
<212> TYPE: DNA
<213> ORGANISM: Artificial Sequence

```
<220> FEATURE:
<223> OTHER INFORMATION: Synthetic Oligonucleotide

<400> SEQUENCE: 535
accctggtgt acac                                                       14

<210> SEQ ID NO 536
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 536
gaccctggtg taca                                                       14

<210> SEQ ID NO 537
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 537
agaccctggt gtac                                                       14

<210> SEQ ID NO 538
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 538
gagaccctgg tgta                                                       14

<210> SEQ ID NO 539
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 539
ggagaccctg gtgt                                                       14

<210> SEQ ID NO 540
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 540
gggagaccct ggtg                                                       14

<210> SEQ ID NO 541
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 541
tgggagaccc tggt                                                       14
```

<210> SEQ ID NO 542
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 542
ctgggagacc ctgg                                                        14

<210> SEQ ID NO 543
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 543
actgggagac cctg                                                        14

<210> SEQ ID NO 544
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 544
tactgggaga ccct                                                        14

<210> SEQ ID NO 545
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 545
gtactgggag accc                                                        14

<210> SEQ ID NO 546
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 546
tgtactggga gacc                                                        14

<210> SEQ ID NO 547
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 547
atgtactggg agac                                                        14

<210> SEQ ID NO 548
<211> LENGTH: 14
<212> TYPE: DNA
<213> ORGANISM: Artificial Sequence
<220> FEATURE:
<223> OTHER INFORMATION: Synthetic Oligonucleotide

```
<400> SEQUENCE: 548
actcgatgta ctgg                                                    14

<210> SEQ ID NO 549
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 549
cagccactcg atgt                                                    14

<210> SEQ ID NO 550
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 550
ttttgcagcc actc                                                    14

<210> SEQ ID NO 551
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 551
tgagcttttg cagc                                                    14

<210> SEQ ID NO 552
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 552
gctcgcagga ggac                                                    14

<210> SEQ ID NO 553
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 553
cagccttggc tttc                                                    14

<210> SEQ ID NO 554
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 554
aggctcagct gggc                                                    14

<210> SEQ ID NO 555
```

```
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 555
taaggaggct cagc                                                        14

<210> SEQ ID NO 556
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 556
tgggcttggc tgaa                                                        14

<210> SEQ ID NO 557
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 557
gccagcagat cacg                                                        14

<210> SEQ ID NO 558
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 558
ctgaggccag caga                                                        14

<210> SEQ ID NO 559
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 559
gcagcctgag gcca                                                        14

<210> SEQ ID NO 560
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 560
gcaatgaagg caga                                                        14

<210> SEQ ID NO 561
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 561
```
tggagtcagc atcg                                    14

<210> SEQ ID NO 562
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 562
acacatggag tcag                                    14

<210> SEQ ID NO 563
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 563
acagcacaca tgga                                    14

<210> SEQ ID NO 564
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 564
taaacaaccg cctt                                    14

<210> SEQ ID NO 565
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 565
gtgagagcta aaca                                    14

<210> SEQ ID NO 566
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 566
gaaaagtgag agct                                    14

<210> SEQ ID NO 567
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 567
ctgaattgtc tgaa                                    14

<210> SEQ ID NO 568
<211> LENGTH: 14
<212> TYPE: DNA

```
<213> ORGANISM: Artificial Sequence
<220> FEATURE:
<223> OTHER INFORMATION: Synthetic Oligonucleotide

<400> SEQUENCE: 568
atgcttctga attg                                                    14

<210> SEQ ID NO 569
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 569
tggtgatgct tctg                                                    14

<210> SEQ ID NO 570
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 570
atgcatggtg atgc                                                    14

<210> SEQ ID NO 571
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 571
gtgcagcccg gcac                                                    14

<210> SEQ ID NO 572
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 572
cagaggatga gcac                                                    14

<210> SEQ ID NO 573
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 573
catctcagag gatg                                                    14

<210> SEQ ID NO 574
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 574
tcatttcagt gatg                                                    14
```

<210> SEQ ID NO 575
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 575
agggttcatt tcag                                                  14

<210> SEQ ID NO 576
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 576
atgtgagggt tcat                                                  14

<210> SEQ ID NO 577
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 577
gcctcaaaca tcta                                                  14

<210> SEQ ID NO 578
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 578
ctacagcctc aaac                                                  14

<210> SEQ ID NO 579
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 579
gggagctaca gcct                                                  14

<210> SEQ ID NO 580
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 580
attgacaagg gctg                                                  14

<210> SEQ ID NO 581
<211> LENGTH: 14
<212> TYPE: DNA
<213> ORGANISM: Artificial Sequence
<220> FEATURE:

<223> OTHER INFORMATION: Synthetic Oligonucleotide

<400> SEQUENCE: 581
atatcattga caag                                                    14

<210> SEQ ID NO 582
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 582
tcccagggtc tctg                                                    14

<210> SEQ ID NO 583
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 583
cagccagggc ctgg                                                    14

<210> SEQ ID NO 584
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 584
cactgcagcc aggg                                                    14

<210> SEQ ID NO 585
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 585
cttgccaggt cctc                                                    14

<210> SEQ ID NO 586
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 586
tgcagcttgc cagg                                                    14

<210> SEQ ID NO 587
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 587
aagagtgcag cttg                                                    14

```
<210> SEQ ID NO 588
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 588
tcagcaagag tgca                                                       14

<210> SEQ ID NO 589
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 589
gggactcagc aaga                                                       14

<210> SEQ ID NO 590
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 590
tgcccaggac ggcc                                                       14

<210> SEQ ID NO 591
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 591
tgcctgagtg cccc                                                       14

<210> SEQ ID NO 592
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 592
tccatggaca ctaa                                                       14

<210> SEQ ID NO 593
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 593
ggtcagctgg tctg                                                       14

<210> SEQ ID NO 594
<211> LENGTH: 14
<212> TYPE: DNA
<213> ORGANISM: Artificial Sequence
<220> FEATURE:
<223> OTHER INFORMATION: Synthetic Oligonucleotide
```

```
<400> SEQUENCE: 594
gggcccgcca ctgg                                                    14

<210> SEQ ID NO 595
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 595
ctcggacaaa agag                                                    14

<210> SEQ ID NO 596
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 596
atttcccatt ggca                                                    14

<210> SEQ ID NO 597
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 597
gctggagctg agcc                                                    14

<210> SEQ ID NO 598
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 598
tggccagtgg cctc                                                    14

<210> SEQ ID NO 599
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 599
gctcatggca gaca                                                    14

<210> SEQ ID NO 600
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 600
tggagagacc aatg                                                    14

<210> SEQ ID NO 601
<211> LENGTH: 14
```

<210> SEQ ID NO 601
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 601
tggtgtgcac acat                                                        14

<210> SEQ ID NO 602
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 602
tggccactgc ctca                                                        14

<210> SEQ ID NO 603
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 603
tgccgtagtg gccg                                                        14

<210> SEQ ID NO 604
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 604
cttggccagt gtgg                                                        14

<210> SEQ ID NO 605
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 605
acaggccagg ctgg                                                        14

<210> SEQ ID NO 606
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 606
aggtgacccg tgag                                                        14

<210> SEQ ID NO 607
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 607

```
cctgtgagtg tgag                                             14
```

<210> SEQ ID NO 608
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 608

```
ggtccccatc actg                                             14
```

<210> SEQ ID NO 609
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 609

```
ggacctgcca tgga                                             14
```

<210> SEQ ID NO 610
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 610

```
caacaggacc tgcc                                             14
```

<210> SEQ ID NO 611
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 611

```
gtgctcgccc agca                                             14
```

<210> SEQ ID NO 612
<211> LENGTH: 23
<212> TYPE: DNA
<213> ORGANISM: Artificial Sequence
<220> FEATURE:
<223> OTHER INFORMATION: Primer

<400> SEQUENCE: 612

```
aatgaggaac agtgctcctt tga                                   23
```

<210> SEQ ID NO 613
<211> LENGTH: 25
<212> TYPE: DNA
<213> ORGANISM: Artificial Sequence
<220> FEATURE:
<223> OTHER INFORMATION: Primer

<400> SEQUENCE: 613

```
tgtaaacaat ccagaactgc ttggt                                 25
```

<210> SEQ ID NO 614
<211> LENGTH: 22
<212> TYPE: DNA
<213> ORGANISM: Artificial Sequence

```
<220> FEATURE:
<223> OTHER INFORMATION: Probe

<400> SEQUENCE: 614
cccgggagat cttcaagagc cc                                              22
```